(12) United States Patent
Wu et al.

(10) Patent No.: US 10,830,672 B2
(45) Date of Patent: Nov. 10, 2020

(54) APPARATUS FOR COLLECTING LIQUID SAMPLE

(71) Applicant: Hangzhou Biotest Biotech Co., LTD., Hangzhou (CN)

(72) Inventors: John Wu, San Diego, CA (US); Liang Hong, Hangzhou (CN); Yangyu Zhu, San Diego, CA (US); Lorraine C. Cogan, San Diego, CA (US); Shujiang Wu, Hangzhou (CN)

(73) Assignee: Hangzhou Biotest Biotech Co., LTD., Hangzhou (CN)

( * ) Notice: Subject to any disclaimer, the term of this patent is extended or adjusted under 35 U.S.C. 154(b) by 332 days.

(21) Appl. No.: 16/044,283

(22) Filed: Jul. 24, 2018

(65) Prior Publication Data

US 2019/0250075 A1 Aug. 15, 2019

Related U.S. Application Data

(60) Provisional application No. 62/629,803, filed on Feb. 13, 2018.

(30) Foreign Application Priority Data

Feb. 13, 2018 (CN) .......................... 2018 1 0150485
Jun. 29, 2018 (CN) .......................... 2018 1 0712719
(Continued)

(51) Int. Cl.
*G01N 1/18* (2006.01)
*B01L 3/00* (2006.01)
(Continued)

(52) U.S. Cl.
CPC ............. *G01N 1/18* (2013.01); *A61B 10/007* (2013.01); *A61B 10/0051* (2013.01);
(Continued)

(58) Field of Classification Search
CPC ....... G01N 1/18; B01L 3/502; A61B 10/0045; A61B 10/007
See application file for complete search history.

(56) References Cited

U.S. PATENT DOCUMENTS 6,251,660 B1 * 6/2001 Muir ....................... B01L 3/502
 422/236
7,320,260 B2 1/2008 Belgardt
(Continued)

FOREIGN PATENT DOCUMENTS

| CN | 1897869 A | 1/2007 |
|---|---|---|
| CN | 104697811 A | 6/2015 |
| WO | WO 9525948 A1 | 9/1995 |

OTHER PUBLICATIONS

International Search Report and Written Opinion of PCT/CN2018/096954 dated May 13, 2019, 8 pp.

*Primary Examiner* — Brian J. Sines
(74) *Attorney, Agent, or Firm* — Thomas|Horstemeyer LLP

(57) ABSTRACT

The present invention provides an apparatus for collecting and detecting liquid samples comprising a first chamber and a second chamber. The first chamber is used for collecting liquid samples for initial detection, and the second chamber is used for collecting liquid samples for second confirmatory detection. The first chamber and second chamber of the apparatus are detachable. When a second confirmatory detection is necessary, the second chamber can be separated from the first chamber, and then sent to a detection agency for confirmatory detection. It can avoid the contamination of liquid samples caused by contacting with test strip of a traditional apparatus; thus, it can effectively reduce the space required for storing liquid samples and greatly reduce the risk of leakage of liquid sampled during transportation.

19 Claims, 65 Drawing Sheets

(30) Foreign Application Priority Data

| Jun. 29, 2018 | (CN) | 2018 1 0714355 |
| Jun. 29, 2018 | (CN) | 2018 1 0714500 |
| Jun. 29, 2018 | (CN) | 2018 1 0714562 |
| Jun. 29, 2018 | (CN) | 2018 1 0715825 |
| Jun. 29, 2018 | (CN) | 2018 1 0717088 |
| Jun. 29, 2018 | (CN) | 2018 1 0717252 |

(51) Int. Cl.
  *A61B 10/00* (2006.01)
  *B01L 9/06* (2006.01)

(52) U.S. Cl.
  CPC ........ *A61B 10/0096* (2013.01); *B01L 3/502* (2013.01); *A61B 10/0045* (2013.01); *B01L 9/06* (2013.01); *B01L 2200/0621* (2013.01); *B01L 2200/0689* (2013.01); *B01L 2300/0609* (2013.01); *B01L 2300/0663* (2013.01); *B01L 2300/0672* (2013.01); *B01L 2300/0832* (2013.01); *B01L 2400/0478* (2013.01); *B01L 2400/0633* (2013.01)

(56) References Cited

U.S. PATENT DOCUMENTS

| 7,988,935 | B2 | 8/2011 | Yuan et al. | |
| 9,327,284 | B2 | 5/2016 | Rosman et al. | |
| 2002/0030064 | A1* | 3/2002 | Lacout | B65D 81/3211 222/145.1 |
| 2002/0137199 | A1* | 9/2002 | Jobin | B01L 3/0293 435/287.2 |
| 2002/0197631 | A1* | 12/2002 | Lawrence | B01L 3/502 435/270 |
| 2003/0049833 | A1* | 3/2003 | Chen | B01L 3/502 435/287.2 |
| 2007/0292858 | A1* | 12/2007 | Chen | B01L 3/502 435/6.18 |
| 2008/0260581 | A1* | 10/2008 | Rosman | B65D 81/3211 422/68.1 |

* cited by examiner

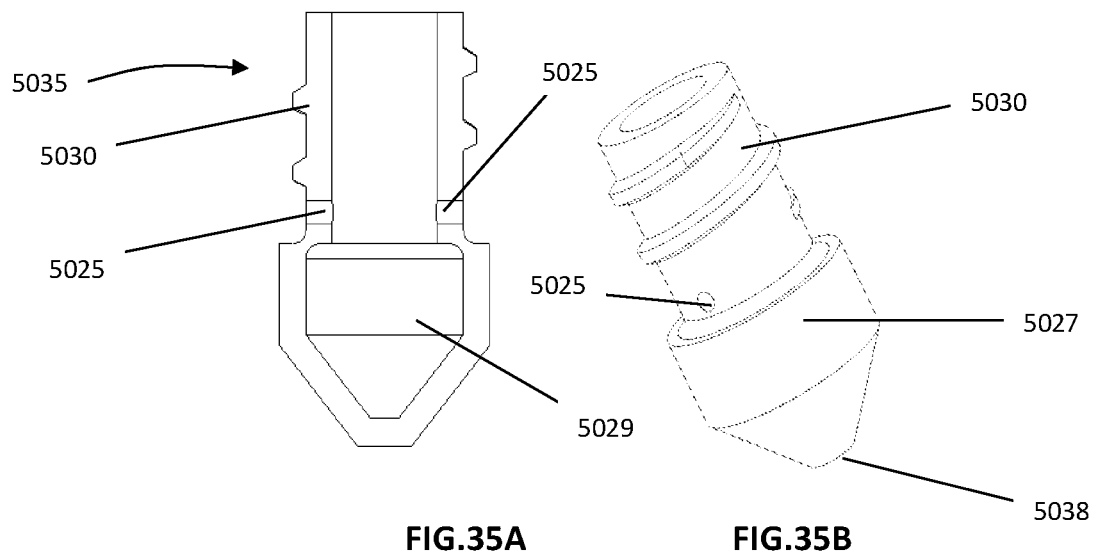
FIG.35A  FIG.35B
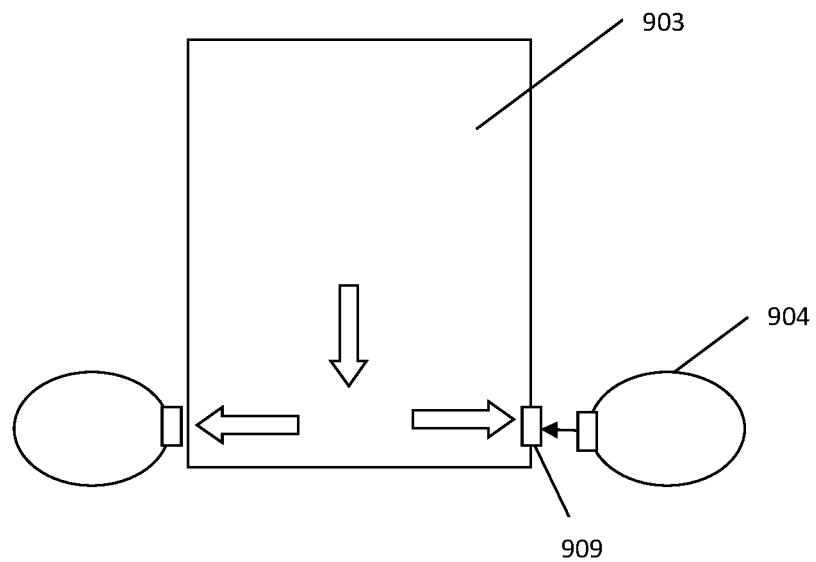
FIG.36

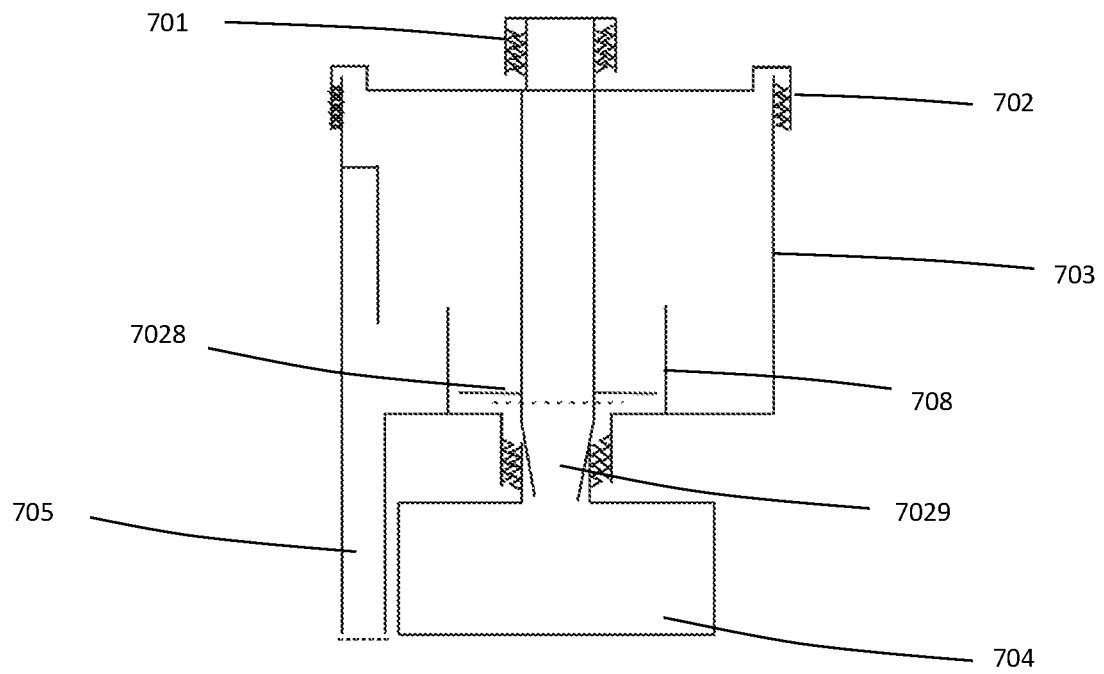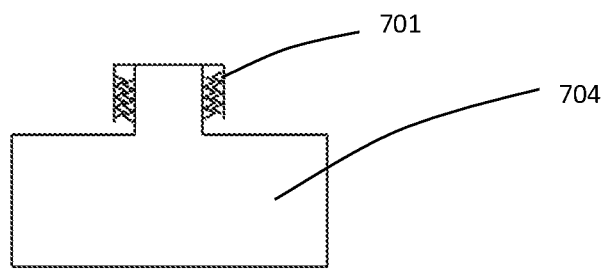
FIG.40

APPARATUS FOR COLLECTING LIQUID SAMPLE

RELATED APPLICATIONS

This application claims priority to Chinese Patent Application No. 201810150485.0, filed on Feb. 13, 2018, U.S. provisional application No. 62/629,803, filed on Feb. 13, 2018, and Chinese Patent Application Nos. 201810714500X, 2018107172524, 2018107170887, 201810715825X, 2018107143555, 2018107145620, 201810712719.6, filed on Jun. 29, 2018, each of which is incorporated herein by reference in its entirety.

FIELD OF THE INVENTION

The present invention relates to an apparatus for collecting liquid samples, in particular, an apparatus for collecting and detecting an analyte in liquid samples in the field of rapid diagnosis, such as a urine collection and detection apparatus.

BACKGROUND OF THE INVENTION

At present, the detection apparatus for detecting the presence or absence of analyte in sample is widely used in hospitals or homes, and such apparatus for rapid diagnosis comprises one or more test strips, such as early pregnancy detection, drug abuse detection, etc. The apparatus is very convenient, and the detection result can be obtained from the test strip after one minute or no more than ten minutes.

The drug detection is widely used by drug control department, Public Security Bureau, drug rehabilitation centers, physical examination centers, the national conscription offices, etc. The drug detection is diverse and frequent, so the urine detection cups that can automatically separate the tested samples and remaining samples have a huge need in the markets. Currently, for the urine detection cups available in the markets, the samples in the cup will be contaminated and unable to be used for the second confirmatory detection, for example, the U.S. Pat. No. 7,300,633.

In conventional technique, the samples to be tested can be separated from the collected samples, but it is expensive and not easy to operate. For example, the piston cup for urine detection in the U.S. Pat. No. 7,300,633. When pushing the piston forwards, the liquid samples in the collection chamber, such as urine, move from the collection chamber to the detection chamber; because there are testing elements for detecting analytes in the samples in the detection chamber, the liquid samples in the collection chamber are separated by a piston, so that samples in the two places will not be confused, which can be used for confirmatory detection in the future. Although this allows the samples to be tested are separated from the collected samples, this kind of piston cup is expensive and not easy to operate. The piston pushing needs a great force, because the piston wall needs to be liquid-sealed to reach the samples; while, to achieve sealing effect, the piston needs to be closely linked with the piston chamber. In addition, when performing a secondary test, the entire apparatus must be sent to a detection agency.

For another example, U.S. Pat. No. 8,992,855 describes an apparatus for collecting liquid samples, which comprises a piston structure integrated with the cover and moving together. Although the samples to be detected are separated from the collected samples, it needs to overcome a great pressure to enter the detection chamber; moreover, the sizes of the cover and cup port need to be precisely designed, so that the piston integrally coupled with the cover can be accurately inserted into the separation chamber.

In addition, for the traditional collection and detection apparatus, if subsequent confirmatory detection after initial detection is necessary, the entire collection and detection apparatus must be sent to a confirmatory detection agency for further confirmatory detection. This will at least bring the following problems: first, most of the existing collection and detection apparatuses only have preliminary detection chambers. If subsequent confirmatory detection is required, the entire apparatus containing the urine and test strip needs to be sent to a confirmatory detection agency for testing, and the samples in the urine cups may be contaminated by the test reagents. Second, there is a risk of liquid spillage due to a large cup port when the entire apparatus is sent to a confirmatory detection agency, which requires more costs to maintain a better sealing effect of the apparatus and minimize the risk of spillage; third, the confirmatory detection agency needs a large low-temperature storeroom to store the entire detection apparatus to prevent the deterioration of the liquid samples and get ready for further confirmatory detection, which will result in a substantial rise in costs for the confirmatory detection agency (also known as secondary detection agency).

The above technical problems need to be improved, so it is required to provide an alternative way to solve the shortcomings of the prior art.

SUMMARY OF THE INVENTION

To overcome the shortcomings in the prior art, an object of the present invention is to provide a first design, for example, the design as shown in 1-40. Therefore, the present invention provides a detection apparatus capable of separating initial detection samples and confirmatory detection samples (second detection). After the liquid samples are collected in the apparatus and before and after detection, the initial detection samples and confirmatory detection samples can be brought into two chambers, for example, the first chamber and the second chamber, and then the second chamber can be separated from the initial collection chamber (first chamber) before or after the initial detection is completed, to achieve a detachable separation of the second chamber and the chamber for initial collection of samples. The second chamber, after separated from the initial collection chamber, can be used for subsequent second detection or confirmatory detection, so as to achieve effect separation of initial detection samples collected and subsequent possible confirmatory detection samples (second detection), and achieve the purpose of at least twice detections for one-time collection.

It can also be considered that, the collection apparatus comprises two chambers, and the two chambers receive liquid samples such as urine simultaneously or sequentially. One of the chambers, for example, the first chamber is used to collect a part of liquid samples, and the other chamber, for example, the second chamber, is used to collect other liquid samples. When collected or during collecting, the liquid in the first chamber can be used to contact the testing element to complete the first test, and the second chamber can be separated from the first chamber for a second detection.

In one aspect of the present invention, an apparatus for collecting liquid sample is provided, comprising a first chamber and a second chamber, wherein the first chamber used for collecting liquid samples and the second chamber is used for collecting liquid samples for confirmatory detection; and the first chamber and the second chamber are detachably combined, assembled or connected.

In some preferred embodiments, before the second chamber is separated from the first chamber, the first chamber and the second chamber are in a fluid communication state; or when the first chamber and the second chamber are combined, the first chamber and the second chamber are in fluid communication state. By this way, regardless of whether the first chamber or the second chamber collects or receives a liquid sample, the liquid can flow in both chambers in an active flow way or a passive flow way.

In some preferred embodiments, the active flow means that liquid can flow from the first chamber to the second chamber or from the second chamber to the first chamber without external force. In some preferred embodiments, passive flow means that liquid can flow from the first chamber to the second chamber or from the second chamber to the first chamber through external force. Here, the external force refers to negative pressure, pressure that can press liquid, allowing the liquid to flow.

In some preferred embodiments, the first chamber and the second chamber are not in fluid communication while the second chamber is to be separated from the first chamber or after separated, thus the liquid will not flow between the two chambers. In some preferred embodiments, the first chamber and the second chamber are not in fluid communication while the second chamber is to be separated or before separated from the first chamber. Alternatively, in some preferred embodiments, after the second chamber is separated from the first chamber, liquid chambers from the first chamber are stored in the second chamber. In some preferred embodiments, the second chamber also collects liquid samples from the first chamber, either during or after collection of liquid samples by the first chamber. In some preferred embodiments, the second chamber also collects liquid samples from the first chamber while the first chamber collects the liquid samples.

In some other embodiments, the first chamber and the second chamber are detachably combined by a combination position, and then separated by the combination position. Here, the two chambers are separated before use, and assembled together during use. After use, they are separated again. Alternatively, the first chamber and the second chamber can be combined directly or indirectly through a structure. The combination position can be a place where the first chamber is in physical contact with the second chamber. Therefore, in another aspect of the invention, the first chamber is initially assembled with the second chamber, and after the liquid sample is collected, the second chamber is separated from the first chamber. The first chamber can be used for the first detection, while the second chamber can be used for the second detection or confirmatory detection. Alternatively, the first chamber and the second chamber are initially separated and not assembled. After collecting liquid samples, the second chamber is combined with the first chamber to allow some of the liquid to communicate or flow between the first chamber and the second chamber. When second detection is required, the two chambers are separated. The first chamber can be used for the first detection and the second chamber can be used for the second detection or confirmatory detection.

In a second aspect of the present invention, an apparatus for collecting liquid samples is provided, comprising a first chamber and a second chamber, wherein the first chamber is used for collecting liquid samples and the second chamber is used for collecting liquid samples for confirmatory detection; and the first chamber and the second chamber are detachably combined, assembled or connected.

In some preferred embodiments, the second chamber and the first chamber are in fluid communication through a connecting channel. In some preferred embodiments, the first chamber and the second chamber are in fluid communication through the connecting channel before the second chamber is separated from the first chamber. In some preferred embodiments, the first chamber and the second chamber are not in fluid communication while the second chamber is separated from the first chamber or after separated, and the channel is sealed. In some preferred embodiments, after the second chamber is separated from the first chamber, liquid chambers from the first chamber are stored in the second chamber. In some preferred embodiments, the second chamber also collects liquid samples from the first chamber through the connecting channel, either during or after collection of liquid samples by the first chamber. In some preferred embodiments, the second chamber also collects liquid samples from the first chamber through the connecting channel while the first chamber collects the liquid samples.

In one of all the foregoing embodiments, the first chamber comprises an opening for collecting liquid samples through which the liquid samples enter the first chamber. In some preferred embodiments, the connecting channel is in fluid communication with the first chamber and the second chamber, and the liquid samples can exchange liquid between the first chamber and the second chamber via the connecting channel. In some preferred embodiments, liquid samples can flow from the first chamber to the second chamber through the connecting channel. In some preferred embodiments, the connecting channel has a first opening and a second opening, wherein the first opening is in liquid communication with the first chamber and the second opening is in liquid communication with the second chamber. In some preferred embodiments, the connecting channel is located on the first chamber or in the first chamber. The second chamber is detachably connected, combined or assembled with the first chamber via the connecting channel. Therefore, the connecting channel allows the first chamber and the second chamber to be combined, assembled or connected together in an indirect and detachable manner.

In some preferred embodiments, the connecting channel comprises a structure that connects the first chamber and the second chamber, and a structure that separates the first chamber from the second chamber, wherein the structure that connects the first and second chambers is the space or the pipe that makes up the channel. In other preferred embodiments, alternatively, the connecting channel has two states: sealed or unsealed state. In the unsealed state, the liquid can flow from the first chamber to the second chamber. Preferably, the liquid in the first chamber cannot flow to the second chamber from the connecting channel. Therefore, the state of liquid exchange between the first chamber and the second chamber is limited by sealing or non-sealing of the connecting channel. When the connecting channel is not sealed, the fluid exchange exists between two chambers; and when the connecting channel is sealed, no fluid exchange exists between two chambers.

Therefore, in a third aspect of the present invention, a sealing element is provided. The sealing element can seal the connecting channel to allow the connecting channel in a sealed state. In a preferred embodiment, the connecting channel is connected to the first chamber and the second chamber, so that the second chamber and the first chamber are in a non-fluid communication state through the sealing by the sealing element. In some preferred embodiments, the apparatus further comprises a sealing element that seals the connecting channel. In some preferred embodiments, when the sealing element seals the channel or after sealing, partial liquid samples in the second chamber are discharged. Preferably, the liquid samples discharged are delivered to the first chamber. Alternatively, partial liquid samples (if any) are discharged to the place out of the connecting channel, such as the first chamber or elsewhere, while the sealing element seals the connecting channel. In some preferred embodiments, the sealing element further comprises an elastic seal ring that allows the sealing element to contact with the inner wall of the connecting channel, thereby allowing the sealing element tighter. In other preferred embodiments, the sealing element is more flexible than the connecting channel, thus, when any one is deformed or squeezed through contact between them, the sealing element is in close contact with the connecting channel, playing the role of sealing. For example, the sealing element is elastic and the connecting channel is rigid, and when the sealing element is forced to enter the connecting channel by an external force, the elastic element is squeezed and deformed, thereby sealing the connecting channel.

In other embodiments, the sealing element and the connecting channel are sealed by means of screw threads. For example, the sealing element has an external thread, and the connecting channel has an internal thread, and the sealing element seals the connecting channel by a way of relative rotation. In other preferred embodiments, the sealing element is a cover body-like structure with an internal thread, while the outer edge of the first opening of connecting channel has an external thread, by this way, the sealing element and the connecting channel can play a role of sealing.

In a fourth aspect of the present invention, the apparatus further comprises a discharge element. Before the sealing element seals the first opening of the connecting channel, part of the discharge element enters the second chamber. In some preferred embodiments, after the sealing element seals the opening of the connecting channel, part of the discharge element enters the second chamber. Alternatively, before the sealing element seals the first opening of the connecting channel, part of the discharge element enters the second chamber through a connecting channel.

Therefore, in a fourth aspect of the present invention, a discharge element is provided, which is used to discharge a portion of the liquid in the second chamber. Preferably, a portion of discharge element enters the second chamber before the sealing element seals the first opening of the connecting channel. In some preferred embodiments, after the sealing element seals the opening of the connecting channel, a portion of discharge element enters the second chamber. Alternatively, the discharge element enters the second chamber through the connecting channel, thereby discharging part of liquid from the second chamber. In some preferred embodiments, the discharge element and the sealing element are connected as an integral structure. In some embodiments, the discharge element enters the liquid connecting channel prior to the sealing element. Preferably, the second chamber is detachably coupled, combined or connected to the first chamber by a second opening of a liquid connecting channel. Alternatively, the discharge element is close to the first opening of the connecting channel earlier than the sealing element, wherein the first opening is in fluid communication with the first chamber. In some preferred embodiments, the sealing element is connected to the discharge element as an integral structure or a detachable combination, or in some embodiments, the sealing element can serve as two functions: sealing and discharging; optionally, the discharging element can also serve as two functions: sealing the connecting channel while discharging. Here, the different name only represents different function. Of course, the two functions can be realized by one element.

In a fifth aspect of the present invention, the apparatus further comprises a drain channel. The liquid is discharged outside of the connecting channel and/or the second chamber by the discharge element or sealing element. The said "outside" includes the first chamber or other locations, such as a receiving chamber. In some preferred embodiments, a liquid receiving chamber is included in the sealing element, and the liquid samples discharged from the second chamber enter the receiving chamber of the sealing element through a drain channel. The "receiving chamber" herein is used to collect surplus liquid that is discharged by the discharge element or the sealing element. Thus, the receiving chamber may be the first chamber or other locations, such as a space in a sealing element or a discharge element. In this way, the discharged liquid enters the receiving chamber through a drain channel. In some preferred embodiments, the drain channel has one or more liquid inlets located downstream of the first opening of the connecting channel. Alternatively, the drain channel has one or more liquid inlets located on the sealing element, allowing the liquid inlet to enter the connecting channel prior to the sealing element. In some preferred embodiments, after the connecting channel is sealed by a sealing element, the opening of the drain channel liquid inlet is located in the second chamber. In some preferred embodiments, the receiving chamber is located in the sealing element. In some preferred embodiments, the liquid inlet of the drain channel is located on the wall of the sealing element. In some preferred embodiments, the liquid inlet of the drain channel is located at the end of the sealing element.

In some preferred embodiments, the sealing element and the discharge element are connected as a whole, wherein the discharge element enters the connecting channel prior to the sealing element. In some preferred embodiments, a portion of the discharge element enters the second chamber and the sealing element seals the connecting channel. Preferably, the sealing element is located in the connecting channel. In some embodiments, the liquid inlet of the drain channel is located between the sealing element and the discharge element, or below the sealing element, or above the discharge element. In some embodiments, the liquid inlet of the drain channel is arranged at the end of the discharge element, either entering the connecting channel prior to the discharge element or entering the second chamber prior to the discharge element.

In a sixth aspect of the invention, the present invention provides a first cover body for covering the opening of the first chamber that collects liquid samples, wherein the sealing element for sealing the connecting channel is connected to the cover body, or the sealing element and cover body are combined as an integral structure. Thus, when the first cover body covers the opening of the first chamber, the sealing element enters the connecting channel, to seal the connecting channel. In some preferred embodiments, the first cover body comprises a sealing element. In some preferred embodiments, while the first cover body covers the first chamber opening, the sealing element connected to the first cover body seals the first opening of the connecting channel. The covering of first chamber opening by the first cover body is substantially synchronous with the sealing of the first opening of the connecting channel by the sealing element. Alternatively, when the sealing element is integrated with the discharge element, or the sealing element and the discharge element are provided on the first cover body, the three components can be connected as a whole or a detachable combination. Thus, when the cover body covers the opening of the first chamber, the sealing element seals the opening of the connecting channel and the discharge element discharges part of liquid from the second chamber (if any) during the covering process. The excessively discharged liquid enters the receiving chamber through the drain channel.

In some preferred embodiments, the central axis of the sealing element on the cover body is substantially on the same line as the central axis of the connecting channel. When the first cover body covers the opening of the first chamber, the sealing element can seal the connecting channel. In some preferred embodiments, the sealing element is connected to the cover body in a detachable manner. In some embodiments, the sealing element is connected to the cover body by means of a screw thread. In some embodiments, the sealing element is connected to the cover body by a connecting rod, so that the first chamber has a certain depth. When the cover body covers the opening of the first chamber, the sealing element is located at or near the opening of the connecting channel, when the first chamber is covered by the cover body, the sealing element connected by the connecting rod enters the connecting channel from the first opening close to the connecting channel, thereby sealing the connecting channel.

It can be understood that the sealing element is connected to one end of the connecting rod, and the other end of the connecting rod is connected with the cover body, and the movement of the cover body drives the sealing element to move synchronously, for example, when the cover body rotation drives the rotation of the sealing element or the cover body moves from top to bottom, it drives the sealing element to move from top to bottom. It can be further understood that, when the sealing element seals the connecting channel through the piston, its synchronous motion can seal the connecting channel. Of course, if the sealing element and the connecting channel move through screw threads, the synchronous rotation can also allow the sealing element to seal the connecting channel.

In some embodiments, the present invention provides a first cover body for covering the opening of the first chamber to collect liquid samples, wherein the first cover body comprises a sealing element and a discharge element, or the sealing element and the discharging element are connected with the cover body, or integrated with the cover body as an integral structure. In some preferred embodiments, when the first cover body covers the opening of the first chamber, the sealing element connected to the first cover body seals the first opening of the connecting channel, and the discharging element enters the second chamber. It can be understood that the movement of the first cover body drives the sealing element and the discharge element to move together.

In a seventh aspect of the invention, in some preferred embodiments, the apparatus of the present invention may further comprise a second cover body for sealing the opening of the second chamber. In some embodiments, the second cover body is disposed on the first cover body, and when it is necessary to seal the opening of the second chamber, the second cover body is removed from the first cover body to seal the opening of the second chamber. Therefore, in some embodiments, the second cover body is located on the first cover body and disposed on the first cover body by a way of screw thread, pin or bolt, etc. In other preferred embodiments, the second cover body is detachably located on the first cover body so that the second cover body can be easily removed from the first cover body.

In some preferred embodiments of all foregoing embodiments, the second chamber has an opening that collects liquid samples. In some preferred embodiments, the opening of the second chamber is in fluid communication with the second chamber opening of the connecting channel. In some preferred embodiments, the second chamber is detachably connected to the connecting channel by a screw thread. In some preferred embodiments, the opening of the second chamber has an internal thread and an external thread, wherein the internal thread is matched and connected with the external thread of the connecting channel. The external thread of the second chamber opening is matched and connected with the second cover body that covers the second chamber opening. Optionally, the second chamber and the second channel of the connecting channel can also be detachably connected together by clamping without a screw thread.

In some preferred embodiments, the apparatus further comprises a testing element, and the testing element is in fluid communication with the first chamber. In some preferred embodiments, the apparatus further comprises a detection chamber, and the testing element is located in the detection chamber.

In an eighth aspect of the present invention, a method of collecting liquid samples is provided. The apparatus for collecting liquid samples as foregoing described is provided, comprising a first chamber and a second chamber, wherein the first chamber is used for collecting liquid samples and the second chamber is used for collecting liquid samples for confirmatory detection; and the first chamber and the second chamber are detachably combined, assembled or connected. Liquid samples enter the first chamber through the opening of the first chamber, then the liquid samples enter the second chamber from the first chamber.

In some preferred embodiments, the apparatus comprises a connecting channel for liquid communication between the first chamber and the second chamber.

In some preferred embodiments, the method provides a sealing element, which seals the connecting channel after the liquid enters the second chamber.

In some preferred embodiments, the second chamber separates from the first chamber after the sealing element seals the connecting channel.

In some preferred embodiments, after the second chamber is separated from the first chamber, the opening of the second chamber is covered with a cover body.

In some preferred embodiments, the method comprises making the first chamber not in fluid communication with the second chamber after the second chamber has been separated from the first chamber. In some preferred embodiments, liquid samples from the first chamber are stored in the second chamber after the second chamber has been separated from the first chamber. In some preferred embodiments, when or after the first chamber collects liquid samples, the second chamber collects liquid samples from the first chamber. In some preferred embodiments, the second chamber collects liquid samples from the first chamber while the first chamber collects liquid samples.

In some preferred embodiments, the method includes allowing the first chamber and the second chamber to be in fluid communication through a connecting channel. In some preferred embodiments, the first chamber and the second chamber are allowed to be in fluid communication through the channel before the second chamber is separated from the first chamber. In some preferred embodiments, the first chamber and the second chamber are not in fluid communication while the second chamber is being separated from the first chamber or separated, and the connecting channel is sealed. In some preferred embodiments, liquid samples from the first chamber are stored in the second chamber after the second chamber is separated from the first chamber. In some preferred embodiments, the second chamber also collects liquid samples from the first chamber through the connecting channel, either during collection of liquid samples by the first chamber or after collection. In some preferred embodiments, the second chamber also collects liquid samples from the first chamber through the connecting channel while the first chamber collects liquid samples.

In some preferred embodiments, the first chamber comprises an opening for collecting liquid samples through which liquid samples enter the first chamber. In some preferred embodiments, the first chamber is connected to the second chamber by the connecting channel, so that liquid samples are in fluid communication between the first chamber and the second chamber via the connecting channel. In some preferred embodiments, the liquid samples can flow from the first chamber to the second chamber through the liquid channel. In some preferred embodiments, the connecting channel has a first opening and a second opening, wherein the first opening is in liquid communication with the first chamber and the second opening is in liquid communication with the second chamber. In some preferred embodiments, the connecting channel is located on the first chamber or in the first chamber, so that the second chamber is detachably connected, combined or assembled with the first chamber through the liquid channel.

In some preferred embodiments, the connecting channel has a structure that connects the first chamber and the second chamber, and a structure that separates the first chamber from the second chamber, wherein the structure that connects the first chamber and second chambers is the space that makes up the channel. Alternatively, the connecting channel has two states, sealed or unsealed, allowing liquid to flow from the first chamber to the second chamber when in an unsealed state; and allowing liquid not to flow from the first chamber to the second chamber via the connecting channel when the connecting channel is in a sealed state.

In some preferred embodiments, the method includes: the apparatus comprises a first cover body for covering liquid samples collected by the first chamber, wherein the sealing element and the cover body are connected and combined. In some preferred embodiments, the first cover body comprises a sealing element. In some preferred embodiments, the sealing element connected to the first cover body seals the second chamber opening of the connecting channel while/during/after the first cover body covers the opening of the first chamber. In some preferred embodiments, the cover body comprises a second cover body for sealing the opening of the second chamber. In some preferred embodiments, the sealing element is detachably connected with the cover body. In some embodiments, the sealing element is connected to the cover body by a screw thread.

In some preferred embodiments, the second chamber has an opening that collects liquid samples. In some preferred embodiments, the opening of the second chamber is in fluid communication with the second chamber opening of the connecting channel. In some preferred embodiments, the second chamber is detachably connected to the connecting channel by a screw thread. In some preferred embodiments, the opening of the second chamber has an internal thread and an external thread, wherein the internal thread is matched and connected with the external thread of the connecting channel. The external thread of the second chamber opening is matched and connected with the second cover body that covers the second chamber opening.

The first chamber and second chamber are detachably connected by a structural design of the connecting channel and the second chamber, and the detachable connection is a direct connection. In some preferred embodiments, the second chamber can be detachably connected, combined or assembled with the first chamber by a screw thread. When the second chamber and the first chamber are detachably assembled together, the first chamber and second chamber are in fluid communication. Preferably, the first chamber and the second chamber are in fluid communication via the connecting channel. In some preferred embodiments, the opening of the second chamber is in fluid communication with the second opening of the connecting channel. In some preferred embodiments, the second chamber is disposed on a base that forms a detachable combination with the first chamber. Alternatively, the second chamber and the base also form a detachable combination. In this way, the opening of the second chamber is in fluid communication with the connecting channel when the base and the first chamber are combined together directly. When the base is separated from the first chamber, the second chamber on base is separated from the second chamber along with base. Preferably, when base is separated from the first chamber, the second chamber on the base is separated from the connecting channel along with the base. In some preferred ways, the second chamber is separated from the base when base and the second chamber on the base are separated from the first chamber. In some preferred embodiments, when the second chamber is separated from the base, the opening of the second chamber is covered with a second cover body.

In a sixth aspect of the present invention, a method of collecting liquid samples is provided. An apparatus for collecting liquid sample as described above is provided, comprising a first chamber and a second chamber, wherein the second chamber and the first chamber are detachably connected, the first chamber is used to collect liquid samples, to allow liquid samples to flow into the second chamber.

In some preferred embodiments, when the second chamber collects liquid samples, the second chamber is separated from the first chamber, so that the opening of the second chamber is covered by a second cover body.

In some preferred embodiments, the first chamber and the second chamber are connected together by a connecting channel, wherein the first opening of the connecting channel is in liquid communication with the first chamber and the second opening of the connecting channel is in liquid communication with the second chamber.

In some preferred embodiments, the apparatus further comprises a sealing element. Before the second chamber is separated from the first chamber, the connecting channel is sealed by the sealing element.

In some preferred embodiments, the apparatus further comprises a cover body, wherein the cover body and the sealing element are integrated so that the cover body drives the sealing element to seal the second opening of the connecting channel when covering the first chamber opening.

In some preferred embodiments, the cover body drives the sealing element to enter the connecting channel. In some preferred embodiments, the second chamber is separated from the first chamber after the sealing element seals the connecting channel.

In some preferred embodiments, a discharge element for discharging a portion of liquid from the second chamber is further disposed on the cover body, and the cover body drives the discharge element to enter the second chamber. In some preferred embodiments, a sealing element and a discharge element are disposed on the cover body, and the discharge element enters the second chamber prior to the sealing element.

In some preferred embodiments, the apparatus further comprises a drain channel. The liquid samples discharged from the discharge element are discharged to the outside of the second chamber through the drain channel. In some preferred embodiments, the sealing element is brought into the connecting channel, and the liquid discharged from the sealing element is drained out of the connecting channel through the drain channel.

In some preferred embodiments, the liquid discharged by the sealing element or the discharge element is drained to the first chamber through the drain channel. In some preferred embodiments, a receiving chamber is provided on the cover body, the receiving chamber is in fluid communication with the drain channel, wherein the liquid discharged by the sealing element or the discharge element is discharged to the receiving chamber through the drain channel.

In a ninth aspect of the present invention, a method of detecting the presence or absence of an analyte in a liquid sample is provided. The method includes a liquid collection apparatus described in any one of the above ways. When liquid samples are collected in the first chamber, liquid samples from the first chamber are detected by the testing element. After obtaining the test results, the second chamber is separated from the first chamber according to any one of the above methods.

In some embodiments, the apparatus further comprises a detection chamber for accommodating the testing element. The detection chamber is in fluid communication with the first chamber. When the first chamber collects liquid samples, the liquid flows into the detection chamber. When the detection chamber includes a testing element, the second chamber is separated from the first chamber after the testing is completed by the testing element. In some preferred embodiments, liquid samples enter the detection chamber from the first chamber firstly, then enter the second chamber. Such a structure, as described above, is designed so as to prevent liquid that enters the detection chamber from entering the second chamber, to avoid contamination of liquid samples in the second chamber.

In a tenth aspect herein, the present invention provides a cover body having a sealing element for sealing a connecting channel. In some preferred embodiments, a seal ring is provided on the sealing element. In some preferred embodiments, the sealing element and connecting channel are of the same or different materials. In some preferred embodiments, the sealing element is made of a flexible material and the connecting channel is made of a rigid material. In some preferred embodiments, the sealing element and the first cover body are connected as an integral structure through the connecting rod. In some preferred embodiments, the sealing element also comprises an opening of the drain channel. In some preferred embodiments, the opening of the drain channel is located under the sealing element, or the opening of the drain channel enters the connecting channel prior to the sealing element. In some preferred embodiments, the cover body further comprises a receiving chamber that is in fluid communication with the drain channel. The receiving chamber is in communication with the opening of the drain channel. In some preferred ways, the receiving chamber is located in the sealing element.

In other preferred embodiments, a discharge element is further disposed on the first cover body, and the discharge element is further from the first cover body than the sealing element. Alternatively, the discharge element is disposed below the sealing element, or, the sealing element and the discharge element are disposed such that the discharge element enters the second chamber prior to the sealing element or the discharge element enters the connecting channel prior to the sealing element. Alternatively, when a connecting rod is disposed on the cover body to connect the first cover body and sealing element, the sealing element is connected with the discharge element. Alternatively, the connecting rod and sealing element and discharge element are an integral structure.

The present invention provides a second design, as specifically illustrated in FIGS. 41-78. The technical problem to be solved by the present invention is to provide an apparatus for collecting samples capable of separating the collected samples and separating the samples requiring the second confirmatory detection from samples for initial detection. It can be sealed independently and sent to a detection agency for confirmatory detection. The sample collection apparatus of the present invention can divide the collected samples into different chambers, and these chambers can realize partial communication or partition according to the needs of collection, separation or detection. Samples are obtained by one-time collection and stored separately. No contaminations will occur between samples for confirmatory detection and samples for initial detection and the testing elements, to ensure that it will not affect the effect of secondary confirmation.

In order to solve the above technical problem, in a first aspect of the invention, a sample detection apparatus is provided, comprising a first chamber for collecting liquid samples and a second chamber for collecting samples for confirmatory detection. The first chamber and the second chamber can be in a fluid communication or partition state. When the first chamber is in fluid communication with the second chamber, the liquid in the first chamber can be transferred to the second chamber under an external force.

In some preferred embodiments, the external force can be gravity. In some preferred embodiments, the external force is a force other than gravity. In some preferred embodiments, forces other than gravity include contact and/or non-contact pressure, thrust, squeezing force, and etc. In some preferred embodiments, the external force may be a force that overcomes gravity. In some preferred embodiments, the external force may be a force other than overcoming gravity, such as breaking an obstruction or passing through an opening. In some preferred embodiments, the external force may be a force generated inside the structure. In some preferred embodiments, the external force may be a force formed inside the structure by a structure or a matching, for example, a driving force generated by a pressure difference or an attractive force generated by a negative pressure or a vacuum. In some preferred embodiments, the second chamber can be set to a vacuum. When the first chamber can be in liquid communication with the second chamber, the liquid may flow from the first chamber to the second chamber due to the differential pressure. In some preferred embodiments, the second chamber is not necessarily an absolute vacuum. As long as the internal pressure of the second chamber is smaller than the first chamber, the foregoing pressure difference effect can be achieved. In some preferred embodiments, the first chamber can be pressurized, to achieve the foregoing pressure difference effect.

In some preferred embodiments, the first chamber can directly collect samples, or the first chamber can communicate with another chamber to receive samples directly or indirectly. But in which way, the receiving way does not require external force. For example, the first chamber has an opening that can receive the sample, or the first chamber has an opening that is in liquid communication with other chamber that directly receives samples. Samples can slide into the first chamber through other chamber under gravity. This process can be naturally realized by the process of collection, without requiring an external force.

In some preferred embodiments, the first chamber and the second chamber are in a liquid partition state without an external force, that is, in this case, there is no liquid communication between the first chamber and the second chamber; when an external force is applied, liquid communication can be achieved between the second chamber and the first chamber. In the state where the first chamber and the second chamber are in fluid communication, the samples in the first chamber can be transferred to the second chamber under a certain pressure, that is, it is necessary to exert an external force for transferring samples in the first chamber to the second chamber. This process cannot be achieved by natural power (such as gravity). When the second chamber collects appropriate amount of samples, the external force is removed, and the first chamber and the second chamber resume the liquid partition state. In some preferred embodiments, the external force that causes the first chamber and the second chamber to achieve the liquid communication state may be the same as that of transferring the samples in the first chamber to the second chamber. In some preferred embodiments, the external force that causes the first chamber and the second chamber to achieve the liquid communication state is different from that of transferring the samples in the first chamber to the second chamber.

As a possible implementation manner, for example, the first chamber has an opening to the second chamber, which has the characteristics of being normally closed without pressure and opened with pressure. By this way, when the liquid collected in the first chamber is subject to a pressure, the liquid can enter the second chamber through this opening. When the pressure is removed, the opening is closed again, to complete the transfer of samples in the first chamber to the second chamber.

As a possible implementation manner, a connector can be disposed between the second chamber and the first chamber. The connector can make the first chamber to communicate with the second chamber internally under certain conditions (for example, subjecting to a pressure), so that the first chamber is in liquid communication with the second chamber. In such case, the samples in the first chamber can be transferred to the second chamber. After the transfer, the connector can be removed and the second chamber is closed.

As a possible implementation manner, the connector can have a puncture, the second chamber has a sealing port, and the sealing port can be pierced by the puncture. When the connector is removed, the sealing port can restore the liquid seal, for example, sealed with rubber material. The puncture can pierce the sealing port under the action of external force, so that the first chamber is in communication with the second chamber, and the liquid in the first chamber can enter the second chamber through the puncture under pressure.

In a second aspect of the present invention, a third chamber for collecting samples initially is provided. The third chamber and the first chamber can be in a fluid communication or partition state.

In some preferred embodiments, the third chamber can be in a natural liquid communication with the first chamber, that is, the liquid in the third chamber can naturally flow into the first chamber without an external force. In some preferred embodiments, the liquid in the first chamber can also naturally flow into the third chamber without an external force.

In some preferred embodiments, the third chamber and the first chamber are in a fluid communication state under the action of external force, that is, the fluid in the third chamber does not actively flow into the first chamber, and an external force needs to be exerted to achieve fluid flowing from the third chamber to the first chamber. In some preferred embodiments, the fluid in the first chamber does not actively flow into the third chamber, and an external force needs to be exerted to achieve fluid flowing from the first chamber to the third chamber.

In some preferred embodiments, the third chamber and the first chamber are in a liquid partition state, that is, the liquid in the first chamber cannot flow into the third chamber, and the liquid in the third chamber cannot flow into the first chamber, and the partition state can be broken by an external force, that is, when possible, the liquid communication between the first chamber and the third chamber can be achieved by an external force. For example, in some preferred embodiments, when collecting sample initially, the samples collected in the third chamber will not enter the first chamber without an external force.

In some preferred embodiments, the third chamber can be used as a chamber for initially collecting the sample. As described in the first aspect, the first chamber or the third chamber can be used as a chamber for initially collecting the sample, and the liquid communication can be achieved between the first chamber and the third chamber. By this way, liquid samples collected in the third chamber can flow into the first chamber to achieve sample collection in the first chamber.

In some preferred embodiments, a first channel is provided for liquid communication between first chamber and the third chamber. Fluid can enter the third chamber from the first chamber or enter the first chamber from the third chamber through the first channel. In some preferred embodiments, this first channel is located at the bottom of the third chamber, so that the samples entering the third chamber can naturally flow into the first chamber under the action of its own gravity.

In some preferred embodiments, the first channel between the first chamber and the third chamber may be closed. When the first channel is closed, the first chamber and the third chamber are in a liquid partition state, for example, in some preferred embodiments, the samples first enter the third chamber, and flow into the first chamber along the first channel, the liquid in the first chamber can enter the second chamber under the action of an external force. In some preferred embodiments, when the first chamber and the second chamber are in a fluid communication state, the first channel can be closed.

In some preferred embodiments, the first chamber is located at the bottom of the third chamber. When the first chamber and the third chamber are in a fluid communication state, the liquid in the third chamber can flow directly into the first chamber under the action of its own gravity.

In some preferred embodiments, the fluid in the third chamber cannot naturally flow into the first chamber under the action of gravity. For example, the first chamber and the third chamber are partitioned in a natural state, and the communication port between the first chamber and the third chamber can be opened only under a certain pressure. In such case, samples will be loaded into the third chamber preferentially, and under a certain pressure, for example, the compression force generated by covering of the cover body, samples in the third chamber will be squeezed down, and forced to enter the first chamber.

In some preferred embodiments, the third chamber is preferentially loaded into samples. In some preferred embodiments, samples in the third chamber can enter the first chamber under the action of an external force.

In some preferred embodiments, the first chamber may be provided with a third channel passing through the third chamber. During the initial collection, the third channel is not loaded into the samples. In some preferred embodiments, the second chamber and the assembly structure of the second chamber may be assembled to the third channel. In some preferred embodiments, the second chamber can be assembled directly onto the third channel. In some preferred embodiments, the third channel and the third chamber have a common opening, but when the sample is loaded, attention should be paid to prevent samples from entering the third channel. In some preferred embodiments, when the sample is initially collected, the third channel can be closed, for example, it can be plugged with a plug, or sealed with a film.

In some preferred embodiments, the bottom of the third chamber is provided with openings that can communicate with the first chamber. In some preferred embodiments, the first chamber is in communication with the third chamber via the pressure port. When the third chamber is pressurized, the pressure port is opened, the fluid can directly enter the first chamber from the third chamber, and the pressure port can restore to be closed when the pressure is removed. In some preferred embodiments, the pressure port can withstand the liquid pressure of the third chamber in the filled state, that is, only the samples loaded in the third chamber are not enough to open the pressure port by their dead weight. In some preferred embodiments, the pressure port can be opened when the samples collected reach a certain amount. In some preferred embodiments, the pressure that the pressure port can withstand can be configured according to actual needs.

In a third aspect of the invention, a fourth chamber for collecting samples is provided. The fourth chamber and the first chamber can be in a fluid communication or partition state.

In some preferred embodiments, the third chamber can be in a natural liquid communication with the fourth chamber, that is, the liquid in the third chamber can naturally flow into the fourth chamber without an external force. In some preferred embodiments, the liquid in the fourth chamber can also naturally flow into the third chamber without an external force.

In some preferred embodiments, the third chamber and the fourth chamber are in a fluid communication state under the action of external force, that is, the fluid in the third chamber does not actively flow into the fourth chamber, and an external force needs to be exerted to achieve fluid flowing from the third chamber to the fourth chamber. In some preferred embodiments, the fluid in the fourth chamber does not actively flow into the third chamber, and an external force needs to be exerted to achieve fluid flowing from the fourth chamber to the third chamber.

In some preferred embodiments, the third chamber and the fourth chamber are in a liquid partition state, that is, the liquid in the first chamber cannot flow into the third chamber, and the liquid in the third chamber cannot flow into the fourth chamber, and the partition state can be broken by an external force, that is, when possible, the liquid communication between the fourth chamber and the third chamber can be achieved by an external force.

In some preferred embodiments, as stated in the foregoing second aspect, the third chamber can be used as a chamber for initially collecting the sample and the liquid communication can be achieved between the fourth chamber and the third chamber. By this way, liquid samples collected in the third chamber can flow into the fourth chamber to achieve sample collection in the fourth chamber.

In some preferred embodiments, a second channel is provided for liquid communication between fourth chamber and the third chamber. Fluid can enter the third chamber from the fourth chamber or enter the third chamber from the fourth chamber through the second channel. In some preferred embodiments, this second channel is located at the bottom of the third chamber, so that the samples entering the third chamber can naturally flow into the fourth chamber under the action of its own gravity.

In some preferred embodiments, the second channel between the fourth chamber and the third chamber may be closed. When the second channel is closed, the fourth chamber and the third chamber are in a liquid partition state, for example, in some preferred embodiments, the samples first enter the third chamber, and flow into the fourth chamber along the second channel, the liquid in the fourth chamber can enter the testing area under the action of an external force. In some preferred embodiments, when the fourth chamber and the testing area are in a fluid communication state, the second channel can be closed.

In a fifth aspect of the invention, the present invention provides a cover body for covering a sample collection port. In some preferred embodiments, the cover body can be used as the sealing element of the whole apparatus. In some preferred embodiments, the cover body can cover the sample collection port of the sample collection apparatus.

As foregoing stated, the second chamber and the first chamber can be in a fluid communication state, then there is a position and matching relationship between the second chamber and the first chamber. In some preferred embodiments, the second chamber and the first chamber may be combined or separated. In some preferred embodiments, the second chamber and the third chamber may be combined or separated.

In some preferred embodiments, the second chamber is mounted on the cover body. In some preferred embodiments, the second chamber is detachably connected to the cover body. In some preferred embodiments, an assembly channel of the second chamber is provided on the cover body. In some preferred embodiments, the second chamber is detachably connected to the assembly channel. In some preferred embodiments, assembly channel can be sealed.

In some preferred embodiments, the cover body can be assembled to the third chamber. In some preferred embodiments, when the cover body is covered with the third chamber, the second chamber and the first chamber can achieve liquid communication. In some preferred embodiments, when the cover body is covered with the third chamber, the connector pierces the second chamber to achieve liquid communication between the first chamber and the second chamber. In some preferred embodiments, when the cover body is covered with the third chamber, the assembly channel is combined with the first channel to seal the first channel, so that the third chamber and the first chamber are in a liquid partition state.

In some preferred embodiments, the cover body can be assembled to the first chamber. In some preferred embodiments, when the cover body is covered with the first chamber, the second chamber and the first chamber can achieve liquid communication accordingly. In some preferred embodiments, when the cover body is capped with the first chamber, the connector pierces the second chamber to achieve liquid communication between the first chamber and the second chamber.

In the fifth aspect of the invention, the present invention provides an assembly structure of the second chamber that can match with the channel in the cover body, to load/remove the second chamber into/from the cover body. In some preferred embodiments, the assembly structure is detachably combined or connected with the cover body. In some preferred embodiments, the detachable combination is a screw thread connection. In some preferred embodiments, the detachable combination is a plug fit.

In some preferred embodiments, the assembly structure is capable of fixing the second chamber therein. In some preferred embodiments, the assembly structure has a handle member that facilitates combination or separation of the assembly structure and the cover body. In some preferred embodiments, the assembly structure has a knob member that facilitates combination or separation of the assembly structure and the cover body. Whether it is a handle member or a knob member, its role is to facilitate the combination or separation of the assembly structure and the cover body. In some preferred embodiments, when the assembly structure and the cover body are separated, the cover body can be plugged with a plug. In some preferred embodiments, before the assembly structure and the cover body are assembled, the cover body may be plugged with a plug to prevent the space in the cover body for accommodating the assembly structure from dusts or contamination.

In some preferred embodiments, the assembly structure is provided with some hollow structure through which a certain external force, such as squeezing, can be applied to the second chamber to cause samples to flow out.

In a sixth aspect of the invention, the present invention provides a connector for communicating the first chamber or a second chamber or for achieving liquid communication between the first chamber and the second chamber. In some preferred embodiments, the connector itself has a chamber (which can be called a communicating chamber). In some preferred embodiments, when the connector communicates with the first chamber, its internal chamber and first chamber are in liquid communication. In some preferred embodiments, when the connector communicates with the second chamber, the communicating chamber inside the connector is in liquid communication with the second chamber. In some preferred embodiments, both the communicating chamber inside the connector and the first chamber are in liquid communication with the second chamber.

In some preferred embodiments, the connector and the second chamber can be combined or separated. In some preferred embodiments, the connector pierces the second chamber to achieve liquid communication with the second chamber. In some preferred embodiments, after the connector is separated from the second chamber, the second chamber is naturally closed. In some preferred embodiments, the connector is detachably combined with the second chamber.

In some preferred embodiments, the connector can be mounted directly on the first channel. In some preferred embodiments, the connector can be mounted on the first channel with the cover body. In some preferred embodiments, the connector is a detachably combined or connected with the assembly channel on the cover body. In some preferred embodiments, the connector can be mounted on the assembly channel. At this time, the connector and the cover body move synchronically. With the covering of the cover body, the connector can be placed on the first channel. In some preferred embodiments, samples that need to be collected by the second chamber can enter the connector from the first channel, and then enter the second chamber from the connector.

In some preferred embodiments, the connector communicates with the first chamber through the first channel. In some preferred embodiments, the connector enables the first channel and the third chamber to be in a liquid partition state when in communication with the first chamber.

In a seventh aspect of the invention, the present invention provides a second chamber for collecting samples for second confirmatory detection. The second chamber is used for collecting and storing samples for second confirmatory detection. In some preferred embodiments, the second chamber obtains samples from the first chamber. In some preferred embodiments, the second chamber is capable of natural sealing. In some preferred embodiments, the second chamber can be sealed after a sufficient amount of sample has been collected. In some preferred embodiments, the volume of the second chamber is variable. In some preferred embodiments, the second chamber may be a flexible chamber. In some preferred embodiments, the second chamber may be in a vacuum state before being loaded into samples. In some preferred embodiments, the second chamber can be sealed by a rubber plug. In some preferred embodiments, the connector can pierce the rubber plug, and when the connector is removed, the rubber plug can maintain sealing under a certain pressure condition, so that the second chamber has the function of sealing and storing the liquid samples.

In some preferred embodiments, the second chamber is directly detachably combined or connected to the first chamber. In some preferred embodiments, the second chamber is detachably combined or connected to the first chamber by the cover body. In some preferred embodiments, the second chamber is detachably combined or connected to the cover body by an assembly structure.

In some preferred embodiments, the second chamber is detachably connected to the assembly structure. In some preferred embodiments, the second chamber can be placed in the assembly structure. In some preferred embodiments, the assembly structure is provided with a hollow structure through which a certain external force, such as squeezing, can be applied to the second chamber to cause the samples to flow out. In some preferred embodiments, the second chamber has an opening which can be kept closed without being subjected to pressure or within a certain pressure range, so that a certain amount of sample can be stored in the second chamber, and the hydraulic pressure of the samples is insufficient to open the opening; moreover, the opening can be opened under sufficient pressure to allow the second chamber to achieve liquid communication with outside or other chamber. The sufficient pressure can be, for example, squeezing or other means of compression.

In some preferred embodiments, the second chamber may be a rigid chamber. In some preferred embodiments, the second chamber may be a flexible chamber. In some preferred embodiments, the second chamber changes its shape and volume after being loaded into the samples. In some preferred embodiments, the second chamber can be configured to have a small internal pressure, for example, the internal pressure is smaller than that in the first chamber or the third chamber, so that the driving force generated by the differential pressure or the attractive force generated by the negative pressure or vacuum can transfer the samples in the first chamber or third chamber to the second chamber. In some preferred embodiments, the second chamber can be set to a vacuum. When the first chamber and the second chamber are capable of liquid communication, the liquid may flow from the first chamber to the second chamber due to the differential pressure. In some preferred embodiments, the second chamber is not completely vacuumed, as long as the internal pressure of the second chamber is smaller than that of the first chamber, the pressure difference effect described above can be achieved. In some preferred embodiments, the first chamber can be pressurized, and the differential pressure effect described above can also be achieved.

In an eighth aspect of the invention, the invention provides a pipetting element capable of transferring liquid from a first chamber into a second chamber. In some preferred embodiments, the pipetting element is capable of transferring liquid in the fourth chamber to the testing area.

In some preferred embodiments, the pipetting element comprises a first pipetting element for transferring samples in the first chamber to the second chamber, and a second pipetting element for transferring the samples in the fourth chamber to the testing area. In some preferred embodiments, the first pipetting element is capable of moving under the action of an external force to squeeze samples in the first chamber, thereby generating pressure to transfer them to a desired direction or a chamber. In some preferred embodiments, the second pipetting element is capable of moving under the action of an external force to squeeze samples in the fourth chamber, thereby generating pressure to transfer them to a desired direction or a chamber.

In some preferred embodiments, the first pipetting element and the first chamber are in the same pipetting channel, and the first pipetting element is pushed to achieve the above extrusion. In some preferred embodiments, the second pipetting element and the fourth chamber are in the same pipetting channel, pushing the second pipetting element to achieve the above extrusion. In some preferred embodiments, first pipetting element, second pipetting element, first chamber, and fourth chamber are in the same pipetting channel, and pushing one of the first pipetting element or the second pipetting element can simultaneously achieve the above extrusion, in this case, the first pipetting element and the second pipetting element can achieve the linkage state level by level. For example, when the first pipetting element is pushed, the first pipetting element is first forced to move and squeeze the sample in the first chamber. The resistance for moving the second pipetting element may be greater than that for moving the liquid in the first chamber, at this time, the sample in the first chamber is preferentially transferred. When the sample in the first chamber is discharged to the first pipetting element and the force on the second pipetting element is greater than the resistance of the second pipetting element, the second pipetting element begins to squeeze the sample in the fourth chamber so that the sample in the fourth chamber is also transferred, or, in other cases, the second pipetting element is pushed and first forced to move and squeeze the sample in the fourth chamber. At this time, the resistance of the first pipetting element may be greater than the resistance of the liquid in the fourth chamber, and the sample in the fourth chamber is preferentially transferred. When the sample in the fourth chamber is discharged to the second pipetting element, and the force on the first pipetting element is greater than the resistance of moving the first pipetting element, the first pipetting element begins to squeeze the sample in the first chamber so that the sample in the first chamber is also transferred. In some cases, we hope that, when the first pipetting element and the second pipetting element are in the linkage state as described above, the liquid in the first chamber is preferentially transferred.

In some preferred embodiments, the pipetting channel can be in fluid communication or partitioned with the second chamber. In some preferred embodiments, the pipetting channel can be in fluid communication or partitioned with the testing area. In some preferred embodiments, first pipetting element and second pipetting element separate the pipetting channel into a first chamber and a fourth chamber. In some preferred embodiments, the fourth chamber is partitioned with the second chamber by a second pipetting element.

In some preferred embodiments, when the sample in the first chamber is transferred into the second chamber, the volume of the first chamber decreases accordingly. In some preferred embodiments, when the volume of the first chamber is reduced, the first pipetting element and the second pipetting element are approaching. In some preferred embodiments, when the sample in the fourth chamber is transferred to the test area, the volume of the fourth chamber is reduced. In some preferred embodiments, when the liquid in the first chamber is transferred, the liquid communication state between the first chamber and the second chamber is blocked. In some preferred embodiments, when the liquid in the fourth chamber is transferred, the liquid communication state between the fourth chamber and the third chamber is blocked. In some preferred embodiments, the communication state of the fourth chamber and the third chamber is blocked by sealing the second channel during the movement by the second pipetting element.

In some preferred embodiments, the initial volume of the fourth chamber is fixed, that is, the amount of samples that are loaded in the fourth chamber can be determined before the fourth chamber is stressed. In some preferred embodiments, the second pipetting element is fixed at the initial position within the pipetting channel. In some preferred embodiments, the initial volume of the first chamber is fixed, that is, the amount of sample that are loaded in the first chamber can be determined before the first chamber is stressed. In some preferred embodiments, first pipetting element is fixed at the initial position in the pipetting channel. In some preferred embodiments, the first pipetting element and the second pipetting element are fixed relative to the initial position in the pipetting channel.

In some preferred embodiments, the pipetting channel has a pipetting opening through which an external force can be applied to the pipetting channel to achieve the above extrusion. In some preferred embodiments, the pipetting opening can be sealed by a first pipetting element or a second pipetting element. In some preferred embodiments, the pipetting element further comprises a pipetting plug capable of pushing the first pipetting element and/or the second pipetting element. In some preferred embodiments, the pipetting plug can be inserted into the pipetting channel through the pipetting opening. In some preferred embodiments, the first pipetting element and/or the second pipetting element is provided with a socket matching the pipetting plug.

In some preferred embodiments, a sealing element is provided between the pipetting element and the pipetting channel to ensure that no samples will leak from the place between the pipetting element and the inner wall of the pipetting channel when the pipetting element moves within the pipetting channel.

In a ninth aspect of the invention, the invention provides a method of collecting a liquid sample. The method uses An apparatus for collecting samples as described previously. The sample collection apparatus comprises a first chamber for collecting a liquid sample and a second chamber for collecting samples for confirmatory detection. The first chamber and the second chamber can be in a fluid communication state or in a partitioned state. When the first chamber and the second chamber are in a fluid communication state, the liquid in the first chamber can be transferred to the second chamber.

In some preferred embodiments, the apparatus further comprises a third chamber for collecting samples. The third chamber and the first chamber are in a fluid communication state or in a partitioned state. Initial samples can be collected in the third chamber, and the samples collected in the first chamber may be transferred to the second chamber for second detection.

In some preferred embodiments, when the first chamber and the third chamber are in fluid communication state, the liquid collected in the third chamber can enter the first chamber at the same time, that is, when initial samples are collected in the third chamber, the initially collected samples can also be loaded in the first chamber.

In some preferred embodiments, when the liquid in the first chamber is transferred into the second chamber, the first chamber and the third chamber are in a liquid partition state. Since the sample in the second chamber is used for second confirmatory detection, in order to ensure that the sample in the second chamber is not contaminated, the first chamber is isolated from the other chambers prior to transfer.

In some preferred embodiments, it further comprises a fourth chamber for collecting the sample to be detected, and the fourth chamber being in fluid communication with or partitioned with the third chamber.

In some preferred embodiments, when the fourth chamber is in fluid communication with the third chamber, the liquid collected in the third chamber can enter the fourth chamber at the same time. The fourth chamber can also be in communication with the third chamber when collecting samples initially, by this way, the fourth chamber can basically complete the required samples synchronously with the third chamber. The samples collected in the fourth chamber are mainly used for initial detection. The initial detection can be performed directly in the fourth chamber, or can be transferred to other areas through the fourth chamber, for example, to the testing area.

In some preferred embodiments, it further comprises a testing area. The fourth chamber is in fluid communication with or partitioned with the testing area. When initially collecting samples in the fourth chamber, the fourth chamber can be separated from the testing area, that is, sample collection and detection can be carried out independently.

In some preferred embodiments, when the fourth chamber is in fluid communication with the testing area, the fourth chamber and the third chamber are in a liquid parturition state, which, on one hand, can ensure that the testing area is not affected by contamination of other chambers, and on the other hand, the quantitative detection can be achieved. As long as the volume of the fourth chamber is set, the quantitative detection of samples entering the testing area can be achieved.

In some preferred embodiments, the second chamber and the third chamber can be combined or separated. In some preferred embodiments, the second chamber and the first chamber can be combined or separated. Since the second chamber needs to acquire the collected samples from the first chamber or the third chamber, the second chamber must establish a liquid communication relationship with the first chamber or the third chamber or one of them. After the desired samples are acquired, the second chamber must be independently sealed and preserved, or even transported independently and sent to a second detection agency. So, the second chamber must be separated from the first chamber or the third chamber or one of them, in some preferred embodiments, the second chamber can be detachably combined or connected to the first chamber or the third chamber or one of them.

In some preferred embodiments, it further comprises a communicating device between the first chamber and the second chamber. The communicating device provides a convenient channel and path for the samples in the first chamber to enter the second chamber.

In some preferred embodiments, when samples are collected initially, the communicating device is not mounted. When a secondary confirmatory test is required, the communicating device is mounted.

In some preferred embodiments, the communicating device can allow the first chamber and the second chamber to be in a fluid communication state or in a partition state.

In some preferred embodiments, the communicating device can block the communication between the first chamber and the third chamber. After initial collection of samples is completed, the first chamber and the third chamber may be partitioned to ensure that the samples for a second confirmatory test are not contaminated.

In the present invention, since the initially collected samples cannot naturally enter the second chamber, an external force must be exerted. In such cases, it is necessary to take a force on the initially collected samples.

Therefore, in some preferred embodiments, the method of the present invention further provides a pipetting element. After the initial collection is completed, there is a sufficient amount of samples in the first chamber, at this time, the pipetting element is pushed to squeeze the samples in the first chamber, to allow samples to enter the second chamber directly or through a communicating device, while the volume of the first chamber itself is reduced. In some preferred embodiments, the pipetting element can also transfer samples in the fourth chamber. In some preferred embodiments, samples in the fourth chamber can be transferred after the first chamber. In some preferred embodiments, the first chamber and the fourth chamber may be extruded using different pipetting elements, respectively. In some preferred embodiments, a linkage can be achieved for pipetting elements between the first chamber and the fourth chamber.

In some preferred embodiments, the method of the present invention further provides a pipetting channel. The foregoing pipetting elements can be moved in the pipetting channel to squeeze the liquid in the first chamber or the fourth chamber. In some preferred embodiments, the first chamber or the fourth chamber may be a segment within the pipetting channel that is separated by different pipetting elements to form a chamber. In some preferred embodiments, the first chamber can be in fluid communication with the second chamber. In some preferred embodiments, the fourth chamber can be in fluid communication with the testing area. In other words, the pipetting channel itself can be in communication with the second chamber or testing area or both.

In some preferred embodiments, the method of the present invention further provides a pipetting plug, which is mainly used to provide power for moving the pipetting element, so that the pipetting element generates an extrusion force on samples in the first chamber and/or the fourth chamber when moving in the pipetting channel, to transfer these samples.

In some preferred embodiments, the method of the present invention further provides a sealing structure between the pipetting element and the pipetting channel, to ensure that no gap is generated between the pipetting element and the inner wall of the pipetting channel when the pipetting element is forced to move, and no sample leakage occurs.

In a tenth aspect of the present invention, it provides a method for detecting the presence or absence of an analyte in a liquid sample. The detection method comprises An apparatus for collecting samples of any one of the foregoing embodiments. By collecting samples to be detected with An apparatus for collecting samples, after samples are collected in the fourth chamber, samples are detected. In some preferred embodiments, after samples are collected in the third chamber, the samples are detected. In some preferred embodiments, the samples in the fourth chamber are transferred to the testing area for detection. In some preferred embodiments, the samples in the third chamber are transferred to the testing area for detection. After obtaining the detection results, the second chamber is separated from the sample collection apparatus in any of the foregoing ways.

The present invention can achieve the following beneficial effects. The foregoing structure in the invention is simple and reasonable. The material cost is low and its performance is excellent. The structure is convenient for second detection. In particular, when subsequent confirmatory detection is necessary, only the second chamber rather than the entire detection apparatus is required to be sent to a testing agency for detection, so it is safe, space-saving, cost-saving and environmentally friendly.

The present invention provides a third design, as specifically illustrated in FIGS. 79-93.

In a first aspect, the present invention provides a sample collection and detection apparatus, comprising a first chamber for collecting liquid samples and a second chamber for collecting liquid samples for confirmatory detection, and the first chamber and the second chamber can be combined or separated, that is, the combination of the first chamber and the second chamber can be a detachable combination, to ensure that the first chamber and the second chamber can be separated under certain conditions. In some preferred embodiments, the first chamber and the second chamber are combined in an initial state, and the first chamber and the second chamber should be fluid communication in the combined state, that is, the liquid sample to be collected can enter the second chamber while entering the first chamber, or enter the first chamber while entering the second chamber, to achieve the one-time collection rather than separate collection for the first chamber and the second chamber. In some preferred embodiments, the first chamber has an external opening, and the opening of the second chamber is in communication with the inside of the first chamber.

As the first chamber and the second chamber have a process from combination to separation during use, the shape of the second chamber needs to be designed to be partially detached from the first chamber. For example, a part of the second chamber can be exposed outside of the first chamber, further, in some preferred embodiments, as the second chamber is separated from the first chamber, the portion of the second chamber exposed outside of the first chamber can gradually withdraw from the space of the first chamber.

When the first chamber and the second chamber are in the combined state, only one of the chambers can be sealed because they have a common opening. When the first chamber and the second chamber have been separated, the second chamber needs to be sealed independently, so a separate sealing device is required for the second chamber. During the separation of the first chamber and the second chamber, the first chamber will inevitably generate a new opening other than the original opening that may leak liquid due to the withdrawal of the second chamber. At this time, the opening needs to be sealed to prevent the liquid samples from flowing out, so a sealing device is required for the separation portion.

In some preferred embodiments, the second chamber collects samples through the first chamber, the second chamber can be detachably connected or combined with the first chamber, and the second chamber is combined with the first chamber during sample collection, and after sample collection, the second chamber is pushed out of the first chamber.

In some preferred embodiments, the second chamber includes a second collection port for collecting samples, and the second collection port is in fluid communication with the interior of the first chamber when collecting samples in the second chamber. In some preferred embodiments, the second chamber is disposed at the bottom of the first chamber. In some preferred embodiments, the first chamber has a first collection port for collecting samples. In some preferred embodiments, the opening direction of the first collection port is the same as that of the second collection port.

In some preferred embodiments, while the liquid samples are loaded into the first chamber, the liquid samples can naturally enter the second chamber. In some preferred embodiments, while the liquid samples are loaded into the first chamber, the liquid samples can enter the second chamber under an external force.

In some preferred embodiments, the bottom of the first chamber is provided with a channel capable of assembling a second chamber. In some preferred embodiments, the second chamber can move within the channel. In some preferred embodiments, the second chamber and the channel are detachably combined or connected. In some preferred embodiments, the first channel is in fluid communication with the interior of the first chamber. In some preferred embodiments, when the second chamber channel collects the sample, the second chamber is assembled in the channel. In some preferred embodiments, after the sample collection is completed, the second chamber can move in a direction separating from the first chamber under an external force.

In a second aspect, the present invention provides a specific sealing structure which may comprise a second sealing element for sealing the second chamber, and a third sealing element for sealing the separation portion of the first chamber and second chamber when the first chamber is separated from the second chamber.

It should be noted that the first, the second, and the third in the present invention do not represent the actual number. For example, the present invention may include only the second and/or third, and does not necessarily include the first, or, it may also include only the first and/or the third, and does not necessarily include the second, or may include only the first and/or the second, and does not necessarily include the third. The qualifiers of "the first", "the second" and "the third" are merely for the convenience of expression and the correspondence between the parts. Here, the first, second and third do not represent the number or sequence according to the actual quantity.

In some preferred embodiments, the openings of the first sealing element and the first chamber are sealed by a first thread structure, the openings of the second sealing element and the second chamber are sealed by a second thread structure, and the third sealing element and the separation portion are sealed by a third thread structure seal. In some preferred embodiments, these sealing structures may also include a first sealing element for sealing the first chamber.

In some preferred embodiments, the first sealing element is linked with the second sealing element. When the first sealing element seals the first chamber, the second sealing element can seal the second chamber. Possibly, when the first sealing element completes sealing, the second sealing element also completes the sealing, or, before the first sealing element completes sealing, the second sealing element has completed the sealing.

In some preferred embodiments, the first sealing element is linked with the third sealing element. When the first sealing element seals the first chamber, the third sealing element can seal the separation portion. Possibly, when the first sealing element completes sealing, the second sealing element also completes the sealing, or, before the first sealing element completes sealing, the third sealing element has completed the sealing.

In some preferred embodiments, the second sealing element is linked with the third sealing element. When the second sealing element seals the second chamber, the third sealing element can seal the separation portion. Possibly, when the second sealing element completes sealing, the third sealing element also completes the sealing, or, before the third sealing element completes sealing, the second sealing element has completed the sealing.

As a linkage relationship should be established between the first sealing element, the second sealing element, and the third sealing element, some linkage structures must be set between these sealing elements.

In a third aspect, the present invention provides a linkage structure of a sealing element, comprising a sealing element of a sample collection apparatus. The linkage of sealing process is achieved through a linkage element between sealing elements.

In some preferred embodiments, the linkage structure comprises a first sealing element for sealing the first chamber and a second sealing element for sealing the second chamber, and the first sealing element is linked with the second sealing element via a first linkage element. In some preferred embodiments, the linkage structure comprises a first sealing element for sealing the first chamber and a third sealing element for sealing the channel, and the first sealing element is linked with the third sealing element via a first linkage element. In some preferred embodiments, the linkage structure comprises a second sealing element for sealing the second chamber and a third sealing element for sealing the channel, and the second sealing element is linked with the third sealing element via a second linkage element. In some preferred embodiments, the linkage structure comprises a first sealing element for sealing the first chamber and a second sealing element for sealing the second chamber, and a third sealing element for sealing the channel, the first sealing element is linked with the second sealing element via a first linkage element and the second sealing element is linked with the third sealing element via a second linkage element. In some preferred embodiments, the linkage structure comprises a first sealing element for sealing the first chamber, a second sealing element for sealing the second chamber, and a third sealing element for sealing the channel. The first sealing element is linked with the second sealing element via a first linkage element and the second sealing element is linked with the third sealing element via tight fitting or fixed connection.

In some preferred embodiments, the linkage between the second sealing element and the third sealing element may be implemented by a fixed connection. In some preferred embodiments, the linkage between the first sealing element and the third sealing element may be implemented by a fixed connection.

In some preferred embodiments, the first linkage element is a linkage pole. In some preferred embodiments, the second linkage element is a linkage pin. In some preferred embodiments, the linkage refers to synchronous rotation. In some preferred embodiments, the linkage refers to moving in a direction close to the inside of the sample synchronically.

In some preferred embodiments, the first linkage element is a linkage rod, and the first sealing element and the third sealing element are respectively connected to the two ends of the linkage rod, so that when one of the first sealing element and the third sealing element is rotated, the other one can be driven to rotate accordingly. The subsequent rotation can be either synchronous or intermittent, but usually in the same direction. In some preferred embodiments, the inner cover surface of the first sealing element is provided with a shaft hole into which the linkage rod is inserted. In some preferred embodiments, the outer cover surface of the third sealing element is provided with a shaft hole into which the linkage rod is inserted. In some preferred embodiments, the linkage rod will connect the first sealing element and the third sealing element by passing through the first chamber.

In some preferred embodiments, the linkage rod has a certain shape. Generally, the shape is not a perfect circle, and may be, for example, a square, a semicircle, or a triangle. Accordingly, the shaft holes on the first sealing element and the third sealing element are of the same shape, then the circumferential limit between the linkage rod and the shaft hole is achieved through such shape, without relative rotation, thus, the linkage rod can drive the first sealing element and the third sealing element to rotate through the two shaft holes, to achieve linkage. In some other embodiments, the linkage rod and the shaft hole can also be tightly fitted round holes, at this time, the force of linkage comes from the friction between the linkage rod and the shaft hole abutting surface. In other possible embodiments, the linkage rod and the shaft hole can also be in a step-by-step linkage relationship. In this step-by-step linkage relationship, the linkage rod or the shaft hole can be rotated independently by a certain angle, and then rotated synchronically. While rotating, the first sealing element seals the first chamber, and the third sealing element seals the separation portion during sealing the first chamber by the first sealing element.

As another implementation form of linkage, the linkage rod is provided with a shaft hole, and the first sealing element or the third sealing element is provided with a matching component that links with the shaft hole. The matching component has the same shape as the shaft hole, and the shape is deviated from the axis core of the linkage rod, or non-circular, so that the linkage rod and the mating component can realize the linkage. In some preferred embodiments, the linkage rod can also be matched with mating component by stepwise linkage.

In some preferred embodiments, the linkage structure may also comprise a second linkage element that links the second sealing element and the third sealing element. The second linkage element is a linkage pin or a similarly shaped short object. The linkage pin can be attached to one of the second sealing element or the third sealing element, and the other one is provided with a linkage hole matching the linkage pin, similarly, the linkage pin and the linkage hole also have a shape similar to that of the linkage rod, which can be offset from the self-rotation center of the second sealing element or the third sealing element, or a non-circular shape. The shape can be, for example, a square or a semicircle, or a triangle, etc., so that one of the linkage pin and/or the linkage hole can drive the other one to rotate synchronously or intermittently. The rotation can be in the same direction or in the opposite direction. The third sealing element can seal the separation portion while rotating, and the second sealing element can seal the second chamber during the sealing of the separation portion by the third sealing element.

As a specific implementation manner of linkage matching, a linkage hole is disposed on the inner cover surface of the third sealing element, the linkage pin is inserted in the linkage hole, and the other end is fixed on the outer cover surface of the second sealing element, or A linkage hole is provided on the outer cover surface of the second sealing element, one end of the linkage pin is inserted in the linkage hole, and the other end is fixed on the inner cover surface of the third sealing element. In this implementation manner, the linkage of the second sealing element and the first sealing element is driven by the third sealing element, that is, during sealing of the first chamber by the first sealing element, the third sealing element can seal the separation portion, and the second sealing element can seal the second chamber.

In some preferred embodiments, no second linkage element is disposed on the second sealing element and the third sealing element, but the linkage is achieved by their structural matching, for example, a face of the second sealing element is fixedly connected together with a face of the third sealing element, so that the two sealing element can rotate synchronously.

In a fourth aspect, the invention provides a specific form of a separation portion. In some preferred embodiments, the separation portion may be in the form of a channel, for example, a channel that allows the second chamber to be plugged in and that can be sealed. In some preferred embodiments, the channel is located at the bottom of the first chamber (that is, the channel and the port of the first chamber for collecting the liquid samples are located at the ends of the first chamber, respectively), by this way, when collecting liquid samples, the port is usually upward and the channel is facing downwards, which facilitates the liquid samples to directly enter the second chamber due to the natural action of gravity while entering the first chamber. In some preferred embodiments, the bottom of the first chamber may be provided with a slope that is slightly inclined toward the channel, and then the liquid samples will flow along the slope to the channel, and the angle of inclination may be within 5°.

In some preferred embodiments, the second chamber is installed in the channel before the product is used. Of course, the installation method must be detachable. For example, the second chamber is inserted in the channel, and its outer wall is closely matched with the inner wall of the channel. In some preferred embodiments, the close matching between the second chamber and the channel must be sealed. The sealing must be achieved by its own material after assembly, or achieved by adding a sealing member to the matching surface.

In some preferred embodiments, the channel has an opening that communicates with the first chamber, and the second chamber also has an opening for collecting the samples. After the second chamber is assembled in the channel, the opening in the second chamber must coincide with the opening of the channel, so that the liquid samples can be collected in the second chamber. In some preferred embodiments, the opening in the second chamber is flush with the surface of the opening of the channel. In other preferred embodiments, the surface of the opening of the second chamber is slightly above the surface of the opening of the channel. In other preferred embodiments, the surfaces of opening of the second chamber and the opening of the channel form a smooth transition and a slope downwardly from inside out. The main function of the design and matching of the structure at the opening is to avoid the liquid samples from accumulating in the gap between the second chamber and the channel as much as possible, because the accumulation easily causes the second chamber and the channel to generate leakage of liquid samples during the separation process. Through the structural layering, liquid samples can flow to other locations at the bottom of the first chamber along the structure, rather than accumulated in the junction of the second chamber and the channel. Except the sealing of the matching surface, the seal can be reinforced by the structural design at the opening to avoid any leakage as much as possible.

In some preferred embodiments, it is necessary to limit the matching between the second chamber and the channel. Otherwise, the second chamber may slide into the first chamber through this channel. This situation must be eliminated, since the exposed part of the second chamber may enter the first chamber to cause contamination to the liquid samples, moreover, the channel itself is an opening for the first chamber, and the second chamber can be used as a plug for the channel. If the second chamber falls into the first chamber, it will inevitably cause a hole in the channel, and a large amount of liquid samples will leak. In some preferred embodiments, a matching limiting structure is provided at the inner wall of the channel and the outer wall of the second chamber. The limiting structure limits the limit position of the second chamber to a certain position in the channel, and once the second chamber is mounted, it will not continue to move inside.

As a specific implementation manner of the limiting structure, an outer stepped surface is disposed on the inner wall of the channel, and using the outer stepped surface as the dividing line, the inner diameter of the portion close to the first chamber is larger than that of the portion close to the outer portion. At the same time, an inner stepped surface that matches with the outer stepped surface is provided on the outer wall of the second chamber. Using the inner stepped surface as the dividing line, the inner diameter of the portion close to the first chamber is smaller than the inner diameter of the portion close to the outer portion, then through the matching of the inner stepped surface and the outer stepped surface, the limit installation position of the second chamber can be limited to this mating point. When the second chamber is loaded, the stepped surface is snapped and unable to move further inward, to achieve the limit of the second chamber.

The channel is a structure that allows the first chamber to be assembled with the second chamber. The channel can be regarded as a part of the first chamber. In some preferred embodiments, after installation, the second chamber does not extend beyond the outer surface of the channel. By this way, the first chamber and the second chamber form an integral part before use. However, in such case, the second chamber cannot be removed, so, in some preferred embodiments, when the first chamber, the second chamber, and the separation portion are sealed by the sealing element, the second chamber can be gradually ejected outwards, when all the sealing processes (including the sealing of the first chamber by the first sealing element, sealing of the second chamber by the second sealing element, and the sealing of the separation portion by the third sealing element), a part of the second chamber protrudes beyond the external contour of the first chamber, the second chamber can be separated from the first chamber by the extended portion, and the second chamber at the separation portion is a chamber that has been sealed. The liquid samples inside can be used for second confirmatory detection, and the second chamber can be transported separately to a second detection agency after detaching from the first chamber.

In a fifth aspect, the present invention provides a testing element, the testing element is disposed in the first chamber, and has a relatively independent space in the first chamber, for example, a side wall of the first chamber is provided with a testing area that can separate from or communicate with the first chamber, and the testing element is placed in the testing area. The liquid samples first enter the first chamber, and then enter the testing area from the first chamber to react with the testing element, to perform the detection.

The reason for separating the testing area from the main chamber of the first chamber is to separate part of the samples from the testing element, thereby ensuring that at least a portion of the liquid samples is not in contact with the testing element. This portion of samples is not contaminated by the testing element and can be collected into the second chamber for second confirmatory detection.

In some preferred embodiments, the location where the testing element is located is visible.

In a sixth aspect, the present invention provides a blocking element for blocking or opening a communication relationship between a first chamber and a test area. When collecting the initial state of the sample, the blocking element partitions the first chamber from the test area, and the liquid sample Unable to enter the test area, the testing element does not come into contact with or react with the liquid sample. When a certain degree is collected or at a timer, the blocking element opens the entrance of the first chamber communication test area, allowing a portion of the liquid sample to enter the test area from the inlet. And through the testing element for initial inspection, a preliminary test result is obtained.

In some preferred embodiments, the bottom of the first chamber is provided with an inlet that communicates the testing area, and the blocking element is placed at the inlet. In some preferred embodiments, the blocking element is linked with the second sealing element. When the second sealing element completes the sealing of the second chamber, the blocking element is activated to open the inlet that communicates the testing area, at this time, the sealing of the second chamber is completed, ensuring that the liquid samples in the second chamber will not have any contact with the samples in the testing area, ensuring the accuracy of the second detection.

In some preferred embodiments, the blocking element is linked with the third sealing element, while the third sealing element completes the sealing of the separation portion, the blocking element is activated to open the inlet that communicates with the testing area. Since the second sealing element has sealed the second chamber during the sealing of separation portion by the third sealing element, the second chamber has been sealed when the third sealing element completes the sealing of the separation portion. Therefore, when the opening of the testing area is opened, the liquid samples in the second chamber will not have any contact with the samples in the testing area, to ensure the accuracy of second detection.

In a seventh aspect, the present invention provides a method for collecting test samples. The method uses An apparatus for collecting samples as previously described. The apparatus comprises a first chamber for collecting liquid samples and a second chamber for collecting liquid samples for confirmatory detection, and the first chamber and the second chamber can be combined or separated. The sample detection apparatus further comprises a second sealing element for sealing the second chamber, and a third sealing element for sealing the separation portion of the first chamber and the second chamber when the first chamber is separated from the second chamber.

In some preferred embodiments, it further comprises a first sealing element for sealing the first chamber.

In some preferred embodiments, the second chamber can be sealed by a second sealing element while the first sealing element seals the first chamber.

In some preferred embodiments, the separation portion can be sealed by a third sealing element while the first sealing element seals the first chamber.

In some preferred embodiments, either the second sealing element or the third sealing element is linked with the first sealing element, and the second sealing element is linked with the third sealing element; or both the second sealing element and the third sealing element are linked with the first sealing element.

In some preferred embodiments, the method for collecting samples further comprises a first linkage element that links the first sealing element and the third sealing element.

In some preferred embodiments, the method for collecting samples further comprises a second linkage element that links the second sealing element and the third sealing element.

In some preferred embodiments, the separation portion comprises a channel that is sealed by the second chamber prior to sample collection.

In some preferred embodiments, the second chamber can move in the channel, and a limiting structure is provided in the channel to prevent the second chamber from slipping into the first chamber.

In some preferred embodiments, during the sealing process, the second chamber and the first chamber are capable of relative movement such that a portion of the second chamber is pushed out of the first chamber.

In some preferred embodiments, a blocking element is provided in the first chamber that can prevent liquid samples from flowing into the testing area. The blocking element is capable of opening or closing the inlet that can communicate the first chamber and the testing area, thereby preventing or releasing the liquid samples from flowing into the testing area; while the third sealing element seals the separation portion, the blocking element is triggered to open the inlet of the testing area.

In some preferred embodiments, the method comprises: allowing the first chamber and the second chamber to achieve liquid communication through the channel, and the liquid samples can flow from the first chamber to the second chamber through the channel or a port of the channel, thereby the liquid samples can naturally flow into the second chamber while loading them to the first chamber. In some preferred embodiments, the channel is sealed before the first chamber is separated from the second chamber. In some preferred embodiments, the channel is sealed during the first chamber is separating from the second chamber.

In some preferred embodiments, the method comprises sealing a first chamber and a second chamber in which samples are collected. During the sealing process, the first chamber and the second chamber move relatively such that a portion of the second chamber is pushed out of the first chamber. In some preferred embodiments, a portion of the second chamber is exposed outside the first chamber during the sealing process. In some preferred embodiments, the sealing of the first chamber is accompanied by sealing of the second chamber.

In some preferred embodiments, the method comprises a process of sealing the channel that communicates the first chamber and the second chamber, during the process, the first chamber and the second chamber move relatively such that a portion of the second chamber is pushed out of the first chamber. In some preferred embodiments, a portion of the second chamber is exposed outside the first chamber during the sealing process. In some preferred embodiments, the sealing of the first chamber is accompanied by the sealing of channel. In some preferred embodiments, the sealing process of channel is after the sealing process of the second chamber. In some preferred embodiments, the second chamber is pushed out while sealing the channel.

In an eighth aspect, the present invention provides a sample detection method for detecting the presence or absence of an analyte in a collected liquid sample. The detection method comprises collecting the samples to be detected by using the foregoing collection apparatus or collecting method, and performing initial detection on the samples in the first chamber after collected.

In some preferred embodiments, firstly perform sealing on the second chamber that completes the sample collection, and then conduct detection on samples in the first chamber by the testing element.

In some preferred embodiments, firstly separate the first chamber and the second chamber, then conduct detection on samples in the first chamber by the testing element. Since the liquid samples collected by the second chamber are used for second detection, the second chamber is first separated to prevent contamination on the liquid samples for second detection in the second chamber by the testing elements in the initial detection.

In some preferred embodiments, firstly seal the channel that communicates the first chamber and the second chamber, and then conduct detection on samples in the first chamber by the testing element.

In some preferred embodiments, the testing area and the sample collection area are separated by a blocking element during the sample collection, and after the sample collection is completed, the partition between the testing area and the sample collection area by the blocking element is removed, so that samples can enter the testing area.

In some preferred embodiments, a testing area is provided in the first chamber. In some preferred embodiments, the testing element is provided in the testing area. In some preferred embodiments, an inlet that can communicate or close between the testing area and the first chamber is provided. In some preferred embodiments, the inlet can match with the blocking element, and it can be closed by a blocking element or opened to communicate the testing area with the first chamber.

The following manners should also be included in the technical solutions of the present invention:

The apparatus comprises a first chamber for collecting liquid samples and a second chamber for collecting liquid samples for confirmatory detection, and the first chamber and the second chamber can be combined or separated. The sample detection apparatus further comprises a second sealing element for sealing the second chamber, and a third sealing element for sealing the separation portion of the first chamber and the second chamber.

In some preferred embodiments, when the first chamber and the second chamber are combined, the first chamber and the second chamber can be in a fluid communication state.

In some preferred embodiments, the third sealing element seals the separation portion of the third sealing element after the second sealing element seals the second chamber.

In some preferred embodiments, the third sealing element completes the sealing of the separation portion after the second sealing element completes the sealing of the second chamber. in some preferred embodiments, it further comprises a first sealing element for sealing the first chamber.

in some preferred embodiments, the second chamber can be sealed by a second sealing element while the first sealing element seals the first chamber.

in some preferred embodiments, the separation portion can be sealed by a third sealing element while the first sealing element seals the first chamber.

in some preferred embodiments, either the second sealing element or the third sealing element is linked with the first sealing element, and the second sealing element is linked with the third sealing element.

In some preferred embodiments, both the second sealing element and the third sealing element are linked with the first sealing element.

In some preferred embodiments, the sample detection apparatus further comprises a first linkage element that links the first sealing element and the third sealing element.

In some preferred embodiments, the linkage refers to synchronous rotation.

In some preferred embodiments, the linkage refers to moving in a direction close to the inside of the sample.

In some preferred embodiments, the separation portion comprises a channel, and the second chamber can move in the channel.

In some preferred embodiments, a limiting structure of a second chamber is provided in the channel.

In some preferred embodiments, after the second chamber is sealed, it can move along the channel in a direction away from the first chamber.

In some preferred embodiments, it comprises a testing area for collecting initial samples, and the testing area can be opened or closed.

In some preferred embodiments, when the second chamber does not collect samples or when samples are collected, the testing area is closed. When the second chamber completes collection and is sealed, samples can enter the testing area.

In some preferred embodiments, it further comprises a blocking element, and the blocking element is capable of opening or closing the detection inlet.

In some preferred embodiments, the blocking element can be linked with the third sealing element, and the opening of the testing area can be opened when driven by the third sealing element.

In some preferred embodiments, the blocking element can be linked with the second sealing element, and the opening of the testing area can be opened when driven by the second sealing element.

In some preferred embodiments, the blocking element can be linked with the first sealing element, and the opening of the testing area can be opened when driven by the first sealing element.

A method for collecting samples, firstly samples enter the chamber, and samples for initial detection and samples for second confirmatory detection are stored in different chambers. After samples are collected, the samples for second confirmatory detection are firstly separated individually, and then samples for initial detection are detected.

A method for collecting samples, providing an apparatus for collecting samples, wherein the apparatus comprises a first chamber for collecting liquid samples and a second chamber for collecting samples for confirmatory detection, the first chamber and the second chamber can be combined or separated; the sample detection apparatus further comprises a second sealing element for sealing the second chamber, and a third sealing element for sealing the separation portion of the first chamber and the second chamber.

In some preferred embodiments, first load samples into the first chamber, and then load samples into the second chamber.

In some preferred embodiments, samples are loaded into the first chamber and the second chamber simultaneously.

In some preferred embodiments when the first chamber and the second chamber are combined, the first chamber and the second chamber can be in a fluid communication state.

In some preferred embodiments, the second sealing element seals the second chamber after the second chamber completes sample collection.

in some preferred embodiments, the third sealing element seals the separation portion after the sealing of the second chamber.

in some preferred embodiments, the third sealing element seals the separation portion while sealing the second chamber.

in some preferred embodiments, it further comprises a first sealing element for sealing the first chamber.

In some preferred embodiments, after sample collection in the first chamber and the second chamber, the first chamber is sealed with a first sealing element.

In some preferred embodiments, the second chamber is sealed with a second sealing element while the first chamber is sealed with a first sealing element.

In some preferred embodiments, the separation portion is sealed with a third sealing element while the first chamber is sealed with a first sealing element.

In some preferred embodiments, the second sealing element and the third sealing element are linked and sealed.

In some preferred embodiments, the first sealing element and the second sealing element are linked and sealed.

In some preferred embodiments, the first sealing element and the third sealing element are linked and sealed.

In some preferred embodiments, the linkage refers to synchronous rotation.

In some preferred embodiments, the linkage refers to moving in a direction close to the inside of the sample.

In some preferred embodiments, the separation portion comprises a channel, and the second chamber can move in the channel.

In some preferred embodiments, after the second chamber is sealed, it can move along the channel in a direction away from the first chamber.

A sample detection method, comprising a testing area by collecting samples using the foregoing method, and the testing area can be opened or closed.

In some preferred embodiments, when the second chamber does not collect samples or when samples are collected, the testing area is closed. When the second chamber completes collection and is sealed, the testing area is opened to allow samples to enter for detection.

In some preferred embodiments, it further comprises a blocking element, and the blocking element is capable of opening or closing the detection inlet.

In some preferred embodiments, the blocking element can be linked with the third sealing element, and the opening of the testing area can be opened when driven by the third sealing element.

In some preferred embodiments, the blocking element can be linked with the second sealing element, and the opening of the testing area can be opened when driven by the second sealing element.

In some preferred embodiments, the blocking element can be linked with the first sealing element, and the opening of the testing area can be opened when driven by the first sealing element.

The present invention can achieve the following beneficial effects. The foregoing structure in the invention is simple and reasonable. The material cost is low and its performance is excellent. The structure is convenient for second detection. In particular, when subsequent confirmatory detection is necessary, only the second chamber rather than the entire detection apparatus is required to be sent to a testing agency for detection, so it is safe, space-saving, cost-saving and environmentally friendly.

BENEFICIAL EFFECTS

The foregoing structure in the invention is simple and reasonable. The material cost is low and its performance is excellent. The structure is convenient for second detection. In particular, when subsequent confirmatory detection is necessary, only the second chamber rather than the entire detection apparatus is required to be sent to a testing agency for detection, so it is safe, space-saving, cost-saving and environmentally friendly.

BRIEF DESCRIPTION OF THE DRAWINGS

FIG. 35A and FIG. 35B are structural views of a sealing element, a discharge element, or a sealing element exchanged or defaulted shown in FIG. 33.

FIG. 36 is a schematic structural view showing the separation and combination of a first chamber and a second chamber according to another embodiment of the present invention.

FIG. 40 is a perspective structural view of a separate and combined first chamber and second chamber according to another embodiment of the present invention.

Figure 1:
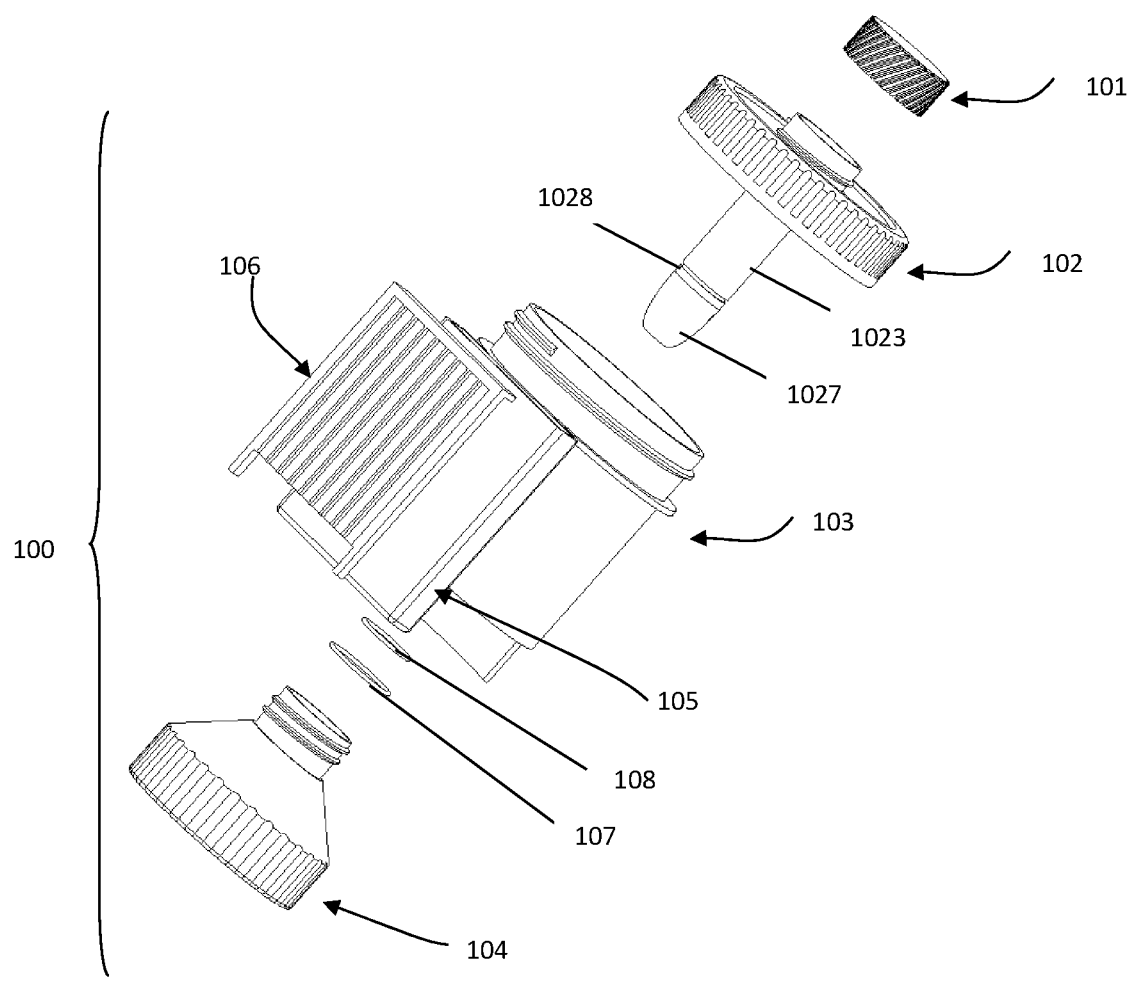
FIG. 1 is a schematic structural exploded view of a collection apparatus according to an embodiment of the present invention.

Note: First chamber 41, second chamber 42, third chamber 43, fourth chamber 44, testing area 45, detection inlet 46, first channel 47, second channel 48, collection port 49, collecting tank 50, pipetting channel 51, first pipetting element 52, second pipetting element 53, detection inlet partition 54, opening end 55, opening 56, seal 57, connector 58, piercing element 59, communicating chamber 60, stepped surface 61, assembly structure of second chamber 62, cover body 63, tapered surface 64, testing element inlet 65, seal connection cover 66, first cover 67, second cover 68, connecting portion matching with a cover body 69, assembly channel 70, outer wall of assembly structure 71, inner chamber of assembly structure 72, hollow structure 73, retaining ring 74, assembly connecting part 75, sealing element 76, pipetting opening 77, pipetting plug 78, first moving chamber 79, support leg 80, sealing groove 81, third channel 82, pressure port 83.

Figure 79:
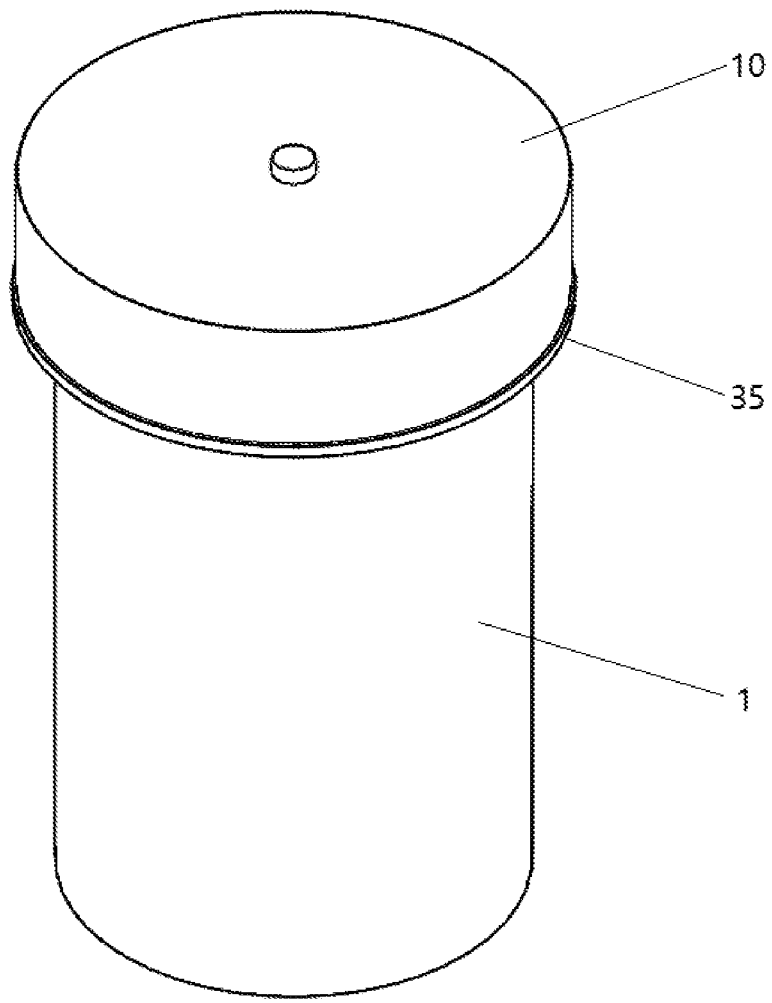

FIG. 79 is a view showing the overall configuration of the present invention.

Figure 80:
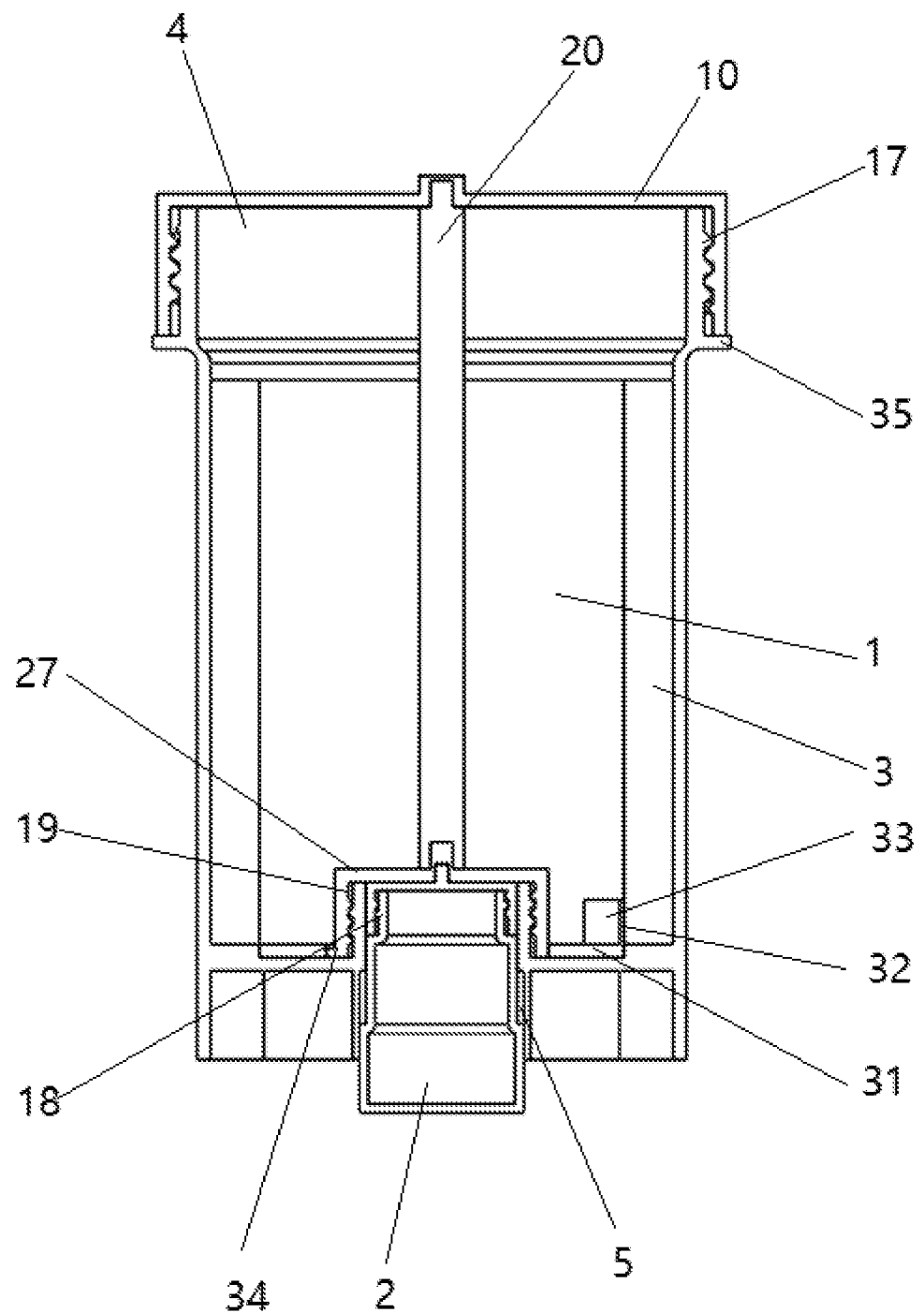

FIG. 80 is a cross-sectional view showing the overall structure of the present invention after completion of sealing.

Figure 81:
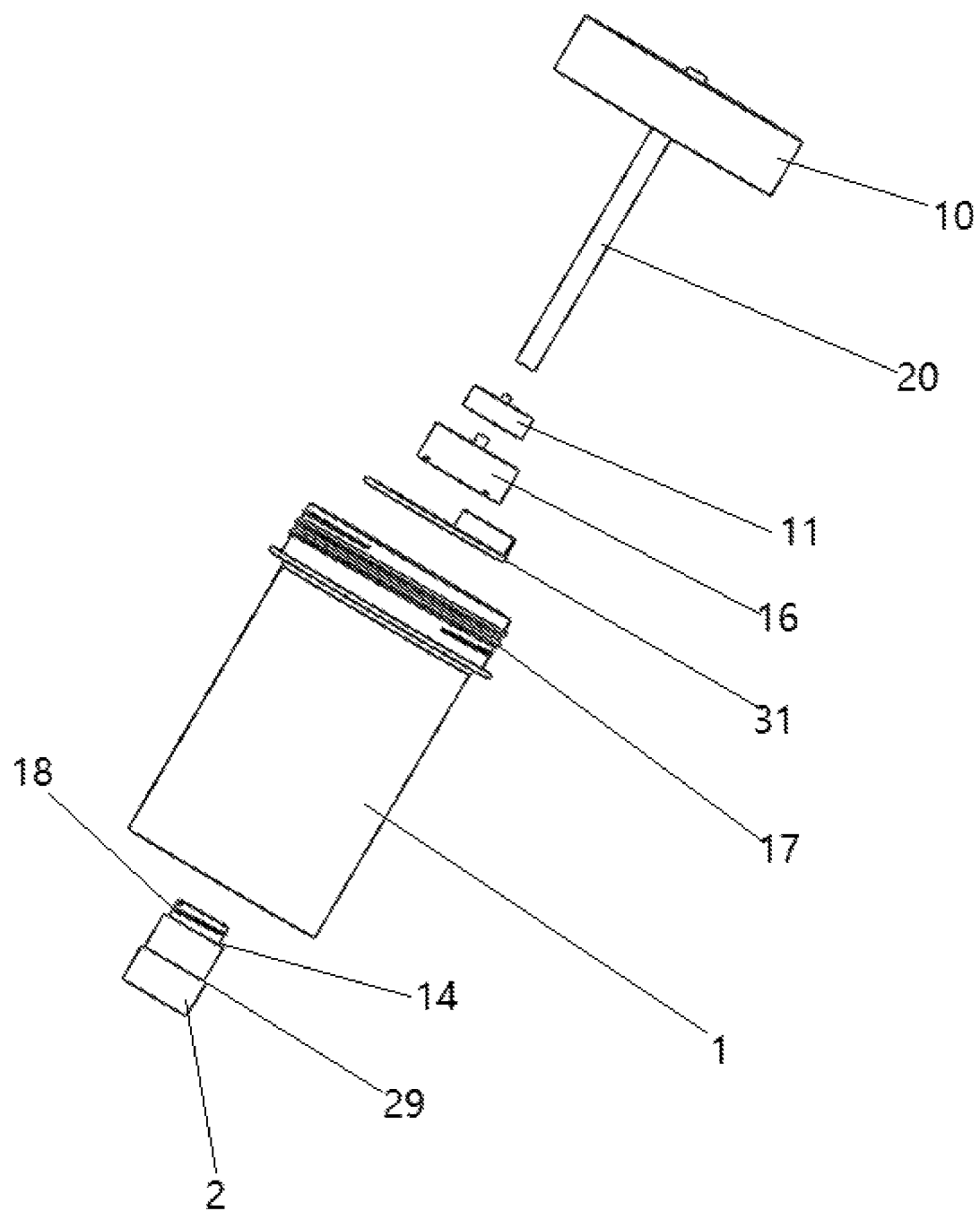

FIG. 81 is an exploded view of the overall structure of the present invention.

Figure 82:
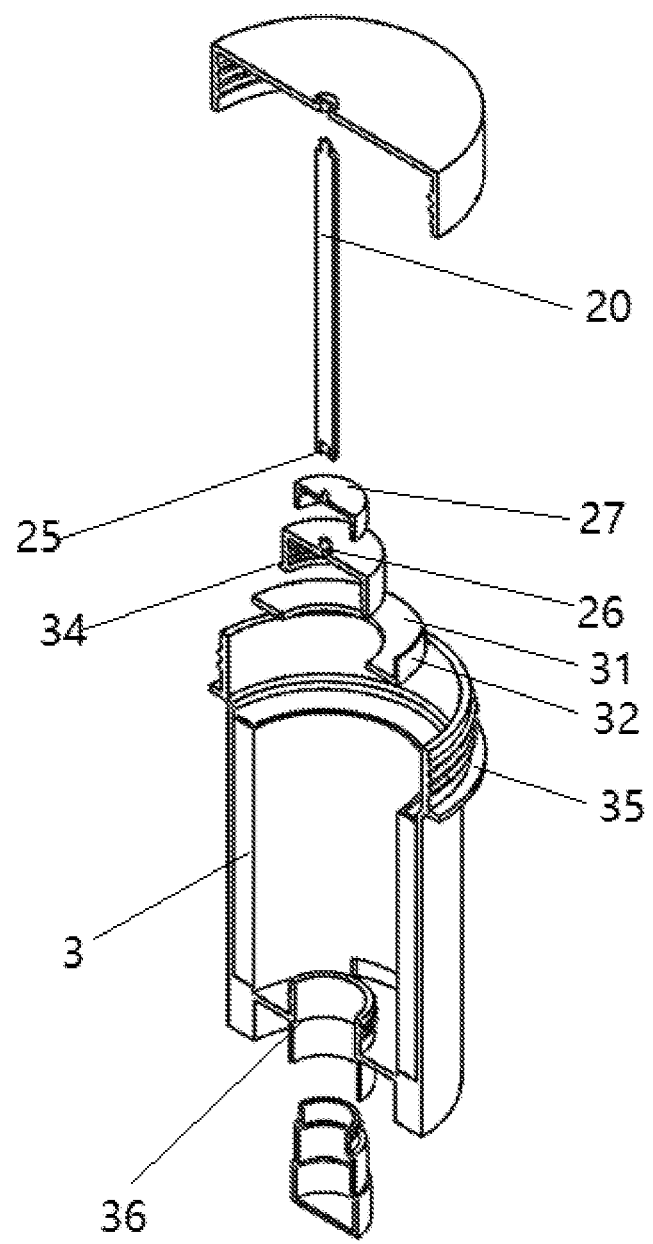

FIG. 82 is a cross-sectional exploded view of the overall structure of the present invention.

Figure 83:
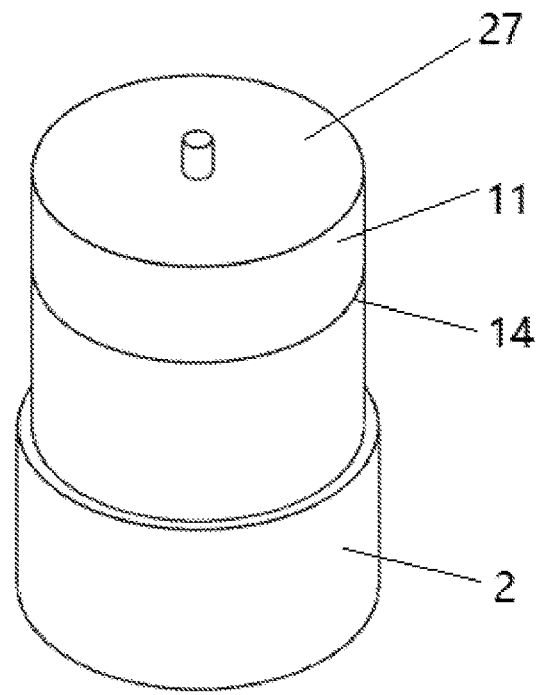

FIG. 83 is an overall configuration view of the second chamber after being sealed.

Figure 84:
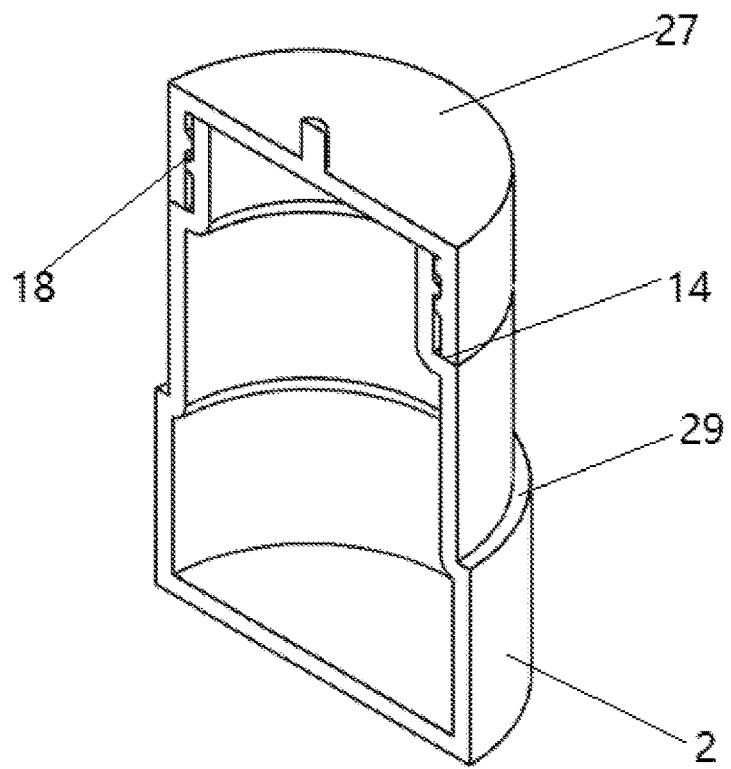

FIG. 84 is a cross-sectional view showing the entire structure in which the second chamber is sealed.

Figure 85:
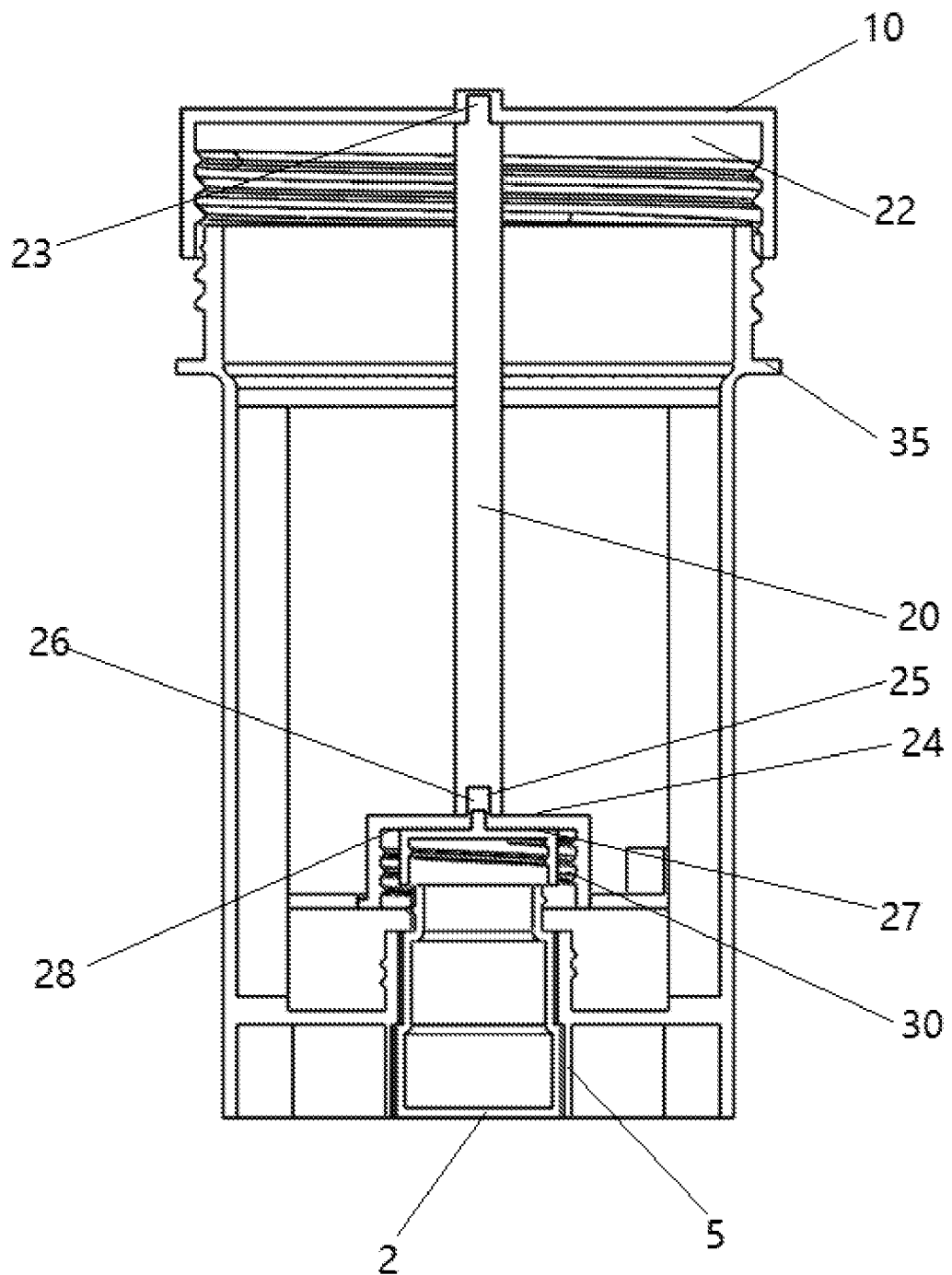

FIG. 85 is a cross-sectional view showing the entire structure before sealing.

Figure 86:
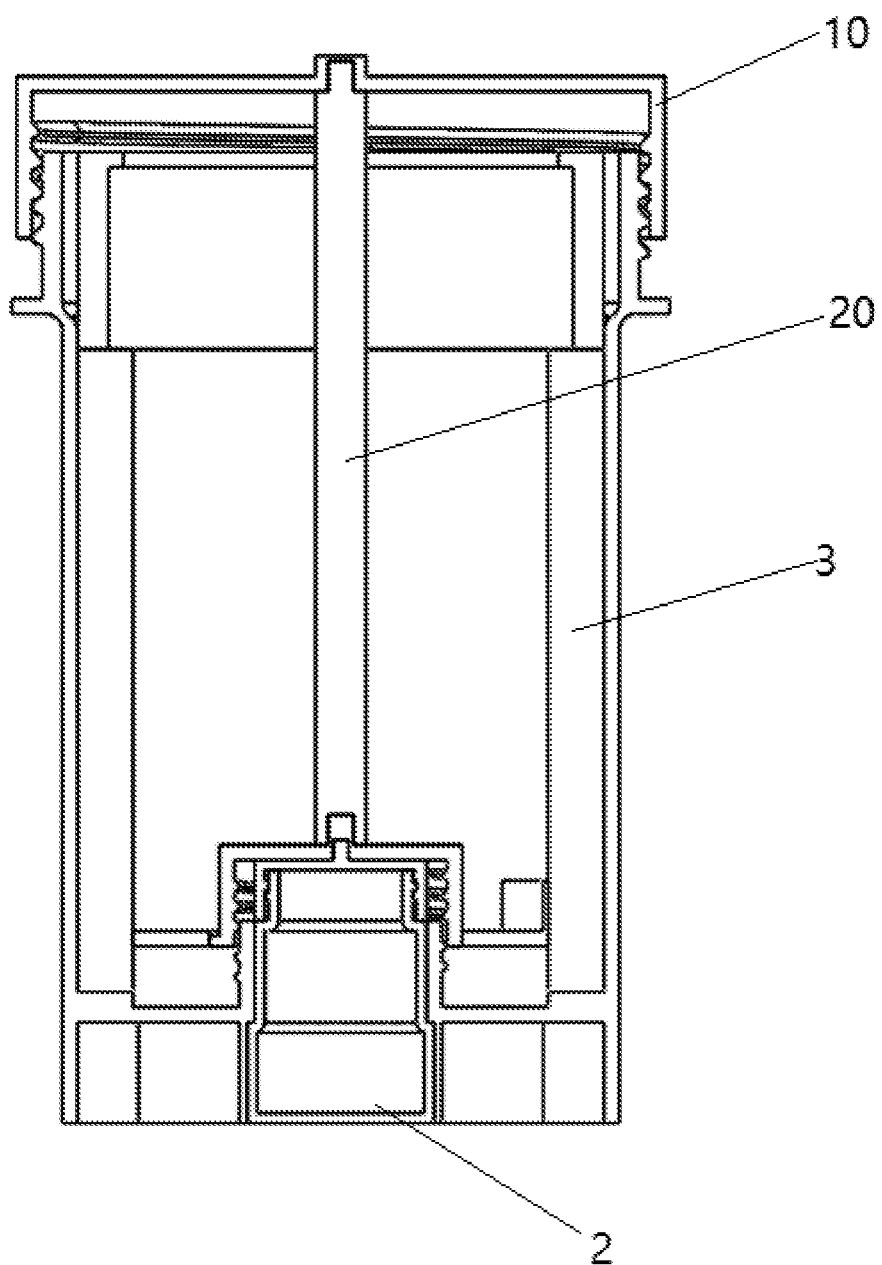

FIG. 86 is a cross-sectional view showing the overall structure of the first stage of sealing.

Figure 87:
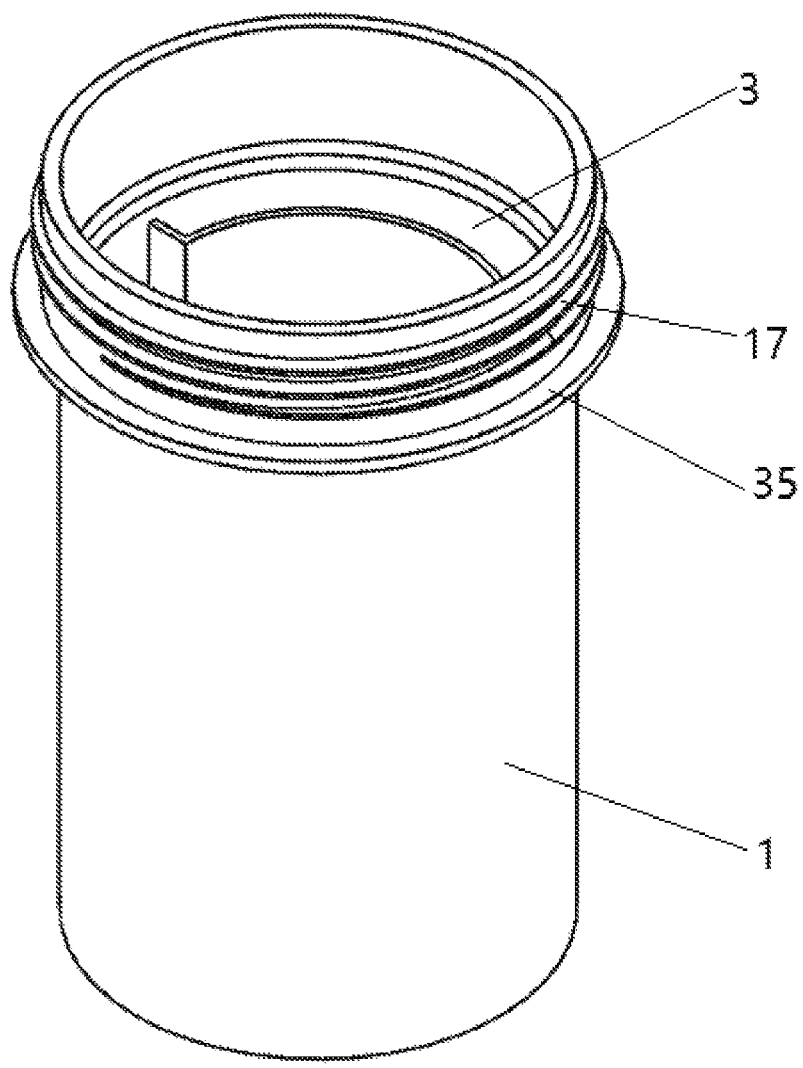

FIG. 87 is a perspective view of the first chamber.

Figure 88:
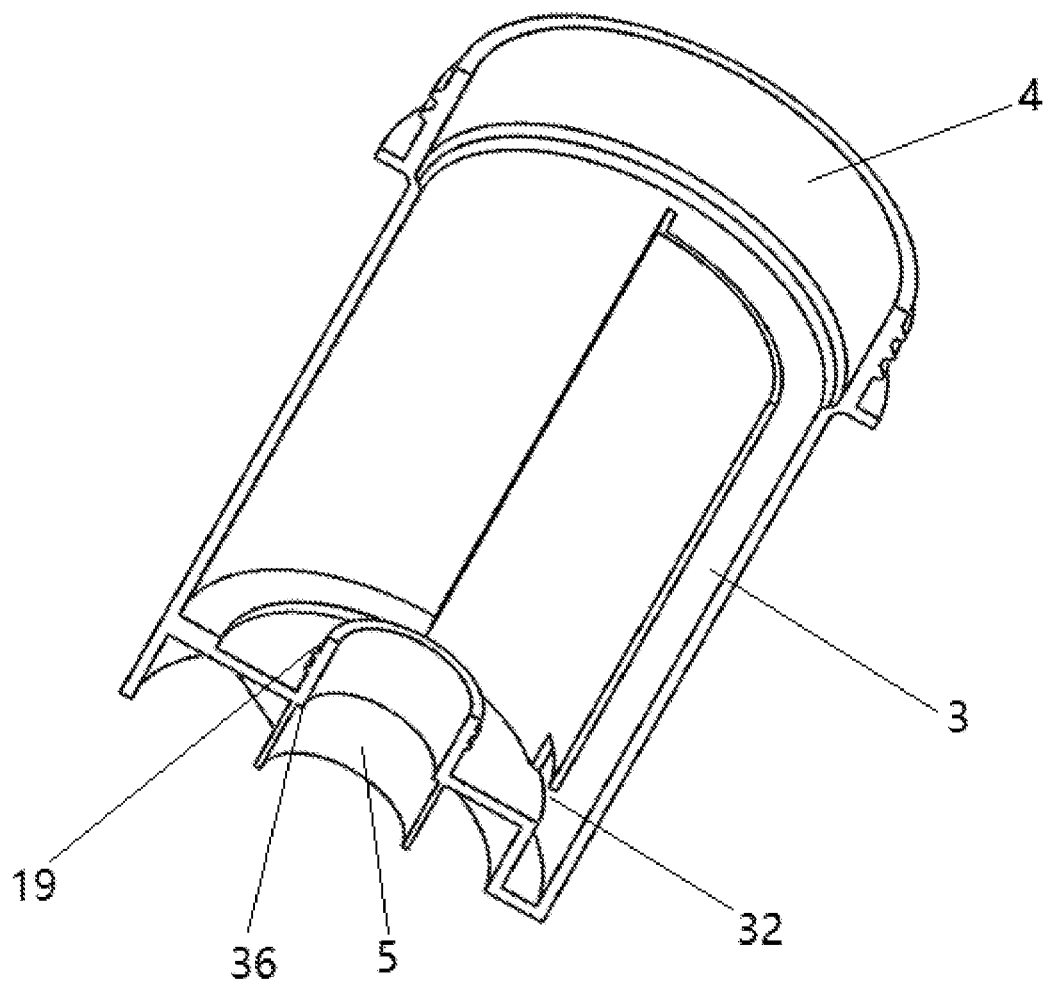

FIG. 88 is a cross-sectional view of the first chamber.

Figure 89:
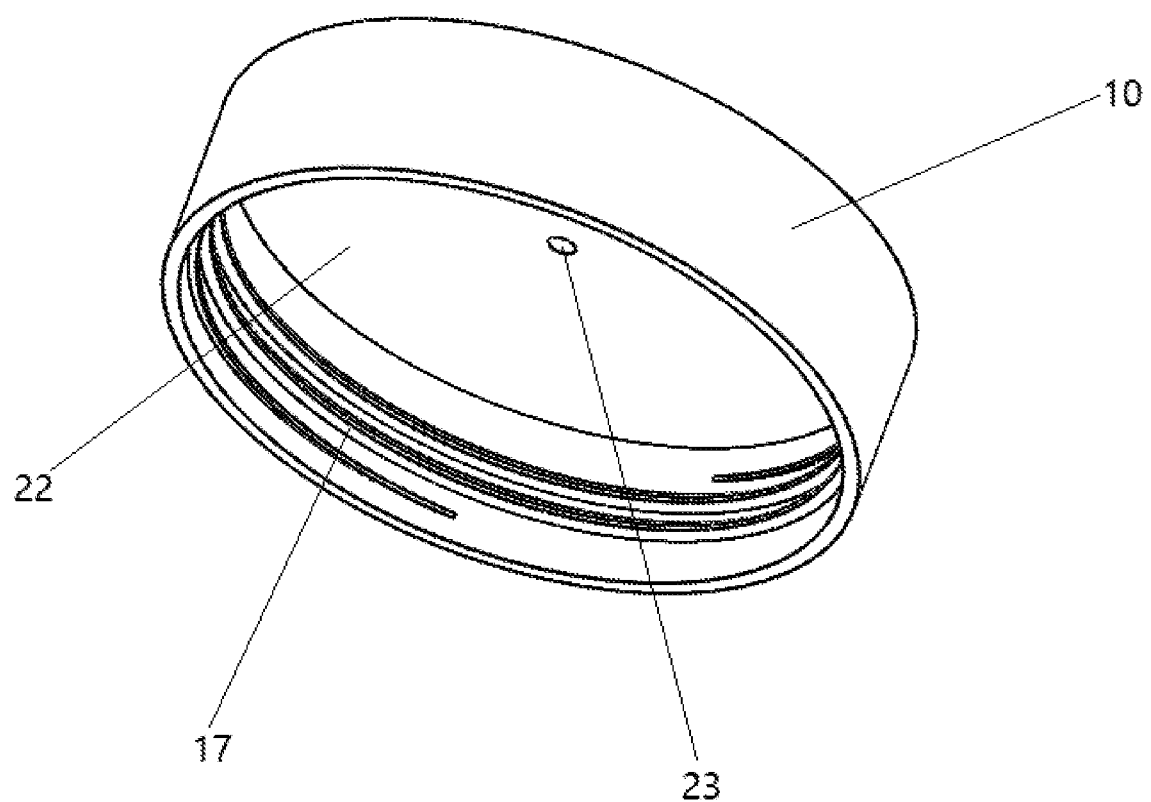

FIG. 89 is a structural diagram of the first sealing element.

Figure 90:
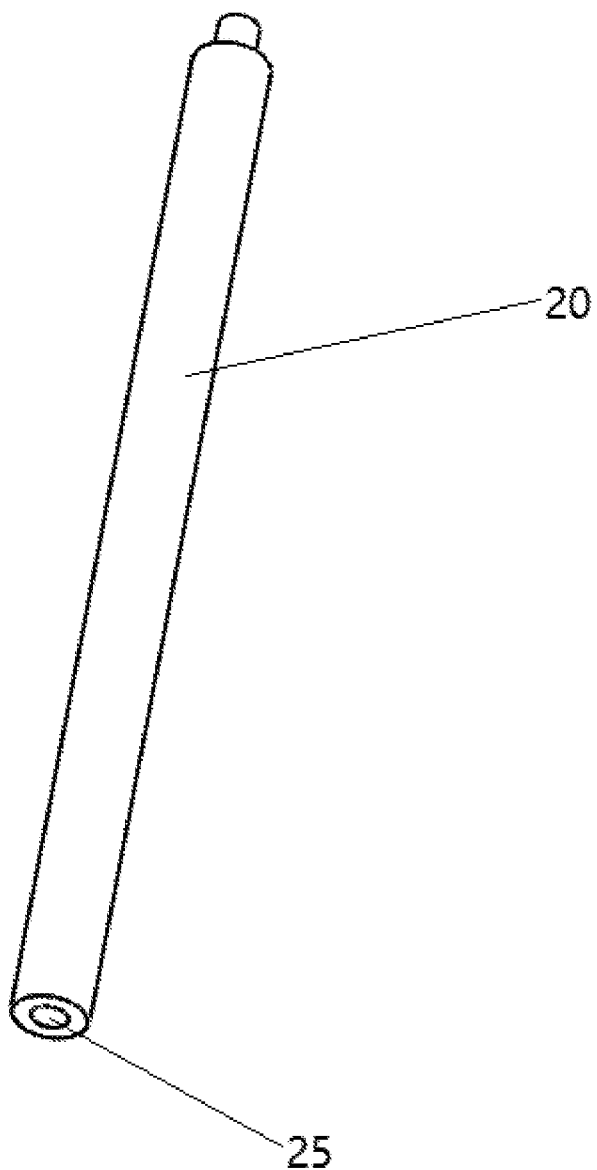

FIG. 90 is a schematic diagram of the first linkage element.

Figure 91:
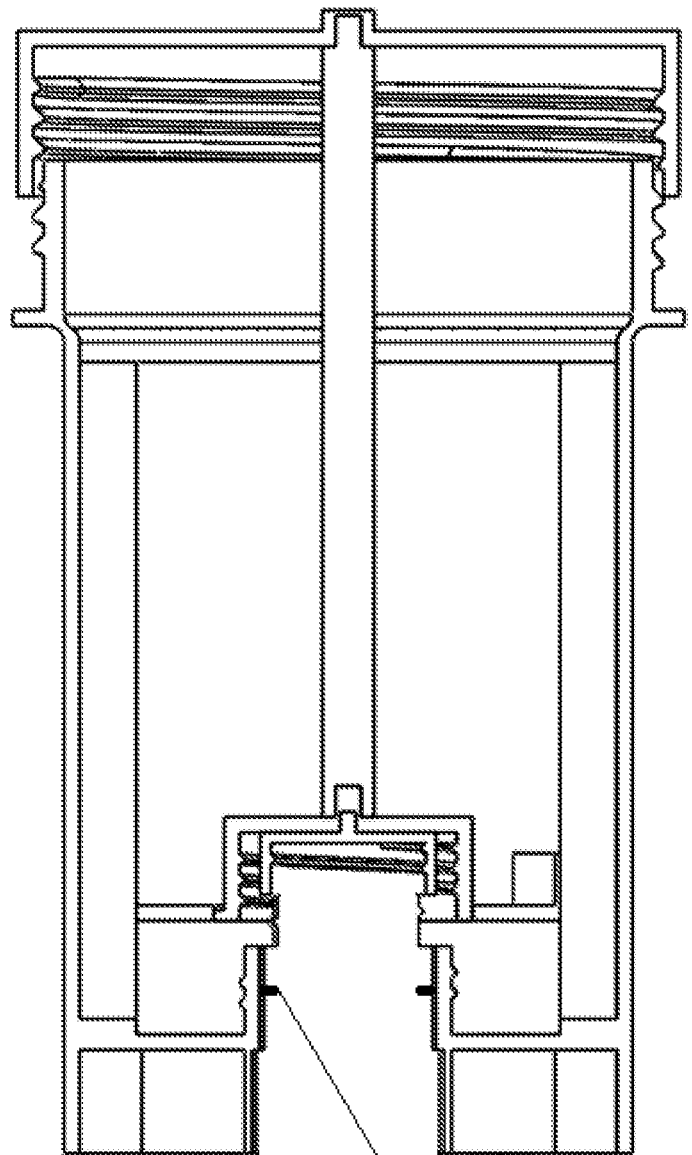

FIG. 91 is a cross-sectional view of the second chamber of the present invention showing the position of the seal retainer.

Figure 92:
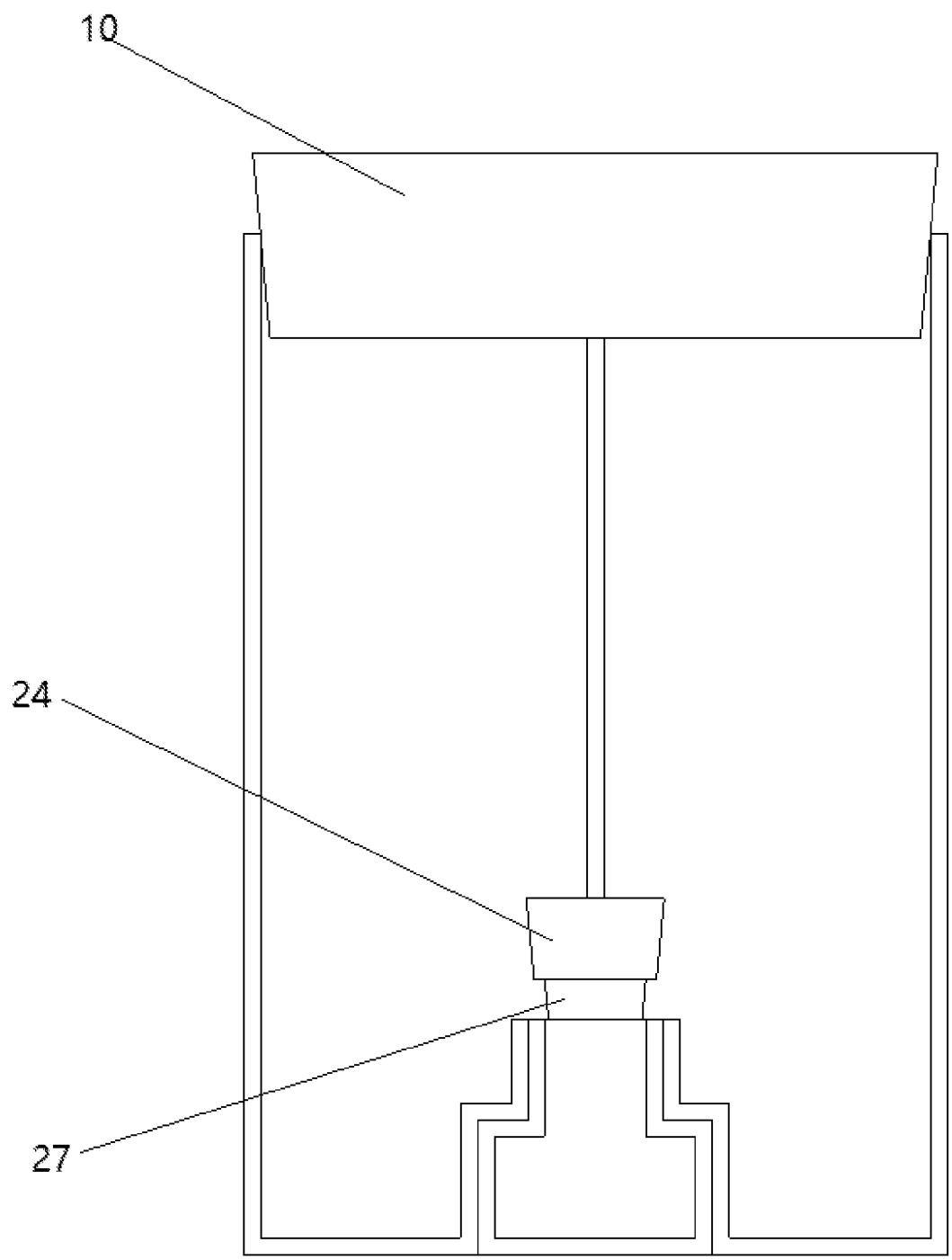

FIG. 92 is another implementation of the sealing element.

Figure 93:
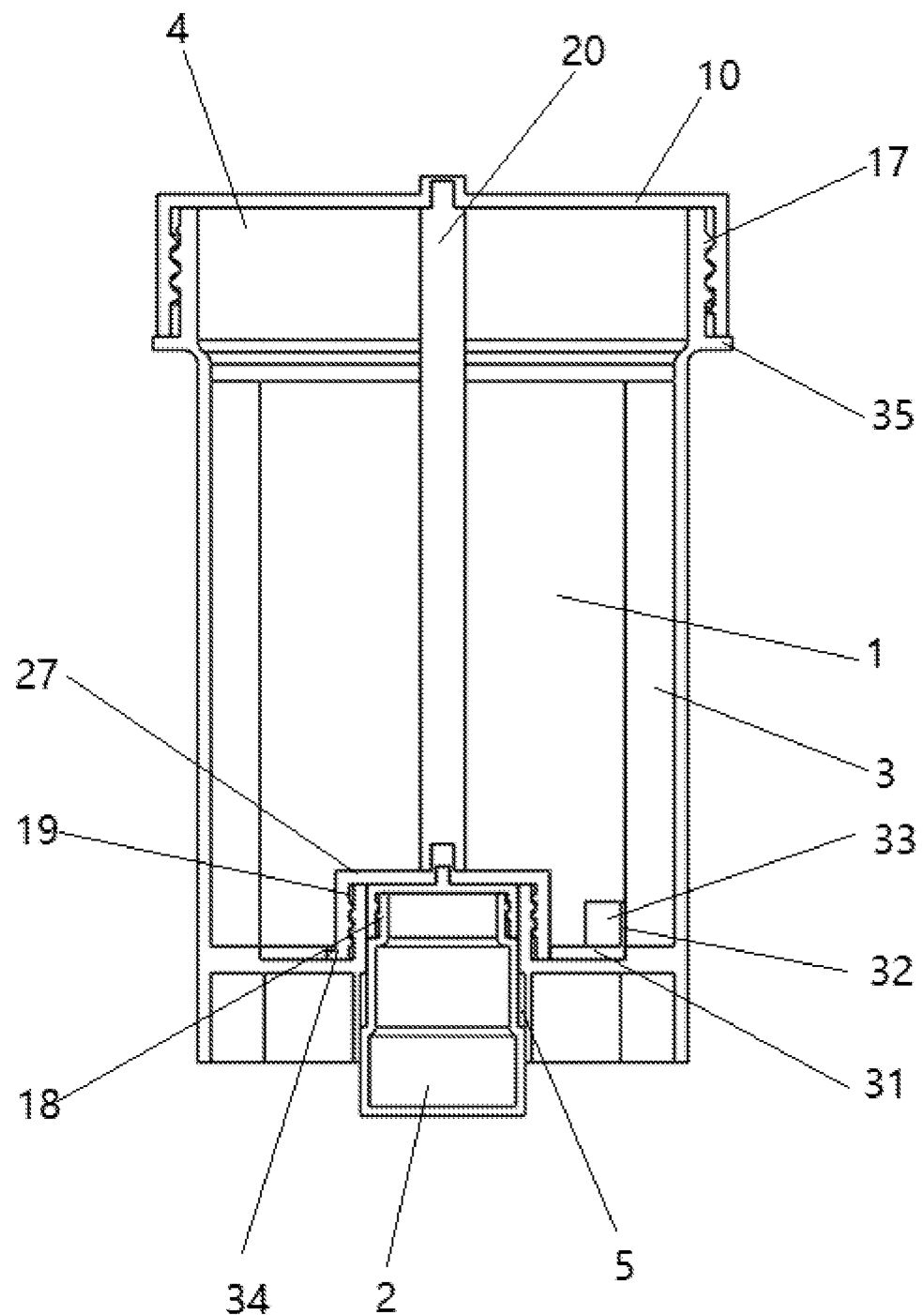

FIG. 93 is a perspective view according to an embodiment of the present invention.

Notes: First chamber 1, second chamber 2, testing area 3, sample inlet 4, channel 5, first collection port 6, second collection port 7, outer stepped surface 8, inner stepped surface 9, first sealing element 10, second sealing element 11, first sealing portion 12, second sealing portion 13, shoulder 14, opening 15 of channel 5, third sealing element 16, first thread structure 17, second thread structure 18, third thread structure 19, first linkage element 20, second linkage element 21, inner cover surface 22, inner shaft hole 23, outer cover surface 24, linkage hole 25, coupling pin 26, upper cover surface of second sealing element 27, lower cover surface of third sealing element 28, inner stepped surface 29, gap 30, blocking element 31, inlet of testing area 3 32, blocking piece 33, protrusion portion 34, spacing ring 35, outer stepped surface 36, seal retainer 37.

DETAILED DESCRIPTION OF THE EMBODIMENTS

The structures or technical terms used in the present invention are further described in the following. Unless otherwise indicated, they are understood or interpreted according to ordinary terms and definitions in the art.
First Design, Second Design and Third Design The mentioned first design, second design and third design are only the division of different designs. In the present invention, some terms that describe the first design shall be understood according to the context of the first design, and similarly, the second design and the third design shall be understood according to the technical terms that describe them. If different technical terms are used in the first design and the third design and the second design to describe some technical features, they shall be understood according to their respective descriptions. If the range represented by the technical terms in these three designs is different, they shall be understood according to the largest range. If the descriptions of these three designs are contradictory, they shall be understood reasonably according to their respective meanings.
Detection Detection means to assay or test the presence or absence of a substance or material, including but not limited to chemical substances, organic compounds, inorganic compounds, metabolic products, medicines or drug metabolites, organic tissues or metabolites of organic tissues, nucleic acids, proteins or polymers. Additionally, detection means to test the quantity of a substance or material. Furthermore, assay also means immunodetection, chemical detection, enzyme detection, and etc.

Confirmatory detection can also be called second detection or second confirmatory detection, which is relative to initial detection. When the first detection result shows that it is possibly positive or weakly positive or it is unable to determine accurately, in order to ensure the accuracy of detection results or to obtain more accurate detection results, samples of the same batch (preferably, collected from the same batch) shall be sent to off-site or further places with confirmatory detection qualification for the second detection so as to verify the detection results. The purpose of the confirmatory detection is to confirm the field or initial detection results. The detection apparatus may be more precise, and the detection method may be more rigorous, but the basic principle is the same as or similar to that of the initial detection. The confirmatory detection is only a re-detection on the basis of the initial detection.

Sample

The sample that can be detected by the detection apparatus of the present invention includes a biological fluid (eg, a case fluid or a clinical sample). Liquid samples can be derived from solid or semi-solid samples, including fecal material, biological tissue and food samples. Solid or semi-solid samples can be converted to liquid samples using any appropriate method, such as mixing, crushing, macerating, incubating, dissolving or digesting the solid samples in a suitable solution (such as water, phosphate solution or other buffer solutions) with the enzymolysis. "Biological samples" comprise samples from animals, plants and food, such as urine, saliva, blood and its components, spinal fluids, vaginal secretion, sperms, excrement, sweat, secreta, tissues, organs, tumors, cultures of tissues and organs, cell cultures and media from human or animals. The preferred biological sample is urine. Food samples comprise food processed substances, final products, meat, cheese, liquor, milk and drinking water; and plant samples comprise samples from any plants, plant tissues, plant cell cultures and media. "Environmental samples" come from the environment (such as liquid samples coming from lake or other water bodies, sewage samples, soil samples, underground water, sea water and effluent samples), and can also comprise waste water or other sewage water.

Any analyte can be detected using the present invention and appropriate testing elements. Preferably, the present invention is used to detect small drug molecules in saliva and urines. Of course, any form of samples, either initially solid or liquid, can be collected by the collection apparatus in the invention. As long as the liquid or liquid samples flow into the first chamber, the liquid samples can flow into the second chamber either simultaneously or later; since the second chamber can be detachably combined, assembled or connected with the first chamber, the second chamber is separated from the first chamber when a subsequent confirmatory detection is necessary, so that the second chamber can be used for a second detection while the liquid in the first chamber can be used for an initial detection. Alternatively, the liquid in the second chamber can be used for initial detection while the liquid in the first chamber can be used for a second detection.

Alternatively, after the liquid sample or the treated sample as liquid is collected into the first chamber, a portion of liquid samples in the first chamber need to be extracted by the second chamber for subsequent confirmatory assays before the initial assay or after the assay. The first chamber can be combined with the second chamber initially, or they can be combined at the time of use and then separated.
Downstream and Upstream Downstream and upstream are divided according to the flow direction of liquid, and generally, liquid flows from upstream to downstream regions. The downstream region receives liquid from the upstream region, and also, liquid can flow to the downstream region along the upstream region. Here we often divide the regions according to the flow direction of liquid. For example, on some materials that use capillary force to promote liquid to flow, liquid can flow against the gravity direction, at this time, the upstream and downstream regions are still divided according to the flow direction of liquid. For example, for the collection apparatus of the present invention, in some preferred embodiments, the first chamber acts as a chamber for collecting liquid samples and the second chamber is in fluid communication with the first chamber. The liquid that enters the first chamber flows into the second chamber. The first chamber may be called upstream, while the second chamber may be called downstream. Of course, this flow is the natural flow of liquid under the force of gravity. Optionally, this natural flow is the flow of liquid from the first chamber to the second chamber. Of course, the liquid can also flow passively from the upstream to the downstream, for example, when the liquid is subjected to reaction force, the liquid is forced to flow from upstream to downstream, or from a low position to a high position. The reaction force may be capillary action or external pressure, to allow liquid to flow from a low position to a high position. The division of the upstream and downstream here is not dependent on the existence of liquid. It means that it flows according to the flow sequence in case of the presence of liquid.

Gas Flow or Liquid Flow

Gas flow or liquid flow means that liquid or gas can flow from one place to another place. The flow process may pass through some physical structures, to play a guiding role. The "passing through some physical structures" here means that passing through the surface of these physical structures or their internal space and flow to another place passively or actively, where passivity is usually caused by external forces, such as the flow of the capillary action. The flow here may mean flow of gas or liquid due to self action (gravity or pressure), or passive flow. Here, the flow does not mean that a liquid or a gas is necessarily present, but indicates a relationship or state between two objects under some circumstances. In case of presence of liquid, it can flow from one object to another. Here it means the state in which two objects are connected. In contrast, if there exists no gas flow or liquid flow state, and liquid exists in or above one object but cannot flow into or on another object, it is a non-flow, non-liquid or non-gas flow state.

Detachable Combination

A detachable combination means that the connection relationship of two parts is in several different states or locations, for example, when two physical parts are separated initially, they can connect or combine together at an appropriate first condition; and at an appropriate second condition, the two parts can be separated, and the separation is a separation of physical space, without contact. Or, the two parts are combined together initially, and when appropriate, the two parts can be separated physically, or two objects are separated initially, and when required, they combine together to complete some functions, and then separate, or combine again for some purposes subsequently. In a word, the combination or separation of two parts is easy, and such combination or separation can be repeated for many times, of course, it can be one-time combination or separation. In addition, the combination may be a detachable combination between two parts, or a mutually detachable combination between three or more parts, for example, with three parts, the first part is detachably combined with the second part, and the second part can also be detachably combined with the third part, and the first part can also be detachably combined with or separated from the third part. Moreover, the combination between them can be achieved by two detachable objects or indirectly through another object.

Testing Element

The "testing element" used herein refers to an element that can be used to detect whether a sample or a specimen contains an interested analyte. Such testing can be based on any technical principles, such as immunology, chemistry, electricity, optics, molecular science, nucleic acids, physics, etc. The testing element can be a lateral flow test strip that can detect a variety of analytes. Of course, other suitable testing elements can also be used in the present invention.

Various testing elements can be combined for use in the present invention. One form of the testing elements is test paper. The test papers used for analyzing the analyte (such as drugs or metabolites that show physical conditions) in samples can be of various forms such as immunoassay or chemical analysis. The analysis mode of non-competition law or competition law can be adopted for test papers. A test paper contains a water absorbent material that has a sample application area, a reagent area and a testing area. Samples are added to the sample application area and flow to the reagent area through capillary action. If analyte exists in the reagent area, samples will bind to the reagent. Then, samples continue to flow to the testing area. Other reagents such as molecules that specifically bind to analyte are fixed in the testing area. They react with the analyte (if any) in the sample and bind to the analyte in this area, or bind to a reagent in the reagent area. Marker used to display the detection signal exists in the reagent area or the detached mark area.

Typical non-competition law analysis mode: if sample contains analyte, signal will be generated; and if not, no signal will be generated. Competition law: if no analyte exists in the sample, signal will be generated; and if analyte exists, no signal will be generated.

The testing element can be a test paper, which can be water absorbent or non-absorbing materials. The test paper can contain several materials used for liquid sample transmission. One material can cover the other material. For example, the filter paper covers the nitrocellulose membrane. One area of the test paper can be of one or more materials, and the other area uses one or more other different materials. The test paper can stick to a support or hard surface for improving the strength of holding the test paper.

Analyte is detected through the signal generating system. For example, one or more enzymes that specifically react with this analyte is or are used, and the above method of fixing the specifically bound substance on the test paper is used to fix the combination of one or more signal generating systems in the analyte testing area of the test paper. The substance that generates a signal can be in the sample application area, the reagent area or the testing area, or on the whole test paper, and one or more materials of the test paper can be filled with this substance. The solution containing signifier is added to the surface of the test paper, or one or more materials of the test paper is or are immersed in the solution, and the test paper containing the solution is made dry.

Each area of the test paper can be arranged in the following way: sample application area, reagent area, testing area, control area, area determining whether the sample is adulterated, and liquid sample absorbing area. The control area is located behind the testing area. All areas can be arranged on a test paper that only uses one material. Also, different areas can use different materials. Each area can directly contact the liquid sample, or different areas are arranged according to the flow direction of liquid sample, with the tail end of one area connected to and overlapped with the front end of the other area. Materials used can be those with good water absorption such as filter papers, glass fibers or nitrocellulose membranes. The test paper can also be in the other forms.

The nitrocellulose membrane test strip is commonly used, that is, the testing area comprises a nitrocellulose membrane on which specific combination molecule is fixed to display the detecting result; and other test strips such as cellulose acetate membrane or nylon membrane test strips can also be used. The test strips and similar apparatuses with test strips disclosed in the following patents can be applied to the testing elements or detection apparatuses in this invention for analyte detection, such as the detection of the analyte in the sample: U.S. Pat. Nos. 4,857,453; 5,073,484; 5,119,831; 5,185,127; 5,275,785; 5,416,000; 5,504,013; 5,602,040; 5,622,871; 5,654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620 and 6,403,383.

The test strips used in the present invention can be those what we commonly called lateral flow test strip, whose specific structure and detection principle are well known by general technicians in the prior art. Common test strip comprises a sample collecting area, a labeled area, a testing area and a water absorbing area, wherein the sample collecting area comprises a sample receiving pad, the labeled area comprises a labeled pad, the water absorbing area can comprise a water absorbing pad, and the testing area comprises necessary chemical substances for detecting the presence or absence of analyte, such as immunoreagents or enzyme chemical reagents. The nitrocellulose membrane test strip is commonly used, that is, the testing area comprises a nitrocellulose membrane on which specific combination molecule is fixed to display the detecting result; and other test strips such as cellulose acetate membrane or nylon membrane test strips can also be used. Of course, in the downstream of the testing area there can also be a detecting result control area. Generally, test strips appear on the control area and the testing area in the form of a horizontal line, that is a detection line or a control line, and such test strips are traditional. Of course, they can also be other types of test strips using capillary action for detection. In addition, there are often dry chemical reagent components on the test strip, such as fixed antibody or other reagents. When the test strip meets liquid, the liquid flows along the test strip with the capillary action, and the dry reagent components are dissolved in the liquid, then the liquid flows to the next area, the dry reagents are treated and reacted for necessary detection. The liquid flow mainly relies on the capillary action. These testing elements are described and documented in the following documents: Li Fogang, "The Regeneration of Nitrocellulose Membrane and Its Absorption of Proteins", Ma Hongyan, Li Qiang et al., "Analysis of Performance of Chromatographic Membrane Materials in Colloidal Gold Diagnostic Kits"; Wang Yong, Wang Lu Hai et al. "a new type of colloidal gold immunochromatographic strip." Here, all of them can be applied to the detection apparatus of the present invention or can be disposed in contact with the liquid samples in the detection chamber or used to detect the presence or absence of analyte in the liquid samples that enter the detection chamber.

Figure 9:
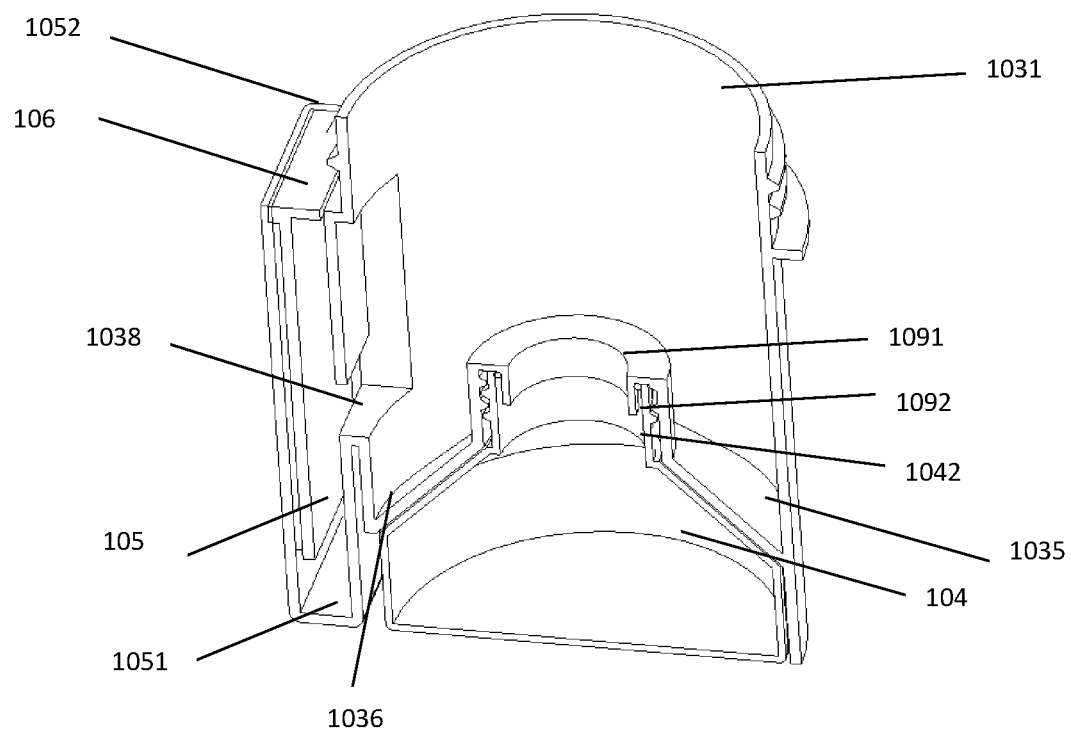
FIG. 9 is a perspective structural view of a combination of a first chamber and a second chamber according to an embodiment of the present invention.

In addition to the foregoing test strip or lateral flow test strip which is used to contact with the liquid in the first chamber to test whether the liquid samples contain analytes, in some preferred embodiments, the testing element is disposed on some carriers, such as some cards 106 having a plurality of grooves. The testing element is located in the groove, and the entire test card is disposed in the detection chamber 105, so that the sample application area of the testing element is located at the bottom 1051 of the detection chamber to contact with liquid samples. These liquid samples may come from the first chamber 103, for example, liquid samples are in liquid communication through the through hole 1038 between the detection chamber 105 and the first chamber (eg, as shown in FIGS. 9 and 1). It is also possible to complete the testing of analyte by disposing the sample application area in the sample collection area of the detection chamber to contact the liquid samples.

Figure 16:
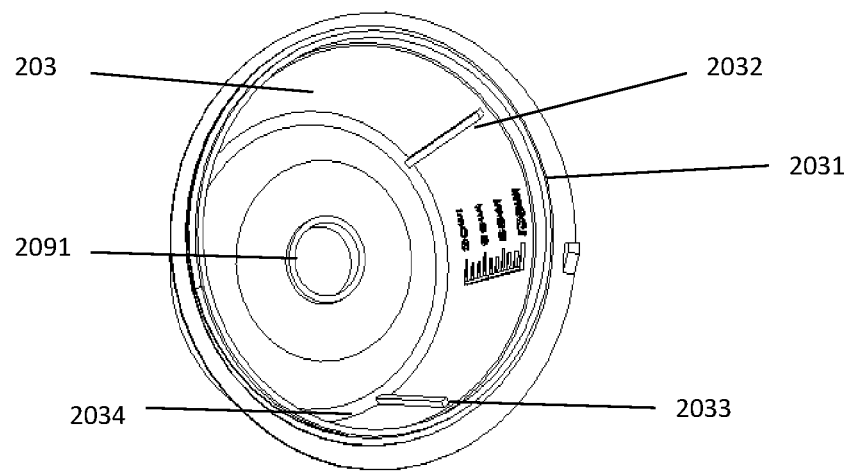
FIG. 16 is a perspective structural view of a first chamber according to an embodiment of the present invention.
Figure 17:
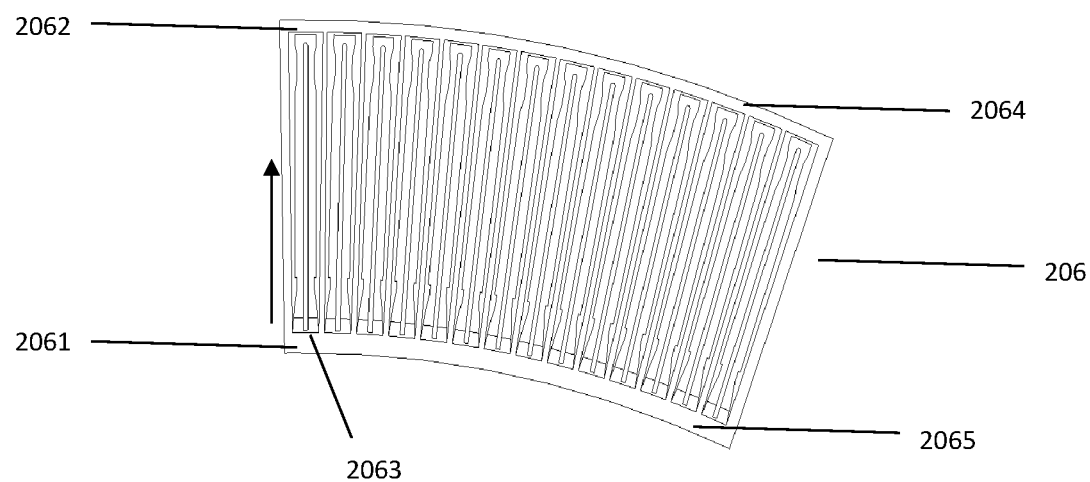
FIG. 17 is a perspective structural view of a testing element carrier according to an embodiment of the present invention.

In another embodiment, for example, as shown in FIGS. 16 and 17, a carrier 206 is provided that has a plurality of channels on one end of sealing 2062 and another end of opening 2063. One or more test strips are disposed in the channel, the sample application area of the test strip is located at one end of the opening 2063. The carrier 206 has one or more channels that accommodate test strips, and each channel is provided with a testing element; when there are multiple channels, testing elements can be disposed in each channel to analyze different analytes, in this way, multiple analytes can be detected using the same sample. The carrier 206 is disposed on the first chamber 203 with two limiting strips 2032 and 2033 on the wall. The carrier 206 is inserted or snapped into two limiting grooves so that one end 2065 of the channel with the opening is close to the bottom of the first chamber, with one end 2064 of the sealing channel close to the opening 2031 (FIG. 16) of the first chamber. When liquid samples flow into the first chamber through the opening 2031 of the first chamber, the liquid samples contact the sample application area of the test strip to complete the test. Such a carrier is specifically described in U.S. patent application Ser. No. 15/644,148 and Chinese Patent Application Nos. 2016106132817 and 2011606079834 filed by the present applicant. Of course, in addition to the carriers disclosed in the above patents, other carriers may also be employed in the present invention as carriers for carrying test strips.

For example, in some embodiments, the first chamber may collect liquid samples and then test analytes in the liquid samples in the first chamber using testing elements. The test strips or cards with test strips or carriers can be inserted into the first chamber for detection. Those skilled in the art can understand that the test strips may not be disposed on the carrier but exist independently according to the present invention. The detection chamber 105 of the present invention may also be absent in some cases, and the test strips may be absent in some cases. Details will be described in the following text.

Analyte

Examples that can use the analyte related to this invention include small-molecule substance, including drugs (such as drug abuse). "Drug abuse" (DOA) means to use drugs (often to paralyze the nerves) for non-medical purposes, which will lead to physical and mental damages, and people who use drugs will be dependent on, addicted to drugs and/or die. Examples of drug abuse include abuse of cocaine, amphetamine AMP (e.g. Black Beauty, white amphetamine tablets, dextroamphetamine, dextroamphetamine tablets, Beans); methylamphetamine MET (crank, meth, crystal, speed); barbiturate BAR (such as Valium, Roche Pharmaceuticals, Nutley, N.J.); sedatives (i.e. sleeping adjuvants); lysergic acid diethylamide (LSD); inhibitors (downers, goofballs, barbs, blue devils, yellow jackets, methaqualone); tricyclic antidepressants (TCA, i.e. imipramine, amitriptyline and doxepin); methylene dioxymetham-phetamine MDMA; phencyclidine (PCP); tetrahydrocannabinol (THC, pot, dope, hash, weed and etc.); opiates (i.e. morphine MOP or opium, cocaine COC, heroin, OXY); antianxiety drugs and sedative hypnotics, the antianxiety drugs are drugs mainly used to relieve anxiety, tension, fear and stabilize emotions, having the function of hypnosis and sedation, including BZO (benzodiazepines), atypical BZ, fused dinitrogen NB23C, benzodiazepines, ligand of BZ receptors, open-loop BZ, diphenylmethane derivatives, piperazine carboxylate, piperidine carboxylate, quinazolinones, thiazines and thiazole derivatives, other heterocyclic, imidazole sedatives/painkillers (such as OXY, MTD), propanediol derivatives—carbamates, aliphatic compounds, anthracene derivatives and etc. The detection apparatus provided in this invention can also be used to detect medicines that are easy to overdose for the medical purpose, such as tricyclic antidepressants (imipramine or analogues) and acetaminophen. These medicines will be resolved into different micromolecular substances after being absorbed by human body, and these micromolecular substances will exist in blood, urine, saliva, sweat and other body fluids or in some of the body fluids.

For example, the analyte detected by the present invention includes but not limited to creatinine, bilirubin, nitrite, (non-specific) proteins, hormones (such as human chorionic gonadotropin, progesterone hormone, follicle-stimulating hormone), blood, leucocytes, sugar, heavy metals or toxins, bacterial substances (such as proteins or sugar substances against specific bacteria, such as *Escherichia coli* 0157:H7, *staphylococcus, salmonella, fusobacterium, campylobacter, L. monocytogenes, vibrio* or *Bacillus cereus*) and substances relevant with the physiological features in the urine sample, such as pH and specific gravity. For any other clinical urine chemical analysis, the detection can be made by combining the lateral flow detection form and the apparatus provided in this invention.

Flow of Liquid

Generally, the flow of liquid means that liquid flows from one place to another place. Under normal circumstances, liquid flows from a high place to a low place due to gravity in the natural world. Such flow relies on an external force, i.e. gravity, which can be called a flow due to gravity. In addition to gravity, liquid can also flow from a low place to a high place by overcoming the gravity. For example, liquid flows from a low place to a high place due to extraction, oppression or pressure, or by overcoming its gravity due to pressure.

For example, according to FIGS. 9, 19, 22 and 27, the first chamber is located above the second chamber, or the second chamber is located below the first chamber. When liquid flows into the second chamber, liquid can flow from the first chamber to the second chamber by relying on its gravity, or flows from upstream to downstream position naturally.

For example, according to FIG. 47-49, the third chamber is located above the first chamber and the fourth chamber, or the fourth chamber is located below the third chamber, when liquid flows into the third chamber, liquid can flow from the third chamber to the first chamber and the fourth chamber by relying on its gravity, or flows from upstream to downstream position naturally. When the whole apparatus shakes, the flow direction of liquid may change due to the change of gravity direction.

Communication and/or Partition

In the present invention, communication refers to a state of fluid communication, that is, in this structure, fluid can flow from one area to another area, or from one part to another part of the structure, or from one chamber to another chamber of the structure. The "flow" mentioned is achieved through the flowability of the fluid itself. Specifically, communication refers to fluid communication, i.e. gas communication or liquid communication which means that liquid or gas can flow from one place to another place, and in the flowing process, it may flow through some physical structures and play a guiding role. Generally, liquid flows through the surface or internal space of these physical structures, and passively (due to external force such as capillary action) or positively flows to another place. The "flow" mentioned can also refer to the flow of liquid or gas due to its own action (gravity or pressure), or passive flow. The communication mentioned does not show that there must be liquid or gas, and it only shows the connected relation or state between two objects in some cases, and if there is liquid, liquid can flow from one object to another object. Here, it refers to the connected state between two objects. On the contrary, if there is no liquid communication or gas communication state between two objects, and if liquid is in or on one object, liquid cannot flow to inside or above another object. Such state is a non-communication state, i.e. non liquid or gas communication state. In the present invention, sometimes, this gas communication or liquid communication state is called fluid communication or communication, which does not require the actual presence of fluids (such as liquid or gas) in the structure, and only shows that the structure is in such a state. Correspondingly, the partition mentioned in the present invention refers to the state opposite to communication (fluid communication), i.e. non-communication. In other words, under the partition state, fluids are unable to flow from one area to another area due to flowability, or from one part to another part of the structure, or from one chamber to another chamber of the structure. Similarly, partition does not require the actual presence of liquid in the structure, and can only show a state of the structure.

Detection Apparatus or Collection Apparatus

Detection apparatus is used to detect the presence of analytes in the samples. Collection apparatus is used for collection and storage of liquid samples. The detection apparatus may comprise a collection apparatus, and the collection apparatus may also comprises a detection apparatus, or the collection apparatus may be separated from the detection apparatus. At the time of detection, the collection apparatus and the detection apparatus may be combined to complete the detection. It is also possible that the collection apparatus and the detection apparatus are an integral structure, and once liquid samples are collected, the test can be performed immediately, to get the test results; and at the same time, the samples to be tested are separated from the collected samples, to perform a second detection (if necessary). Here, the detection apparatus can be interchangeable with the detection chamber, and the collection apparatus can be interchangeable with the collection chamber. For example, the invention may not include a detection chamber or not include a testing element when it comes to the collection apparatus, but the collection apparatus may include a testing element or a carrier with a testing element, and the collection apparatus with the testing element may also be called a detection apparatus. Of course, the collection apparatus can contain the space used to set up the testing element, but it does not necessarily contain the testing element. The testing element can be combined with the collection apparatus at any subsequent appropriate time to form a detection apparatus. For example, the collection apparatus may include a space for accommodating the testing element, for example, containing a detection chamber 105 (FIG. 7), or a testing element or carrier containing a testing element is disposed at an appropriate location of the chamber of the collection apparatus for collecting liquids (FIG. 16). Therefore, the present invention may be merely an apparatus for collecting liquid samples or a detection apparatus for detecting while collecting samples.

Detachable Combination, Assembly or Matching of a First Chamber and a Second Chamber The first chamber and the second chamber can form a detachable combination. Before liquid collection, the first chamber and the second chamber have combined together, and after the liquid sample collection, the second chamber can be separated from the first chamber. Alternatively, the first chamber and the second chamber are detached, and if it is necessary to collect liquid samples, they can be combined together, and after the collection, they can be separated. In some embodiments of the present invention, as shown in FIGS. 1-14, the present invention provides a detection apparatus for detecting the presence or absence of analytes in the liquid samples, or an apparatus for collecting liquid samples, comprising a first chamber 103 and a second chamber 104. The first chamber 103 can be used as a collection chamber for collecting liquid samples, wherein the first chamber and the second chamber are detachably combined or connected or assembled.

In fact, the "combination, connection or assembly" mentioned represents the same meaning, and is only different in their forms of expression. Such combination is relative to "separation". Combination and separation can be chosen freely under any conditions. In some embodiments, when the first chamber is combined with the second chamber, the first chamber and the second chamber are in a state of liquid circulation. In some other embodiments, before or when or after the first chamber is separated from the second chamber, the first chamber and the second chamber are not in a state of liquid circulation.

In some preferred embodiments, the apparatus further comprises a connecting channel, and a detachable connection, combination or assembly of a first chamber and a connecting channel. Thus, the detachable connection, combination or assembly of a second chamber an a connecting channel can be achieved. As shown in FIG. 9, the first chamber 103 is used as a collecting chamber, which comprises an opening 1031 for collecting or receiving liquid samples. Liquid samples flow into the first chamber 103 through the opening. A connecting channel 109 is provided on the bottom of the first chamber, and the connecting channel comprises a first opening 1091, and a second opening 1092 on the other end. The first opening 1091 of the connecting channel 109 and the first chamber 103 are in a state of liquid circulation. Liquid samples in the first chamber can flow into the connecting channel 109 through the opening 1091, then flow out from the second opening 1092 on the other end. So, the present invention provides a chamber for collecting fluid samples, and the chamber comprises an opening 1031 for allowing fluid samples to flow into the chamber 103. A channel is provided on the bottom of the collecting chamber, and the channel comprises a first opening and a second opening. Some liquid samples can flow into the connecting channel through the first opening 1091, and flow out from the second opening 1090, that is to flow to the outside of the first chamber 103. Preferably, liquid that flows out from the connecting channel enters the second chamber 104. Therefore, the collection apparatus can further comprise a second chamber, and generally, the first chamber has an opening, a side wall and a base to form a chamber body. The connecting channel is generally located on the bottom of the first chamber. In the present specific embodiment, the connecting channel is located on the bottom area. However, its position is not restricted. It can be located on the side wall, or the junction between the base and the side wall, or other positions as long as liquid samples entering the collecting chamber 103 can enter the connecting channel.

Figure 4:
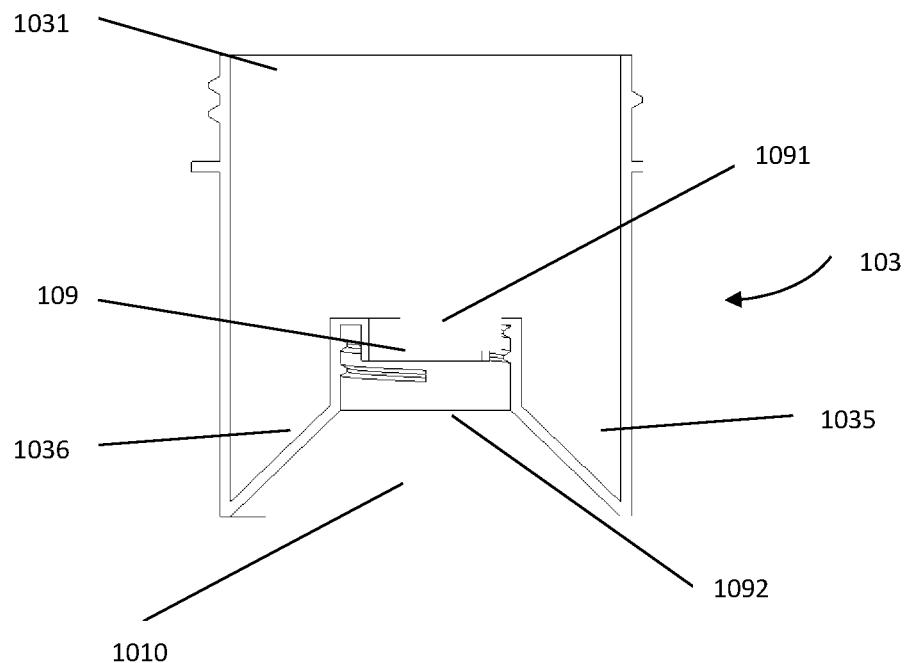
FIG. 4 is a longitudinal cross-sectional view of a combination of a first chamber (excluding a detection chamber) according to an embodiment of the present invention.

Generally, the "connecting channel" refers to a structure for connecting the first chamber and the second chamber. If required, the first chamber and the second chamber are connected or combined. In some cases, the second chamber and the first chamber can be detached. In fact, the connecting channel mentioned herein has two functions: the first one is to connect the first chamber and the second chamber in a detachable manner, and the second one is to let liquid communicate between the first chamber and the second chamber, i.e. liquid can flow between the two chamber bodies through the structure such as a tube, groove or others. Therefore, the use of the "connecting channel" is a preferred embodiment in the present invention. It can be understood that in the relatively preferred solutions, the structure has two different functions: connecting the first chamber and the second chamber, and allowing liquid to communicate between the two chambers, for example, the tubular structure in the present invention. The connecting channel shown in FIG. 9 or FIG. 9 and FIG. 4 is a structure for connecting the second chamber to the first chamber, and allowing liquid to communicate. It can be understood that the connecting channel structure can be defective, which will be described in detail in another embodiment below. Of course, the "connecting channel" can only play the connecting role, that is to connect or combine the second chamber and the first chamber in a detachable manner, without the function of allowing liquid to communicate between the second chamber and the first chamber; preferably, the "connecting channel" can also only have the function of allowing liquid to communicate between the second chamber and the first chamber, without the function of connecting the first chamber and the second chamber. Optionally, the "connecting channel" can have both of the two functions as described above.

In some preferred embodiments, an external thread is provided on the outer side of the second opening of the connecting channel, and a second chamber 104 is provided, and the second chamber 104 comprises an opening 1042. The outer diameter of the second opening 1042 is equal to or slightly greater than that of the connecting channel. An internal thread is provided on the inner side of the opening of the second chamber 104. In this way, through the matching between the external thread of the connecting channel and the external thread of the second chamber, the detachable matching, combination or connection between the second chamber and the first chamber can be achieved. In other words, in case of combination, the second chamber is connected to the connecting channel directly through a screw thread; and in case of disassembly, the screw thread is rotated reversely to separate the second chamber 104 from the connecting channel, and thus from the collecting chamber 103. Alternatively, an internal thread is provided inside the second opening 1092 of the connecting channel, and an external thread is provided outside the opening 1042 of the second chamber 104, and through the matching between the internal thread of the channel opening and the external thread of the second chamber, the first chamber and the second chamber can be assembled or connected in a detachable manner. After the second chamber is separated from the first chamber, the second cover body is used to cover the opening 1042 of the second chamber and thus to seal the second chamber.

Figure 8:
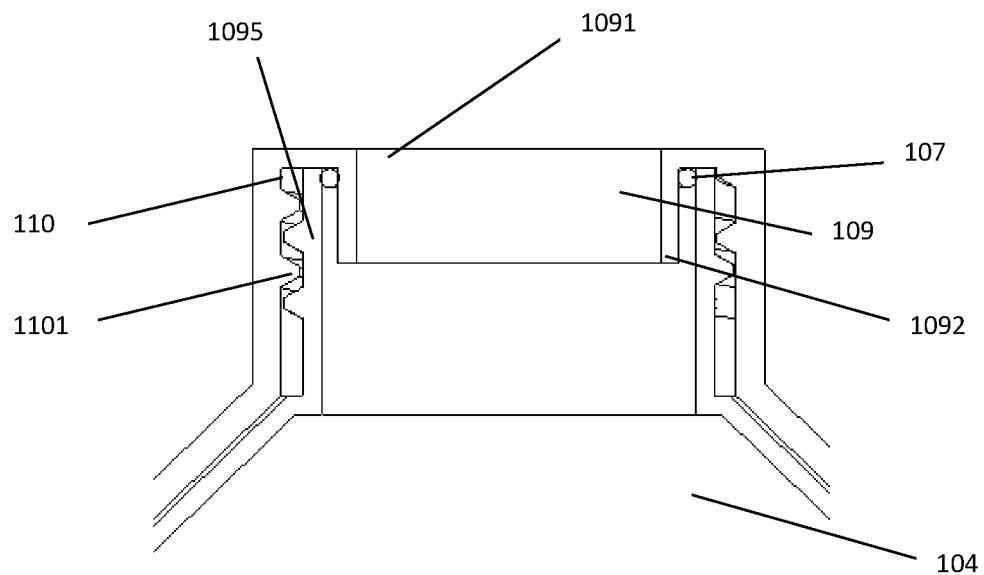
FIG. 8 is a partially enlarged schematic structural diagram of a combination of a first chamber and a second chamber according to an embodiment of the present invention.

Of course, as an alternative, as shown in FIG. 9, the outer wall of the second opening 1092 of the connecting channel is not provided with a screw thread, but an elongated space is provided on the outer wall of the second opening 1092 of the connecting channel 109. The elongated space is just matching with the opening of the second chamber 104, i.e. matching with the thickness of the second chamber opening. For example, the elongated space is formed by an outer wall 1905 of the second opening 1092 of the connecting channel and the corresponding wall 110 (eg, as shown in FIG. 8), and a screw thread structure is provided on the wall 110 that matches with an external thread at the opening 1042 of the second chamber 104, so that the external thread of the second chamber matches with the screw thread on the wall 110, to achieve the combination of the first chamber and the second chamber, which is also accomplished by the engagement of the inner wall of the second chamber opening with the outer wall of one end 1092 of the connecting channel. The second chamber 104 and the first chamber 103 are detachably assembled, combined or connected. In order to provide a better sealing fit between the first chamber and the second chamber, a second seal ring 107 can be provided inside the opening of the second chamber, which allows the inner wall of the opening of the second chamber to fit more closely to the outer wall of the connecting channel, to prevent leakage of liquid samples in the second chamber 104 (as shown in FIGS. 8 and 9). A person skilled in the art should understand that "detachably" as used herein means that two objects can be combined together to form an integral structure when needed, and they can be easily separated when the two objects need to be separated, and such separation is mainly of no physical contact in the space structure.

This kind of detachable ways, in addition to the threaded connection, may be any other way, such as the forms of snapping, piston, plugging, or locking, etc., as long as the first chamber and second chamber can be combined or connected together when necessary, to obtain some liquid samples from the first chamber, and they can be separated from each other when necessary. For example, in the form of a screw thread, it is to rotate in an opposite direction, so as to be separated from the first chamber; alternatively, in the forms of drawing or unlocking, the second chamber 104 can be easily separated from the first chamber after obtaining liquid samples. By this kind of way, the first chamber 103 and the second chamber 104 keep in fluid communication when they are connected or combined together.

Of course, in specific embodiments, and also in preferred embodiments, the connecting channel 109 and the first chamber 103 are formed by one-time injection molding, while the second chamber 104 is formed by another injection molding, and is combined, connected or assembled with the connecting channel in a detachable manner. It can be understood that the connecting channel 109 and the second chamber 104 are formed by one-time injection molding, while it is feasible to combine, connect or assemble the connecting channel 109 and the second chamber 104 with the first chamber 103 in a detachable manner.

Therefore, the "connecting" function can be completed by an independent structure, and the function of allowing liquid to communicate between the first chamber and the second chamber can be completed by the other structure. It is easily understood that such way is adopted. For example, a connecting mechanism is used to connect the first chamber and the second chamber in a detachable manner, while liquid cannot flow between the second chamber and the first chamber through this connecting mechanism, but through the other structure such as a channel, through which liquid flows from the first chamber to the second chamber. Thus, it can be understood that in some preferred embodiments, the apparatus further comprises a connecting structure, through which the first chamber is connected, combined or assembled with the second chamber in a detachable manner. When the connection is achieved by this connecting structure, allow the first chamber and the second chamber to be in a state of liquid circulation which can be achieved by another structure, such as tubes, channels and grooves.

Figure 25:
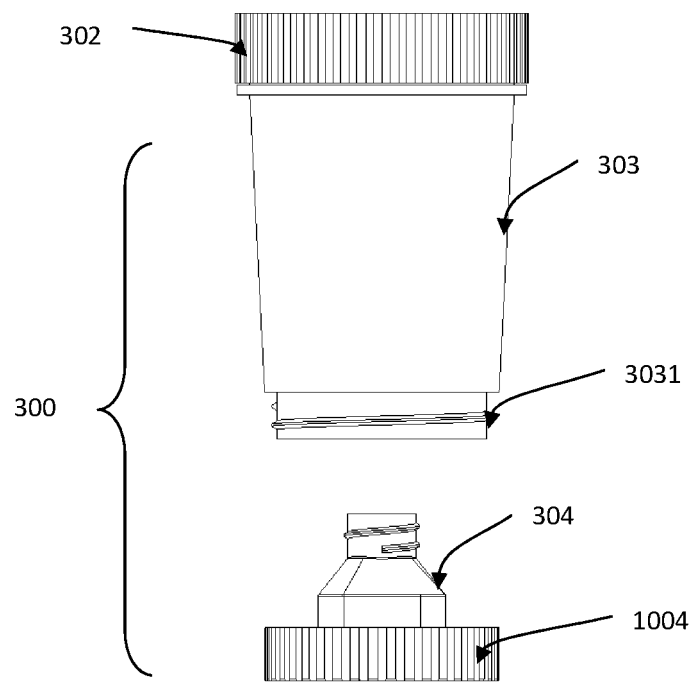
FIG. 25 is a perspective structural view of a second chamber combined with a first chamber in a detection or collection apparatus according to another embodiment of the present invention (second chamber is located in a tray structure).
Figure 26:
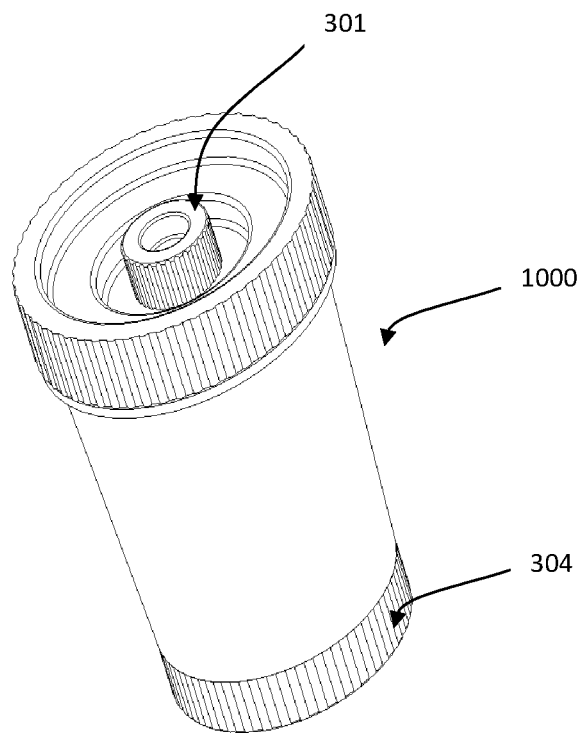
FIG. 26 is a structural view of a detection or collection apparatus of the present invention in which a first chamber is combined with a tray.
Figure 27:
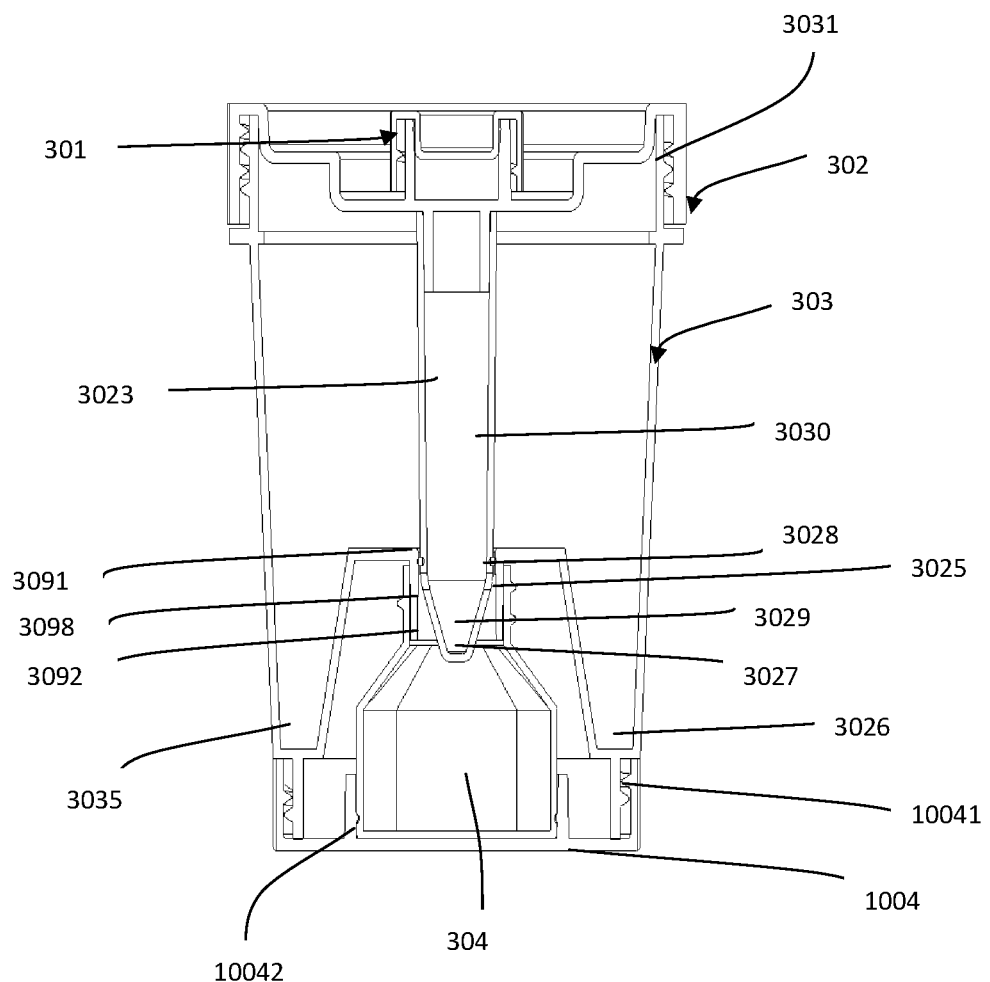
FIG. 27 is a cross-sectional view of the structure shown in FIG. 26 in the detection or collection apparatus of the present invention.
Figure 37:
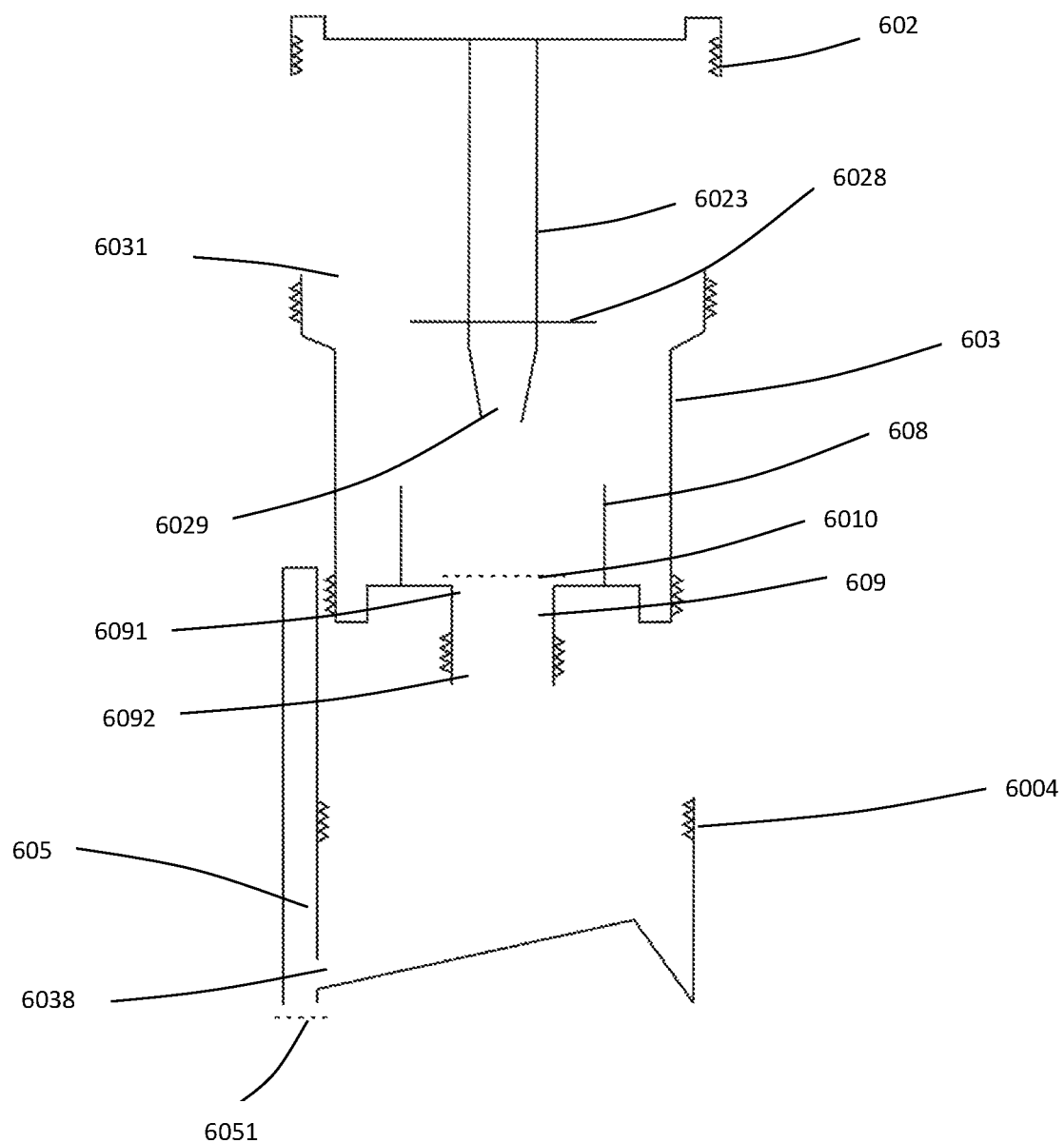
FIG. 37 is a structural view showing combination of a first chamber and a second chamber according to another embodiment of the present invention.
Figure 38A:
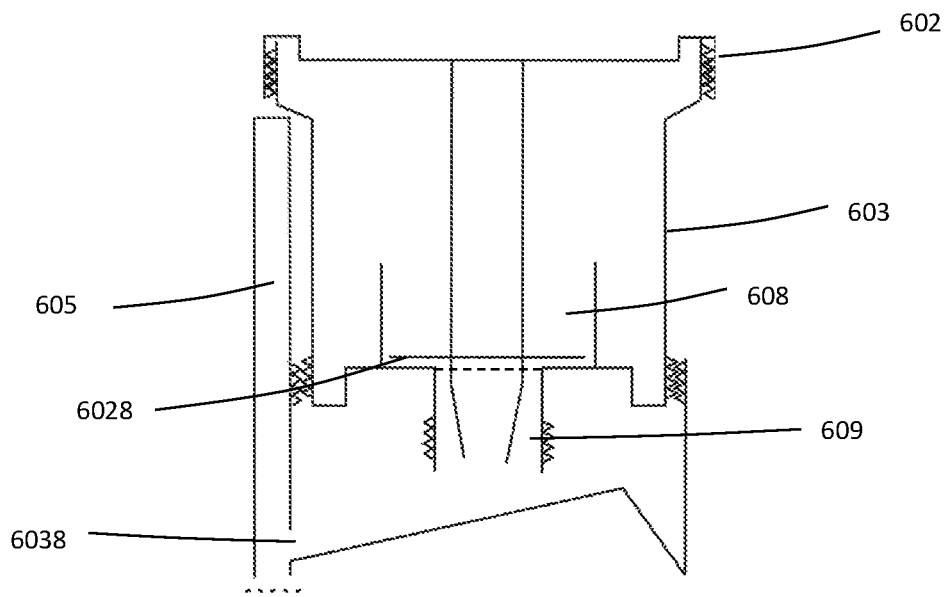
FIG. 38A and FIG. 38B are structural views showing that the first chamber is separated from the second chamber and the first chamber is used for second confirmatory detection.
Figure 38B:
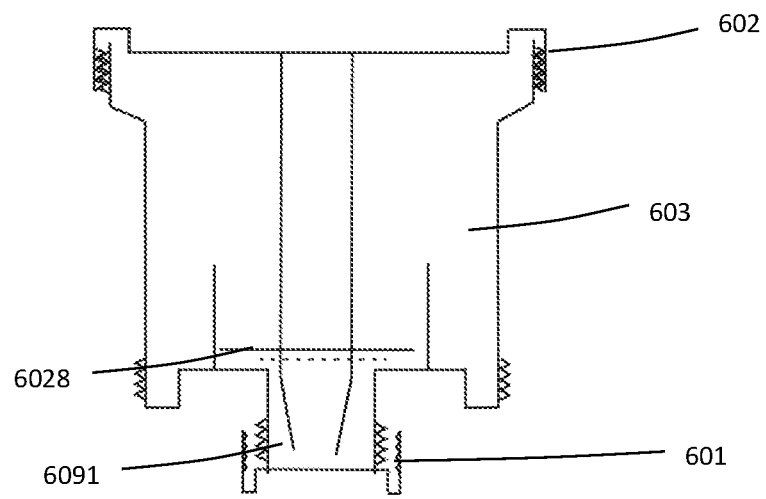

It will be understood by an ordinary person skilled in the art that the connecting channel 109 may be omitted herein provided that the liquid samples can flow to the second chamber from the first chamber when the first chamber collects liquid samples, and the second chamber can be easily separated from the first chamber when necessary. By this way, an ordinary person skilled in the art can know the essence of the prevent invention and envisage other appropriate ways. For example, as shown in FIG. 36, a hole 903 is provided in the side wall of the first chamber 903, and the hole is sealed by a puncturable film, or sealed by self-sealing silicone, rubber or soft plastic initially, and when it is required to collect samples, samples are collected by the first chamber 903; after samples are collected, a second chamber 904 (not connected to the first chamber initially) is provided to allow to pierce the sealing film (not shown) of the first chamber at the opening of the second chamber, so that the liquid in the first chamber flows into the second chamber, and then the second chamber is separated from the first chamber, to use the liquid in the second chamber for second detection. For another example, as shown in FIGS. 37-38, the first chamber and the second chamber are not detachably combined through a connecting channel, but the first chamber and the second chamber are detachably combined by mutually engaging screw structure. Further, as illustrated in FIGS. 25-27, the detachable combination is achieved by a tray structure, which will be described in detail below.

Optionally, referring to FIG. 8, the present invention designs the connecting channel 109 to connect the opening 1042 of the second chamber 104, of course, the connecting channel 109 may not be necessary, but the opening 1042 of second chamber 104 acts as a connecting channel, and its opening 1042 is directly connected with the inner portion of first chamber in the form of snapping, piston, or locking. At this time, a hole is provided at the bottom of the first chamber, as long as the opening 1042 of the second chamber corresponds to the hole, the liquid can flow through the first chamber to the second chamber. Preferably, the first chamber and the second chamber are connected together before the first chamber collects samples, and the first chamber is easily separated from the second chamber when necessary.

Figure 33:
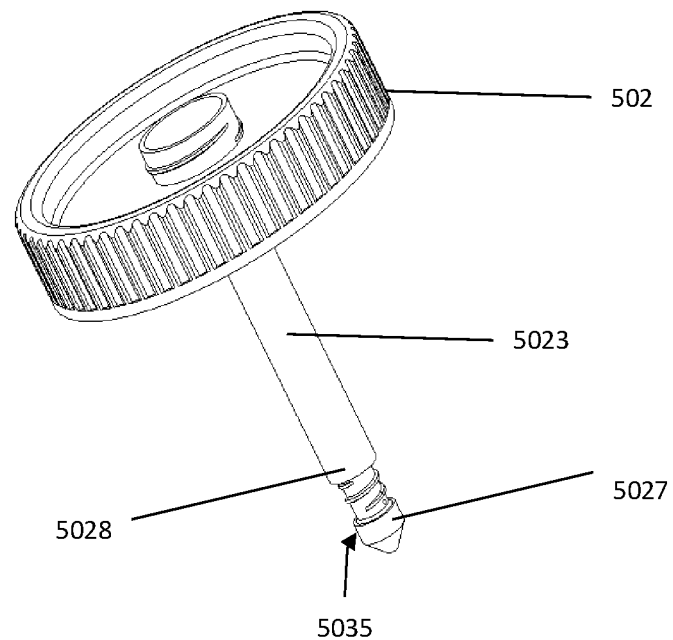
FIG. 33 is a structural view of a sealing element according to another embodiment of the present invention.

In some other preferred embodiments, the detachable connection, combination or assembly between the first chamber and the second chamber is not in the situation shown in FIG. 33 where the first chamber and the second chamber are directly connected in a detachable manner without using the other structure, or in the situation shown in FIGS. 8-9, 1 and 22-23 where the first chamber and the second chamber are indirectly connected in a detachable manner through a connecting channel, instead, it is the detachable connection or combination shown in FIGS. 25-30. Below are detailed descriptions.

As a result, the other aspect of the present invention provides a collection or detection apparatus, which comprises a first chamber for collecting liquid samples; and a second chamber for performing the confirmatory second detection, wherein the apparatus further comprises a tray structure which is connected, combined or assembled with the first chamber in a detachable manner. In some embodiments, the second chamber is located on the tray, that is, the detachable combination or connection between the second chamber and the first chamber is achieved indirectly through the detachable combination or connection between the tray and the first chamber, the movement of the tray structure and the second chamber is in the form of linkage. Generally, the linkage means that the movement of the tray drives the movement of the second chamber, thus achieving the separation from the first chamber. Then, after the linkage, separating or not separating from the tray structure can be achieved.

At this time, there can be one or no connecting channel. So, the communication structure is not a must. For example, as shown in FIG. 25-30, the second chamber is located on a base structure or a tray structure 1004, and liquid can still communicate between the opening of the second chamber and the connecting channel (there is a connecting channel). However, it is unnecessary to achieve liquid communication by direct connection between the second chamber and the connecting channel relying on its own structure as described above. In the present specific embodiment, we only need to connect the opening of the second chamber and the second outlet of the connecting channel, and connect the base structure 1004 and the bottom of the first chamber 103 through a matching structure (FIG. 27) such as a screw thread. In this way, the base structure has a screw thread, for example, an external thread, while the bottom of the first chamber has an internal thread, and the two are combined together in the form of a screw thread, and through the binding force of the screw thread, the second chamber is closely matched with the connecting channel. To be specific, it is achieved in the following way, for example, as shown in FIGS. 25-28, the second chamber 304 is located on a base tray 1004, and the base tray 1004 is connected with the first chamber in a detachable manner, and the second chamber 304 is combined with the base tray 1004 in a detachable manner. Specifically, the tray structure 1004 has an internal thread which cooperates with the external thread 3031 extended from the bottom of the first chamber 303 to achieve the detachable combination between the tray structure 1004 and the first chamber 303. In this way, if there is still a connecting channel, as shown in FIG. 27, the connecting channel 309 can still have a first opening 3091 through which liquid can flow from or to the first chamber and a second opening 3092 through which liquid can flow from or to the second chamber, while the connecting channel has an extension 3098 which goes deep into the opening 3052 of the second chamber, and contacts the inner wall of the opening 3041, and they can be connected together by snapping, that is, the outer diameter of the extended area matches with the inner diameter of the opening 3041. Although the second chamber and the first chamber can also be connected through the connecting channel 109 by snapping as shown in FIG. 27, such connection is not required to be very firm, or as close as that shown in FIGS. 8-9 (by a screw thread or other ways). This is because the tray structure 1004 matches with the external thread 3031 of the extension of the first chamber 103 through the screw thread 10041, so no matter how many liquids are collected by the second chamber 304, the leakage problem between the connecting channel 109 and the opening 1042 of the second chamber will not caused. Therefore, the inner diameter of the connecting channel 109 can be less than that of the opening 1042 of the second chamber, so that the connecting channel can be easily inserted into the opening 3042 of the second chamber, as shown in FIG. 27. A screw thread is only set at the outer edge of the opening 3042 to cover the second cover body (as shown in FIG. 27). At this time, the connection between the connecting channel and the opening of the second chamber only needs to ensure no liquid leakage when collecting liquid samples, that is to ensure liquid can enter the second chamber, and more structural constraints are not required. Such connection can be achieved in the forms of snapping, piston or locking. In fact, the detachable combination, connection or assembly between the first chamber and the second chamber is completed in an indirect way.

Figure 29:
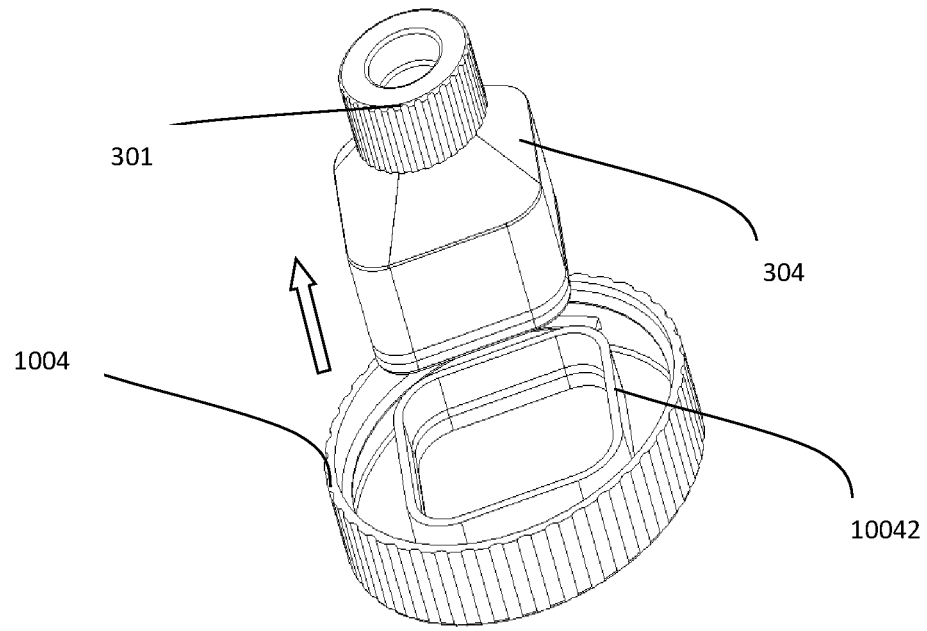
FIG. 29 is a structural view of a second chamber leaving away a tray.

After the collection is completed, and after the connecting channel is sealed or/and the drainage function of the second chamber is conducted according to the method described below, if it is necessary to perform the second confirmatory test, separate the tray structure 1004 from the first chamber 103, for example, reversely rotate the screw thread structure of the tray that matches with the bottom of the first chamber, then the second chamber 104 on the tray is also separated from the first chamber 103 together with the tray structure, as shown in FIG. 27, at this time, take down the second cover body 101 to cover the opening 3042 of the second chamber. Then, let the second chamber separate from the tray 1004 (as shown in FIG. 29). Because the bottom of the second chamber and the bottom of the tray have a snapping structure 10042, so the tray and the second chamber will separate from the first chamber 103 together. Then, disassemble the tray 1004 from the second chamber 304, and connect or combine the tray 1004 alone with the first chamber 103 again. At this time, the integrity of the first chamber shall be still maintained, while the second chamber can be sent to the approved assay agency for the second confirmatory test. To allow the second chamber 304 to separate from the first chamber with the movement of the tray, a snapping ring 10042 is provided on the tray. The shape of the snapping ring is suitable for the shape of the second chamber 304, for example, the second chamber is U-shaped, and the snapping ring 10042 is also U-shaped. In this way, the second chamber 304 will rotate when the tray structure 1004 rotates. The second chamber can slightly and closely cooperate with the snapping ring, so naturally, the second chamber 304 and the tray structure 1004 can separate from the first chamber 303 together. Of course, in some embodiments, the second chamber is a structure similar to a cube, and 4 snap joint structures are set on the tray. The second chamber is connected to the snap joint structure by snapping, so that the movement of the tray can drive the movement of the second chamber, and the second chamber can be separated from the first chamber.

At this time, to ensure the safety after the second chamber is covered by the second cover body, a strip seal can be pasted on the second chamber, which covers the second cover body and part of the second chamber so as to ensure the samples in the second chamber will not be replaced maliciously, and allow the liquid in the second chamber to keep consistent with the original samples in the first chamber. Of course, optionally, the tray 1004 and the second chamber can be packed and transported together, and the strip seal shall cover the second chamber and the tray, and seal the cover body of the second chamber, so as to transport them as an integral structure. It can be understood that, the base structure 1004 and the second chamber 104 are an integral structure, and a structure formed by one-time injection molding. In this way, when the base 1004 combines with the first chamber 104, the second chamber 104 combines with the connecting channel 109.

Optionally, there can be no connecting channel and extension 3098, and we only need to open a hole on the bottom of the first chamber 103, with its size less than or equal to the opening 3042 of the second chamber 304, so the connecting channel is not required to have an extension (as shown in FIG. 27). The first opening 3091 of the connecting channel can play the role of the bottom hole. In this way, when the second chamber is combined with the first chamber through the tray, the opening 1042 of the second chamber corresponds to the position of the bottom hole of the first chamber 103 (like the position 3091 shown in the figure), and by relying on the cooperation between the tray 1004 and the first chamber 303, the opening of the second chamber 304 and the area around the hole form a close matching or contact, so that the second chamber and the first chamber form a state of liquid circulation, that is, when liquid is collected in the first chamber, liquid will flow into the second chamber. If it is necessary to separate the second chamber from the first chamber 103, the bottom hole (like the position 3091 as shown in FIG. 27) of the second chamber shall be sealed, so that the tray 1004 can be separated from the first chamber 103, driving the second chamber 103 to separate from the first chamber. In this way, the same function is achieved. Optionally, at the beginning, this hole is sealed by a sealing material that is easily pierced, and after liquid is collected or detection is started, this sealing material is pierced to allow liquid to flow into the second chamber. The ways of the sealing element will be described specifically below.

After liquid is collected in the first chamber, the second chamber can be separated from the first chamber. The second chamber can be stored or transported to the detection agency for second confirmatory detection, and the liquid in the first chamber can be used for first or initial detection. Alternatively, after liquid is collected in the first chamber, the second chamber can be separated from the first chamber, after separation, the liquid in the first chamber can be detected. After the detection result is obtained, the second chamber can be stored or sent directly to a detection agency for second confirmatory detection. Further alternatively, after collection of liquid samples, the liquid samples in the first chamber are detected. When the results of initial detection are obtained, the second chamber is separated from the first chamber, and the separated second chamber is used for storage or subsequent second confirmatory detection.

Of course, the liquid in the first chamber can be stored for initial detection at an appropriate time. In some preferred embodiments, it is desirable that initial or initial detection is performed when the liquid is collected in the first chamber, and when the detection ends, a second confirmatory detection can be carried out if necessary. The initial test is just to detect whether there is analyte in the sample and its sensitivity is generally low. Sometimes, when the analyte in the sample is at the critical threshold, the result of the initial test cannot be used as an affirmative result. At this time, it is expected to conduct a second confirmatory detection for the same part of samples.

As for the issue that the second chamber or the first chamber is used for the confirmatory second detection after they are separated, for example, the first chamber can be used for performing the second detection, while the liquid samples in the second chamber are used for the initial detection, which can be achieved. So, it is not restricted that only the second chamber can be used for the confirmatory detection. In some embodiments, for example, as shown in FIG. 37 and FIG. 38, the present invention provides a first chamber 603 for collecting liquid samples and a second chamber 604 for performing the initial detection, wherein the second chamber comprises a detection chamber 605, and the detection chamber and the second chamber have a liquid communication through hole 6038. The first chamber comprises an opening 6031, and a connecting channel 609 is provided on the bottom of the first chamber. The connecting channel comprises a first opening 6091 through which liquid communicates with the first chamber, and a second opening 6092, wherein the first opening is sealed by a sealing element, the sealing element can be easily pierced, such as thin film, double faced adhesive tape, and aluminum foil. In this way, when the first chamber is used to collect the liquid sample, liquid will not flow out from the first opening of the connecting channel at the very start. After liquid sample is collected in the first chamber, the first chamber is combined with the second chamber, for example, the combination is achieved by using the external thread 6031 of the first chamber and the internal thread of the second chamber, or, at the beginning, the first chamber and the second chamber have been combined together through a screw thread, and the first chamber 603 is used to collect liquid samples directly. After the collection is completed, the piercing element 6029 is used to pierce the sealing element 6028 that seals the first opening of the connecting channel, so as to release liquid to the second chamber 604 for the initial detection. This liquid enters the detection chamber 605 for the initial assay and detection. If it is necessary to perform the second confirmatory detection, disassemble the first chamber from the second chamber, and seal the opening of the first chamber with the cover body, so that the liquid sample in the first chamber can be used for the second confirmatory detection. Optionally, the cover body used to seal the first chamber comprises the sealing element 6028 and the piercing element 6029, and inside the first chamber, there is an extended channel 610 corresponding to the first opening 6091 of the connecting channel 609, which extends towards the interior of the first chamber. In this way, when the cover body covers the first chamber, the cover body, the sealing element 6028 and the piercing element 6029 form a relationship of linkage, thus the former will drive the movement of the sealing element and the piercing element. When the piercing element pierces the sealing element that seals the first opening 6091 of the connecting channel, the sealing element pushes the liquid in the channel 610 to flow into the second chamber for the initial assay, then the cover body seals the opening of the first chamber, as shown in the above figure in FIG. 38. When it is necessary to perform the second confirmatory assay, separate the first chamber 603 from the second chamber 604, then seal the second opening of the connecting channel with the second cover body, for example, by using a screw thread, then send the first chamber 603 to the detection agency for the second confirmatory detection, as shown in the below figure in FIG. 38.

Of course, the piercing element can also have a function of discharging some liquids in the second chamber, then the piercing element can further comprise a drain channel, a liquid inlet and a receiving chamber. In this way, after the sealed first opening 7091 of the connecting channel is pierced, the piercing element is directly inserted into the second chamber in part, so that the liquid can flow into the receiving chamber through the liquid inlet of the drain channel in addition to discharging liquid, for example, the receiving chamber is located in the piercing element. It will be understood clearly according to the detailed descriptions on such combination below.

In some optional embodiments, when it is regarded as a detection apparatus, the collection apparatus further comprises a testing element which can test the collected samples. For example, the collection apparatus comprises a detection chamber, wherein liquid communicates between the detection chamber and the first collecting chamber, that is, liquid sample in the first chamber can flow into the detection chamber. Of course, it is only a preferred embodiment that the detection apparatus mentioned comprises a detection chamber. When it is regarded as a collection apparatus, there can be no detection chamber, or the detection apparatus comprises a detection chamber and no testing element, and when the detection is needed, a detecting element is inserted into the detection chamber. In some specific embodiments, a detection chamber 105 is provided outside the side wall of the first chamber, and the first chamber 103 and the detection chamber 105 is in a state of fluid communication (as shown in FIG. 9). If there is liquid sample in the first chamber 103, liquid communication can be achieved through the through hole 1038 set on the detection chamber 105 and the collecting chamber 103, so that liquid can enter the detection chamber for necessary initial assay or detection.

Generally, the sensitivity of detection of liquid samples in the first chamber 103 (first or initial detection) is not higher than that of the second confirmatory detection, or the specificity of the first or initial detection is not as accurate as that of the second confirmatory detection. Thus, the second detection can be used to basically confirm whether the initial detection is really accurate. For example, the initial detection is performed according to immune and chemical methods, while the second confirmatory detection is generally mass spectrometry (GS), gas or liquid chromatography detection. Such second detection often uses liquid samples in the second chamber separated from the first chamber. This is because the first chamber and the second chamber both aim at the same sample, and their nature is the same and they are only divided into different parts. Thus, the second detection can confirm the accuracy of the initial detection.

In some preferred embodiments, when the first chamber 103 collects the liquid samples or shortly after collection, the liquid in the first chamber is detected immediately. Therefore, in a preferred embodiment of the present invention, the first chamber 103 is in fluid communication with the detection chamber 105 and the detection chamber comprises the testing element. In some preferred embodiments, these testing elements are disposed on a carrier. In a preferred embodiment, the detection chamber comprises a testing carrier 106, and a plurality of card slots 1061 are provided on the testing carrier, and a testing element is provided in each of the card slots. For example, as shown in FIG. 9, when the liquid samples are collected in the first chamber 103, a part of the liquid samples flows into the detection chamber 105 via the through hole 1038 to contact with the testing element, thereby completing the detection of the analyte. The other part of the liquid samples flow into the second chamber 104 through the opening 1091 of the connecting channel 109. After the detection element in the detection chamber finishes the detection, the initial detection results are obtained. When it is considered necessary to perform a second confirmatory detection, the second chamber 104 is separated from the first chamber 103, then the opening 1042 of the second chamber 104 is sealed by a second cover body 101, and the second chamber 104 is stored or directly sent to a detection agency for further confirmatory assay. the liquids in the first chamber 103 and the detection chamber 105 for the initial detection can be discarded or disposed of.

The separation of initial detection and second confirmatory detection can overcome some drawbacks of traditional detection apparatus. For the traditional detection apparatus, if the second assay is required after the detection is completed, it is necessary to store the entire detection apparatus (with the first chamber as a chamber for collecting the liquid and/or with a detection chamber, or a testing element in the detection chamber), or pack and transport the entire detection apparatus (by vehicle, by sea or by air) to a detection agency for the second confirmatory detection. This needs to guarantee that any structure or any place of the entire detection apparatus has no leakage of liquid samples, since the leakage will result in external contamination or mutual contamination of samples, producing uncertain results of the second confirmatory detection. This will inevitably require sealing of each structure that may cause leaks, which will increase the costs and design difficulty for the manufacture of such a detection apparatus. Because these detection apparatuses used for initial detection are usually disposable plastic products, it is very difficult to achieve no liquid leakage of the apparatus, and even it can guarantee no leakage, the cost will be very high. Ideally, it is required to reduce the costs as much as possible and guarantee no leakage of liquid samples, bringing a great challenge to manufacturers. This requires, for example, a complex design of the first cover body 102 that seals the opening 1031 of the first chamber to ensure that liquid cannot leak through the opening 1031. If the apparatus further comprises a testing element, it requires a more elaborate processing or design of the chamber (if any) for accommodating the testing element, to ensure that liquid samples do not leak through the test chamber. In particular, these apparatuses usually require air transportation, it will bring great challenges to the production and design to guarantee no leakage under a condition of high pressure or negative pressure. Traditionally, to avoid leaks, seal rings or silicone pads are used as sealing parts. However, once the apparatus is stored too long, these silica gels or plastics may be oxidized or aged, causing liquid leakage during use. Second, if the samples with initial detection results need to be stored, more space is required to accommodate a large-volume detection apparatus; this will certainly increase the space; and for a professional detection agency, the sample size is very big, which will require enough space to store the samples after initial detection. These samples after initial detection are contained in large detection apparatuses, requiring a greater area or volume for the storage space. Third, the volume of these apparatuses for completing the initial detection is big, so the transportation cost is increased significantly, and the cost for transportation and packaging is increased, after all, the traditional detection apparatuses are huge and are all packaged and transported separately. Fourth, if the detection apparatus comprises a testing element at the beginning, then during the transportation, the collected liquid always contacts the testing element, and the testing element contains chemical substances. These chemical substances do not exist in the liquid sample itself, so the liquid sample will be polluted if it contacts the testing element for a long time, and it is possible to cause a negative effect on the subsequent second detection. In a word, whatever the reason is, the traditional detection apparatus or collection apparatus has one or more drawbacks as described above.

For the apparatus in the present invention, the volume of the second chamber is generally smaller than that of the first chamber, even it is one tenth or a fraction of the conventional detection chamber. Usually 1 to 50 ml of samples stored in the second chamber are enough for a second detection, for example, 0.1 ml, 0.2 ml, 0.3 ml, 0.4 ml, 0.5 ml, 0.6 ml, 0.7 ml, 0.8 ml, 0.9 ml, 1 ml, or just 1.2 ml, 1.4 ml, 1.6 ml, 1.8 ml, 2 ml, or just 3 ml, 4 ml, 5 ml, 6 ml, 7 ml, 8 ml, 9 ml, 10 ml, 11 ml, 12 ml, 15 ml, 25 ml, 30 ml. The first chamber typically has a volume of 5 to 500 ml, for example, 8 ml, 10 ml, 12 ml, 14 ml, 16 ml, 18 ml, 20 ml, 22 ml, 24 ml, 26 ml, 28 ml, 30 ml, 32 ml, 34 ml, 36 ml, 38 ml, 40 ml, 42 ml, 44 ml, 46 ml, 48 ml, 50 ml, 60 ml, 70 ml, 80 ml, 100 ml, 150 ml, 200 ml, 250 ml, 500 ml. Moreover, in general, the second chamber has only one opening 1042; as long as the second opening 1042 is sealed, it can guarantee no leakage of samples. On one hand, the second chamber is small in size and light in weight, so the transportation packaging cost is significantly reduced and the storage space is small. On the other hand, it does not propose high requirements for sealing of first chamber and/or the part containing the detection chamber as conventional apparatus. For example, the sealing requirement for the first cover body to seal the first chamber opening 1031 is much lower and the sealing requirement for detection chamber disposed on testing element is also much lower than conventional apparatus, and even the sealing effect of first cover body on the opening of the first chamber 103 and the sealing effect of the detection chamber itself need not to be considered, since the first chamber 103 and/or the first chamber with the test chamber 105, or even the first cover body 102 can be discarded once the initial detection is completed. Compared with the traditional disposable detection apparatus, it saves a lot of costs and is more safe and reliable. In addition, the nature of the liquid in the second chamber is the same as that of the liquid in the first chamber, thus the effectiveness of the second detection is ensured. Third, the second chamber is small, so special consideration on the storage space is not required, and a small place can store a lot of second chamber bodies, thus the pressure on the confirmatory assay laboratory is reduced and the transportation cost is also reduced, and the safety of the transportation can be ensured since there is no need to worry too much about the risk of liquid leakage.

Figure 6:
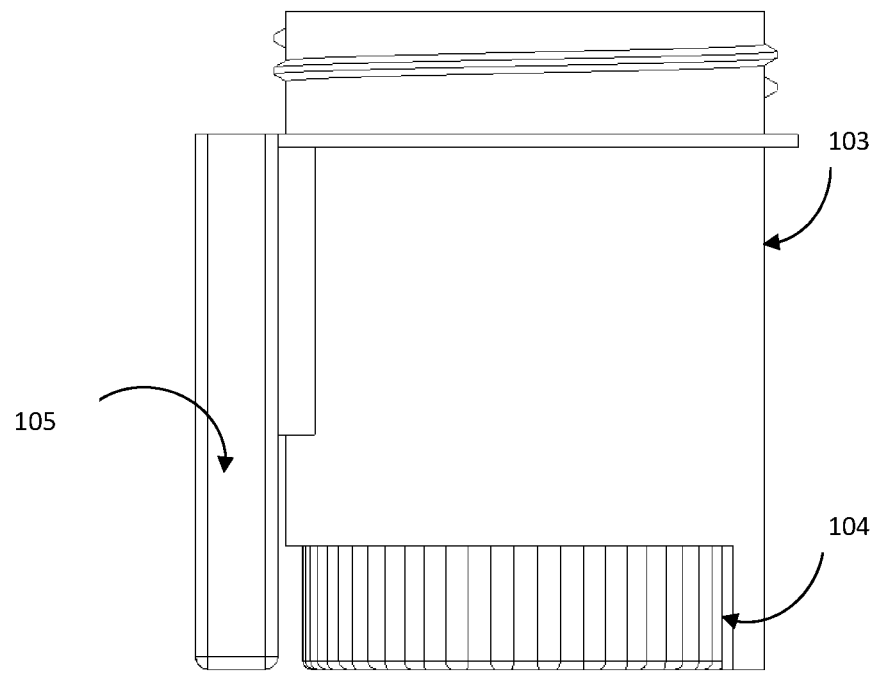
FIG. 6 is a perspective structural view without a first cover body according to an embodiment of the present invention.
Figure 7:
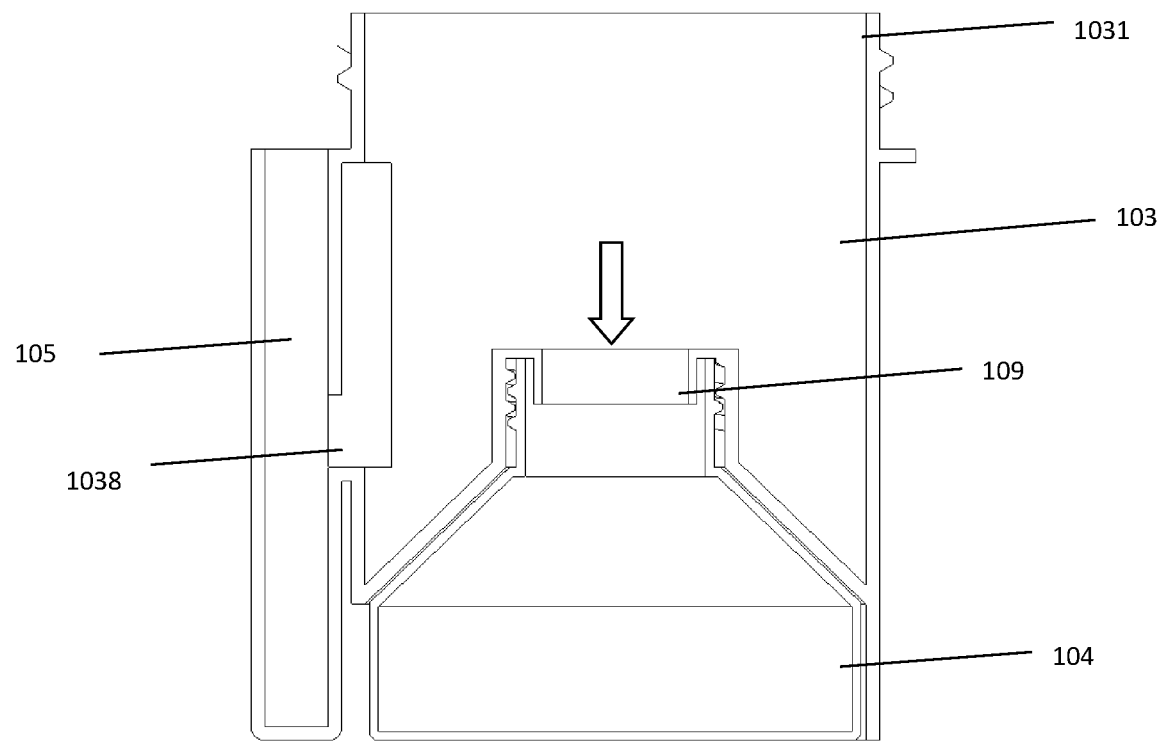
FIG. 7 is a longitudinal cross-sectional view of an apparatus of FIG. 6 in the present invention, wherein the first chamber is combined with the second chamber.

In some preferred embodiments, when the liquid samples collected in the first chamber 103 need to be detected at the same time when the samples for the second confirmation are collected in the second chamber 104, it is hoped that the samples that flow into the detection chamber (if any) will not cause potential pollution to the liquid samples that enter the second chamber 104. Allow the position of the opening 1091 of the connecting channel 109 to be higher than the height of the through hole 1038 (for example, as shown in FIG. 7 and FIG. 6, and FIG. 9), then liquid that flows into the detection chamber will not or can hardly enter the second chamber, so that the liquid in the second chamber 104 is the same as the liquid sample that does not contact the testing element in nature. After all, the liquid sample that contacts the testing element may contain some chemical reagents or other components disposed on the testing element. If these reagents or components enter the second chamber, an adverse effect may be produced on the second test result. It can be understood that if the opening 1091 of the connecting channel is higher than the through hole 1038, or according to the above method, the opening through which liquid flows into the second chamber is higher than the through hole through which liquid flows into the detection chamber (for example, the bottom hole described in the above embodiment, and there is no connecting channel), the liquid sample that contacts the test strip can be prevented from entering the second chamber when the testing element is included in the apparatus and contacts the liquid sample.

In some preferred embodiments, the first chamber comprises a collecting area 1035 or 1036 for collecting liquids. These collecting areas are located on the bottom of the first chamber 103, around the connecting channel 109 or around the first opening 1091 of the connecting channel. In some preferred embodiments, the position of these collecting areas is lower than that of the opening 1091 of the connecting channel. In this way, when liquid enters the first chamber, liquid is collected in the collecting area first, and then enters the detection chamber through the through hole 1038 and contacts the testing element. Therefore, according to the arrival sequence, liquid arrives at the collecting area first, then flows into the through hole 1038 and enters the detection chamber (if any), then arrives at the first opening 1091 of the connecting channel.

Figure 5:
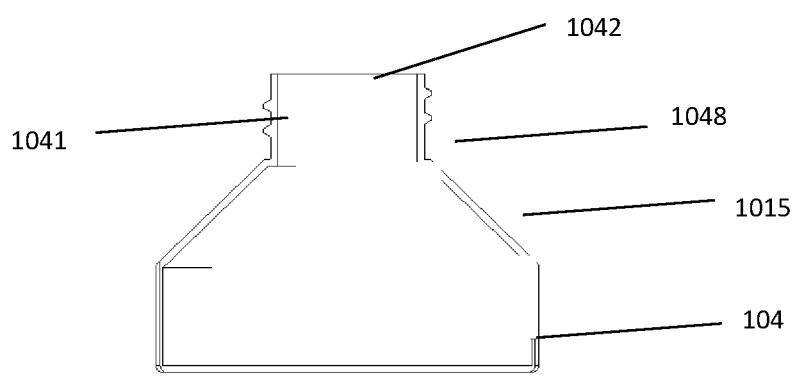
FIG. 5 is a longitudinal cross-sectional view of a second chamber according to an embodiment of the present invention.
Figure 12:
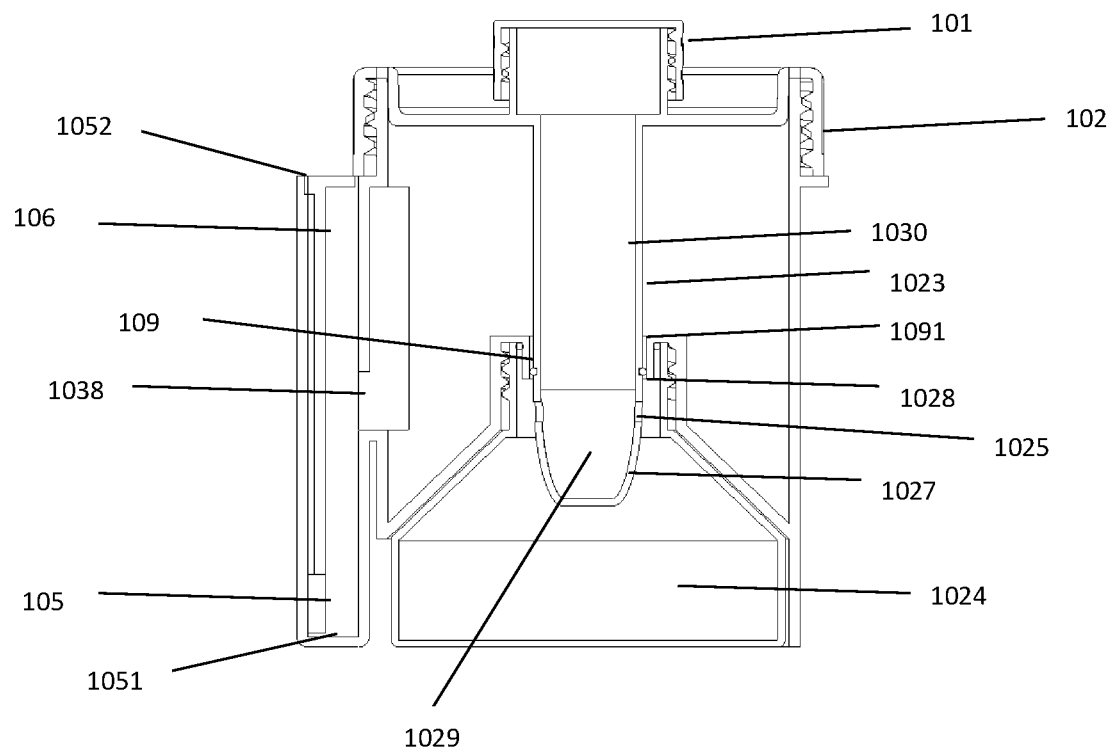
FIG. 12 is cross-sectional structural view of an apparatus shown in FIG. 11 according to an embodiment of the present invention.

In some preferred embodiments, for example, as shown in FIGS. 12, 4, and 5, there is a bulge area in the middle of the bottom of the first chamber, and the space formed by the bulge area is used to accommodate the major structures of some second chamber bodies 104. A connecting channel or hole is provided in the bulge area, then the bulge area also forms a collecting area u (as shown in FIG. 4 and FIG. 5). From the perspective of the bottom of the first chamber (for example, as shown in FIG. 4), the bottom sinks towards the interior of the first chamber 103, and this sunk area is used to accommodate the opening 1042 of some second chamber bodies 104. In this way, as a whole, the materials for the detection apparatus will not be added, and it will not be abrupt. As shown in FIG. 7-11, the opening part of the second chamber is set below the bottom of the first chamber 103, on the whole, it is still much the same as the traditional detection apparatus. In some preferred embodiments, the position of the collecting areas 1036 and 1035 is lower than that of the through hole 1038. In this way, the collected liquid samples first enter the detection chamber (if any) 105 through the through hole 1038, and as long as the detection chamber is filled with the liquid or the liquid seals the through hole 1038, redundant liquids will enter the second chamber 104 through the first opening 1091 of the connecting channel 109. Thus, the liquid that flows into the detection chamber can be prevented, wherever possible, from flowing out from the detection chamber and entering the second chamber. Alternatively, according to the flowing sequence, liquid arrives at the collecting area first for collection, and after it is collected to a certain height, liquid flows into the detection chamber through the through hole 1038 for detection and assay, and after the detection chamber collects the liquid samples, the through hole 1038 will be sealed by liquids. With the increase of liquid volume, the liquid level will reach the position of the opening 1091 of the connecting channel, thus enter the second chamber to fill the second chamber or some liquid samples enter the second chamber for subsequent second confirmatory detection.

Figure 15:
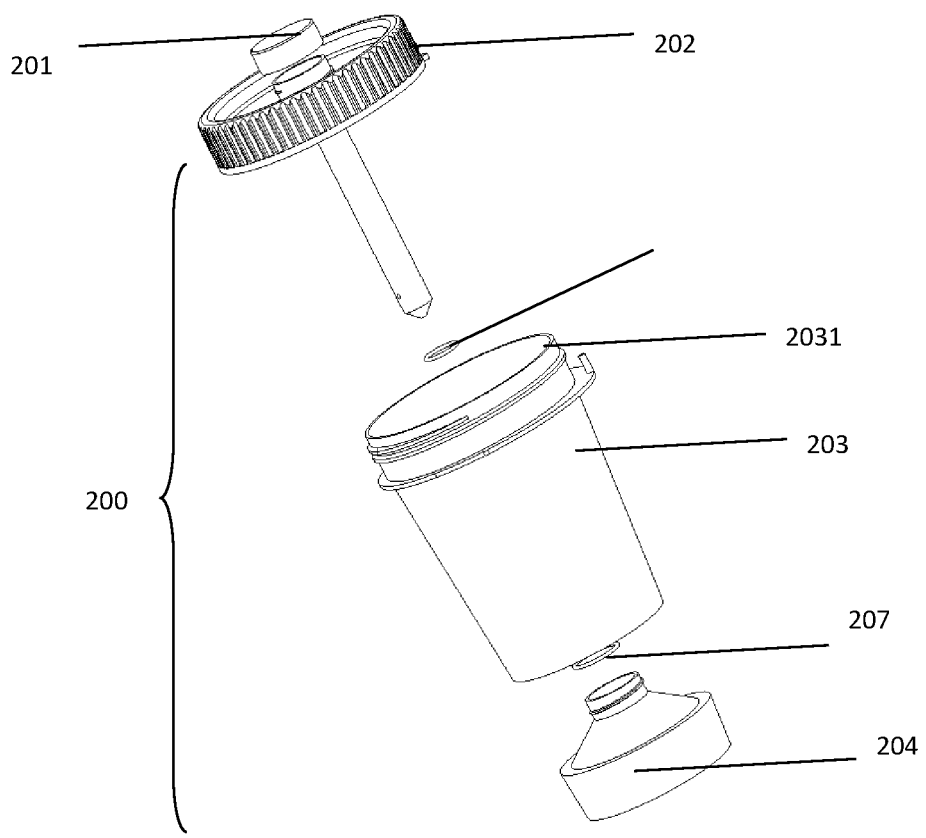
FIG. 15 is a perspective structural view of an apparatus according to an embodiment of the present invention.

In some other embodiments, the detection apparatus does not contain a testing chamber separately (as shown in FIG. 1). For example, as shown in FIGS. 15-17, the side wall of the first chamber 203 comprises an area, for example, as shown in FIG. 16, the first chamber 203 comprises two vertical card strips 2032 and 2033, which restrict such an area where the carrier shown in FIG. 17 is inserted, forming a structure with a testing function. For example, the carrier structure shown in FIG. 17, on which multiple channels 2063 accommodating the testing element are provided, and one end 2062 of the channel is closed and the other end 2061 is opened. Each channel is arranged on the carrier in such compatible direction, and the testing area and the water absorbing area on the testing element are located in the channel, while the sample application area on the testing element is located on one end of the channel opening 2063. The testing element in each channel is set in this way, then the sample application area is located on the tail end 2065 of the carrier. Correspondingly, the testing area of the testing element is located near the closed end of the channel and on the top 2064 of the carrier. Then, the carrier is assembled and combined with the first chamber 103, to let the tail end 2065 of the carrier be close to the bottom 2034 of the first chamber and the top 2064 close to the opening 2031 of the first chamber. In this way, some of the liquid samples entering from the opening of the first chamber 203 can contact the sample application area of the testing element that is close to the bottom 2034 of the first chamber 203, and the detection and assay on the analyte in the liquid samples can be completed. In some other preferred embodiments, for example, as shown in FIGS. 25-30, the detachable combination of the second chamber 304 and the first chamber 303 can be achieved in the ways described above, for example, as shown in FIGS. 1, and 6-13, or in any of the above ways, and also, the sealing or separation can be achieved in any of the subsequent ways.

Figure 22:
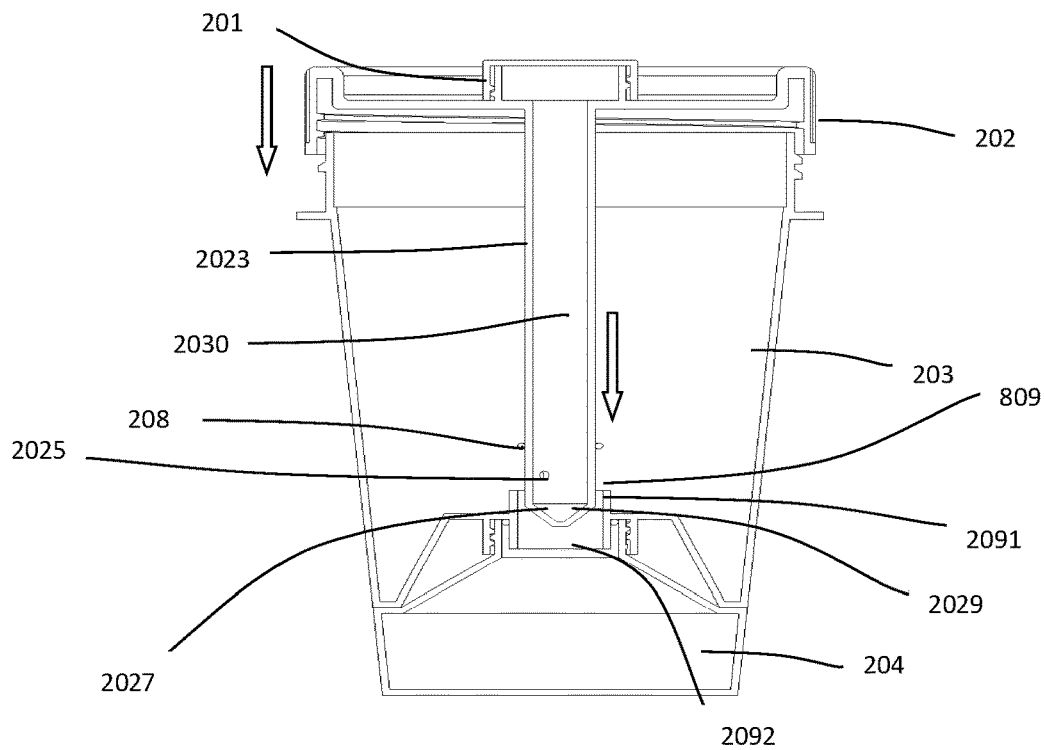
FIG. 22 is a cross-sectional view of the apparatus shown in FIG. 21 of the present invention (the sealing element does not seal the connecting channel and begins to approach the opening).
Figure 23:
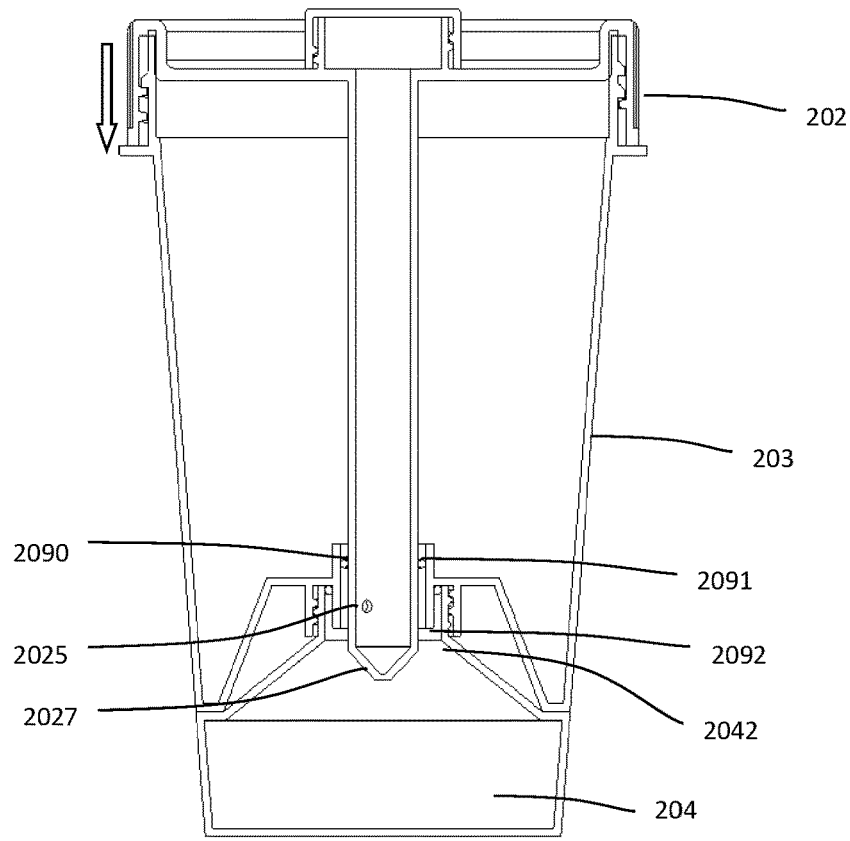
FIG. 23 is a cross-sectional view of an apparatus (when a sealing element enters a connecting channel) according to an embodiment of the present invention.

In some preferred embodiments, a groove structure 2035 is provided at the bottom 2034 of the first chamber, and the groove structure 2035 can allow liquid samples to collect in the first chamber, as shown in FIGS. 22 and 23. In some preferred embodiments, the level of the first opening 2091 of the connecting channel 209 is higher than that of the groove, that is, the opening 2091 of the connecting channel 2091 is the upstream of the groove 2035 so that the liquid samples in the vicinity of the groove, which are in contact with the testing element, flow into the second chamber 204 through the first opening 2091 of the connecting channel. Similarly, when the testing element in the carrier located in the first chamber finishes the first or initial detection and it is necessary to perform subsequent second confirmatory detection, the second chamber may be separated directly from the first chamber, after separated, the opening 2041 of the second chamber 204 is sealed by a second cover body 201, and the second chamber 204 is stored or packaged to send to an detection agency for second confirmatory detection. Correspondingly, the carrier 206 and the first chamber 203 with carrier and the first cover body 202 with the opening 2031 of the first chamber 203 are discarded or disposed of after the initial detection is finished. The volume of the first chamber is typically larger than that of the second chamber, and they can be designed according to the volume difference as foregoing described. Of course, the volume of the first chamber can be equal to that of the second chamber. Alternatively, the volume of the first chamber can also be smaller than that of the second chamber.

In some embodiments, the shape of the first chamber and the second chamber is not specially restricted, for example, usually the first chamber is cylindrical and the second chamber is cylindrical, of course, the first chamber can be a cuboid, a cube, an ellipsoid or a cone, correspondingly, the second chamber can be a cuboid, a cube, an ellipsoid or a cone.

The detachable combination of the first chamber and the second chamber is described above. Generally, the second chamber is located inside or on the bottom of the first chamber, or, at the beginning, the first chamber and the second chamber are combined together, and after the liquid is collected, the first chamber and the second chamber are separated. Of course, the specific position of the second chamber is not restricted, and the second chamber can be in other forms.

Sealing Element

In some preferred embodiments, after the first chamber is separated from the second chamber, or before they are about to separate or before they separate, allow liquid not to flow between the two chambers which are originally in a state of liquid communication, so as to prevent liquid communication between the two chamber. Alternatively, there are the following states about whether liquid communicates between the first chamber and the second chamber: the first state is that liquid does not communicate, and the second state is that liquid communicates; or, the first state is that liquid communicates, and the second state is that liquid does not communicate. With regard to different states between the first chamber and the second chamber for different purposes or in different operating processes, fluid communication or non-communication can be designed and selected at will. For example, when the first chamber collects fluid samples or liquid samples, the first chamber is in liquid communication with the second chamber; before or when separation is needed, the second chamber is not in liquid communication with the first chamber. Alternatively, when the first chamber collects fluid samples or liquid samples, the first chamber is not in liquid communication with the second chamber; before or when separation is needed, the second chamber is in liquid communication with the first chamber, to allow the second chamber to collect the liquid from the first chamber, then the first chamber and the second chamber are not in a liquid communication state, so as to separate the second chamber from the first chamber.

Therefore, in some embodiments, a sealing element is provided. If the first chamber 103 is combined with the second chamber 104 in a detachable manner through the connecting channel 109, the sealing element seals the connecting channel so that the liquid in the first chamber will not enter the second chamber, or the liquid in the first chamber will not flow out from the channel through which liquid enters the second chamber. Not allowing liquid to flow out from the connecting channel means that the connecting channel is sealed or the junction between the first chamber and the second chamber is sealed. The two chambers can be connected indirectly through the connecting channel, or in other ways. In these embodiments, after, when or before the second chamber is separated from the first chamber, the junction between the first chamber and the second chamber is sealed, so that liquid will not enter the second chamber, or after the second chamber is separated, liquid samples will not leak to outside of the first chamber through the junction. In some preferred embodiments, liquid cannot leak to the outside of the first chamber containing a detection chamber through the junction, or liquid cannot leak to the outside of the first chamber containing a testing element through the junction. It can be understood easily that the connection and liquid communication are not achieved through the preferred way of the present invention, i.e. connecting channel, instead, they are achieved through two independent structures, i.e. connecting structure and communication channel. After the first chamber is separated from the second chamber through the connecting structure, liquid can flow as long as the sealing element is used to seal the communication channel. Therefore, the function of the sealing element is to allow the first chamber not to be in liquid communication with the second chamber, and to change the state from liquid communication to non-communication.

In some preferred embodiments, when the second chamber is detachably connected to the first chamber by a connecting channel, and the connecting channel is sealed by the sealing element while the second chamber is separating from the first chamber, or after or before separation. The sealing element can seal the first opening 1091 of the connecting channel, as described in FIG. 12. Here, the sealing element, like a plug, blocks the opening 1091 of the connecting channel, thereby preventing the liquid from entering the second chamber or preventing liquid from flowing out of the first chamber from the first opening 1091 of the connecting channel. Here, the sealing element can be matched or adapted to the shape of the opening of the connecting channel, to seal the connecting channel. The "adapted" here means that the sealing element mutually matches with the connecting channel by means of appropriate size, material or shape or their combination, to play a role of liquid seal. For example, the first opening of the connecting channel is circular, the sealing element is also circular, or the connecting channel is plastic, the sealing element is also plastic, which is sealed relying on the mechanical elasticity of the material itself, alternatively, the sealing element is rigid, the connecting channel is elastic, further alternatively, the sealing element is rigid, the connecting channel is rigid; all these ways can achieve the sealing effect, so as to achieve the functions described above. For example, the sealing element is elastically deformed, and the connecting channel is rigid, and the sealing element is inserted into the connecting channel, thereby sealing the opening of the connecting channel. This type of sealing is optional. The sealing element can be used alone to seal the connecting channel or seal the liquid flow-through places of the first chamber and the second chamber, allowing the first chamber to be in fluid communication with the second chamber.

In some preferred embodiments, the first cover body 102 comprises a sealing element for sealing the connecting channel, and the sealing element seals the opening of the connecting channel while the first cover body covers the opening of the first chamber. In fact, the sealing element and the cover body form a linkage mechanism, and the movement of the cover body drives the movement of sealing element. The movement of the first cover body can seal the opening of the first chamber. When the first cover body is moving, the connecting seal can be sealed by the sealing element, to facilitate the operation. Of course, it can be understood that the covering of the first chamber by the first cover body is not linked with the sealing of connecting channel by the sealing element, and it can be achieved by two steps, which also falls in the scope of the present invention. Preferably, the sealing element seals the first opening of the connecting channel. The movement of the first cover body is linked with the change of the state in which the first chamber and the second chamber are in fluid communication. For example, with the movement of the first cover body, the first chamber and the second chamber that are in fluid communication are changed to a state of non-fluid communication. Alternatively, with the movement of the first cover body, the first chamber and the second chamber that are not in fluid communication are changed to a state of fluid communication, and with the movement, they are changed to non-fluid communication state again.

The "covering" here means that the first cover body matches with the first chamber to cover the opening 1031 of the first chamber, of course, it may also means the cover body seals the opening of the first chamber. The sealing herein may be merely a normal sealing or alternatively, in a unsealed state, but just preventing liquid samples from spilling out of the first chamber, for example, when moving the first chamber, prevent liquid from spillage from the opening 1031 of the first chamber. As previously described, the covering of the first cover body on the opening of the first chamber does not require the sealing effect of a conventional first detection apparatus, since it is not necessary to transport the entire detection apparatus or transport under some extreme conditions. The sealing element is on the cover body. When enough liquid is collected in the first chamber, it is generally necessary to cover the opening of the first chamber with a cover body. When the cover body covers the opening 1031 of the first chamber, the sealing element that connects to the cover body seals the opening of the connecting channel or the connecting channel simultaneously, so that liquid will not enter the second chamber. When the second chamber is separated from the first chamber, the liquid cannot leak through the connecting channel to the outside. By this way, the operation is more convenient, simple and quick, to complete two functions simultaneously by operating one step. Here, the sealing effect of the sealing element on the connecting channel is to temporarily prevent liquid from leaking to outside through the connecting channel, without the sealing effect of a traditional detection apparatus that ensure no leakage under extreme conditions of transport (such as high pressure or vacuum). The samples in the second chamber, as a transport carrier, need a second confirmatory detection, while the liquid in the first chamber need not be transported or stored, but just discarded subsequently. Therefore, the sealing of the first chamber opening 1031 and the connecting channel or the connecting channel opening 1091 is only a general sealing, and it is not necessary to require a sealing state under a negative pressure and vacuum state as conventional apparatus, mainly because the first chamber and liquid in the first chamber need not to be delivered to a professional laboratory or detection agency for second testing.

For the convenience and lowering production cost, the first chamber and the second chamber are made of plastic materials, which are one-time injection-molded. The sealing element and the first cover body are also injection-molded. The sealing element can seal the connection between the first chamber and the second chamber relying on the physical properties of the plastic materials, preferably, the connecting channel that connects the first chamber to the second chamber is sealed. In order to achieve a better sealing effect, the sealing element can be provided with an elastic seal ring 108, for example, an "O" type seal ring, a silicone seal ring. These seal rings can be made of flexible material relative to the sealing element, thus, it can increase the sealing effect when the sealing element seals the first opening 1091 of the connecting channel. It can be understood that when the cover body is linked with the sealing element, the openings of the first cover body and the first chamber are usually joined together by a screw thread. The first cover body covers the opening of the first chamber in a rotating way, and the sealing element enters the connecting channel or seals the opening of the connecting channel, or seals the holes for fluid communication between the first chamber and the second chamber (when the connecting channel is omitted).

It can be understood that the "O" type seal ring is used together with the sealing element. The "O" type seal ring can be separately produced and then assembled to the sealing element, to produce sealing functions. Of course, the structure of the "O" type seal ring can be of the same material as that of the place for installation of "O" type seal ring and it is done by one-time injection molding, to facilitate the processing. Of course, in other circumstances, the "O" type seal ring can be omitted, and sealing can be achieved by different materials of the connecting channel and the sealing element.

Figure 2:
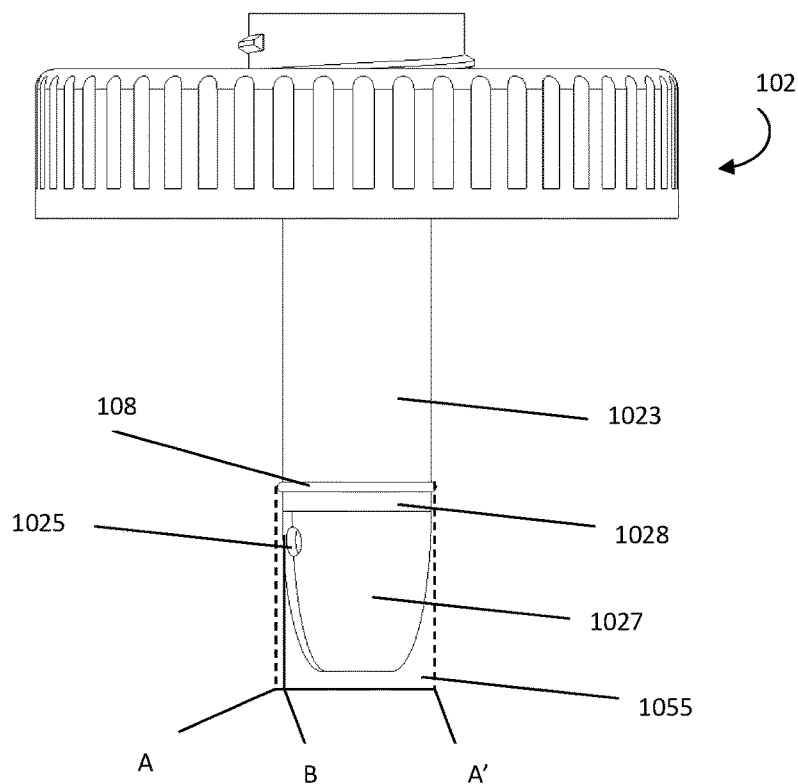
FIG. 2 is a perspective structural view of a cover body according to an embodiment of the present invention.
Figure 3:
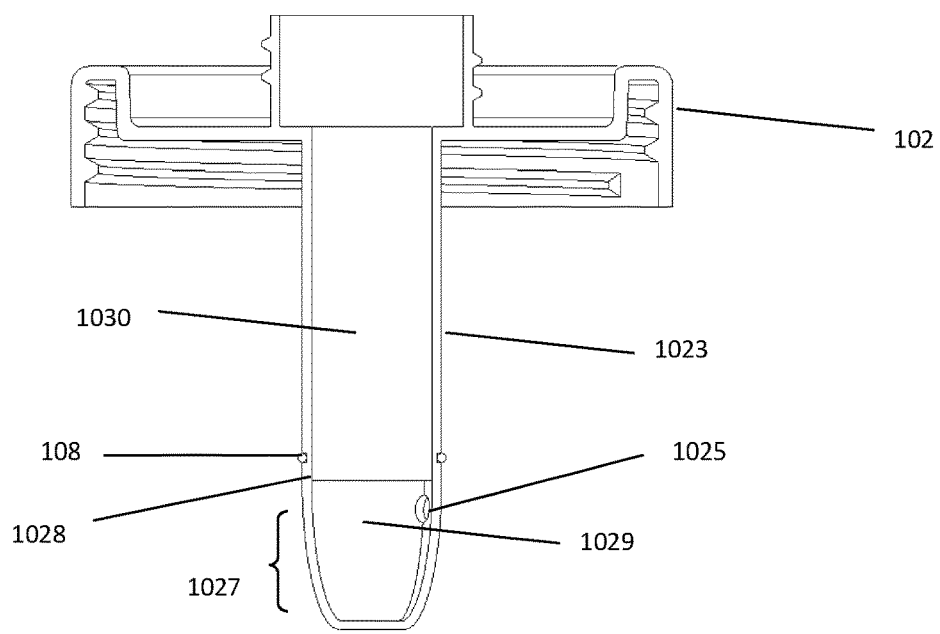
FIG. 3 is a longitudinal cross-sectional view of a cover body in FIG. 2 according to an embodiment of the present invention.

In some preferred embodiments, the sealing element and the first cover body can be connected by one-time injection molding or in a detachable way. For example, as shown in FIGS. 2 and 3, the sealing element 1028 is attached to the first cover body, and the sealing ring 108 is provided on the sealing element, and the sealing element is integrally formed with the cover body 102. In order to better fix the seal ring, a groove structure is provided on the sealing element, so that the sealing element can be flexibly fixed on the groove.

Usually the first chamber needs to accommodate a certain volume of liquid samples, so it has a certain volume. Therefore, the first chamber opening 1031 has a distance from the first opening 1091 of the connecting channel at the bottom of the first chamber. Therefore, the sealing element is connected with the cover body 102 via a connecting structure 1023 to form an integral structure. As shown in FIG. 12, the sealing element 1028 integrated with the cover body rotates together into the connecting channel 109 when the cover body covers the opening 1031 of the first chamber by covering, for example, rotating. With the covering process of the cover body, the sealing element enters the connecting channel, and the sealing element 1028 seals an opening 1091 of the connecting channel, thereby preventing the liquid samples from entering the first chamber. When the second chamber is separated from the first chamber, liquid samples on the first chamber will not leak outside through the connecting channel.

For example, as shown in FIG. 22, the first cover body 202 is connected with a connecting structure 2023, and the connection structure 2023 extends a section as a sealing element 2028 to seal the connecting channel; in the state shown in FIG. 22, when the sealing element 2028 (that is, the location 208 with the seal ring) is not close to the opening 2091, the first chamber and the second chamber are in a liquid flow state. As the position of the cover body changes, the sealing element is close to the position of the opening 2091. As it moves, the sealing element seals the opening 2091, at this time, the sealing effect is achieved, and the liquid in the first chamber will not flow into the second chamber.

It is a preferred way to adopt the linkage between the cover body and the sealing element. In this way, the first chamber is not in fluid communication with the second chamber. Of course, the cover body and the sealing element can be assembled together by one-time injection molding, or multiple injection moldings. For example, the cover body is completed by one-time injection molding, the connecting rod 2023 and the sealing element 2028 are completed by one-time injection molding; then they are combined together by any optional plugging, screw thread or other ways, so that the movement of the cover body can drive the movement of the sealing element, which is called "linkage". In another embodiments, the injection molding for the sealing element, the connecting rod and the cover body is performed respectively, and then they are combined together.

Figure 34:
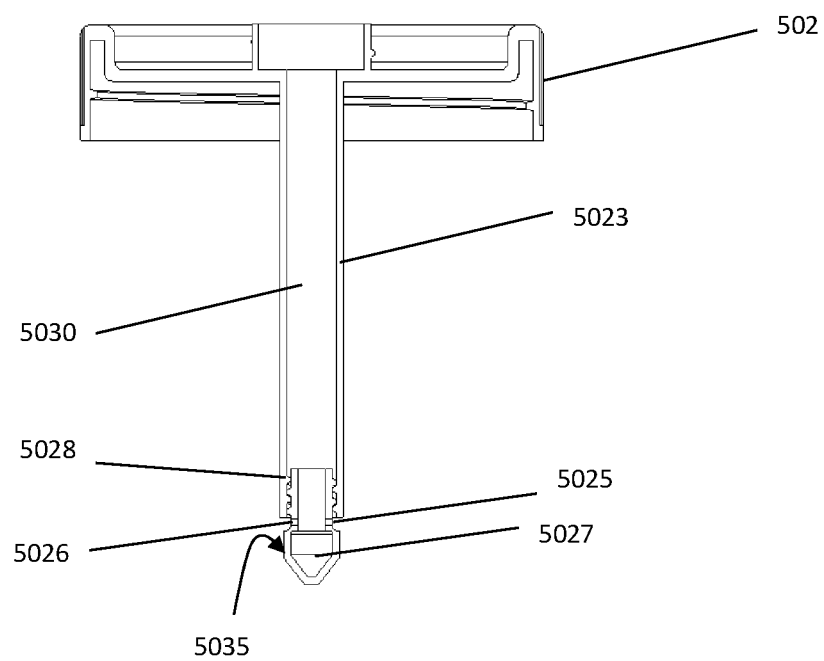
FIG. 34 is a cross-sectional view of the structure shown in FIG. 33.

Thus, in some preferred embodiments, the sealing element is also detachably connected with the cover body. For example, as shown in FIGS. 31-35, the cover body 204 comprises a sealing element 4028 whose shape matches with the shape of the connecting channel or matches with the first opening 1091, 3091, such as the shape of a piston. In this way, a part of the connecting structure 4023 is used as a sealing element 4028, at this time, the seal ring is not necessary. But the material is different. Generally, the material of the sealing element is more elastic. In this way, the flexible sealing element can seal the connecting channel or the first opening of the connecting channel even without a seal ring. For example, the sealing element can be made of latex, silicone, or other elastic materials, or, the sealing element is made of two parts and the inner part is made of relatively rigid material. The rigid material surface is covered with a layer of flexible silicone, rubber, latex and other materials to enhance the sealing effect of the sealing element and the connecting channel or the opening 1091. Meanwhile, when the first cover body 402 covers the opening of the first chambers 103 and 203, the sealing element 4028 can seal the connecting channel or the opening more easily, for example, allowing the sealing element to enter the connecting channel to seal the connecting channel. Or the sealing element 5029 (when the structure of 5029 is used as a sealing element) is connected with the connecting rod 5023 by the screw thread. For example, as shown in FIGS. 33-34, in this embodiment, the sealing element 5029 is provided with an external thread at one end 5030, an internal thread is provided at one end of the connecting structure 5023, and the sealing element is connected to the cover body by a screw thread to form an integral structure. Thus, the material of the sealing element can be different from that of the cover body and the connecting structure. The sealing element can meet different sealing needs through different design forms and ways.

Here, the sealing element can be an independent component or be arranged at the junction between the second chamber and the first chamber to prevent liquid flow between the two chambers. Here, the flow is generally active. In fact, when liquid flows from the second chamber to the first chamber passively, the sealing element is not a must.

Furthermore, just as described above according to FIG. 27, when the connecting channel is not provided between the first chamber and the second chamber, there is only a hole, such as the hole 3091, while there is no extension 3098 of the connecting channel, at this time, the sealing element only needs to seal the opening 3091, and there is no need to let the sealing element enter the connecting channel. For example, the sealing element such as a rubber plug. The rubber plug is provided on the connecting rod 3023 of the cover body, and the linkage of the cover body drives the plug to plug the opening 3091, so as to achieve changes in the liquid communication state between the first chamber and the second chamber.

Besides, the sealing element can seal the first opening of the connecting channel at the beginning. After the first chamber 103 collects liquid samples, or before or after the initial detection is performed on the liquid samples in the first chamber, the piercing element is used to pierce the sealing element or remove the sealing element, so that liquid samples can flow into the connecting channel, and enter the second chamber 104 through the second opening. Moreover, the second chamber and the first chamber are a detachable combination, so the second chamber and the first chamber are separated, to perform the subsequent possible confirmatory assay and test. Therefore, when the sealing element is pierced, here the sealing element can be a structure that can be pierced, for example, such sealing element can be adhesive stickers, double faced adhesive tapes, plastic sheets, etc. Generally, such element will not allow liquid to enter the connecting channel at the very start before being pierced. It can be pierced in various ways, for example, sharp things. In some embodiments, the piercing element can be arranged on the first cover body 102, and the two have a linkage relationship. When the first cover body covers the opening of the first chamber 103, the piercing element pierces the sealing element, then liquid flows from the first chamber to the second chamber. If it is necessary to separate the first chamber from the second chamber, before the separation, another sealing element is used to seal the piercing place, so as to achieve changes in the liquid communication state between the first chamber and the second chamber.

Figure 39:
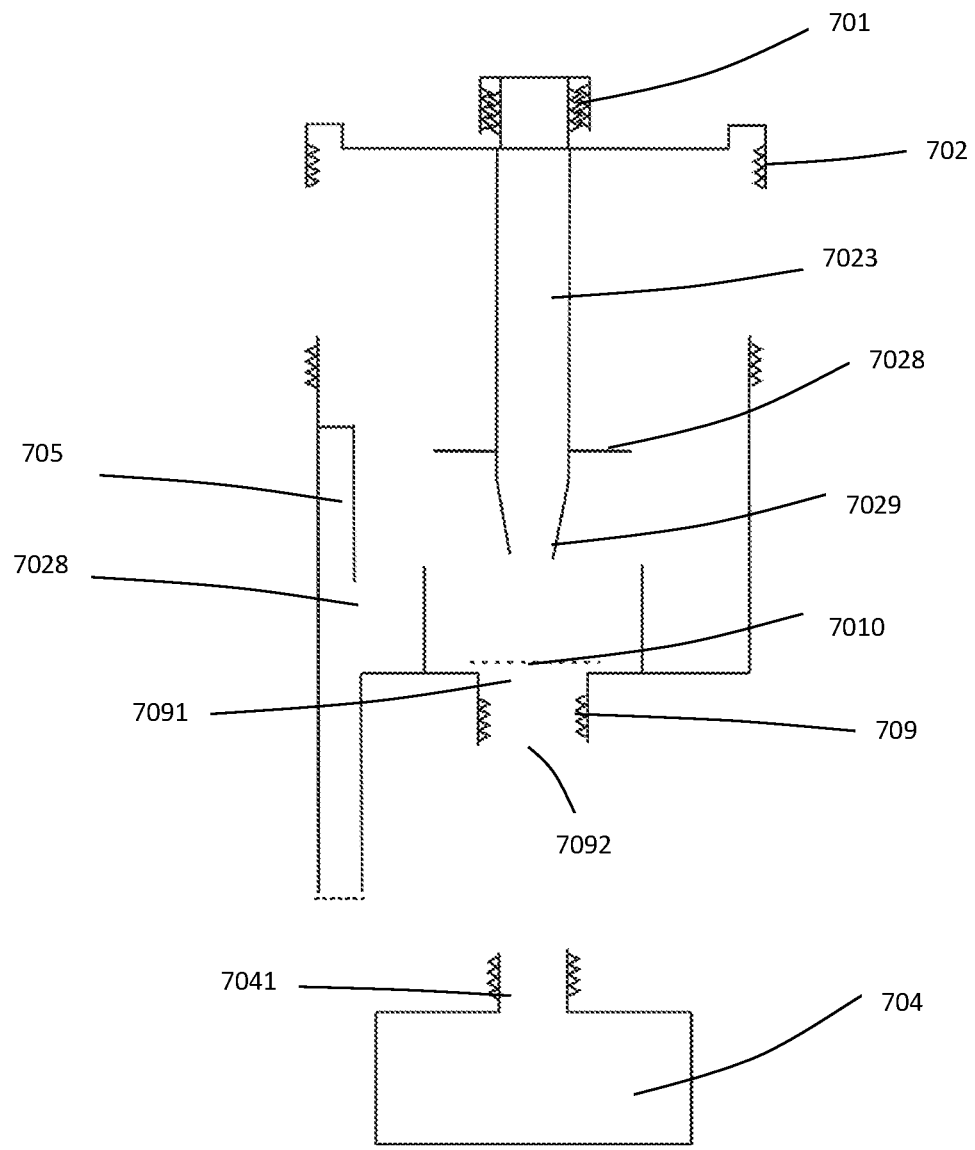
FIG. 39 is a perspective structural view of a first chamber and a second chamber in other embodiments of the present invention.

For example, as shown in FIGS. 39-40, the first chamber 702 comprises an opening 7031 for receiving the liquid samples, and the first chamber comprises a hole which is the first opening 7091 of the connecting channel, and this opening is sealed by the sealing element 70281 that can be pierced and is in liquid communication with the detection chamber 705 through the channel 7038. Different from what is shown in FIGS. 37-38, the first chamber is a chamber for collecting liquid samples for the initial detection, and the second chamber 704 is detachably connected to the second opening 7092 of the connecting channel. When liquid samples are collected, some of the liquids in the first chamber flow into the detection chamber for initial assay and detection, then the first cover body is used to cover the opening of the first chamber. A second cover body is provided on the cover body, and a sealing element 7028 and a piercing element 7029 are provided on the first cover body. In this way, the cover body, the sealing element 7028 and the piercing element 7029 form a linkage mechanism. When the first cover body covers the first chamber, driving the linkage of the sealing element and the piercing element, the piercing element pierces the sealing element that seals the first opening of the connecting channel, then liquid is released to the second chamber, then the opening of the second chamber is sealed with a sealing element. Of course, the piercing element can also have a function of discharging some liquids of the second chamber. At this time, a drain channel, a liquid inlet and a receiving chamber can be provided on the piercing element. In this way, after piercing the sealing element that seals the first opening 7091 of the connecting channel, the piercing element is directly inserted into the second chamber in part, so that liquid can flow into the receiving chamber through the liquid inlet of the drain channel in addition to discharging liquid. For example, the receiving chamber is located in the piercing element. It can be understood clearly according to the detailed descriptions on such combination below. For example, as shown in the above figure in FIG. 40, when the second confirmatory detection is needed, take down the second chamber from the first chamber, for example, by rotating the screw thread, then use the second cover body to seal the opening 7041 of the second chamber 704, for performing the subsequent second confirmatory detection.

To sum up, with regard to allow liquid to flow from the first chamber to the second chamber, liquid can flow to the second chamber at the same time when liquid enters the first chamber, or liquid does not enter the second chamber at the same time when or immediately after liquid samples flow into the first chamber. This is because the second chamber and the first chamber are not in fluid communication at this time, instead, they are in fluid communication at any time later. The opportunity to control the sealing element determines whether they are in fluid communication. For example, piercing the sealing element that seals the first opening 1091 or the second opening 1092 of the connecting channel is to let the two chambers be in a communication state. Of course, in order to separate the second chamber while to ensure the liquid in the first chamber does not continue to flow to the second chamber, sealing is required after piercing.

Thus, in some embodiments, when the first chamber 104 is not used to collect liquid samples, the second chamber and the first chamber are in fluid communication, and when or after liquid samples are collected, they are not in fluid communication. Of course, optionally, when the first chamber 104 is not used to collect liquid samples, the second chamber and the first chamber are not in fluid communication. When or after liquid samples are collected, they are in fluid communication, and when or after liquid samples enter the second chamber, and before the separation is needed, they are not in fluid communication again. In these embodiments above, the sealing element plays different roles at different time, and the sealing can be performed at the right time.

In the above examples where the sealing element is needed, liquid samples can always flow from the first chamber 103 to the second chamber freely (for example, due to gravity, liquid always flows from a high place to low place), and the sealing element is used only for the purpose of preventing the liquid from continuing to flow after the separation of the two chambers; however, in fact, when liquid samples passively flow from a low place to high place by overcoming its gravity, the sealing element may not be a must. For example, in the embodiment in design 3, an independent sealing element is not required.

Drain Channel

The "drain channel" mentioned herein means the channel that discharges liquid, through which liquid is drained or discharged, or flows from one place to another place. Besides, the "drain channel" can also discharge redundant gas so as to relieve the pressure, through which gas is drained or discharged, or flows from one place to another place. Therefore, the "drain channel" can discharge redundant liquid and gas or the mixture of gas and liquid. Generally, the so-called "channel" means a tube-shape channel or a channel of which the periphery is sealed, comprising two openings, with one opening as the liquid inlet and the other as the liquid outlet; or one opening as the gas inlet and the other as the gas outlet; or one opening as the inlet of the mixture of liquid and gas and the other as the outlet of the mixture. Here, one inlet and one outlet only refer to one embodiment. Of course, they can be one or more inlets, or one or more outlets. There is no limitation on the length of the channel itself, and it may be relatively long or short, and it is easily realized according to actual conditions for those skilled in the art.

In some preferred embodiments, the sealing can be achieved by only sealing the holes between the first chamber and the second chamber. However, if a better effect sealing is desired, when connecting the first chamber and the second chamber with a connecting channel, the connecting channel generally has an extension 3094. The extension extends into the opening of the second chamber in FIG. 27. Of course, it is also possible to extend a distance or length into the first chamber at the connecting channel 3091. In order to better achieve the sealing effect, usually a part of the plug-like sealing element needs to be inserted into the connecting channel to seal the connecting channel. Generally, before sealing the connecting channel, the connecting channel contains liquid samples, and the second chamber is also filled with liquid samples. This is because the collected liquid samples need to satisfy the second confirmatory detection and be used for the first test of testing element, and the liquid samples need enough volume. So, in some preferred embodiments, the liquid level of liquid samples in the first chamber is higher than the position of the first opening of the connecting channel, in other words, the first opening of the connecting channel is located below the liquid level. In this way, both the connecting channel and the second chamber are filled with liquid. In such case, it is necessary to let part of the sealing element enter the connecting channel to seal the connecting channel. Due to such liquid sealing, liquid samples will not leak from the first chamber after the second chamber is separated from the first chamber. In this circumstance, it is a little bit difficult to allow the sealing element to enter the connecting channel, because the counter-acting force applied by liquid on the sealing element needs to be overcome when the connecting channel 109 is sealed in spite of the equal size of the sealing element and the connecting channel. This is because it is necessary to let part of the sealing element enter part of the connecting channel in order to achieve a better sealing effect. The sealing process is a dynamic process, during which the sealing element starts to approach the first opening (first state) of the connecting channel first, and then blocks the first opening (a second state, at this time, it can play a sealing effect) completely, and finally enters the connecting channel (a third state, to achieve a better sealing effect). In this process, when it is required to change from the second state to the third state, it actually overcomes the counter-acting force applied by the liquid samples that contact the sealing element in the connecting channel, especially when the sealing element enters the connecting channel, it is required to compress the liquid in the connecting channel, and if the liquid cannot be removed, it is difficult to change from the second state to the third state. The distance from sealing the first opening to entering the connecting channel can be 0.1 mm to 10 mm or more, so as to ensure a better sealing effect. For example, the distance of the sealing element entering the connecting channel can be 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm or 7 to 10 mm. To relieve such counter-acting force, i.e. the pressure applied by liquid to the sealing element, liquid must be discharged by the sealing element to another place smoothly to relieve the pressure on the sealing element, so as to let the sealing element enter the connecting channel more easily. So, it is necessary to discharge some liquids in the connecting channel when the sealing element enters the connecting channel so as to let the sealing element enter the connecting channel smoothly and seal the connecting channel or the opening of connecting channel smoothly. This is similar to the principle of inserting the stopper into a bottle. If the bottle is filled with water, the stopper is difficult to be inserted, and it is necessary to pour a part of the water or liquid of the bottle so that the stopper can be inserted into the bottleneck and seal the opening of the bottle. However, when the second chamber is full of liquid, the connecting channel is also filled with liquid. Sometimes the first opening of the connecting channel is below the liquid level of the first chamber, the sealing element is required to enter or the sealing element is to seal the opening of the connecting channel in a form of piston. At this time, it is necessary to exclude part of the liquid in the connecting channel to another place, so that the sealing element can enter the connecting channel. The best way is to remove some liquid when entering. The sealing element is forced to enter the connecting channel by an external force.

Therefore, in some preferred embodiments, the apparatus further comprises a drain channel, through which the extruding liquid produced when the sealing element enters the connecting channel can be discharged outside the connecting channel, so as to let the sealing element seal the connecting channel smoothly, or through which some liquids in the second chamber are discharged outside the second chamber, but this function is described in detail in the following paragraphs. For example, in some preferred embodiments, the liquid inlet of the drain channel is located above the sealing element. As the sealing element enters the connecting channel, redundant liquids enter the drain channel through the liquid inlet and are discharged outside the connecting channel. Generally, places outside the drain channel refer to places excluding the connecting channel and the detachable second chamber connected to the connecting channel, such as places inside the first chamber or the detection chamber, or other places. Therefore, the apparatus further comprises a receiving chamber for receiving liquid or gas from the drain channel. Generally, the sealing element seals the connecting channel or blocks the first chamber from the second chamber for liquid flow or flow, which is generally divided into two states. First, the first chamber is in communication with the second chamber before the sealing channel is sealed by the sealing element. At this time, the liquid can be exchanged between the two chambers, generally allowing the liquid to naturally flow from the first chamber into the second chamber. Second, when the sealing element begins to seal the connecting channel, for example, the opening of the connecting channel, the first chamber and the second chamber are not communicated. As the sealing element continues to enter the connecting channel, the pressure of the connecting channel and the second chamber will increase. Due to the pressure, liquids in the connecting channel and the second chamber will enter the receiving chamber through the liquid inlet of the drain channel to reduce the former pressure, so as to let the sealing element seal the connecting channel smoothly. Of course, the drain channel here can be set arbitrarily, generally the drain channel and the receiving chamber are in fluid communication. Thus, if the sealing element continues to enter the connecting channel, the liquid discharged enters the receiving chamber through the drain channel.

In some embodiments, for example, as shown in FIG. 3 and FIG. 2, the sealing element 1028 is used to seal the opening 1091 of the connecting channel 109, while the receiving chamber can be located in the sealing element, for example, the sealing element is a hollow structure, thus the discharged liquids can enter the receiving chamber, and the hollow structure 1029 can be used as the receiving chamber. For example, as shown in FIG. 3, the sealing element 1028 further comprises a receiving chamber 1029. When the sealing element enters the connecting channel, redundant liquids will enter the receiving chamber 1029 through the drain channel 1025, thus relieving the pressure. Of course, the drain channel 1025 mentioned herein is very short, because the sealing element is a thin-wall structure or hollow structure. Of course, it can be easily understood that the receiving chamber is not necessarily located on the sealing element. When the connecting rod 1023 is a hollow structure 1030, the hollow structure 1030 communicates with the receiving chamber 1029 to form a big receiving chamber to receive the liquids discharged by the sealing element, or the hollow structure 1030 is used as the receiving chamber, with the equivalent effect. In some preferred embodiments, for example, as shown in FIGS. 2-3, and 12, the sealing element 1028 seals the opening of the connecting channel 1091 and enters the connecting channel 109, while redundant liquids enter the receiving chamber 1029 through the drain channel 1025. In such a embodiment, one opening of the drain channel (liquid inlet) is in liquid communication with the connecting channel, and the other opening (liquid outlet) is in liquid communication with the receiving chamber, so that liquid can enter the receiving chamber. Here, the drain channel is set on the hollow sealing element, so the drain channel is very short. But no matter how short it is, there will always be a liquid inlet and a liquid outlet. In fact, when the receiving chamber is located in the sealing element or the subsequent discharge element, the liquid inlet and the liquid outlet are not divided strictly. Only when the drain channel is long, they are divided. This is because the sealing element or the discharge element is a hollow structure, and the wall is very thin. In fact, the hole opened on the wall plays the role of allowing the liquid to enter the receiving chamber. At this time, the liquid inlet or the liquid outlet is not divided apparently, and this hole can refer to the liquid inlet or the liquid outlet. In a word, the position division is not very obvious.

In some preferred embodiments, as shown in FIG. 12, the liquid inlet of the drain channel is located below the sealing element. In some preferred embodiments, the liquid inlet of the drain channel is located above the sealing element, which enters the connecting channel earlier than the sealing element, so that redundant liquids can be discharged outside the connecting channel, reducing the counteractive resistance of the liquid level to the sealing element. Here, the drain channel can refer to the through hole on the receiving chamber 1029, and there can be one or more such drain channels.

In one preferred embodiment, the liquid inlet of the drain channel enters the connecting channel earlier than the sealing element. Thus, in some embodiments, if the drain channel is long, the first chamber is used as a receiving chamber, and the liquid inlet of the drain channel is located on the sealing element but enters the connecting channel earlier than the sealing element, as the sealing element enters the connecting channel, the discharged liquids enter the drain channel through the liquid inlet of the drain channel, then enter the first chamber through the liquid outlet, or enter the receiving chamber. Here, the first chamber is a specific embodiment for the receiving chamber, and the first chamber can also be a chamber with the function of the receiving chamber. Thus, the receiving chamber is not necessarily located on the sealing element, while the best embodiment is that it is located on the sealing element or in the connecting rod connecting the sealing element and the cover body. In this way, as the sealing element enters the connecting channel, redundant liquids are discharged outside the connecting channel through the liquid inlet of the drain channel, due to the pressure on the liquid level produced when the sealing element enters the connecting channel. Of course, the size of the receiving chamber is related to the discharged liquids, and a suitable volume capacity shall be set to accommodate the discharged liquids.

With regard to the position of the "liquid inlet of the drain channel", if the sealing element needs to enter the connecting channel, it will oppress the liquid samples in the connecting channel, and under such situation, the liquid inlet shall be located below the sealing element. The "below" only means the relative position, and it may not be located on the sealing element. For example, it can be located on the wall of the connecting channel. When the sealing element enters the connecting channel, the liquid inlet on the wall of the connecting channel is located below the sealing element in relative terms. As the sealing element continues to enter the connecting channel, some liquids are forced to enter the liquid inlet and are discharged, thus make the sealing element enter smoothly. Under a situation, the sealing element can continue to enter the connecting channel until the sealing element overlaps with the liquid inlet on the wall of the connecting channel, then liquid will not enter the drain channel through the liquid inlet, thus it is discharged outside the connecting channel. Therefore, in some preferred embodiments, the liquid inlet is located below the sealing element, for example, as shown in FIGS. 2-3, a liquid inlet 1032 is provided under the sealing element 1028, which is the liquid inlet of the drain channel 1025.

Another examples are shown in FIGS. 15, 18, 22, 23 and 27. For example, as shown in FIGS. 15-24, the sealing element 2024 and the connecting structure 2023 are an integral structure. The extended part of the connecting structure is regarded as the sealing element, and the whole connecting structure and the extension structure are hollow structures 2030 and 2029. Such hollow structure is used as a big receiving chamber. The liquid inlet 2025 of the drain channel is an opening located on the side wall of the extension structure, and also under the sealing element. For another example, as shown in FIG. 23, as the sealing element 2028 enters the connecting channel, the inlet 2025 of the drain channel located under the sealing element discharges redundant liquids to the outside, thus reducing the resistance when the sealing element enters. In some preferred embodiments, different from the structure shown in FIG. 31, there is no sealing element 3028 of the seal ring 208, and a part of the connecting structure 3024 is used as the sealing element, at the same time, there is an opening 3025 on the top of the extension structure of the connecting structure, and this opening 3025 communicates with the hollow receiving chamber 2039 in the sealing element. When the sealing element enters the connecting channel, redundant liquid samples will enter the receiving chamber through the inlet 3025 of the drain channel. For example, as shown in FIGS. 33-35B, although the sealing element 4029 and the connecting rod 4024 are a detachable combination, redundant liquids can be discharged through a liquid inlet 4038 provided on the top of the sealing element. It can be understood that in order to better seal the connecting channel, the shape or size of the sealing element shall match with the connecting channel, for example, if the connecting channel is a circular hollow structure, then the sealing element shall be a circular structure, for the convenience of the sealing and cooperation between the two.

Referring to FIGS. 33-35, a connecting rod 5023 is provided on the first cover body 502, and a sealing element 5028 is provided on the connecting rod. This sealing element can be used to seal the connecting channel. If the sealing element 4028 described above is used to seal the connecting channel, a liquid inlet 4038 of the drain channel is provided on the top 4029, and the sealing element 5028 comprises a receiving chamber 5030 for collecting the liquids discharged when the sealing element enters the connecting channel. Of course, the liquid inlet 5025 can be provided under the sealing element 5028. When the sealing element 5028 enters the connecting channel to seal it, redundant liquids enter the receiving chamber through the liquid inlet 5025, that is, the hollow structure is used as the receiving chamber 5030. At this time, the element 4029 is not used to seal but to discharge liquids, while the tail end 4028 of the extension of the connecting rod 4024 plays the role of sealing.

Of course, if the structure 5028 of the connecting rod 5022 is not used as the sealing element, instead, a sealing element 5029 is provided on the structure 5035. As shown in FIGS. 33-35, the sealing element 5029 can connect detachably to the connecting rod, such as by plugging, screw threads or snapping. For example, the element 5035 comprises one end 5030 with an external thread, which matches with the internal thread 5027 of the connecting rod. The sealing element 5029 cooperates with the inner wall of the connecting channel to seal the connecting channel. The liquid inlet of the drain channel is arranged on the top 5038 of the element 5035. When the sealing element 5029 enters the connecting channel, redundant liquids will enter the receiving chamber 4029 inside the sealing element through the liquid inlet 4038, and at this time, there can be no liquid inlet 5025 or it can be omitted.

Figure 31:
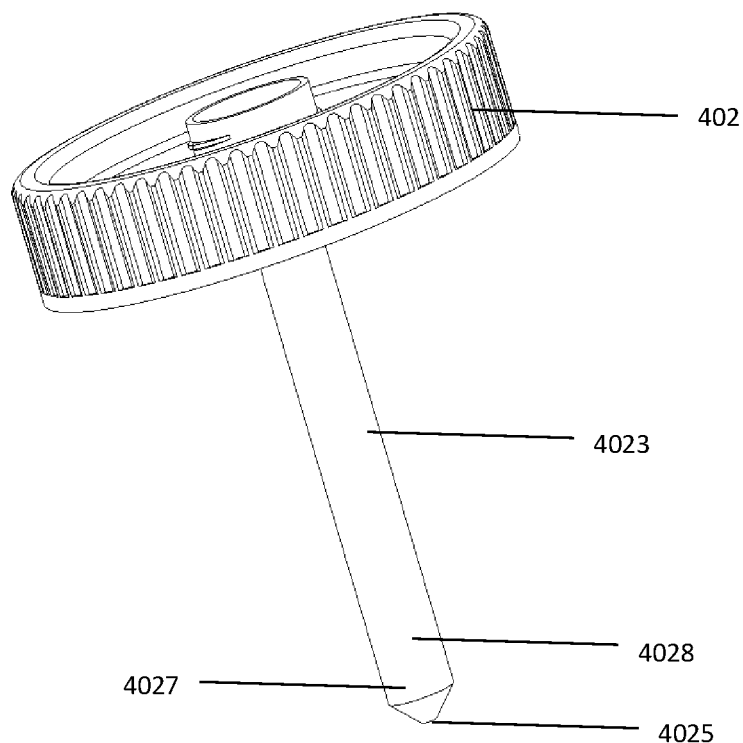
FIG. 31 is a perspective structural view of a first cover body with a sealing element according to another embodiment of the present invention.
Figure 32:
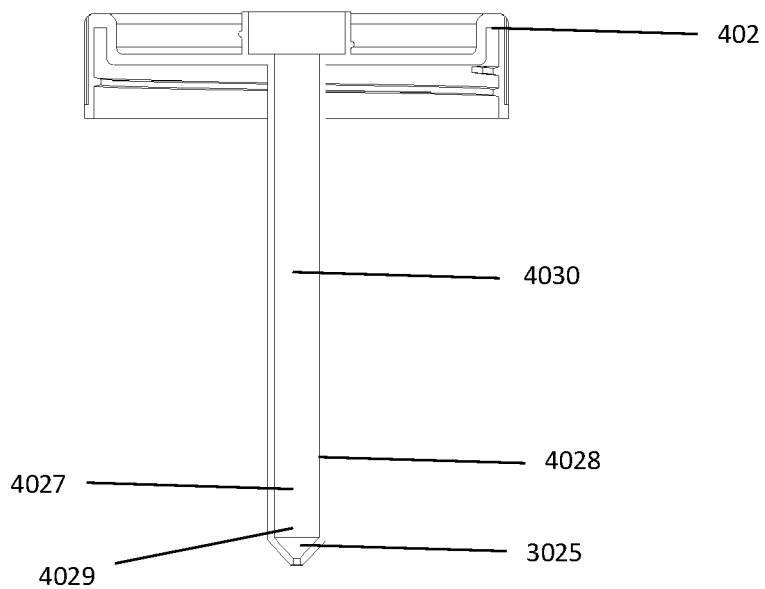
FIG. 32 is a cross-sectional view of a first cover body with a sealing element shown in FIG. 31 according to another embodiment of the present invention.

In some preferred embodiments, in order to easily discharge liquids and allow liquids to enter the liquid inlet effectively, the vertical plane position of the liquid inlet of the drain channel shall be lower than the vertical position of the outermost side of the sealing element. In other words, the horizontal projection area of the position of the liquid inlet of the drain channel is not completely consistent with that of the sealing element. Preferably, the former is located in the latter. In other words, the sealing element needs to contact the inner wall of the connecting channel, and the liquid inlet of the drain channel does not contact the inner wall, because the liquid inlet will be sealed if contact; in this way, liquids can enter the liquid inlet of the drain channel and be discharged. For example, as shown in FIG. 2 and FIG. 3, the diameter of the position on the sealing element where a seal ring 108 is provided is larger than that of the liquid inlet 1025, thus the liquid inlet 1025 will not contact the inner wall of the connecting channel and the smooth entering of liquids in the liquid inlet of the drain channel will not be influenced, then liquids enter the receiving chamber. In FIG. 2, the dotted line area 1055 is the projection area of the sealing element A-A', and the projection area point or area of the liquid inlet 1025 is at B, which is between A-A'. So, based on such principle, in some solutions, the sealing element can have an inverted conical structure (the function of this structure will be described below, i.e. discharge liquids), and the liquid inlet 1025 of the drain channel is located on the surface of the cone. In this way, the liquid inlet of the drain channel will not contact the inner surface of the connecting channel, so that the discharged liquids can be easy to enter the liquid inlet and be discharged. According to FIG. 18, it can also be understood that, the projection of the liquid inlet 2025 in the sealing element 2028 falls within the range of the projection of the seal ring because the sealing element 2028 has a seal ring 208. Similarly, according to FIG. 27, it can be easily understood that, there is an inverted conical structure, and the liquid inlet of the drain channel is provided on the surface of the cone, so that the liquid is easy to enter the drain channel and redundant liquid samples are discharged. For another example, as shown in FIGS. 31-32, the liquid inlet of the drain channel is provided on the top, and the situation where the side wall of the connecting channel seals the liquid inlet will not be considered, but still, the projection of the liquid inlet is in the horizontal projection area of the sealing element. For another example, as shown in FIGS. 33-34, whether the tail end 5028 of the extension of the connecting rod 5023 is used as the sealing element, or the part 5029 is used as the sealing element, the projection of the liquid inlet 5025 or 5027 of the drain channel is still in the horizontal projection area of the sealing element. This is because the liquid inlet will not be sealed or plugged by the side wall of the connecting channel if the liquid inlet 5025 or 5027 is provided at the sunken position. Generally, the inner wall of the connecting channel is flat and smooth, so it will be sealed easily. Thus, by using such structure, liquids will be discharged easily.

In a word, when the sealing element seals the connecting channel, a preferred embodiment is to let the sealing element enter the connecting channel, but in order to relieve the pressure on the sealing element, it is necessary to arrange a drain channel for discharging the liquid discharged by the sealing element when it enters the connecting channel to another places. Just like the specific embodiment described above, the liquid inlet of the drain channel is arranged below the sealing element, and the inlet on one end of the drain channel should enter the connecting channel earlier than the sealing element so that redundant liquids can enter the drain channel. As described above, when the receiving chamber is inside the sealing element or located in other positions, the outlet (liquid outlet) on the other end of the drain channel is connected with the receiving chamber so as to receive the redundant liquids inside the connecting channel.

In some another optional solutions, the first chamber can be used as the receiving chamber, so that the liquid samples discharged by the sealing element in the connecting channel can be discharged to the first chamber through the drain channel. In the above embodiment, the inlet of the drain channel is located above the sealing element, or located above the connecting structure which is connected with the cover body to form an integral structure or below the sealing element. Of course, optionally, the drain channel is not necessarily located above the sealing element, instead, it can be located above the connecting channel, for example, the drain channel is located on the side wall of the connecting channel, and the inlet (liquid inlet) of the drain channel is located on the side wall of the connecting channel while the liquid outlet is connected with the first chamber. When the sealing element enters the connecting channel, redundant liquids discharged due to the entering of the sealing element enter the first chamber through the liquid inlet of the drain channel until the sealing element seals the inlet of the drain channel. It can be imagined by those skilled in the art when reading the embodiments provided in the present invention that regardless of the arrangement of the drain channel such as the arrangement of the positions of inlet and outlet, it will be feasible as long as the liquid samples that are discharged because the sealing element enters the connecting channel can be discharged so as to reduce the resistance on the sealing element (resistance applied by liquid to the sealing element). For example, the liquid inlet of the drain channel can be located above the sealing element or other positions.

In some other embodiments, the size of the liquid inlet can be designed at will. For example, the size enables liquid to enter, but the liquid cannot flow out from the liquid inlet freely. Liquid is often forced to enter the drain channel through the liquid inlet, and after the liquid enters the drain channel, it will not flow out from the liquid inlet due to surface tension. The liquid inlet is generally located under the sealing element. When the second chamber is separated from the connecting channel, the liquid inlet will be exposed. If the liquid in the receiving chamber can flow out from the liquid inlet, liquid samples may pollute the environment. So, it is hoped that the liquid inlet is designed only to allow liquid to enter and not to flow out. Generally, the size of the liquid inlet is 0.1-1-2 mm, and the liquid in the receiving chamber will not flow out from the liquid inlet due to surface tension.

In some embodiments, after the sealing element seals the connecting channel, it can be separated from the first cover body if the sealing element is provided on the cover body. In one embodiment, the sealing element and the cover body are connected or combined together, the sealing element seals the connecting channel as the first cover body covers the opening of the first chamber. After the sealing is completed, if it is necessary to open the first cover body, reversely rotate the first cover body to expose the opening of the first chamber, then let the sealing element still stay in the connecting channel to seal the connecting channel, and take down the first cover body to take some liquid samples from the first chamber for another detection or assay. For example, as shown in FIGS. 33-35, the sealing element 5029 is detachably combined with the cover body through the connecting rod 5023, at this time, the sealing element 5029 is located on the element 5035, and the element 5035 is detachably combined with the connecting rod 5023 of the cover body by plugging other than by screw thread shown in FIGS. 33-35, in other words, one end 5030 of the element 5035 is inserted into one end of the connecting rod. After the first cover body 502 drives the sealing element 5029 to seal the connecting channel, the second chamber can be separated from the first chamber, so that the opening of the second chamber can be sealed, for example, by using the second cover body, and the samples in the second chamber are used for the second test. At this time, the first cover body 502 has covered the first chamber, for example, the opening 1031 of the first chamber 103 as shown in FIG. 9; if it is necessary to take out liquid samples from the first chamber, reversely rotate the first cover body, then the sealing element will closely match with the connecting channel, and the element 5035 is only inserted into the connecting rod, so the first cover body can be separated from the first chamber 103 again, and the element 5035 can still stay in the connecting channel. The advantage of such design is that, if the first chamber is only used to collect samples, then after the samples are collected, the connecting channel is sealed, and the liquid samples are divided, the first cover body can be opened, and some samples can be taken out from the first chamber for assay, and if a confirmatory detection is needed to confirm the assay result, the second chamber can be taken down from the first chamber for the second assay. In fact, samples can be taken out from the first chamber more than once for the detection or assay on different indexes.

Generally, liquids need to be discharged when both the connecting channel and the second chamber are filled with liquid samples. It can be understood that when the second chamber is not filled with liquid samples, there will be no liquid samples in the connecting channel either. When the sealing element enters the connecting channel to seal the connecting channel, the drain channel can discharge some gas oppressed outside the second chamber or relieve the resistance on the sealing element when it enters the connecting channel. At this time, the resistance is the counteracting force hindering the sealing element that is generated because of gas oppression As a result, in some preferred embodiments, in such two cases, when the connecting channel contains liquid, the drain channel plays a role of discharging liquid, and when the second chamber is not filled with liquid, the drain channel is used for air discharge in order to allow the sealing element to better seal the connecting channel. So, the drain channel can play two roles or any of the two roles, in other words, the drain channel can be a channel discharging fluids which refer to liquids or gas or their mixture. Correspondingly, the liquid inlet of the drain channel is also called gas inlet and the liquid outlet is also called gas outlet, or collectively called as fluid inlet or fluid outlet. It can be understood that if the oppressed gas needs to be discharged, it is unnecessary to specially set an exhaust passage, because the drain channel can be used to discharge gas, and also, it is unnecessary to specially design such channel because when there is liquid, the sealing element only needs to reach the degree of liquid seal, and the same is true when there is gas. Therefore, when gas needs to be discharged, the small gap between the sealing element and the connecting channel can be used to discharge gas. Such small gap can be an error between mechanical structures or a structure designed specially, which can allow gas to pass through but can not allow liquid to pass through so that the function of discharging gas can be realized. Of course, the exhaust passage or sub-exhaust structure is not necessary either, because a liquid seal effect is needed but not a gas seal effect is needed when the sealing element seals the connecting channel. Relatively speaking, the gas seal effect is not necessarily reached when the liquid seal effect is reached, but the latter is also reached when the former is reached.

The drain channel is also a preferred embodiment provided in the present invention, because the sealing element better seals the connecting channel, allowing part of the sealing element to enter the connecting channel to achieve better sealing effect. In other embodiments, the sealing element only seals the first opening of the connecting channel, or only needs to enter one end of the connecting channel for a distance with no need to seal the opening. It is also feasible. At this time, the drain channel can be defaulted. If there is something else in the second chamber that is not filled with liquid, the drain channel can also be defaulted because the effect of the sealing opening or the connecting channel is not important, as there is no leakage of liquid.

Also, in another case, it is not necessary to provide a structure similar to a drain channel, for example, as shown in the figure (Design 2, the drain channel is not necessary when the opening of the connecting channel is sealed with a cover).

Discharge Element

In some preferred embodiments, the apparatus of the present invention may further comprise a discharge element for discharging a portion of the liquid samples in the second chamber. The so-called "discharge element" mentioned herein is defined as the following: when an object enters the liquid samples, the object will occupy some space due to its volume, and liquid of a certain volume will be discharged. The volume of the object entering the liquid is exactly the volume of the liquid discharged, and the object entering the liquid can be called as the discharge element. This can be interpreted as the situation in which a steamship floats over the water. Water of a certain volume will be discharged due to the weight of the steamship, and the steamship will occupy the space originally occupied by water. Of course, as described above, if the space contains no liquid but contains gas, then after the discharge element enters the space containing gas, gas rather than liquid will be discharged.

In some other embodiments, for example, when the second chamber is filled with liquid samples, even if the connecting channel is sealed by the sealing element, the second chamber is filled with liquid samples completely and virtually. When the second chamber needs to be disassembled from the first chamber, the liquid filled in the second chamber will overflow due to the mechanical operation, leading to unfriendly operation and contamination to outside or operators. In addition, even if the second chamber filled with liquid samples is carefully removed or disassembled from the first chamber, it will be not easy to seal the opening of the second chamber with the second cover body either. Thus, there may be some leakage risks during the transportation of the second chamber which is filled with liquid. So, in some more preferred embodiments, it is necessary to discharge some liquid samples from inside to outside of the second chamber at the same time when, before or after the connecting channel is sealed by the sealing element. Thus, the second chamber is not completely filled with liquid, and the liquid samples in the second chamber separated from the first chamber will not overflow, which increases the safety and friendliness of the operation, reduces the leakage risks during the transportation for subsequent second detection, and also increases the safety and friendliness of the operation of subsequent second detection.

Figure 13:
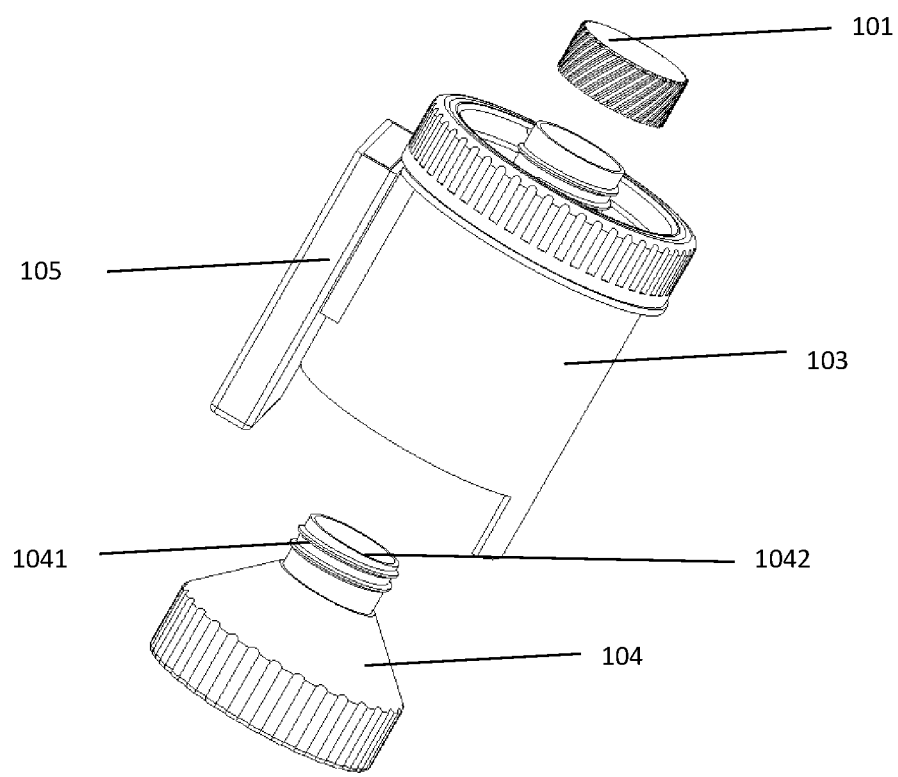
FIG. 13 is a perspective structural view of a second chamber detached from a first chamber and a second cover body detached from a first cover body according to an embodiment of the present invention.

When the second chamber is disassembled from the apparatus, for example, as shown in FIG. 13, some space in the second chamber is reserved, and the second chamber is not completely filled with liquid, thus liquid samples will not overflow from the second chamber, reducing the risk of polluting the outside environment.

In some preferred embodiments, the apparatus further includes a discharge element for discharging the liquid samples outside the second chamber. It can be understood that the discharge element can be any structure or method reducing the volume of liquid samples of the second chamber. In some preferred embodiments, the discharge element is formed by the extending part of the sealing element, or is located on the sealing element. For example, the structures shown in FIGS. 2-3, 18, 23, 27, 31 and 33. For example, in FIGS. 2-3, the sealing element 1028 and the discharge element 2017 are an integral structure, and the discharge structure 1017 is basically the same as the sealing element 1028 in shape, but its longitudinal dimension is slightly larger than that of the sealing element, while the horizontal dimension is smaller than that of the sealing element. At this time, the horizontal projection of the discharge element is located within the horizontal projection of the sealing element or the horizontal projection of a portion of the discharge element is located within the horizontal projection of the sealing element. At this time, when the sealing element enters the connecting channel, the discharge element 2017 enters the connecting channel first. The diameter of the discharge element 2017 is smaller than that of the connecting channel 109, so redundant liquid samples are discharged to the second chamber 104 or the first chamber 103 outside of the connecting channel 109 through the space between the surface of the discharge element and the connecting channel 109 or their gap 809. As the discharge element 1027 further enters the second chamber (see FIGS. 22, 12), the sealing element just starts to seal the opening 1091 of the connecting channel 109, then just as described above, liquid seal is performed on the channel. The discharge element 1027 is located in the second chamber, so some liquid samples in the second chamber are discharged. At the beginning, the sealing element 1028 seals the opening 1091 of the connecting channel. At this time, the liquid sample located under the opening 1091 of the connecting channel cannot be removed by the space between the surface of the discharge element 1027 and the surface of the connecting channel 109. At this time, if the sealing element still needs to move downwards, the liquid samples that the discharge element continues to remove and the liquid sample that the sealing element itself removes enter the drain channel through the entrance of the drain channel, and enter the receiving chamber. Therefore, in some preferred embodiments, the entrance of the drain channel is located on the discharge element. More preferably, the receiving chamber is located in the discharge element. It can be easily understood that the sealing element and the discharge element can be injection molded at one time. At the time of injection molding, the injection molding is to form a hollow structure, thereby forming a receiving chamber to receive the discharged liquid.

As described previously, in order to allow liquid to enter the inlet of the drain channel smoothly and be discharged to the outside, the horizontal diameter of the discharge element shall be less than the inner diameter of the connecting channel. For example, the discharge element can be inverted cone-shaped, like that shown in FIG. 18, i.e. the conical structure where the inlet 3025 of the drain channel locates. For example, as shown in FIG. 27, the discharge element 3027 is an inverted conical structure. FIG. 31 and FIG. 32 show a conical structure 4027 under the sealing element 4029, and FIGS. 33-35 show a conical structure formed by the discharge structure 435. In fact, the discharge structure needs no independent structure. If the sealing element is long enough to go deep into the second chamber, then it can play dual roles, i.e. changing the liquid communication state between the second chamber and the first chamber, and discharging some liquids in the second chamber. Thus, the discharge element only means a functional restriction, and no other structure is needed to achieve this function. In fact, these conical structures can be used as a discharge element, which will be described in detail subsequently.

Figure 24:
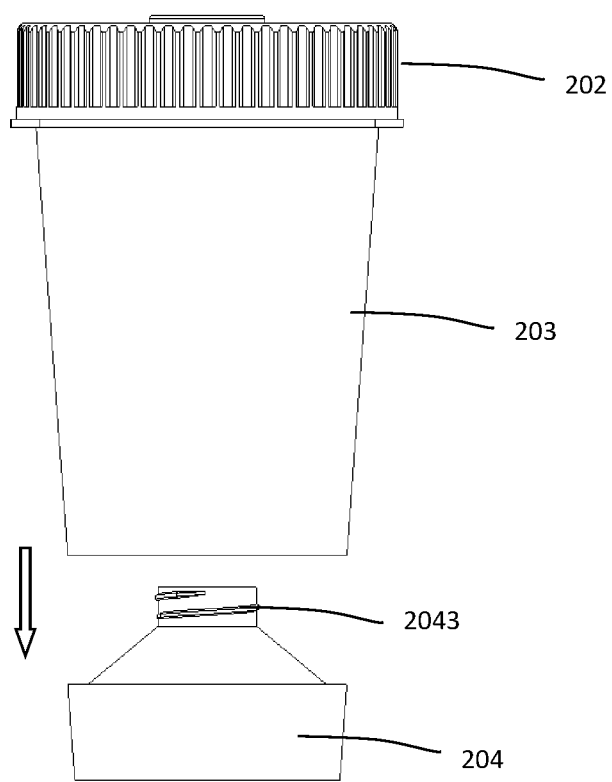
FIG. 24 is a schematic perspective view showing the second chamber being separated from the first cavity and the second cover being separated from the first cover according to an embodiment of the present invention.
Figure 28:
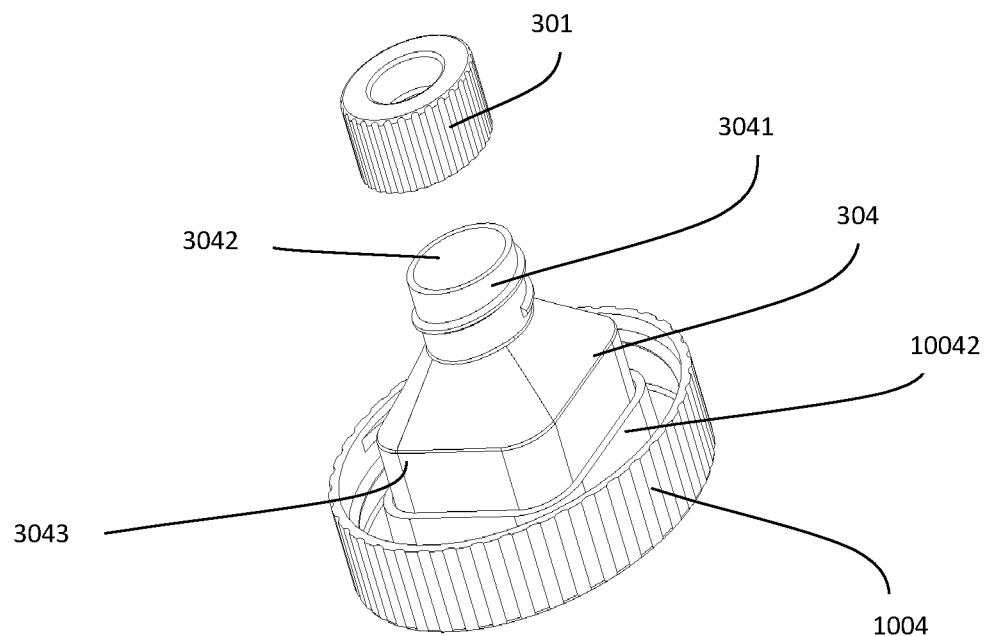
FIG. 28 is a structural view showing sealing of a second chamber by a second cover body according to another embodiment of the present invention.

In some embodiments, for example, referring to FIGS. 15,18,22-23, 27, the discharge elements 2027, 3027 are connected with the sealing elements 2028,3028, which are also formed due to extension of the sealing element. A seal ring 2028 is provided outside the sealing element 2024, in this way, the seal ring 2028 is arranged on the surface of the sealing element and is slightly higher than the outer surface of the sealing element 2014. In this way, even if the diameter of the discharge element 2017 is the same as that of the sealing element 2024, when the discharge element 2027 enters the connecting channel 209 (as shown in FIG. 22), the sealing element and the discharge element enter the connecting channel together. Because the discharge element is located at the terminal and the sealing element is located above the discharge element, so the discharge element first enters the connecting channel. If there is liquid in the connecting channel, the discharge element enters the connecting channel and the discharged liquid enters the first chamber 103 through the gap 809 between the surface of the discharge element and the inner surface of the connecting channel. With the further movement of the sealing element and the discharge element, the discharge element 2027 enters the first chamber and at this time the seal ring may have not sealed the opening 2091 of the connecting channel 209 yet. As the discharge element 2027 further enters the second chamber 204, liquid can still be discharged to the first chamber 203 through the gap 809. When the seal ring 2023 above the sealing element 2024 seals the opening 2091 of the connecting channel 209, liquid can not be discharged to the first chamber through the gap 900. At this time, the sealing element and the seal ring need to continue to move in the connecting channel, so as to reach a stable seal effect. Continual movement requires continual discharge of liquid samples, then redundant liquid samples will be discharged outside the connecting channel and the second chamber through the drain channel. For example, they enter the drain channel through the inlet 2025 of the drain channel, and then enter the receiving chamber 2029 or the first chamber through the liquid outlet of the drain channel. At this time, the second chamber 204 is separated from the device, as shown in FIGS. 24 and 28, and separated from the connecting channel. Since the discharge element 2027 is located in the second chamber, some of the liquid samples in the second chamber are removed. When the second chamber is removed from the apparatus, as shown in FIG. 28, there is a certain space reserved in the second chamber, and the liquid is not filled with the second chamber, so that the liquid samples will not overflow from the second chamber, reducing the risk of polluting the outside.

It can be understood that the size of the discharge element is the same as that of the sealing element, and before the sealing element seals the connecting channel, the liquid in the connecting channel can be discharged to the outside of the connecting channel or the second chamber through the liquid inlet of the drain channel instead of the gap.

In some other embodiments, the sealing element is not differentiated from the discharge element obviously. For example, referring to 31-32, there is no seal ring on the sealing element 5028, and the discharge element 5027 and the sealing element 5028 are located on the extended section of the connecting structure 5023, one end of which is connected with the first cover body 502 and the other end is connected with the sealing element 5028 or the end of the connecting structure, and the sealing element 5028 is connected with the discharge element 5027. While the liquid inlet of the drain channel 5025 is located on the terminal of the discharge element, and the receiving chamber is located in the discharge element or the sealing element or the connecting structure. When the connecting structure, the sealing element and the discharge element are of a hollow structure, the liquid outlet of the drain channel is interlinked with the receiving chamber. Referring to the descriptions above, when such discharge element 5027 enters the connecting channel, the discharged liquid enters the drain channel through the liquid inlet 5038 located on the terminal of the discharge element and then enters the receiving chamber through the liquid outlet of the drain channel. The size of the liquid inlet can be set to let liquid pass through smoothly, but liquid entering the receiving chamber will not be leaked from the liquid inlet because of the liquid surface tension at the liquid inlet. This is because once the discharge element enters the connecting channel 109, 209 through the opening 2091, 1091 of the connecting channel, liquid seal will be formed on the surface of the discharge element 5027 and the inner surface of the connecting channel 209. At this time, the discharge element and the sealing structure are of the same structure, so the discharge element seals the connecting channel and also discharges liquid. With the movement of the discharge element in the connecting channel, a pressure will be generated on the liquid in the connecting channel, and the pressure counteracts the discharge element, so that it will be more difficult for the discharge element 4027 entering the connecting channel. To reduce the counter-acting force of liquid, let redundant liquids enter the liquid inlet 4025 of the drain channel, and then enter the receiving chamber 4029 located in the discharge element 4027.

After the second chamber is separated from the apparatus, the discharge element 1027 is located in the second chamber, so some liquid samples in the second chamber are discharged. When the second chamber is dissembled from the apparatus, for example, referring to FIG. 13, some space in the second chamber is reserved, so it is not filled with liquid completely. Thus, during the disassembly, liquid samples will not overflow from the second chamber, reducing the risk of polluting the outside. In addition, due to the surface tension of the liquid inlet 3025, liquid samples located in the receiving chamber will not leak out through the liquid inlet 3025.

In some embodiments, for example, referring to FIGS. 33-35, the element 5035 is used as a discharge element, located on the connecting rod 5024 together with the sealing element 5028. At this time, the discharging element and the sealing element are detachable connections, and the overall lateral dimension of the discharging element 5035 is smaller than the size of the sealing element 5028, for example, the diameter of the discharge element is smaller than the size of the sealing element 5028 (as shown in FIG. 33), and the discharge element and the sealing element are connected by screw threads, for example, as shown in FIGS. 35A and 35B. The sealing element 5028 is a hollow structure, and the inner surface is provided with internal thread. The discharge element 5035 has an extension 5030 upwards, and an external thread is provided on the extension, so that the discharge element and the sealing element 5028 can be connected together through the internal and external threads. When the sealing element and the discharge element enter the connecting channel 209, as the size of the discharging element is smaller than that of the connecting channel, the discharging element easily enters the connecting channel, and the excess liquid passes through the gap between the discharging element and the connecting channel to enter the first chamber. After the sealing element seals the opening 2091 of the connecting channel 209, the liquid cannot enter the first chamber through the gap. As the sealing element enters the connecting channel, the surplus liquid enters the receiving chamber or the first chamber through the liquid inlet 4025 of the drain channel.

In some preferred embodiments, referring to FIG. 33 and FIG. 35, the size of the discharge element 5035 is equal to or less than the diameter of the sealing element 5028, and the liquid inlet 5025 of the drain channel is arranged on the extended section 5030. According to FIG. 34, the diameter of the place having the liquid inlet 5025 is smaller than that of the sealing element 5028 and that of the discharge element 5029, forming a sunken area at the liquid inlet 5025. In this way, when the discharge element 5035 enters the connecting channel 209, the liquid discharged by the discharge element 5029 is discharged through the liquid inlet 4025 of the drain channel at the sunken area. Similarly, as the discharge element further enters the connecting channel and then enters the second chamber, and the sealing element seals the opening 2091 of the connecting channel and then enters the connecting channel, the liquid discharged by one of the two or by both of them can be discharged through the liquid inlet 5025 of the drain channel, for example, it can be discharged to the receiving chamber or the first chamber. It can be understood that the discharge element here is also a preferred embodiment, and not a necessary way to complete the present invention.

Movement of the Sealing Element or the Discharge Element

As described above, the sealing element seals the connecting channel, and the discharge element will also enter the connecting channel or the second chamber. All of this is a movement process, and to start such movement, external forces or other mechanical structures are needed to allow the sealing element and/or the discharge element to move. Therefore, the sealing element and the discharge element can be moved by a linkage way, for example, the movement of the sealing element drives the movement of the discharge element; for example, the movement of the discharge element drives the movement of the sealing element.

The "linkage" mentioned herein means that the movement of one object will, directly or indirectly, drive the movement of the other object. Generally, the modes of movement of the two objects are the same. For example, the rotary movement of one object drives the rotary movement of the other object; or the plug-in movement of one object drives the plug-in movement of the other object. For another example, one object moves to the final position from the initial position, and during the process, it drives the other object to do the same movement. The rotary movement can be the movement from the initial position to the final position. Of course, rotation and plug-in can be used in combination or alone. Here, movement and motion are interchangeable.

The first cover body and the sealing element or the discharge element move in a linkage form, that is, the movement of the first cover body drives the movement of sealing element, and then drives the movement of the discharge element. Alternatively, the first cover body and the discharge element move in a linkage form, that is, the movement of the first cover body drives the movement of the discharge element, and then drives the movement of the sealing element. In some preferred embodiments, the sealing element is located on the first cover body, when the cover body covers the opening of the first chamber, the cover body drives the sealing element to seal the connecting channel, forming a sealing state. As described above, there are three states as to the sealing of the connecting channel by the sealing element: in the first state, the sealing element will not contact the opening of the connecting channel. For example, as shown in FIG. 22, the first cover body 202 has a sealing element 2028. When the cover body covers the opening 2031 of the first chamber 203, the sealing element 2028 is driven to enter the first chamber, and at this time, the sealing element does not contact the first opening 2091 of the connecting channel (FIG. 22), and the connecting channel connects the first chamber and the second chamber, and the two chambers are in liquid communication. As the cover body covers the opening 2031 of the first chamber, the cover body moves from top to bottom along the direction of the vertical axis of the first chamber, driving the sealing element to gradually get close to the opening 2091 of the connecting channel. With the further covering of the first cover body, the sealing element 2028 contacts the first opening 2091 of the connecting channel 209 and thus seals this opening (FIG. 23). At this time, it can be believed that the connecting channel 209 is sealed. However, in order to seal the connecting channel more stably, it is hoped that the sealing element enters the connecting channel 209 for a distance, and the covering of the cover body is still needed to drive the sealing element 2028 to enter the connecting channel. A similar process is shown in FIG. 1227. No matter for what types of or forms of sealing elements, it is a preferred embodiment that the sealing element and the cover body move simultaneously. Of course, the movement of the cover body and the sealing element can be separated, for example, in the process during which the first cover body is used to cover the opening of the first chamber, the sealing element seals the connecting channel by individual movement.

As for the discharge element, its function is to discharge some liquids in the second chamber. As described above, if the second chamber is filled with liquid, the discharge element is needed to discharge liquid, but if the second chamber is not filled with liquid completely, the discharge element may not be needed. So the discharge element is a preferred embodiment of the present invention and not a necessary way. When the discharge element is needed, the discharge element and the cover body can be connected as an integral structure, and in this way, the movement of the cover body will drive the movement of the discharge element so that it can be inserted into the second chamber to discharge liquid. Of course, as described above, the sealing element and the discharge element are two different elements, and the discharge element enters the second chamber earlier than the sealing element. In a preferred embodiment, the discharge element enters the connecting channel earlier than the sealing element and then enters the second chamber. To achieve such design, the discharge element is located at the terminal of the sealing element and is farther away from the first cover body.

Therefore, in some preferred embodiments of the present invention, the present invention provides a cover body on which a sealing element is provided for sealing the connecting channel. In some preferred embodiments, a seal ring is provided on the sealing element. In some preferred embodiments, the sealing element and the connecting channel have the same or different texture. In some preferred embodiments, the sealing element has flexible texture while the connecting channel has rigid texture. In some preferred embodiments, the sealing element and the first cover body are connected as an integral structure through the connecting rod. In some preferred embodiments, the sealing element further includes an opening of the drain channel. In some preferred embodiments, the opening of the drain channel is located below the sealing element, or it enters the connecting channel earlier than the sealing element. In some preferred embodiments, the cover body further includes a receiving chamber. Liquids in the receiving chamber and the drain channel are connected, and the receiving chamber is connected with the liquid outlet of the drain channel. In some preferred embodiments, the receiving chamber is located in the sealing element.

In some other preferred embodiments, a discharge element is further provided on the first cover body, and the discharge element is farther away from the first cover body than the sealing element. Or, a discharge element is provided below the sealing element, or the sealing element and the discharge element are arranged to allow the latter to enter the second chamber earlier than the former, or allow the latter to enter the connecting channel earlier than the former. Or, when a connecting rod is provided on the cover body for connecting the first cover body and the sealing element, it also connects the sealing element and the discharge element. Or, the connecting rod and the sealing element and the discharge element are an integral structure.

In other embodiments, if at the very start, the first chamber and the second chamber are not in liquid communication, instead, they are in liquid communication after liquid samples are collected in the first chamber, then the cover body can have a first element that allows the first chamber and the second chamber to be in liquid communication, and a second element that allows the first chamber and the second chamber not to be in liquid communication. For example, the reason why the first chamber and the second chamber are not in liquid communication at the very start is that the sealing element has sealed the first opening 1091 of the connecting channel at the very start. If the first element and the second element of the cover body are in a linkage form, let the first element contact the sealing element first, for example, when the sealing element is a structure that is easily pierced, the first element is a sharp piercing structure, and after piercing, liquid in the first chamber enters the second chamber. Subsequently, let the second element seal the first opening, so as to change the liquid communication state. Thus, the second chamber can be separated from the first chamber. It will be understood by an ordinary person skilled in the art that the second element can be an alternative of any sealing element described above, and can also contain a discharge element, or the setting of the drain channel, for example, in the specific embodiment shown in FIGS. 37-40 above.

First Cover Body and Second Cover Body

Here, the first cover body is used to cover the opening of the first chamber, and the second cover body is used to cover the opening of the second chamber. For specific example, the cover body can be of the shape shown in FIGS. 1-28. Of course, the function of the cover body is to cover the opening of the first chamber, but the first cover body does not necessarily need to seal the opening of the first chamber, while the main function of the second cover body is to seal the opening of the second chamber, thus avoiding liquid leakage. So, in some embodiments, the second cover body is located on the first cover body, and the two are a detachable combination, for example, by screw threads or other plugging methods. When the second cover body needs to be used for sealing, and generally for sealing the opening of the second chamber, take down the second cover body from the first cover body.

Method for Detecting or Collecting Liquid Samples

The present invention further provides a method for collecting liquid samples. The method includes providing the foregoing apparatus for collecting liquid samples, and the apparatus includes a first chamber and a second chamber, wherein the second chamber and the first chamber are connected in a detachable manner, and the first chamber is used for collecting liquid samples so as to let liquid samples flow into the second chamber. In some preferred embodiments, after liquid samples are collected in the second chamber, allow the second chamber to separate from the first chamber, so that the second cover body can be used for covering the opening of the second chamber. In some preferred embodiments, before the first chamber is separated from the second chamber, the first chamber is not in fluid communication with the second chamber. In some preferred embodiments, the first chamber is separated from the second chamber by a sealing element, so that the first chamber is not in communication with the second chamber.

In some preferred embodiments, the first chamber is allowed to connect with the second chamber through the connecting channel, wherein liquids in the first opening of the connecting channel are communicated with those in the first chamber, and liquids in the second opening of the connecting channel are communicated with those in the second chamber. By separating the second chamber from the connecting channel, the second chamber is separated from the first chamber; or, the second chamber is connected to the connecting channel detachably, while the connecting channel is not connected to the first chamber detachably; or, the second chamber is connected to the connecting channel detachably, and the connecting channel is also connected to the first chamber detachably.

In some embodiment, when the second chamber is detachably connected to the first chamber through the connecting channel, the sealing element seals the connecting channel. Therefore, in some preferred embodiments, the apparatus further comprises a sealing element. Before the second chamber is separated from the first chamber, allow the sealing element to seal the connecting channel. In some preferred embodiments, the apparatus further comprises a cover body, and the cover body and the sealing element are connected as an integral structure, and the cover body drives the sealing element to seal the first opening of the connecting channel at the same time when the cover body covers the opening of the first chamber. In some preferred embodiments, allow the cover body to drive the sealing element to enter the connecting channel. In some preferred embodiments, the second chamber is separated from the first chamber after the sealing element seals the connecting channel. In some preferred embodiments, a discharge element is provided on the cover body for discharging some liquids in the second chamber, and the discharge element is driven by the cover body to enter the second chamber. In some preferred embodiments, a sealing element and a discharge element are provided on the cover body, and the discharge element enters the second chamber earlier than the sealing element. In some preferred embodiments, the apparatus further includes a drain channel, and the liquid samples discharged by the discharge element are discharged outside the second chamber through the drain channel. In some preferred embodiments, allow the sealing element to enter the connecting channel, and liquids discharged by the sealing element are discharged outside the connecting channel through the drain channel. In some preferred embodiments, allow liquids discharged by the sealing element or the discharge element to discharge to the first chamber through the drain channel. In some preferred embodiments, a receiving chamber is provided on the cover body, and liquids in the receiving chamber are connected with those in the drain channel, wherein liquids discharged by the sealing element or the discharge element are discharged to the receiving chamber through the drain channel.

In some embodiments, the drain channel has a liquid inlet and a liquid outlet, so that the liquid discharged from the sealing element and/or the discharge element enters the liquid inlet, and then enters the receiving chamber through the liquid outlet of the drain channel.

In some other embodiments, the cover body is provided with a sealing element. By covering the opening of the first chamber with a cover body, the connecting channel is sealed by the sealing element. In some embodiments, when the first cover body leaves the opening of the first chamber again, the sealing element remains in the connecting channel, or the sealing element separates from the cover body.

On the other hand, the present invention provides a method for detecting whether or not there is analyte in the liquid samples, and the method includes any of the above liquid collection apparatus. After liquid samples are collected in the first chamber, the testing element is used to detect the liquid samples from the first chamber. After the detection result is obtained, allow the second chamber to separate from the first chamber in any of the above ways. In some specific embodiments, the apparatus further includes a detection chamber for containing the testing element, and fluids in the detection chamber are connected with those in the first chamber. After liquid samples are collected in the first chamber, liquids flow into the detection chamber. When the detection chamber contains the testing element, after the testing element completes the detection, allow the second chamber to separate from the first chamber. In some preferred embodiments, allow liquid samples to enter the detection chamber first from inside the first chamber, and then enter the second chamber. As those described above, such structure can prevent liquids entering the detection chamber from entering the second chamber and polluting the liquid samples in the second chamber.

Detection Chamber

In the present invention, the detection chamber is used for analyzing and detecting whether or not there is analyte in the liquid samples from the first chamber. The detection chamber may be not provided with a detection apparatus. Generally, the detection chamber includes a testing element, and the testing element contacts the liquid samples to assay or test the liquid samples. For traditional products, when the apparatus with a detection chamber is manufactured, the testing element is manufactured first or the testing element is arranged on a carrier and then inserted into the detection chamber, and then the detection chamber is sealed. In such case, the detection chamber generally has an opening to allow the testing element to enter or exit the detection chamber. For example, referring to FIG. 1 and FIG. 9, the detection chamber 105 has an opening 1051 at the position near the opening 1031 of the first chamber 103, and the testing element (not shown) provided on the testing carrier 106 is located in the card slot 1061 of the testing carrier, and then the carrier 106 is inserted into the detection chamber through the opening of the detection chamber. Generally, after it is inserted into the detection chamber, the opening 1051 of the detection chamber needs to be sealed, but the requirements for the sealing effect and quality are very high. As described above, the whole detection apparatus or collection apparatus needs to be transported and packed together, so in order to avoid leakage of liquids in the detection chamber or the first chamber, any position where leakage may occur should be sealed strictly, and a seal test should be performed on each product, which increases the production costs. However, after the second chamber with the second confirmation function provided in the present invention is adopted, there is no need to consider deliberately achieving a good sealing effect, because temporary sealing rather than persistent sealing is enough. For example, referring to FIG. 9, the opening 1051 for detecting the quantity only needs to be sealed conventionally, for example, when a thin film is used for heat seal, it only needs to keep air-tight or leakage-free during detection. After the detection is completed, and after the second chamber is separated from the first chamber, the first chamber and the detection chamber can be discarded, thus it is unnecessary to store and transport the whole detection apparatus.

Design 2 (FIGS. 41-78)

First Chamber for Collecting Liquid Samples

Figure 67:
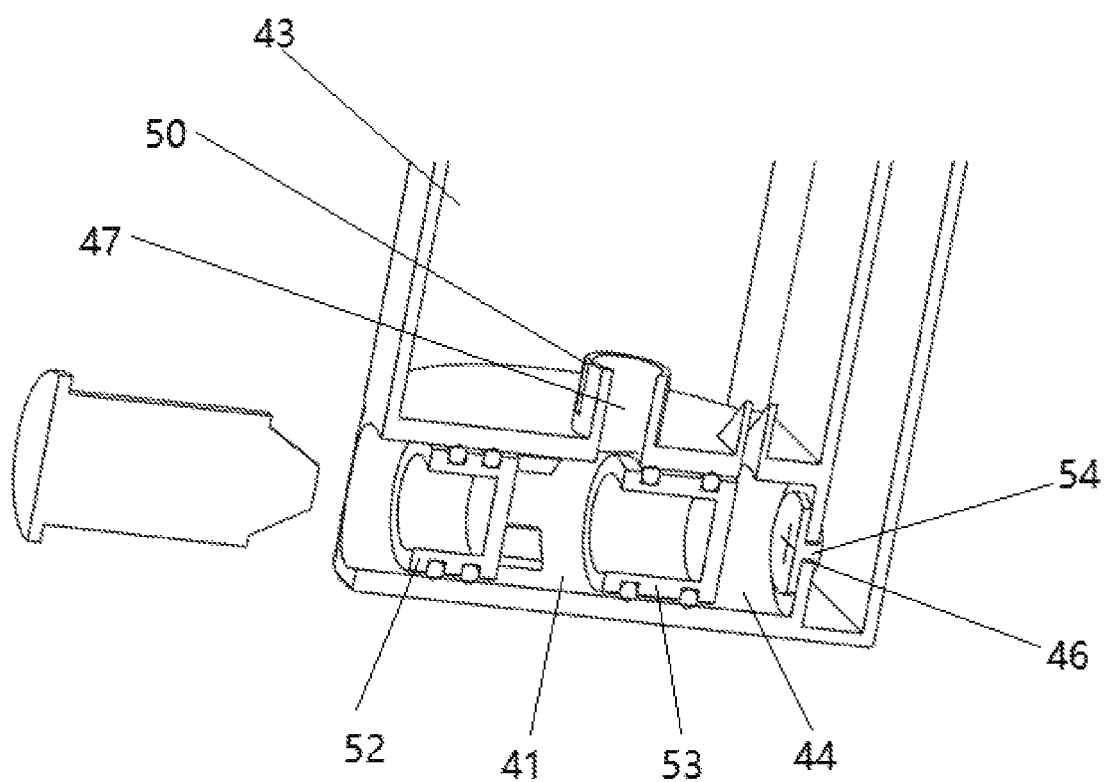
FIG. 67 is a cross-sectional view of a pipetting channel according to an embodiment, in the state shown in the figure, the first pipetting element and the second pipetting element are in a position where the apparatus is not in use, and the first chamber and the fourth chamber are both compressed, the first channel is in fluid communication with the first chamber, and the second channel is in fluid communication with the fourth chamber.
Figure 68:
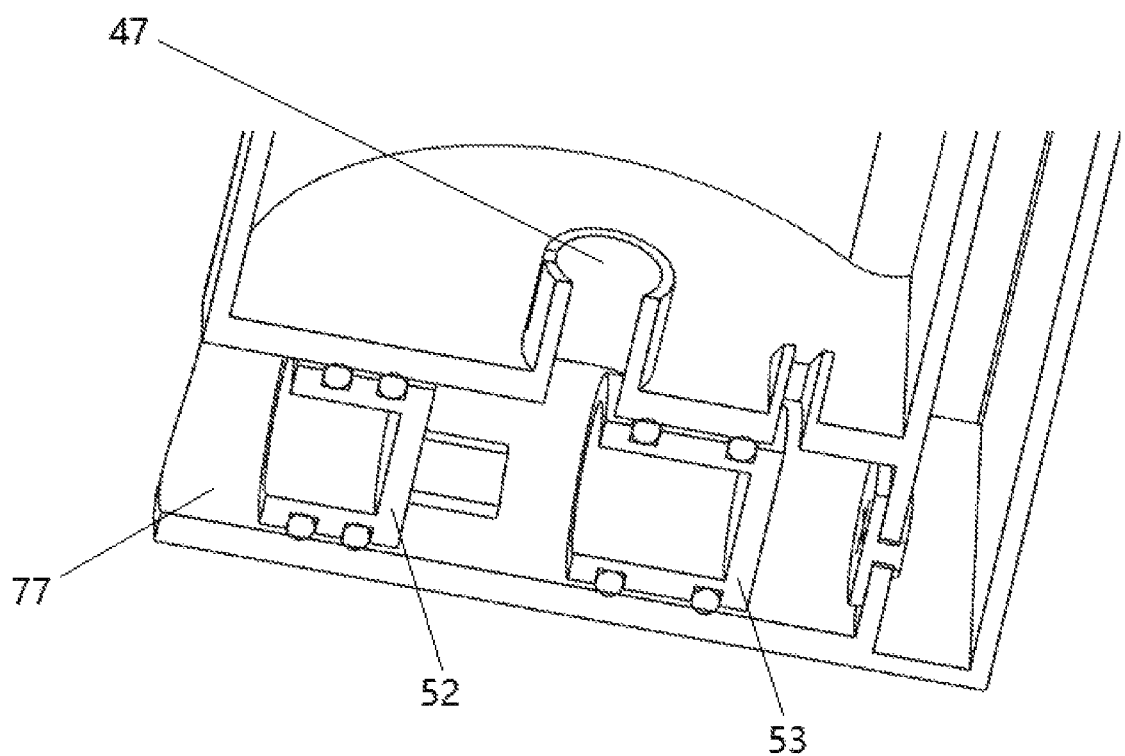
FIG. 68 is a cross-sectional view of a pipetting channel according to an embodiment, in the state shown in the figure, the second pipetting element moves in the direction of pressing the fourth chamber while starting to seal the second channel.
Figure 69:
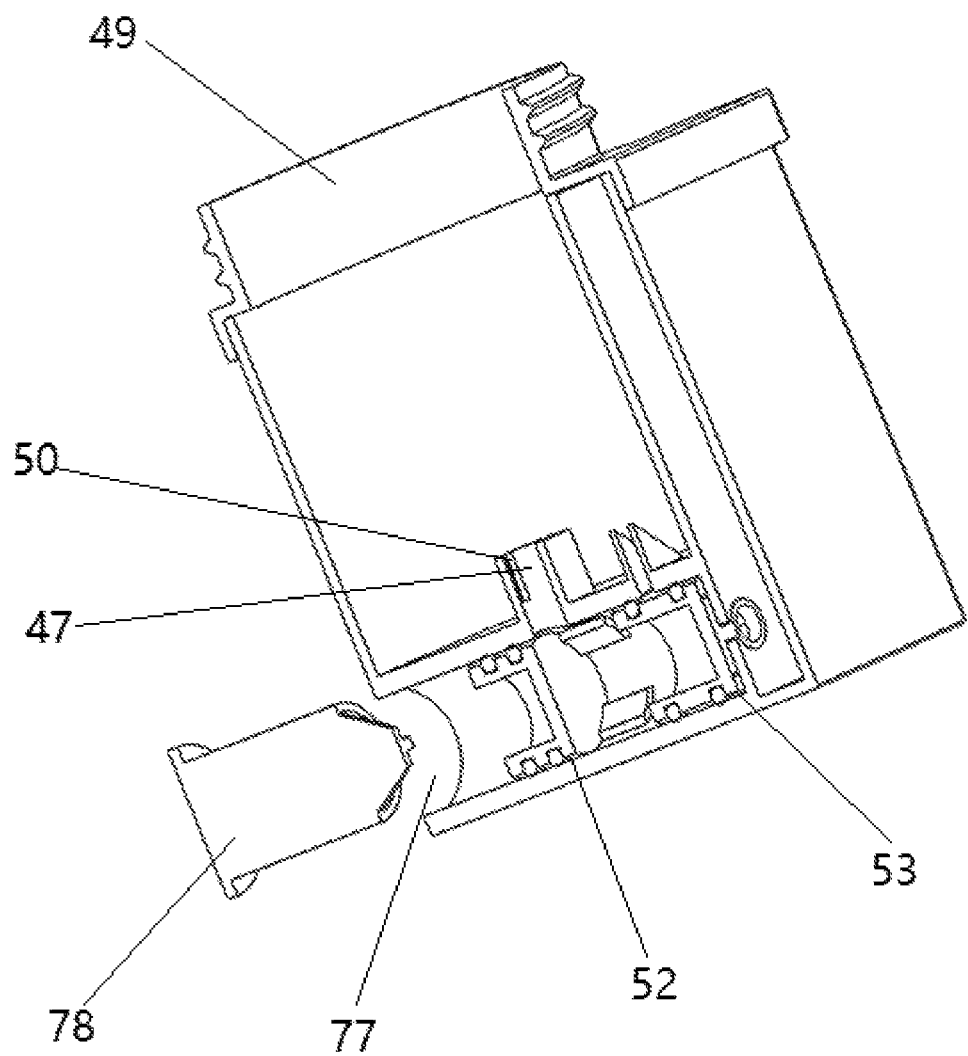
FIG. 69 is a cross-sectional view of a third chamber according to an embodiment, in the state shown in the figure, the first pipetting element and the second pipetting element are pushed to the inward limit position by the pipetting plug. At this time, the fourth chamber and the first chamber are both compressed, the samples in the fourth chamber are pushed into the testing area, the samples in the first chamber are pushed into the second chamber, the first chamber and the first channel are in the liquid partition state, and the fourth chamber and the second channel are in the liquid partition state.
Figure 70:
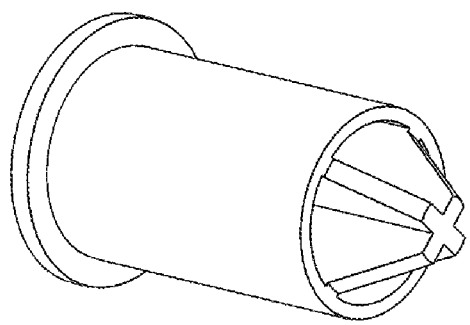
FIG. 70 is a schematic diagram of a pipetting plug according to an embodiment of the present invention.

In some particular embodiments, like the specific embodiments shown in FIGS. 67-69, the present invention provides a collection apparatus for collecting liquid samples, or a detection apparatus for detecting liquid samples, of course, the detection apparatus also has the collecting function or comprises a collection apparatus. The collection apparatus or the detection apparatus comprises a first chamber 41. The first chamber 41 can be used as a chamber for direct collection, or samples can be collected through other chambers such as the third chamber 43.

When the first chamber 41 is used as a chamber for direct collection, the chamber itself can have an opening that is in direct communication with the outside, and samples can be injected or put into the first chamber 41 through the opening, the structure shown in FIG. 26, then the first chamber 41 can collect samples directly from the outside. When samples are collected by other chambers, as shown in FIGS. 27-29, the first chamber 41 is communicated directly with the third chamber 43 through a first channel 47, and the first chamber 41 is located under the third chamber 43, and the third chamber 43 comprises an upward collection port 49 through which liquid samples can enter the third chamber 43 and naturally drop or flow downward due to gravity. The portion of liquid samples that naturally drop and enter the first channel can directly drop into the first chamber 41. During the naturally dropping process, there must be a portion of liquid samples unable to directly fall into the first channel 47, then they can gather on the bottom of the third chamber 43. When the liquid level exceeds the height that the first channel 47 exceeds the bottom of the third chamber 43, this portion of liquids will flow into the first chamber 41 through the first channel 47.

In some preferred embodiments, for example, according to the figure, a collecting tank 50 can be provided on the side wall of the first channel 47, which can be as high as or slightly higher than the bottom of the third chamber 43. The portion of liquid samples that do not enter the first channel 47 during the naturally dropping process will finally gather on the bottom of the third chamber 43. Since the height of the collecting tank is close to that of the bottom of the third chamber 43, the liquid samples on the bottom of the third chamber 43 are very likely to enter the first channel 47 through the collecting tank 50 and flow into the first chamber 41 along the first channel 47. It should be noted that, we do not need all samples in the third chamber 43 to flow into the first chamber 41, instead, we only need a portion. Therefore, as long as enough liquids are collected, a portion of the samples will surely enter the first channel 47. Moreover, in actual application, the whole chamber may be in a non-static state, for example, it is held by a hand, then the collected samples are more likely to enter the collecting tank 50 due to shaking.

In some preferred embodiments, the liquid samples in the first chamber 41 can be directly used for detection. In some preferred embodiments, the liquid samples in the third chamber 43 can be directly used for detection. In some preferred embodiments, the liquid samples in the first chamber 41 can be transferred to other chambers, such as the second chamber 42.

In some preferred embodiments, the volume of the first chamber 41 is variable. For example, in the process shown in FIGS. 27-29, the first chamber 41 is actually a space in the pipetting channel 51, and this space is isolated by the first pipetting element 52 and the second pipetting element 53. When the first pipetting element 52 or the second pipetting element 53 or the two pipetting elements move(s) inside the pipetting channel 51, the volume of the first chamber 41 will change. In some preferred embodiments, the volume of the first chamber 41 can be reduced, then the stored liquid samples will be extruded to other chambers or for other purposes. In some preferred embodiments, the volume of the first chamber 41 can be expanded, under such a situation, an inward attractive force will be produced in the first chamber 41, so that it can collect more liquid samples more quickly, or, in some preferred embodiments, the volume of the first chamber 41 will increase with the increase of the collected samples.

Self-Sealing

The self-sealing means that, when no forces are applied to the chamber other than the pressure that may be produced on the inner wall or outer wall of the chamber by the chamber itself or the objects inside the chamber (including liquids, gas and other substances), the chamber can be in a sealing state, and the fluids are isolated between the interior chamber and the outside or other chambers, and no fluid exchange is allowed (including liquids, gas, etc.). Under some circumstances, the self-sealing means that, other than the pressure that may be produced on the inner wall or outer wall of the chamber by the chamber itself or the objects inside the chamber (including liquids, gas and other substances), even if an external force is applied to the inner wall or outer wall of the chamber, as long as this external force is not large enough or does not reach a certain value, the chamber can still be in the above sealing state. Under some circumstances, there may be an opening or pierced hole on the chamber body, but due to the texture of the materials used for the chamber or the wall thickness, this opening or pierced hole will not be opened under the action of the internal force or if the external force is not large enough. Moreover, when an external force is applied, or the external force is large enough, the chamber can be in liquid communication with the outside or other chambers without the intervention of other components, which can be achieved through the opening or the pierced hole. After the external force is removed, the original fluid isolation state can be recovered. Then, this chamber is called a self-sealing chamber.

Third Chamber for Collecting Liquid Samples

In some particular embodiments, as shown in FIGS. 60-63, the present invention provides a collection apparatus for collecting liquid samples, or a detection apparatus for detecting liquid samples, of course, the detection apparatus also has the collecting function or comprises a collection apparatus. The collection apparatus or the detection apparatus comprises a third chamber 43. The third chamber 43 can be used as a chamber for direct collection or for detection, or for temporary storage, so that the liquid samples can enter other chambers through the third chamber 43, and other chambers can be a collection chamber or a detection chamber.

For example, in specific embodiments shown in FIGS. 67-69, the third chamber 43 is used as a transition chamber for the first chamber 41 to collect liquid samples. By some methods described above, the first chamber 41 can collect the liquid samples entering the third chamber 43. Of course, the third chamber 43 can collect samples through other chambers.

Figure 21:
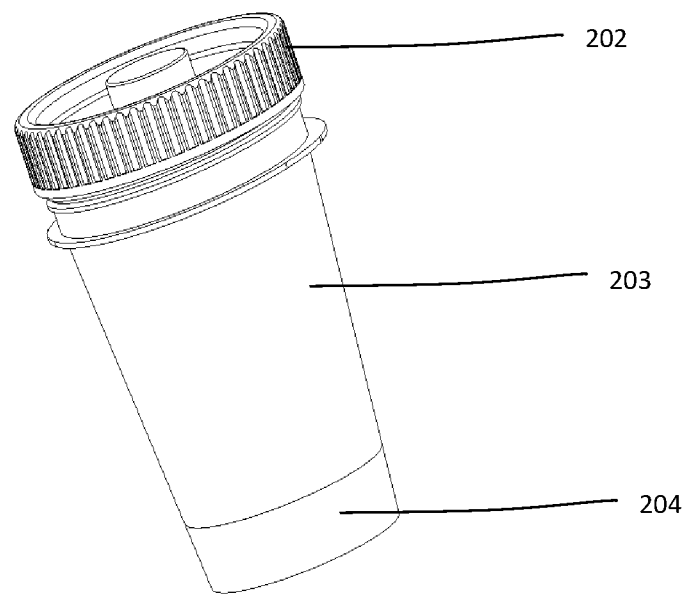
FIG. 21 is a perspective structural view after a first chamber opening is covered by a first cover body according to another embodiment of the present invention (operation process).

When the third chamber 43 is used as a transition chamber, as shown in FIG. 21, a first channel 47 in liquid communication with the first chamber 41 and a second channel 48 in liquid communication with the fourth chamber 44 may be provided on the bottom. Under such a situation, as long as the first channel 47 and the second channel 48 are not closed, the first chamber 41 and the fourth chamber 44 may complete the sample collection basically at the same time when the third chamber 43 completes the collection.

In some preferred embodiments, the third chamber 43 can be in liquid communication with the testing area 45 through a detection inlet 46, and the detection inlet 46 can be adjusted or set as communication or partition. In this way, liquids in the third chamber 43 can be introduced to the testing area 45 as required. A testing element may, or may not be set in the testing area 45. When a testing element is set in the testing area, for the convenience of observation, the testing area can be made from transparent materials.

In some preferred embodiments, a collecting tank 50 can be provided on the side wall of the first channel 47, which can be as high as or slightly higher than the bottom of the third chamber 43. The portion of liquid samples that do not enter the first channel 47 during the naturally dropping process will finally gather on the bottom of the third chamber 43. Since the height of the collecting tank is close to that of the bottom of the third chamber 43, the liquid samples on the bottom of the third chamber 43 are very likely to enter the first channel 47 through the collecting tank 50 and flow into the first chamber 41 along the first channel 47. It should be noted that, we do not need all samples in the third chamber 43 to flow into the first chamber 41, instead, we only need a portion. Therefore, as long as enough liquids are collected, a portion of the samples will surely enter the first channel 47. Moreover, in actual application, the whole chamber may be in a non-static state, for example, it is held by a hand, then the collected samples are more likely to enter the collecting tank 50 due to shaking In some preferred embodiments, the first chamber 41 and the third chamber 43 can be in a liquid isolation state during initial collection, that is, liquid samples collected by the third chamber 43 will not automatically enter the first chamber 41, or can not directly enter the first chamber 41 due to the gravity of the sample. For example, the communication between the first chamber 41 and the third chamber 43 is partitioned by an element, then after a force is applied to the liquid samples in the third chamber 43, the partition of the element can be broken, enabling the sample to enter the first chamber 41 from the third chamber 43. In other words, under such circumstance, the first chamber 41 is not necessarily used as a chamber for initial collection of samples, instead, it can be used as a channel, providing a path for the sample to enter the second chamber 42 from the third chamber 43. Due to the existence of this path, samples can directly enter the second chamber 42, without polluting the outer wall of the second chamber 42.

In some preferred embodiments, the third chamber 43 can be sealed by a cover body. In some preferred embodiments, the cover body can be directly connected to the third chamber 43 and seal the third chamber. In some preferred embodiments, the cover body can directly seal the third chamber including the testing area. In some preferred embodiments, the cover body can be used only for sealing the collection port of the third chamber. In some preferred embodiments, the cover body can be connected to the third chamber through a seal connection piece. For example, as shown in FIGS. 24-25, the collection port 49 and the inlet 65 of the testing element can be sealed by a seal connection cover 66, and the seal connection cover 66 comprises a first cover 67 for covering the sample collection port and a second cover 68 for covering the inlet 65 of the testing element. Through the first cover 67 and the second cover 68, the seal connection cover 66 can cover the collection port 49 and the inlet 65 of the testing element at the same time. The seal connection cover 66 can be connected to the cover body, or if the seal connection piece itself is in a sealing state, as shown in the figure, the first cover 67 and the second cover 68 match with each other in a snapping form at the opening part of the third chamber and the testing area. In addition to the way shown in the figure, a thin film can be used for thermal molding, as long as the film is airtight or does not leak liquids during detection. After the second chamber is separated from the main body of the apparatus after the detection, the main body (including the testing area) can be discarded, with no need to store and transport the whole detection apparatus.

In some preferred embodiments, samples are firstly loaded into the third chamber 43, and the samples are not loaded into the first chamber 41. In some preferred embodiments, the samples in the third chamber 43 can enter the first chamber 41 under a certain external force. For example, as shown in FIG. 37, in some preferred embodiments, the first chamber 41 may be provided with a third channel 82 passing through the third chamber 43, which is not loaded into samples during the initial collection. In some preferred embodiments, the second chamber 42 and the assembly structure of the second chamber can be assembled to the third channel; similarly, a connector 58 can be used to connect the first chamber and the second chamber 42. In some preferred embodiments, the sample in the third chamber 43 can be directly pressed from the first chamber 41 into the third channel 82 under pressure. In some preferred embodiments, the second chamber 42 can be directly assembled to the third channel 82. In some preferred embodiments, the third channel 82 and the third chamber 43 share a common opening, but when the sample is loaded, attention should be paid to prevent the sample from entering the third channel 43. In some preferred embodiments, the third channel 43 may be closed, for example, plugged with a plug, or sealed with a film, to prevent the accidents.

In some preferred embodiments, some open pores that can be in communication with the first chamber are provided on the bottom of the third chamber, and they can be opened under a certain condition. They only communicate the first chamber with the third chamber, and not with other chambers or the outside. In some preferred embodiments, these open pores are provided on the bottom of the third chamber. In some preferred embodiments, these open pores are provided on the wall shared by the first chamber and the third chamber. In some preferred embodiments, these open pores are a pressure port 83. When there is enough pressure in the third chamber 43, the pressure port 83 will be opened, so as to achieve fluid communication between the first chamber and the third chamber, and at this time, samples can directly enter the first chamber from the third chamber. When the pressure is removed, the pressure port 83 will be closed again. In some preferred embodiments, the pressure port can be the self-sealing open pore as described above, for example, like the opening of the "sharp-angled bottle". In some preferred embodiments, the pressure port when closed can bear the liquid pressure from the third chamber when filled with liquids, in other words, samples are only loaded to the third chamber, and the weight of these samples is insufficient to open the pressure port. In some preferred embodiments, when the samples collected reach a certain volume, the pressure port can be opened. In some preferred embodiments, the pressure that the pressure port is able to bear can be configured according to actual needs. In a specific embodiment, the section of the first chamber 41 is wider than that of the third channel 82, thus there is a distance between the third channel 82 and the first chamber 41, and the pressure port 83 is set on this distance. In some preferred embodiments, the pressure inside the third chamber 43 can come from the cover body, for example, a piston is set on the cover body to push or extrude the upper liquid level downward, or the pressure can be produced on the upper liquid level when the cover body covers.

Detection Inlet

The detection inlet 46 is a communication port between the collecting chamber and the testing area. But, it is unnecessary to communicate the testing area and the collecting chamber at every moment. They can be separated, and as required, they can be communicated. Under such circumstance, a detection inlet partition 54 can be set at the detection inlet 46. Through the detection inlet partition 54, the detection inlet 46 can be adjusted or set as communication or partition. In this way, the liquids inside the third chamber 43 can be introduced to the testing area 45 as required.

For example, in the embodiment shown in FIG. 67, the detection inlet partition 54 has a certain hardness and thickness, on which an incision is provided. The sections of the incision match in the form of interference fit. Then, when there is no pressure or the pressure is insufficient, the whole incision is in a closed state, which can partition liquid communication. But, when one side of the incision is under pressure, the incision will open along the direction of the pressure, to relieve pressure naturally. In other words, when there are a certain number of samples on one side of the incision, or samples apply a certain pressure, the incision will be opened, enabling liquid communication between the collecting chamber and the testing area 45. After the pressure is removed, the incision can be closed again.

Testing Area

Figure 64:
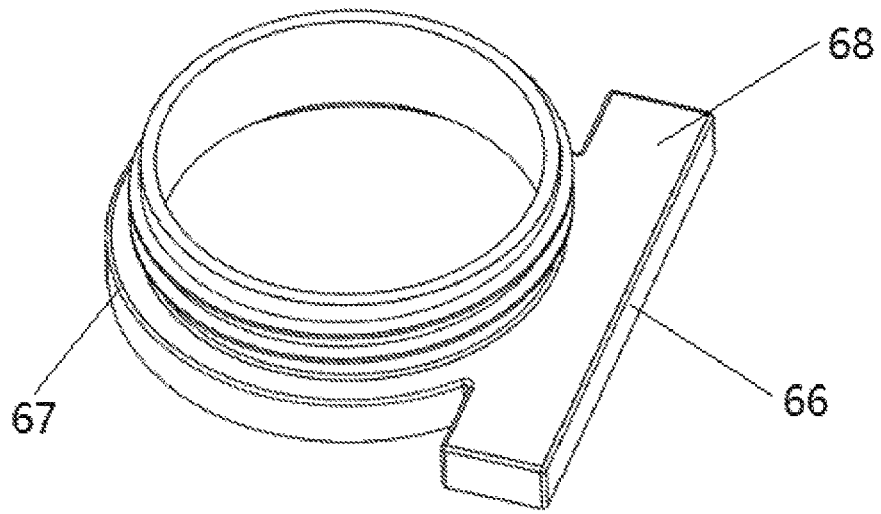
FIG. 64 is a schematic diagram of a seal connection cover on the third chamber shown in FIG. 63.
Figure 65:
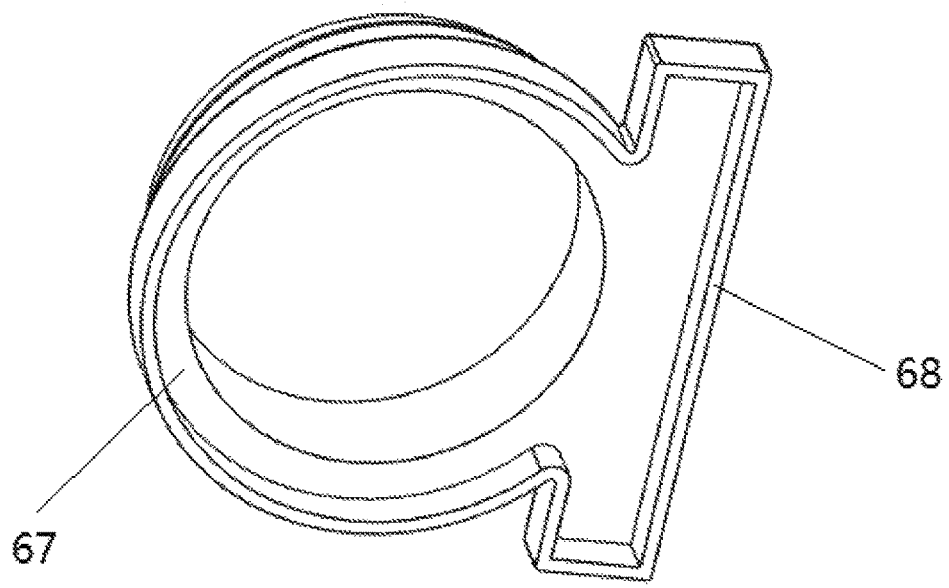
FIG. 65 is a schematic diagram of a seal connection cover shown in FIG. 64 from another angle.
Figure 66:
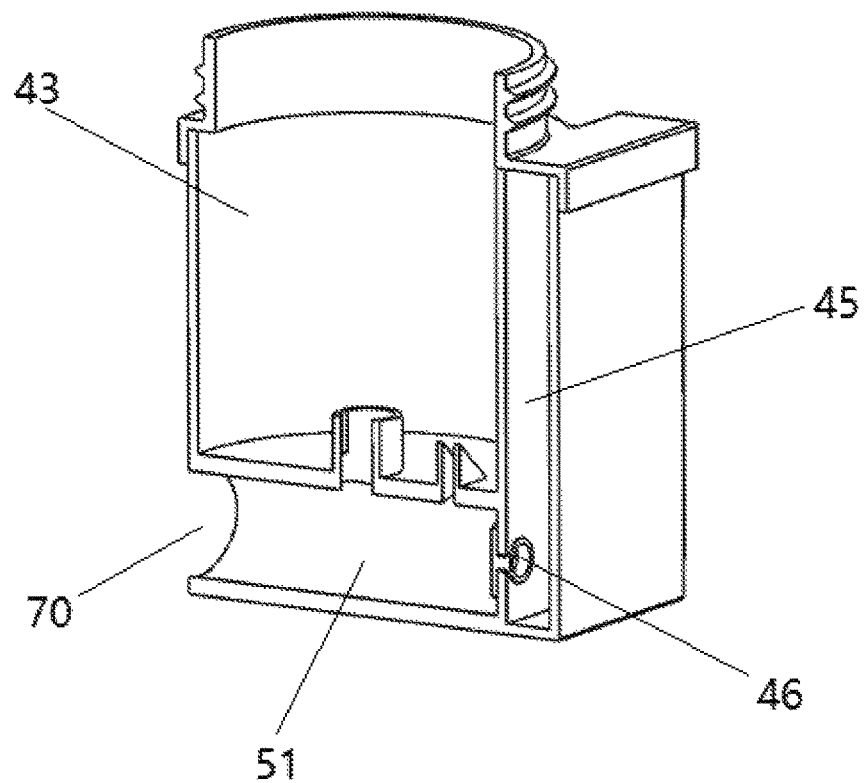
FIG. 66 is a cross-sectional view of a third chamber according to an embodiment, in the state shown in the figure, the first pipetting element and the second pipetting element are not yet installed in the pipetting channel.

In the present invention, the testing area 45 is used to analyze and test the liquid sample to determine the presence or absence of analyte. Generally, the testing area 45 can comprise a testing element. The testing element contacts the liquid sample to assay or test the sample. Among traditional products, when the apparatus with a detection chamber is made, the testing element is made first or it is set on the carrier, and inserted into the testing area, then the testing area is sealed. Under such circumstance, the testing area has an opening to enable the testing element to enter or exit the testing area. For example, as shown in FIGS. 1-2 and 20-21, a testing element inlet 65 is set on the upper end of the testing area 45, as described above, the testing element can be inserted into the testing area 45 through the testing element inlet 65. Under normal conditions, after insertion into the detection chamber, the opening of the testing area needs to be sealed. The requirements for the sealing effect and quality are strict, just as described above, the whole detection apparatus or collection apparatus needs to be transported and packaged together, thus in order to avoid liquid leakage from the testing area or the third chamber, any position that may leak liquids needs to be sealed strictly, and the leakproofness of each product needs to be detected, which will increase the production cost. However, after the second chamber with the ability to perform second confirmation provided in the present invention is adopted, there is no need to consider deliberately the leakproofness of the above positions, and temporary sealing is enough. For example, as shown in FIGS. 64-65, the collection port 49 and the testing element inlet 65 can be sealed by a seal connection cover 66, and the seal connection cover 66 comprises a first cover 67 for covering the sample collection inlet and a second cover 68 for covering the testing element inlet 65. Through the first cover 67 and the second cover 68, the seal connection cover 66 can cover the collection port 49 and the testing element inlet 65 at the same time, so the conventional sealing of the seal connection cover 66 is enough, for example, the first cover 67 and the second cover 68 match with each other in a snapping form at the opening part of the third chamber and the testing area. In addition to the way shown in the figure, a thin film can be used for thermal molding, as long as the film is airtight or does not leak liquids during detection. After the second chamber is separated from the main body of the apparatus after the detection, the main body (including the testing area) can be discarded, with no need to store and transport the whole detection apparatus. In some preferred embodiments, a connecting portion 69 matching with a cover body, as shown in FIGS. 24-25 can be provided on the seal connection cover 66. In some preferred embodiments, the connecting portion 69 can be connected by a screw thread, for example, by the way shown in the figure. Of course, it can also be connected by any other ways, as long as the seal connection cover 66 can be connected with the cover body 63. Of course, the seal connection cover 66 itself can also be used as the cover body of the apparatus, then the connecting portion 69 is not required, instead, the seal connection cover 66 is directly designed as a shape that can seal the whole apparatus.

Second Chamber for Collecting Samples for Confirmatory Detection

In some particular embodiments, the present invention provides a second chamber 42 for collecting samples for confirmatory detection. In some preferred embodiments, the second chamber 42 can collect samples from the same batch as the initial detection samples, in other words, samples from the same batch can be loaded to the second chamber 42 while collecting the initial samples. In some preferred embodiments, samples in the second chamber 42 come from the first chamber 41. In some preferred embodiments, samples in the second chamber 42 come from the third chamber 43. In some preferred embodiments, the second chamber 42 can collect samples directly.

Figure 14:
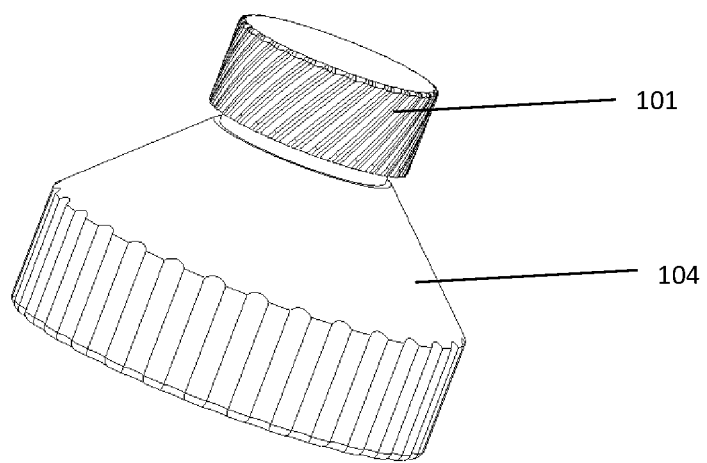
FIG. 14 is a perspective structural view of covering a second chamber by a second cover body according to an embodiment of the present invention.

As a specific embodiment of the second chamber, as shown in FIGS. 52-55, the second chamber 42 is a chamber with variable volume, comprising an opening end 55. In some preferred embodiments, the opening end 55 can not be compressed, as shown in FIG. 13, an opening is provided inside the opening end 55. Through this opening 56, the second chamber 42 can communicate with other chambers and collect samples via other chambers, or this opening can allow the second chamber 42 to collect samples by itself. In some preferred embodiments, this opening 56 can be sealed by a seal 57, as shown in FIG. 14. When being sealed by the seal, the opening 56 can be connected firmly, fitted closely or detachably combined or connected with the seal 57. In some preferred embodiments, the communication between the connector 58 and the second chamber 42 can be achieved by piercing the seal 57 by a piercing element.

In some preferred embodiments, the opening end 55 can be compressed. In such case, the seal may not be set separately, instead, the opening end and the second chamber 42 are connected directly by integrated molding, or a seal that can be compressed together with the opening end 55 is provided, at this time, the seal needs to have elasticity or flexibility to a certain extent.

In some preferred embodiments, the second chamber 42 can have a self-sealing opening. As described previously, this opening can be in a sealing state under the pressure of a certain range, so as to ensure that liquids in the second chamber 42 will not flow out, but when the pressure exceeds a certain value, this opening may be opened, and after the pressure exceeding this value is removed, it will return to a sealing state.

In some preferred embodiments, the seal 57 can be a rubber plug or plastic plug or silica gel plug which is elastic. When being pierced, it can communicate with the outside or other chambers through the piercing element, and after the piercing element is removed, it can return to a sealing state under which liquids will not leak within a certain pressure range.

In some preferred embodiments, the second chamber 42 can be vacuumized, in this way, the second chamber 42 has no internal pressure, thus, once it is communicated with other chambers or the outside, samples will flow towards the second chamber 42.

Figure 18:
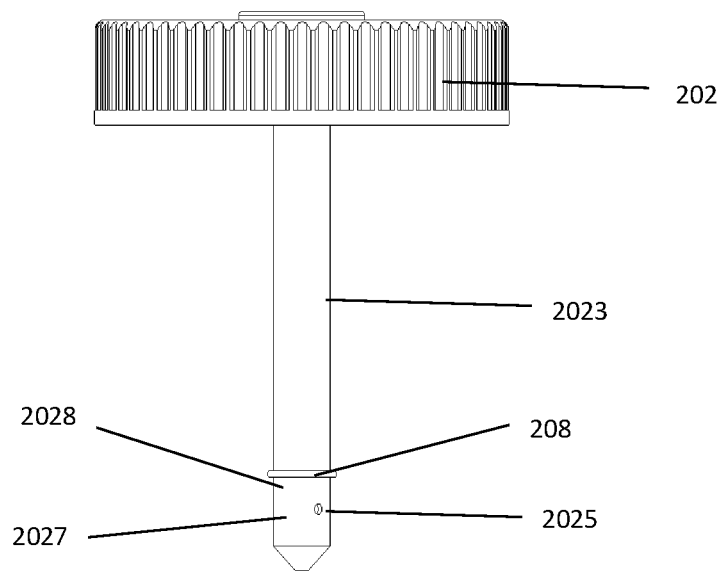
FIG. 18 is a perspective structural view of a first cover body with a sealing element according to an embodiment of the present invention.
Figure 19:
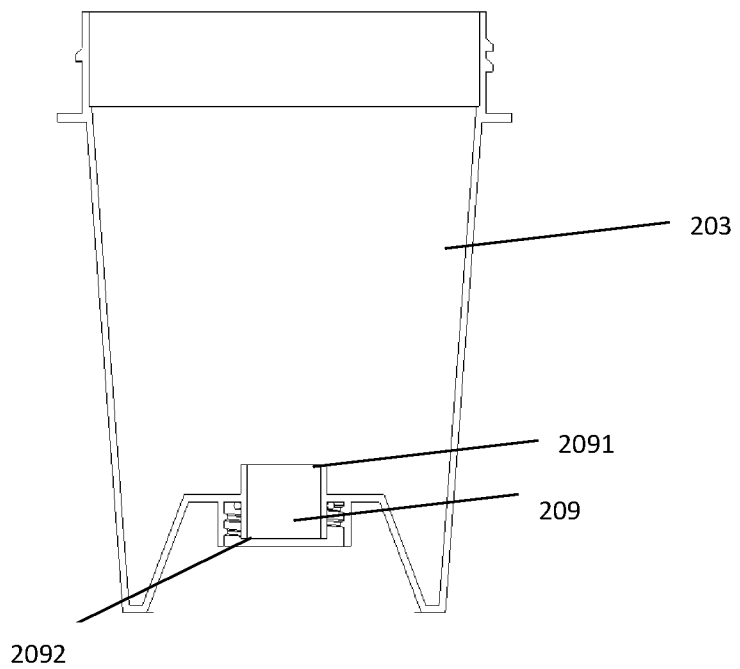
FIG. 19 is a perspective structural view of a first chamber according to an embodiment of the present invention (without a second chamber).
Figure 20:
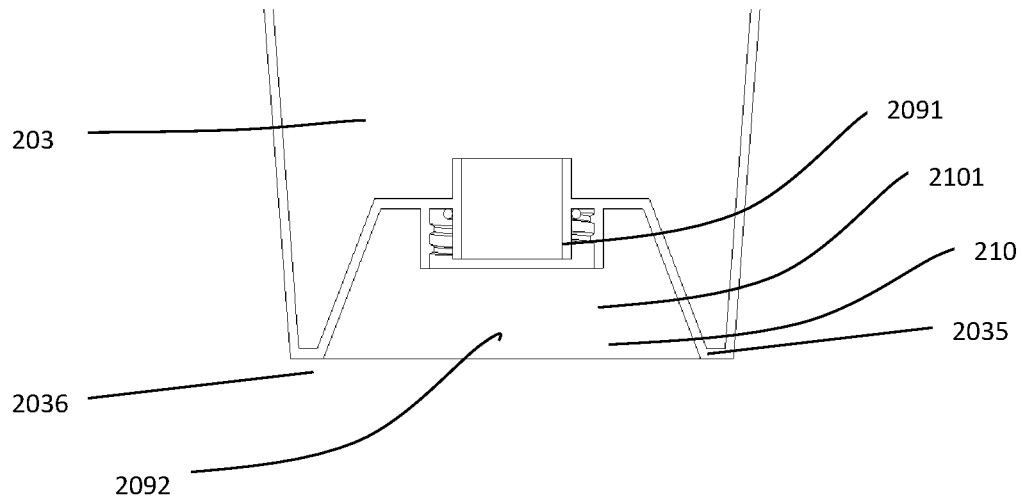
FIG. 20 is a cross-sectional view of a combination of a first chamber and a second chamber (a partially enlarged schematic structural diagram of a detachable combination of a first chamber and a second chamber)

In some preferred embodiments, after liquid samples are loaded to the second chamber 42, its shape and volume will change, as shown in FIGS. 18-19. After a certain number of liquid samples are loaded to the second chamber 42, its shape is expanded to cylinder-shaped from flat-shaped. Due to such flexibility or elasticity, and since its opening end is pierced by a piercing element when samples are loaded to the second chamber 42, the second chamber 42 can be extruded so that samples can flow out from the opening end pierced by the piercing element when samples loaded to the second chamber 42 need to be used.

In some preferred embodiments, the second chamber can a hard chamber, for example, being made from glass or plastic materials, and a self-sealing opening can be provided on the seal 57, for example, an opening similar to "sharp-angled bottle". In some preferred embodiments, the self-sealing opening can be directly provided on the second chamber.

Connector

Figure 49:
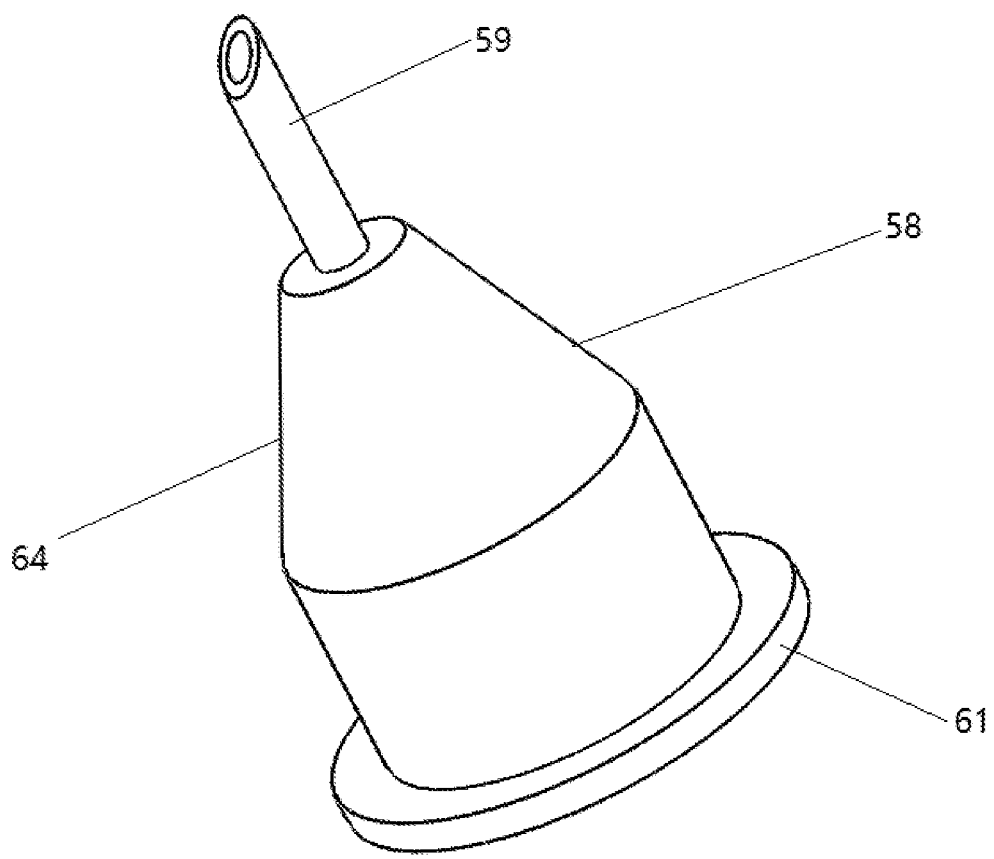
FIG. 49 is a schematic diagram of a connector according to an embodiment of the present invention.
Figure 50:
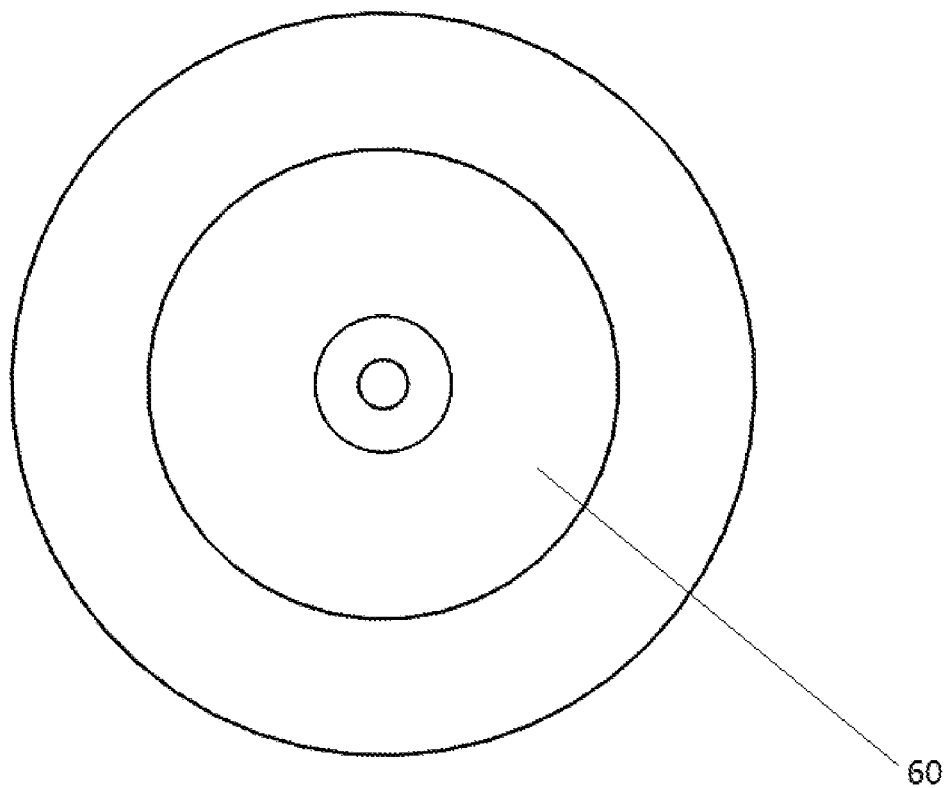
FIG. 50 is a bottom view of a connector according to an embodiment of the present invention.
Figure 51:
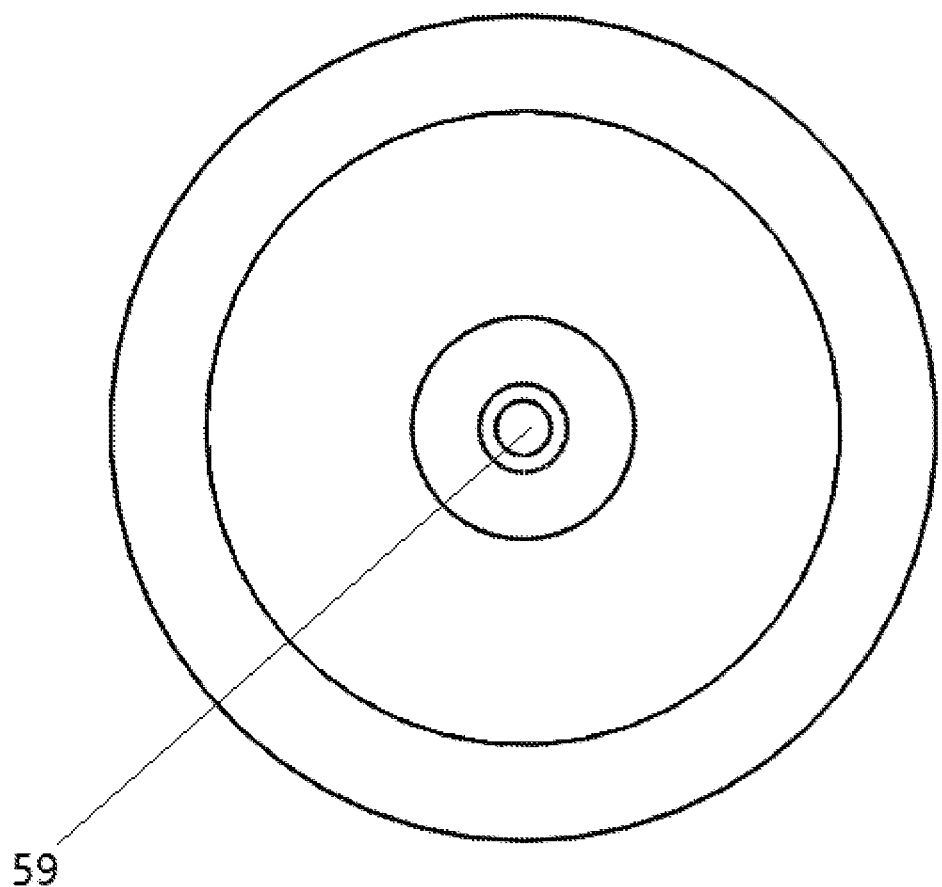
FIG. 51 is a top view of a connector according to an embodiment of the present invention.
Figure 52:
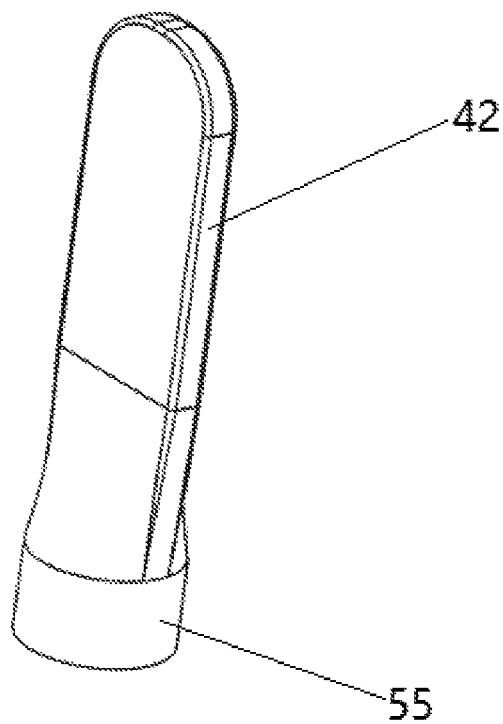
FIG. 52 is a schematic diagram of a second chamber according to an embodiment of the present invention.
Figure 53:
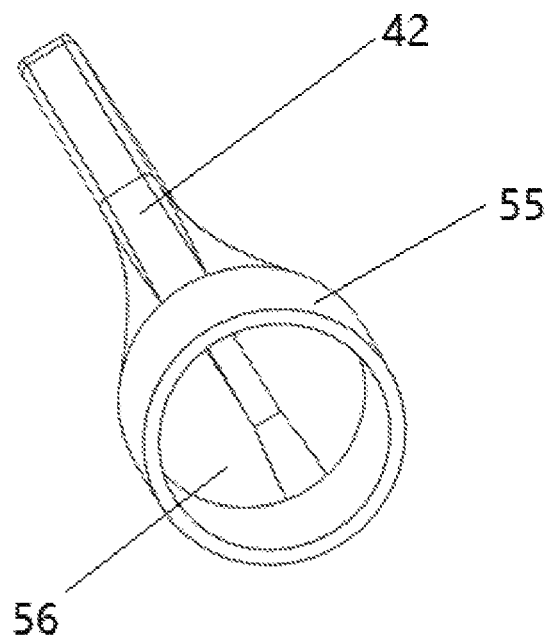
FIG. 53 is a schematic view of a second chamber shown in FIG. 52 from another angle. From the angle of FIG. 13, it can be seen that the bottom of the second chamber has an opening that enables the second chamber to be in fluid communication with outside or other chamber.
Figure 54:
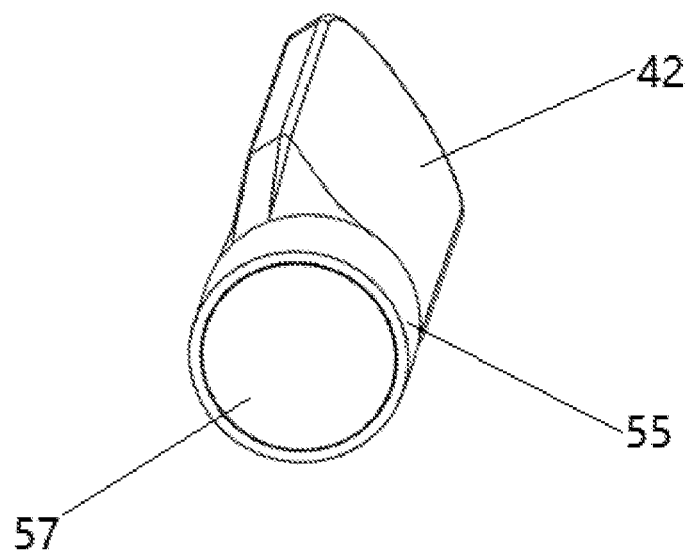
FIG. 54 is a schematic view in which the opening at the bottom of a second chamber shown in FIG. 53 is sealed.
Figure 55:
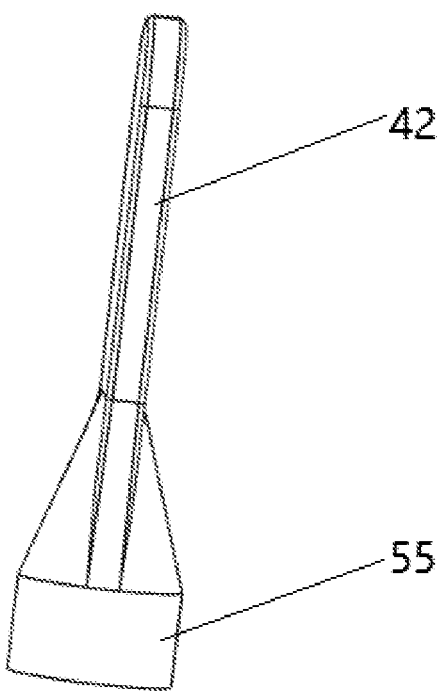
FIG. 55 is a schematic diagram of a second chamber shown in FIG. 52 from another angle. As can be seen from FIG. 15, the second chamber can be shrunk to a flat state when no samples are loaded into the second chamber.

As shown in FIGS. 49-51, in some specific embodiments of the present invention, the present invention further provides a connector 58 for communicating the second chamber 42 and the first chamber 41. In some preferred embodiments, the connector 58 is detachably connected or combined with the second chamber 42. In some preferred embodiments, when the chamber body is connected or combined with the connector, the connector can allow liquid to communicate between interior chamber and other chambers or the outside. In some preferred embodiments, when the chamber body is separated from the connector, the chamber body is in a self-sealing state. In some preferred embodiments, the connector 58 is used for communicating the second chamber 42 and other chambers, such as the first chamber 41, or the third chamber 43. In some preferred embodiments, the connector 58 is used for communicating the second chamber 42 and the outside.

As shown in FIG. 49, the connector 58 can comprise a piercing element 59 which can pierce the second chamber 42 under the action of an external force, establish a channel for the second chamber 42 to communicate with other chambers or the outside. In some preferred embodiments, the piercing element 59 is a needle shown in the figure.

In some preferred embodiments, the connector 58 comprises a communicating chamber 60, and the piercing element 59 communicates with the communicating chamber 60, and the communicating chamber 60 itself can communicate with other chambers, for example, the communicating chamber 60 can communicate with the first chamber 41. When the first chamber 41 is extruded, samples inside can enter the second chamber 42 along the piercing element 59 through the communicating chamber 60. In some preferred embodiments, the communicating chamber 60 can be used as an inlet for directly collecting samples.

In some preferred embodiments, the communicating chamber 60 can contain part of the first channel 47, and this part particularly includes the collecting tank 50 described previously, as shown in FIG. 36, this is a kind of assembly way for the connector and the first channel. Under such assembly way, the connector partitions the first channel and the third chamber 43, so that the first channel can only communicate the second chamber 42 and the first chamber 41, at this time, the second chamber 42 can only receive samples from the first chamber 41. Such way is particularly applicable to the situation under which samples in other chambers are used for detection. This can ensure that samples entering the second chamber 42 for second detection will not be polluted during initial detection, and after the first channel and the third chamber are partitioned, the outer periphery of the second chamber will not be polluted by samples from the third chamber, and after collection is completed and it is taken out, its external surface will not be polluted by samples.

In some preferred embodiments, a limiting structure can be provided for the connector 58 and the cover body 63. This limiting structure can prevent the connector 58 from being separated from the cover body. The outer wall of the connector 58 may contact the sample, so in such case, when the second chamber 42 is taken out, it would be better not to take out the connector 58 along with second chamber 42, otherwise there will be samples. In other words, when the second chamber 42 is taken out, the connector 58 shall be separated from the second chamber 42. Such separation can be achieved by limiting the movement of the connector through a limiting structure. In some preferred embodiments, the limiting structure can be provided on the cover body 63. In some preferred embodiments, the limiting structure can be provided on the connector 58.

In some preferred embodiments, a stepped surface 61 is provided on the end face of the connector 58. The stepped surface 61 can be used as a reference surface for the connector 58 to cover on the first channel 47. In addition, after the second chamber collects samples, the connector 58 will be connected to the second chamber 42 due to the piercing element 59, at this time, an external force shall be applied to separate the second chamber and the connector 58. However, the connector itself has been polluted by samples, so it can not be operated manually. In such case, due to the extrusion of the stepped surface 61, the action of the assembly structure of second chamber 62 on the cover body 63 on the stepped surface 61 can be used to ensure that the connector 58 is still in the apparatus and will not be pulled out along with the second chamber 42 when it is separated. Moreover, the connector 58 further comprises a tapered surface 64 whose primary function is to provide convenience for the installation of the connector 58.

Figure 43:
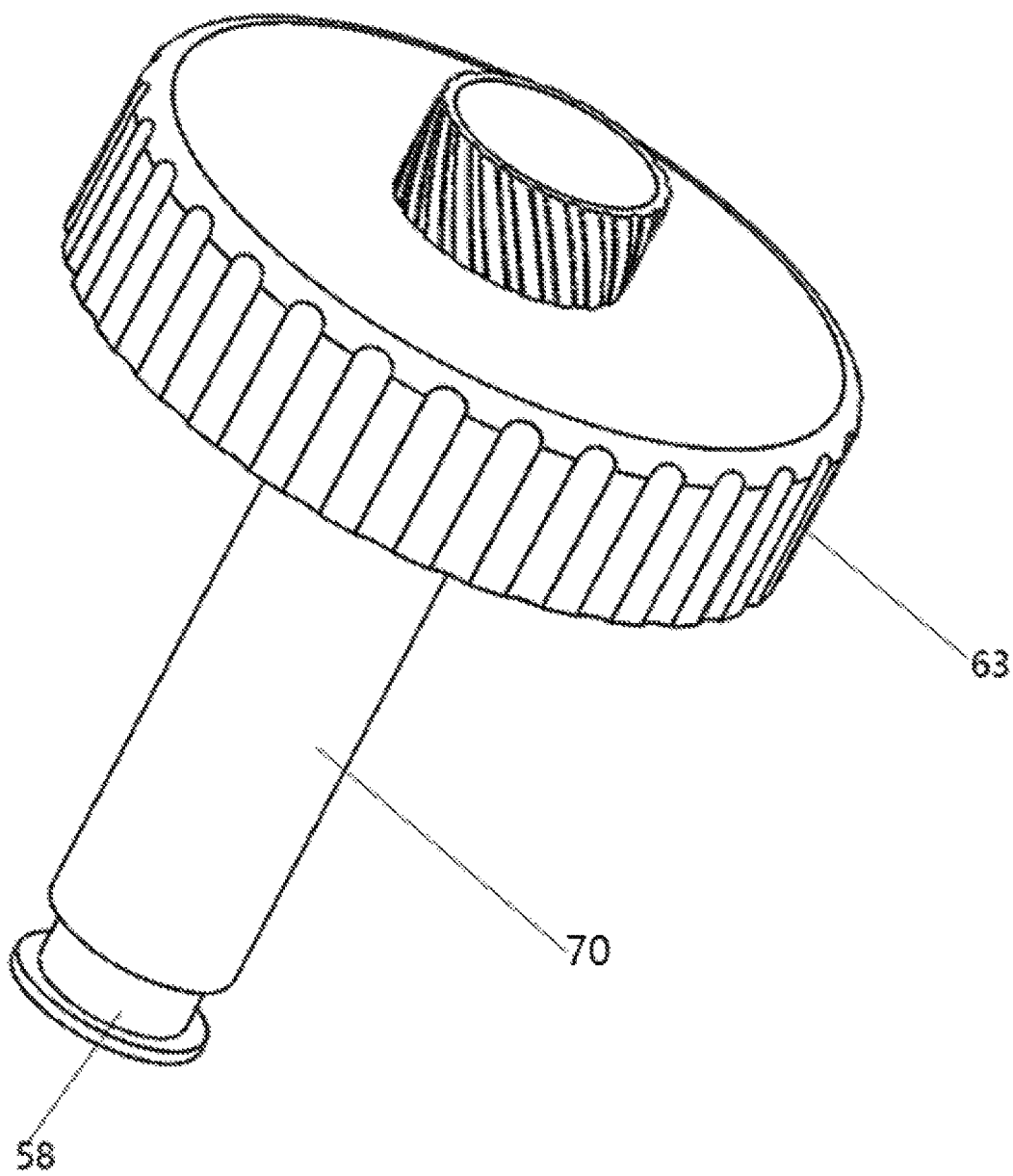
FIG. 43 is a schematic diagram of a cover body according to an embodiment of the present invention, wherein the second chamber and the connector are assembled to the cover body.
Figure 44:
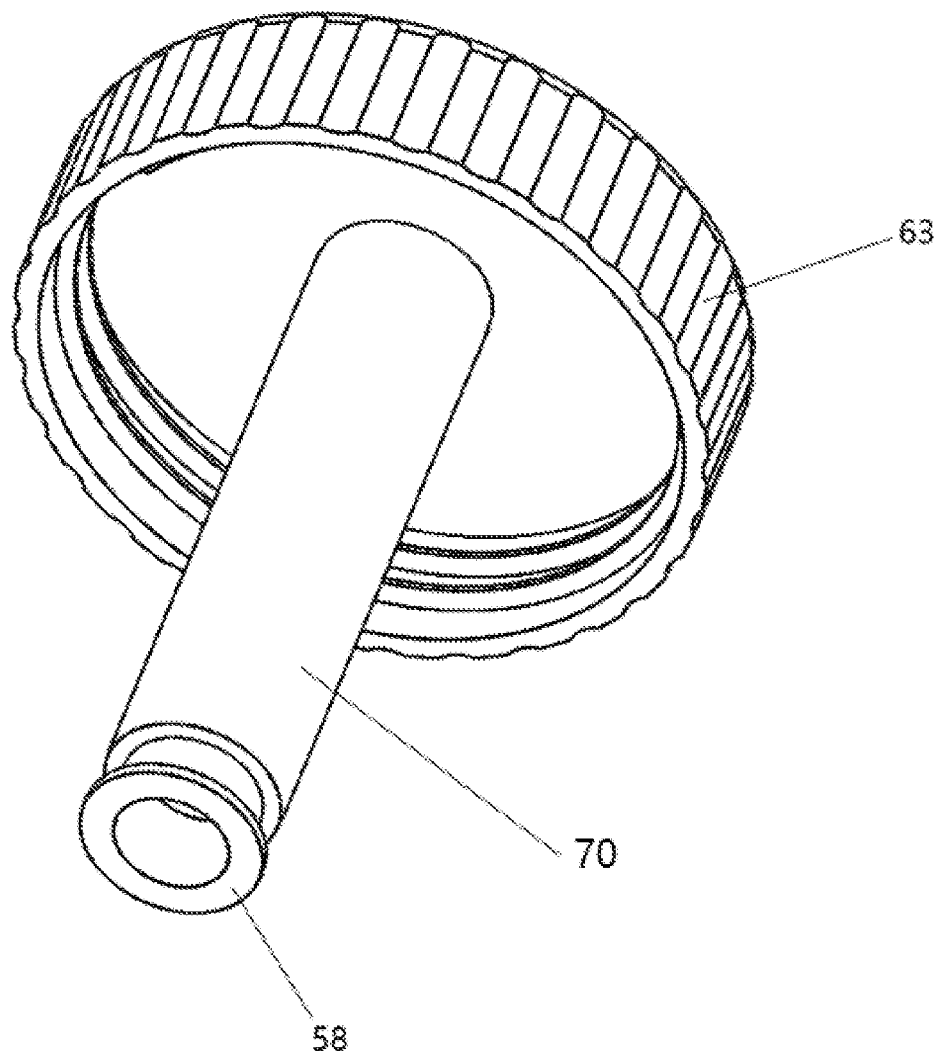
FIG. 44 is a schematic diagram of a cover body shown in FIG. 3 from another angle.
Figure 45:
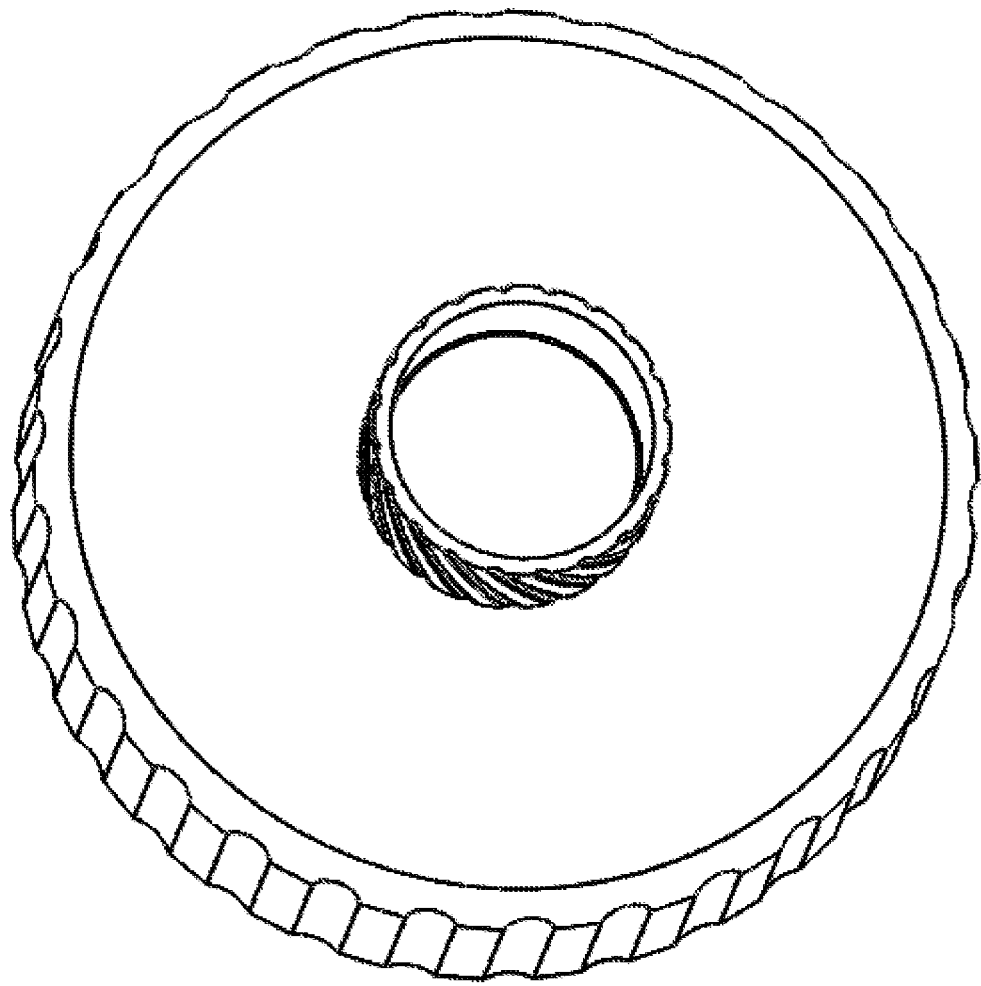
FIG. 45 is a structural view of an upper part of a cover body shown in FIG. 3, showing the assembled handle or knob structure.
Figure 46:
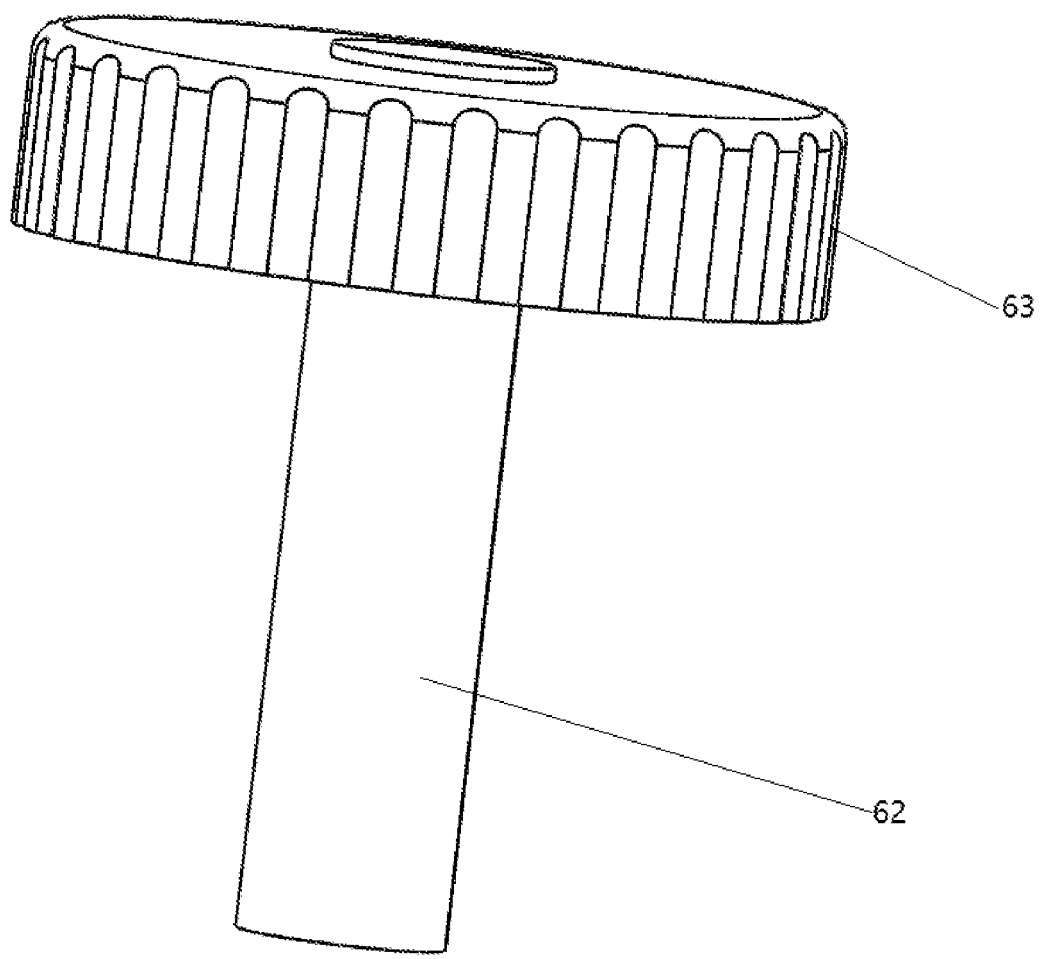
FIG. 46 is a schematic diagram of a cover body according to an embodiment of the present invention, wherein the second chamber has not been assembled to the cover body.

As shown in FIGS. 43-44, in a specific embodiment of the present invention, the connector 58 can be installed at the lower end of the assembly structure of second chamber 62 on the cover body 63 during initial use, and cover on the first channel 47 with the covering of the cover body 63. During initial use or initial assembly, the connector 58 does not communicate the second chamber. Only when it is necessary to collect samples for second confirmatory detection, the connector 58 will communicate the second chamber under a certain action.

For example, the state shown in FIGS. 7-8 and 36 is a state under which the connector 58 has not been communicated with the second chamber 42. At this time, liquid samples have not been collected in the second chamber 42. Under such state, the connector 58 is pushed towards the second chamber 42 through the matching relation or an external force, then the piercing element 59 on the connector 58 can pierce the outer wall of the second chamber or the seal 57 on the second chamber so as to achieve communication with the second chamber. For another example, the state shown in FIG. 19 can be interpreted as a state under which the connector 58 is pulled out from the second chamber. At this time, enough liquid samples have been collected in the second chamber. Then, if the connector 58 is pulled out, the pierced outer wall of the second chamber or the pierced seal 57 on the second chamber can be closed naturally. Such natural closure state can bear the pressure from the liquid samples collected inside. When liquid samples are needed, they can flow out from the pierced position after the second chamber is extruded.

Cover Body

As shown in FIGS. 43-46, in some particular embodiments, the present invention provides a cover body 63. In some preferred embodiments, as shown in FIG. 2, the cover body 63 can be connected to the seal connection cover 66, and such connection can be a detachable combination or connection through a connection part 69, in other words, the cover body 63 can cover on, or be taken down from the seal connection cover 66. In some preferred embodiments, the seal connection cover 66 may not be provided, and the cover body 63 directly covers at the port of the third chamber 43, or the cover body 63 is detachably connected or combined with the port of the third chamber 43. When the cover body 63 covers, the sample collection apparatus provided in the present invention can be sealed overall. As described previously, such sealing can be ordinary sealing or a sealing structure with high requirements according to the actual needs.

In some preferred embodiments of the present invention, the second chamber 42 can be contained in the cover body 63 while cooperating the sealing, so that the second chamber 42 is in a position or state where samples can be collected at any time. Of course, in some preferred embodiments of the present invention, the second chamber 42 can be in a position or state where samples can be collected at any time by other ways. In some preferred embodiments, an assembly structure of second chamber 62 is provided on the cover body 63, and the second chamber 42 can be detachably connected or combined with the assembly structure 62.

Before the apparatus provided in the present invention is used (for example, when it is transported and stored, or sold), the second chamber 42 can be separated from the assembly structure 62 if such separation can reduce the space occupied by the whole structure provided in the present invention, then during use, the second chamber 42 is put into the assembly structure 62, and the second chamber can be installed at a suitable position along with the assembly structure. In some preferred embodiments, an assembly channel 70 is provided on the cover body 63, and the assembly structure of second chamber 62 can be detachably connected or combined with the assembly channel 70, in other words, the second chamber can be put into the assembly structure, and then put into the cover body 63 through the assembly structure.

In some preferred embodiments, the connector 58 will also be put into the assembly structure 62, but this does not mean the connector 58 is directly communicated with the second chamber 42. As described previously, the connector 58 can achieve liquid communication or separation with the second chamber 42 under other cooperations or external forces, according to actual needs.

Assembly Structure of Second Chamber

In some preferred embodiments of the present invention, the present invention provides an assembly structure of second chamber 62. The main function of the assembly structure 62 is to contain the second chamber. In some preferred embodiments of the present invention, the second chamber 42 is a flexible body and its outer wall can be extruded, and the second chamber needs to be detachably connected or combined with the cover body or other chambers. During such detachable connection or combination, a certain external force will surely be applied to the second chamber. If there is no external protection structure for this flexible body, liquids in the second chamber may be extruded out due to improper force, but such situation must be avoided. Therefore, the assembly structure not only bears the second chamber, but also supports and temporarily protects the second chamber.

In some preferred embodiments, the second chamber can be a hard chamber, for example, it is made from glass or plastic materials. In such case, the assembly structure can also play a role of protecting the second chamber, and further, provide a convenient way for taking or holding the second chamber.

Figure 47:
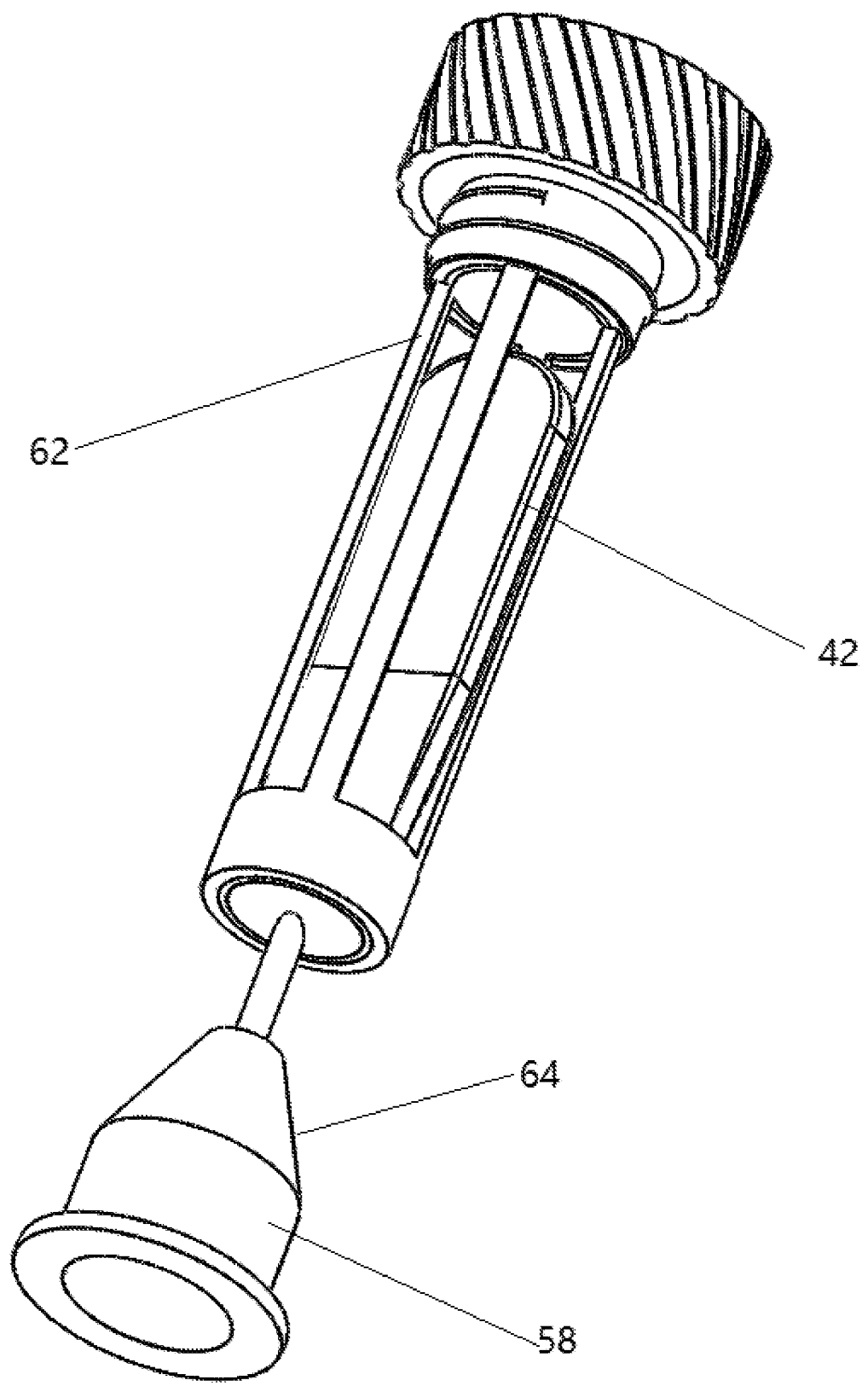
FIG. 47 is an assembly relationship diagram of a second chamber and an assembly structure and a connector according to an embodiment of the present invention.
Figure 48:
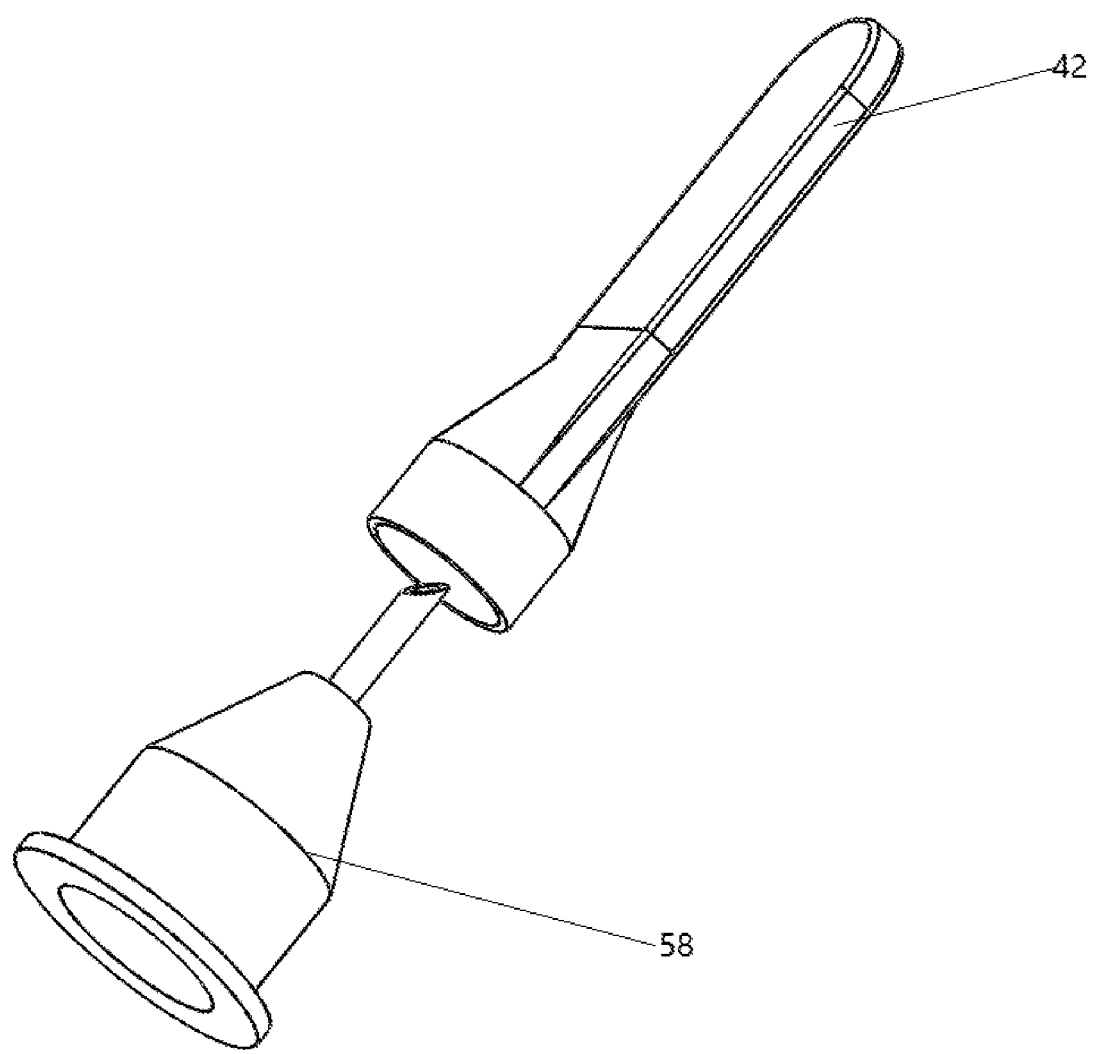
FIG. 48 is an assembly relationship diagram of a second chamber and a connector according to an embodiment of the present invention.
Figure 56:
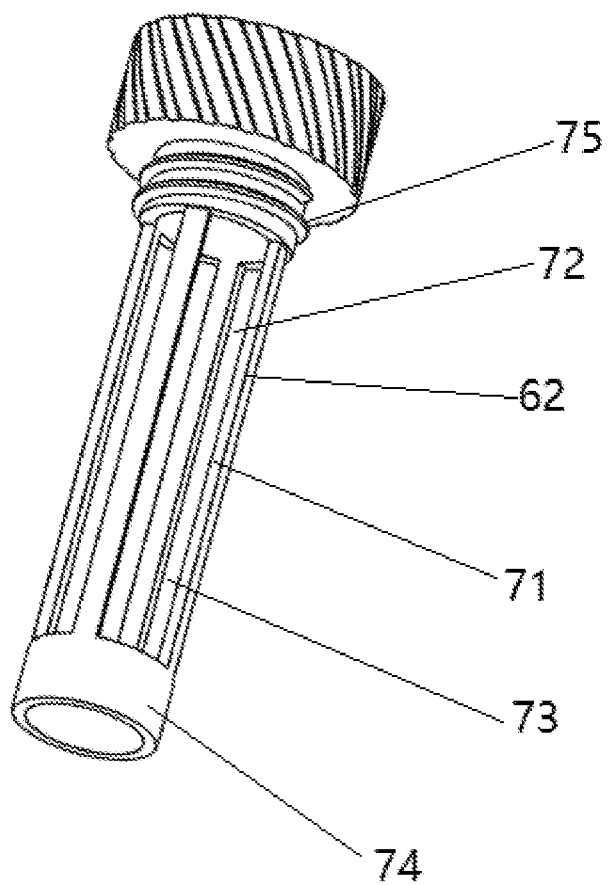
FIG. 56 is a schematic diagram of an assembly structure of a second chamber according to an embodiment of the present invention.
Figure 57:
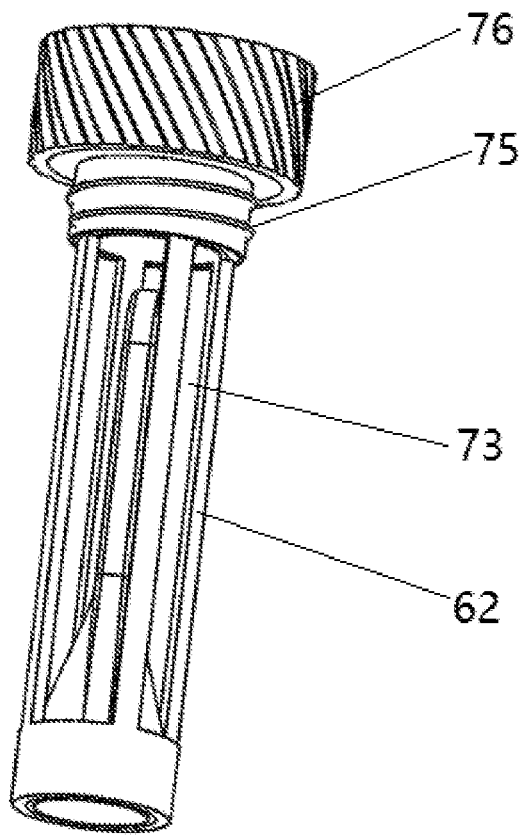
FIG. 57 is a schematic diagram of the combination of an assembly structure and a second chamber according to an embodiment of the present invention.
Figure 58:
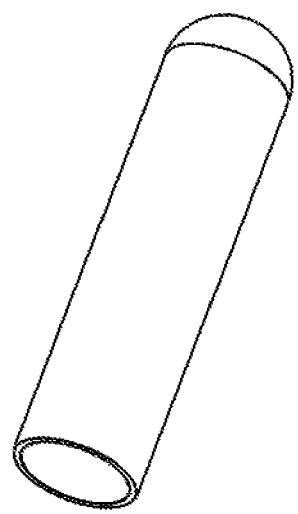
FIG. 58 is a schematic diagram of a second chamber shown in FIG. 57 after being loaded into samples.
Figure 59:
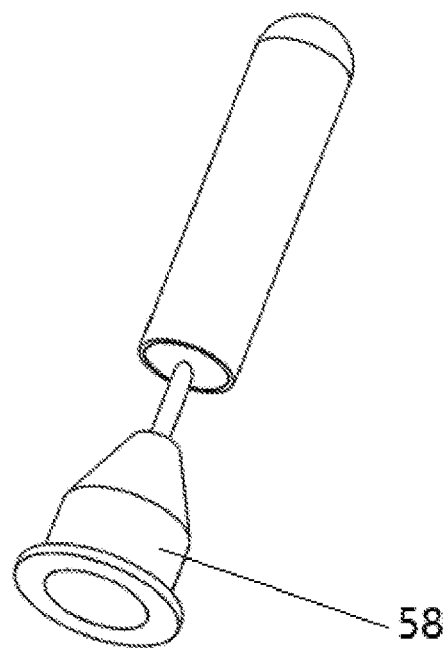
FIG. 59 is a schematic diagram showing separation from a connector after sample collection is completed in a second chamber according to an embodiment of the present invention.
Figure 60:
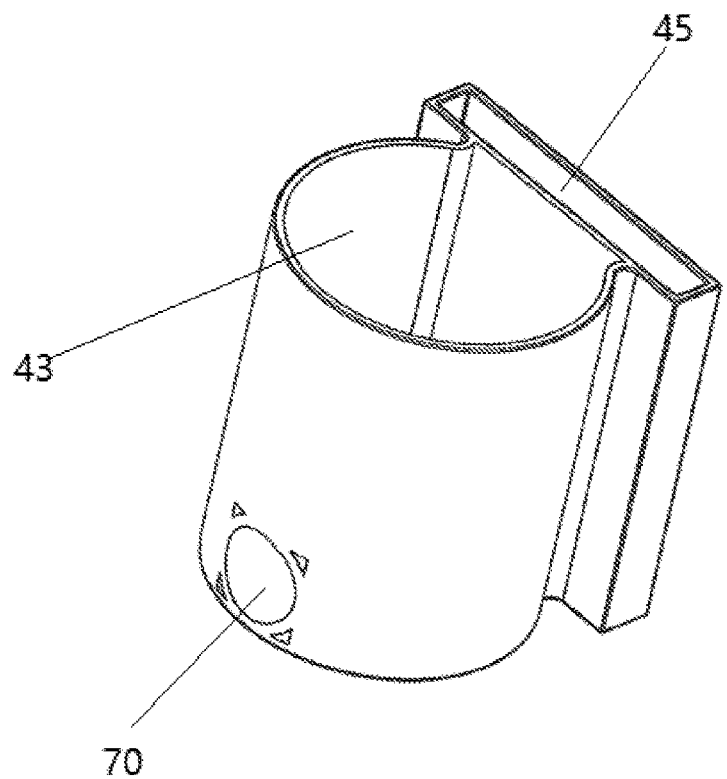
FIG. 60 is a schematic diagram of a third chamber according to an embodiment of the present invention; the third chamber may be a box body. In this specific embodiment, the testing area may be disposed on one side of the third chamber.
Figure 61:
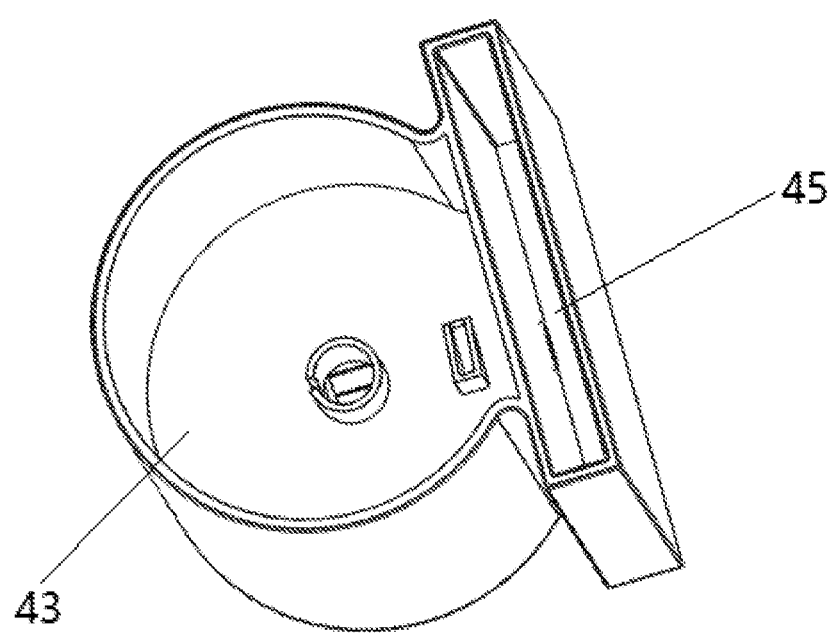
FIG. 61 is a schematic diagram of a third chamber in FIG. 60 from another angle from which the positions of a first channel and a second channel can be shown.
Figure 62:
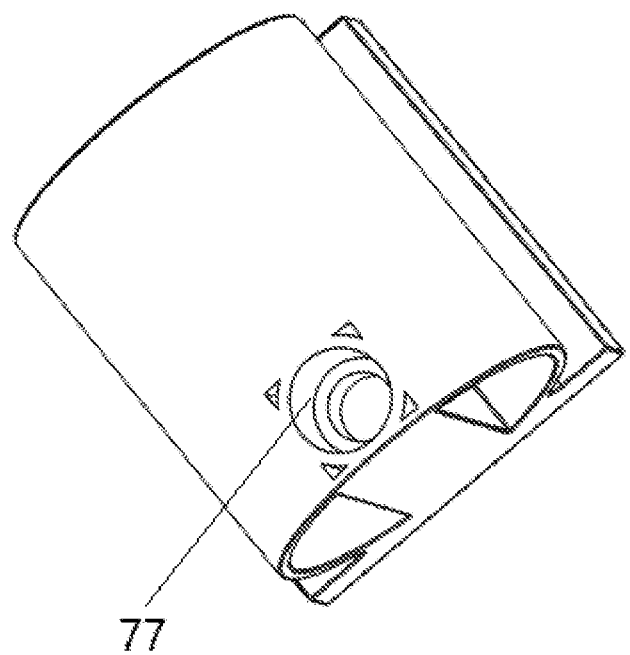
FIG. 62 is a schematic diagram of a third chamber in FIG. 60 from another angle from which a partial structure of a pipetting channel can be shown.
Figure 63:
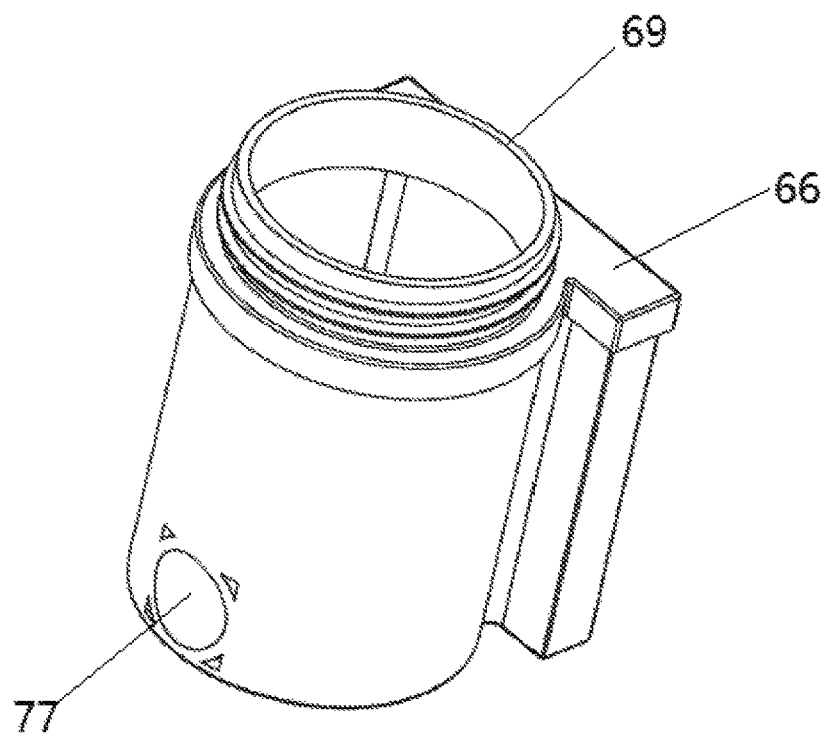
FIG. 63 is a schematic diagram of a third chamber according to another embodiment, wherein a sealing connection cover is mounted on the third chamber.

In some preferred embodiments, as shown in FIGS. 47, and 56-57, the assembly structure comprises an outer wall 71 and an inner chamber 72, and the second chamber can be put into the inner chamber. The second chamber and the inner chamber can be assembled by fixed combination and connection or detachable combination and connection. The purpose of assembly is to allow the second chamber and the assembly structure to be connected or combined with the cover body or other chambers and components as a whole. As described previously, the assembly structure 62 needs to play a role of supporting and protecting the second chamber. Therefore, the outer wall of the assembly structure 62 must have a certain shape and hardness. The shape shall exceed the external shape range of the second chamber, and the hardness shall be able to bear a certain pressure without extruding the second chamber, such as extruding by a finger. Since the second chamber is often moved or manually operated under the working environment, and the second chamber or the assembly structure will not be extruded deliberately during use, thus the requirement for hardness is not too high. Basically, the hardness of common plastic materials can meet this requirement.

In some preferred embodiments, the outer wall of the second chamber may be extruded to release samples, so some hollow structures 73 are provided on the outer wall of the assembly structure, so that the second chamber can be extruded passing through such hollow structures 73. In some preferred embodiments, due to the existence of these hollow structures 73, the assembly structure itself can bear compressional deformation within a certain range. To discharge samples, we only need to extrude the assembly structure, and through the assembly structure, apply pressure to the second chamber.

In some preferred embodiments, a retaining ring 74 that matches with the opening end 55 of the second chamber is provided on the assembly structure 62. The outer wall of the opening end 55 is assembled with the inner wall of the retaining ring 74 by fixed connection and combination or detachable connection and combination, so that the second chamber is fixed on the assembly structure. In some preferred embodiments, the retaining ring 74 and the opening end 55 are both located at the lower end of the second chamber and the assembly structure.

In some preferred embodiments, the assembly structure 62 is detachably connected or combined with the cover body 63. In some preferred embodiments, an assembly connecting part 75 is provided on the assembly structure 62. The assembly connecting part 75 can be detachably connected or combined with the cover body. In some preferred embodiments, the assembly connecting part 75 is detachably connected or combined with the cover body 63 through a screw thread, and in some other preferred embodiments, the assembly connecting part 75 can be connected with the cover body by other detachable connection ways.

Figure 41:
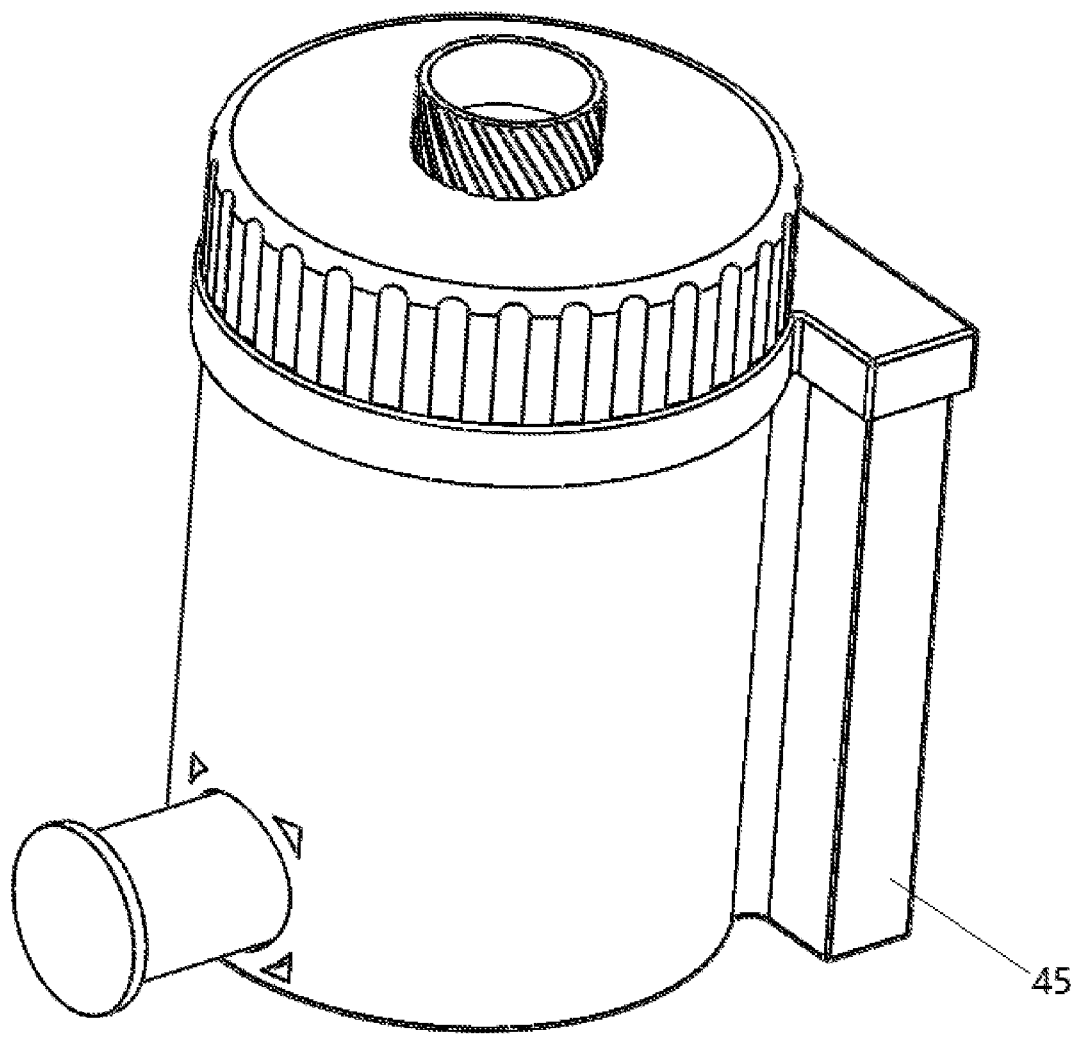
FIG. 41 is an overall structural diagram of a sample detection apparatus according to an embodiment of the present invention.
Figure 42:
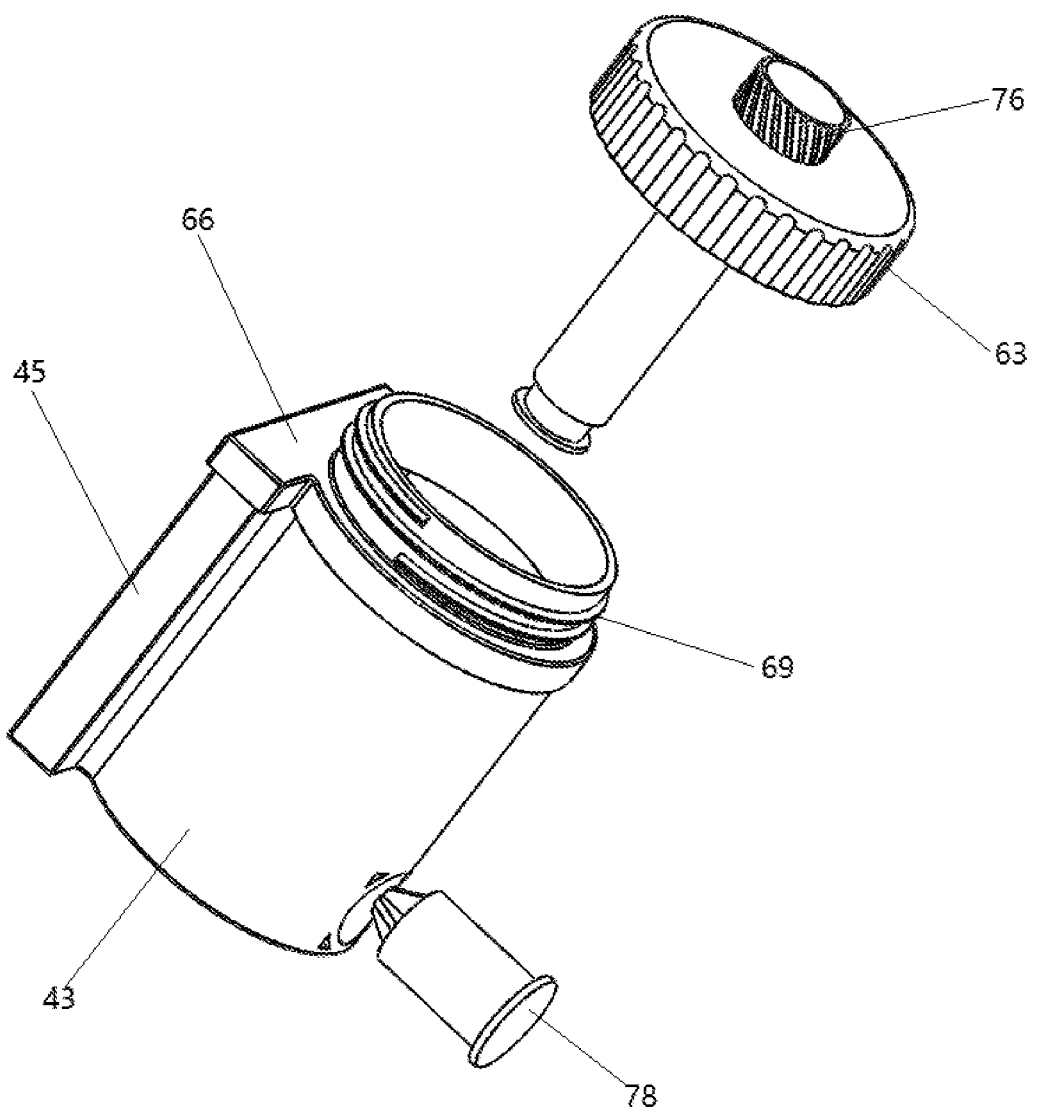
FIG. 42 is a partial exploded view of a sample detection apparatus according to an embodiment of the present invention, in the figure, the cover body is in an opened state and the pipetting plug is not inserted.

In some preferred embodiments, for the convenience of the separation and installation of the second chamber, as shown in FIGS. 56-57, a knob 76 is provided on the assembly structure 62, as shown in FIGS. 41-43, after the assembly structure is put into the cover body 63, the knob 76 is exposed on the outer surface of the cover body, and the assembly structure and the second chamber can be taken out by reversely rotating the knob 76. It should be noted that the knob 76 is only a feasible way, and in fact, this function can also be achieved by a handle, pick or hanging ring, as long as this component can expose on the outer surface of the cover body to provide convenience for the installation and separation of the second chamber. In the present invention, specific ways of this component are not restricted.

In some preferred embodiments, the seal 57 of the second chamber can be fixed on the assembly structure 62, for example, provided at the retaining ring 74, or outside the retaining ring 74, or on other positions where the interior second chamber 42 can be communicated when passing through the seal 57.

First Channel

In some preferred embodiments, the first chamber provided in the present invention does not comprise a direct external collection port, instead, liquid samples are collected through other chambers such as the third chamber 43. In such case, the first chamber and the third chamber are in a fluid communication state. In some preferred embodiments, the first chamber is directly communicated with the third chamber. In some preferred embodiments, the first chamber is communicated with the third chamber through a first channel 47, as shown in FIGS. 27-29, the function of the first channel 47 is to achieve liquid communication between the first chamber and the third chamber, and fluids can enter the first chamber from the third chamber through the first channel. For example, in the way shown in the figure, the first channel 47 is located on the bottom of the third chamber 43. In this way, samples entering the third chamber can naturally flow into the first chamber due to gravity. The first channel 47 is directly communicated with the third chamber 43, the first chamber 41 is located under the third chamber 43, and the third chamber 43 comprises an upward collection port 49 through which liquid samples can enter the third chamber 43 and naturally drop or flow downward due to gravity. The portion of liquid samples that naturally drop and enter the first channel can directly drop into the first chamber 41. During the naturally dropping process, there must be a portion of liquid samples unable to directly fall into the first channel 47, then they can gather on the bottom of the third chamber 43. When the liquid level exceeds the height that the first channel 47 exceeds the bottom of the third chamber 43, this portion of liquids will flow into the first chamber 41 through the first channel 47. In some preferred embodiments, samples can also enter the third chamber from the first chamber.

In some preferred embodiments, for example, according to the figure, a collecting tank 50 can be provided on the side wall of the first channel 47, which can be as high as or slightly higher than the bottom of the third chamber 43. The portion of liquid samples that do not enter the first channel 47 during the naturally dropping process will finally gather on the bottom of the third chamber 43. Since the height of the collecting tank is close to that of the bottom of the third chamber 43, the liquid samples on the bottom of the third chamber 43 are very likely to enter the first channel 47 through the collecting tank 50 and flow into the first chamber 41 along the first channel 47. It should be noted that, we do not need all samples in the third chamber 43 to flow into the first chamber 41, instead, we only need a portion. Therefore, as long as enough liquids are collected, a portion of the samples will surely enter the first channel 47. Moreover, in actual application, the whole chamber may be in a non-static state, for example, it is held by a hand, then the collected samples are more likely to enter the collecting tank 50 due to shaking.

In some preferred embodiments, the first channel 47 can be closed, for example, when samples in the first chamber are transferred to the second chamber, or the second chamber is taken out and put in. The second chamber is used for collecting liquid samples for second confirmatory detection, so when the first channel is closed, the first chamber and the third chamber are in a liquid partition state. For example, in some preferred embodiments, samples first enter the third chamber and can flow into the first chamber along the above first channel, and liquids in the first chamber can enter the second chamber due to external forces. In some preferred embodiments, when the first chamber and the second chamber are in a fluid communication state, the first channel can be closed. In some preferred embodiments, as shown in FIG. 36, the first channel can be closed through a connector. Under such assembly way, the connector partitions the first channel and the third chamber 43, so that the first channel can only communicate the second chamber 42 and the first chamber 41, at this time, the second chamber 42 can only receive samples from the first chamber 41. Such way is particularly applicable to the situation under which samples in other chambers are used for detection. This can ensure that samples entering the second chamber 42 for second detection will not be polluted during initial detection, and after the first channel and the third chamber are partitioned, the outer periphery of the second chamber will not be polluted by samples from the third chamber, and after collection is completed and it is taken out, its external surface will not be polluted by samples.

Fourth Chamber

In some preferred embodiments, the present invention provides a fourth chamber for temporarily storing test samples. As shown in FIGS. 27-28, the samples in the fourth chamber are mainly used for initial detection. In some preferred embodiments, samples are directly detected in the fourth chamber. In some preferred embodiments, the samples in the fourth chamber are pushed into the testing area for detection. In some preferred embodiments, samples can be collected in the fourth chamber directly. In some preferred embodiments, the fourth chamber can collect samples through other chambers.

In some preferred embodiments, when the fourth chamber collects samples through other chambers, the fourth chamber can be in fluid communication with or partition with the third chamber. In some preferred embodiments, when the fourth chamber and the third chamber are in fluid communication state, the liquid collected in the third chamber can enter the fourth chamber simultaneously, or the fourth chamber and the third chamber are in communication state when initially collecting samples, for example, as shown in FIGS. 27-28, the fourth chamber is located at the bottom of the third chamber, and the bottom of the third chamber is provided with an opening that communicates with the fourth chamber, by this way, liquid samples that enter the third chamber can flow directly into the fourth chamber under the force of gravity, and the fourth chamber can substantially complete the samples synchronously with the third chamber. In some preferred embodiments, the fourth chamber can be directly in communication with the third chamber. In some preferred embodiments, the fourth chamber can be in liquid communication with the third chamber via the second channel.

In some preferred embodiments, the fourth chamber can be in fluid communication with or partition with the testing area. When initially collecting samples, the fourth chamber can be separated from the testing area, that is, the collection and detection can be independent of each other. In some preferred embodiments, the partition and communication between the fourth chamber and the testing area can be achieved by the detection inlet. As aforesaid stated, the detection inlet 46 is a port for communication between the collection chamber and the testing area, however, it is not required to always communicate the testing area with the collection chamber, and they can be separated and communicated as necessary. In such circumstance, a detection inlet partition 54 can be disposed at the detection inlet 46 to achieve the function of adjusting or setting the detection inlet 46 as communication or partition. By this way, the liquid in the third chamber 43 can be introduced into the testing area 45 as needed.

For example, in the manner shown in FIG. 67, the detection inlet partition 54 has a certain hardness and thickness, with a notch thereon. The surfaces of the notches are in an interference fit, in case of no pressure or insufficient pressure, the entire notch is in a closed state, to partition the liquid flow, however, when one side of the notch is subjected to pressure, the notch is opened in the direction of pressure to naturally release pressure, that is, when there are a certain amount of samples on one side of the notch or a pressure is exerted on the samples, the notch will be opened to achieve liquid communication between the test chamber and the testing area 45, and when the pressure is removed, the notch will return to the closed state.

In some preferred embodiments, when the fourth chamber 44 and the testing area 45 are in a fluid communication state, the fourth chamber 44 and the third chamber 43 are in a liquid partition state, by this way, it can ensure that the testing area is not affected by contamination caused by other chambers, and achieve the quantitative detection. As long as the volume of the fourth chamber is set, the quantitative detection of samples that enter the testing area can be carried out.

Second Channel

As previously stated, the role of the second channel 48 is to achieve the liquid communication between the fourth chamber 44 and the third chamber 43, thereby the fourth chamber 44 and the third chamber 43 can collect samples simultaneously. In some preferred embodiments, considering that this part of samples should avoid contamination, they should be avoided to contact with samples in other chamber during the detection, and prevent backflow after contacting the testing element of the testing area. When the samples in the fourth chamber are transferred to the testing area, the second channel is also sealed. For example, as shown in FIG. 28, the initial position of the second pipetting element 53 is on the side below the second channel 48. During the collection of samples in the fourth chamber 44, the position of the second channel is unchanged, and when the samples need to be pushed into the testing area, the second pipetting element 53 moves toward the testing area 45, which is also a process of gradually sealing the second channel 48. In some preferred embodiments, the distance between the second channel 48 and the testing area is less than the length of the second pipetting element 53 itself, such that the second channel 48 is still in a state of being closed by the second pipetting element 53 after the pipetting is completed.

First Pipetting Element, Second Pipetting Element, Pipetting Channel and Pipetting Plug The present invention provides a pipetting element, to transfer liquid within the first chamber 41 into the second chamber 42. In some preferred embodiments, the pipetting element is capable of transferring the liquid in the fourth chamber 44 to the testing area 45. The above two types of transfer can be synchronized or independently.

In some preferred embodiments, as shown in FIGS. 67-69, 71-74, the pipetting element comprises a first pipetting element 52 for transferring samples in the first chamber 41 into the second chamber 42, and a second pipetting element 53 for transferring the samples in the fourth chamber 44 to the testing area 45. The first pipetting element 52 and the second pipetting element 53 can be moved independently or can be linked. The first pipetting element 52 and the second pipetting element 53 are usually pushed to move and produce thrust to the liquid in their respective chambers, so that these samples are transferred to other chambers or areas. For example, the first pipetting element 52 can be moved by an external force to squeeze samples in the first chamber 51 and generate pressure, so that the samples are transferred to the desired direction or chamber, for example, entering the second chamber through the connector 58. In some preferred embodiments, the second pipetting element 53 can be moved by an external force to squeeze samples in the fourth chamber 44 and generate pressure, so that the samples are transferred to the desired direction or chamber, for example, entering the testing area 45.

In some preferred embodiments, the first pipetting element 52 and the first chamber 41 are in the same pipetting channel 51, and the first pipetting element is pushed to achieve the above extrusion. In some preferred embodiments, the second pipetting element and the fourth chamber are in the same pipetting channel, pushing the second pipetting element to achieve the above extrusion. In some preferred embodiments, first pipetting element, second pipetting element, first chamber, and fourth chamber are in the same pipetting channel 51, and pushing one of the first pipetting element or the second pipetting element can simultaneously achieve the above extrusion, in this case, the first pipetting element and the second pipetting element can achieve the linkage state level by level. For example, when the first pipetting element is pushed, the first pipetting element is first forced to move and squeeze the sample in the first chamber. The resistance for moving the second pipetting element may be greater than that for moving the liquid in the first chamber, at this time, the sample in the first chamber is preferentially transferred. When the sample in the first chamber is discharged to the first pipetting element and the force on the second pipetting element is greater than the resistance of the second pipetting element, the second pipetting element begins to squeeze the sample in the fourth chamber so that the sample in the fourth chamber is also transferred, or, in other cases, the second pipetting element is pushed and first forced to move and squeeze the sample in the fourth chamber. At this time, the resistance of the first pipetting element may be greater than the resistance of the liquid in the fourth chamber, and the sample in the fourth chamber is preferentially transferred. When the sample in the fourth chamber is discharged to the second pipetting element, and the force on the first pipetting element is greater than the resistance of moving the first pipetting element, the first pipetting element begins to squeeze the sample in the first chamber so that the sample in the first chamber is also transferred. In some cases, we hope that, when the first pipetting element and the second pipetting element are in the linkage state as described above, the liquid in the first chamber is preferentially transferred, then the liquid in the fourth chamber passes through the entrance of the testing area, to ensure that the liquid sample transferred to the second chamber from the first chamber will not be contaminated during the detection. Of course, the transfer of the first chamber and the fourth chamber can also be performed simultaneously. Since the structure is arranged to flow along the liquid flow direction, there is less possibility of backflow or contamination.

In some preferred embodiments, the pipetting channel can be in fluid communication or partitioned with the second chamber. In some preferred embodiments, the pipetting channel can be in fluid communication or partitioned with the testing area. In some preferred embodiments, first pipetting element and second pipetting element separate the pipetting channel into a first chamber and a fourth chamber. In some preferred embodiments, the fourth chamber is partitioned with the second chamber by a second pipetting element. Actually, as shown from the figure, in some preferred embodiments, the first chamber and the fourth chamber are two segments on the pipetting channel.

In some preferred embodiments, when the sample in the first chamber is transferred into the second chamber, the volume of the first chamber decreases accordingly. In some preferred embodiments, when the volume of the first chamber is reduced, the first pipetting element and the second pipetting element are approaching. In some preferred embodiments, when the sample in the fourth chamber is transferred to the test area, the volume of the fourth chamber is reduced. In some preferred embodiments, when the liquid in the first chamber is transferred, the liquid communication state between the first chamber and the second chamber is blocked. In some preferred embodiments, when the liquid in the fourth chamber is transferred, the liquid communication state between the fourth chamber and the third chamber is blocked. In some preferred embodiments, the communication state of the fourth chamber and the third chamber is blocked by sealing the second channel during the movement by the second pipetting element.

Another feature of the present invention is that quantitative detection can be achieved. For example, in some preferred embodiments, the initial volume of the fourth chamber is fixed, that is, the amount of samples that are loaded in the fourth chamber can be determined before the fourth chamber is stressed. In some preferred embodiments, the second pipetting element is fixed at the initial position within the pipetting channel. In some preferred embodiments, the initial volume of the first chamber is fixed, that is, the amount of sample that are loaded in the first chamber can be determined before the first chamber is stressed. In some preferred embodiments, first pipetting element is fixed at the initial position in the pipetting channel. In some preferred embodiments, the first pipetting element and the second pipetting element are fixed relative to the initial position in the pipetting channel.

In some preferred embodiments, the pipetting channel has a pipetting opening 77 through which an external force can be applied to the pipetting channel to achieve the above extrusion. In some preferred embodiments, the pipetting opening can be sealed by a first pipetting element or a second pipetting element. In some preferred embodiments, the pipetting element further comprises a pipetting plug capable of pushing the first pipetting element and/or the second pipetting element. In some preferred embodiments, the pipetting plug can be inserted into the pipetting channel through the pipetting opening. In some preferred embodiments, the first pipetting element and/or the second pipetting element is provided with a socket matching the pipetting plug.

In some preferred embodiments, a sealing element 76 is provided between the pipetting element and the pipetting channel 51, and the sealing element 76 may be a seal ring as shown in FIG. 35. The seal ring may be made of a material having certain elasticity to ensure that there is no leakage of samples from the position between the pipetting element and the inner wall of the pipetting channel when the pipetting element is moving in the pipetting channel. Another function of the sealing element 76 is to increase the friction between the pipetting element and the inner wall of the pipetting channel. Under sufficient friction, the liquid in the first chamber and the fourth chamber is not enough to displace the pipetting element, so as to achieve quantitative collection and quantitative detection.

Figure 71:
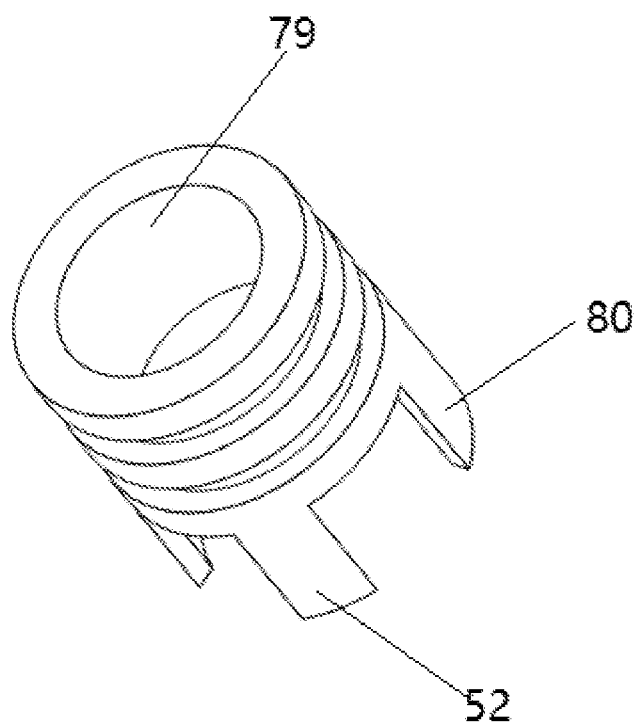
FIG. 71 is a schematic diagram of a first pipetting element according to an embodiment of the present invention.
Figure 72:
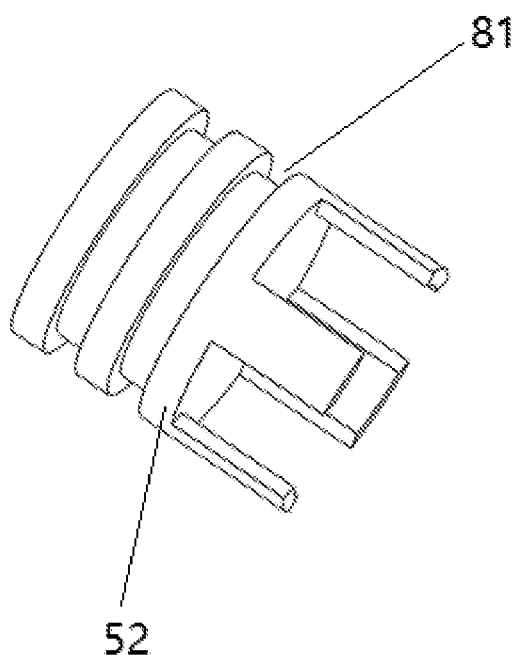
FIG. 72 is a schematic diagram of a first pipetting element from another angle according to an embodiment of the present invention.

As shown in FIGS. 71-72, in a specific embodiment, the first pipetting element 52 comprises a first moving chamber 79. A power component such as a pipetting plug 78, can partially extend into the moving chamber 79, to push the first pipetting element 52, correspondingly, the pipetting plug 78 can also be provided with a taper portion. This chamber can provide a force applying point for power components; at the same time, it can limit the pushing direction to some extent. In some preferred embodiments, the first moving chamber 79 may not be provided. In some preferred embodiments, the first pipetting element 52 is provided with a support leg 80. The support leg 80 can separate the first pipetting element 52 and the second pipetting element 53, to ensure that there is always a certain space between the two pipetting elements. In some preferred embodiments, the first pipetting element may also not be provided with a support leg. In some preferred embodiments, the first pipetting element is provided with a sealing groove 81, and the sealing element 76 is mounted in the sealing groove 81. There may be one or more sealing grooves 81.

Figure 73:
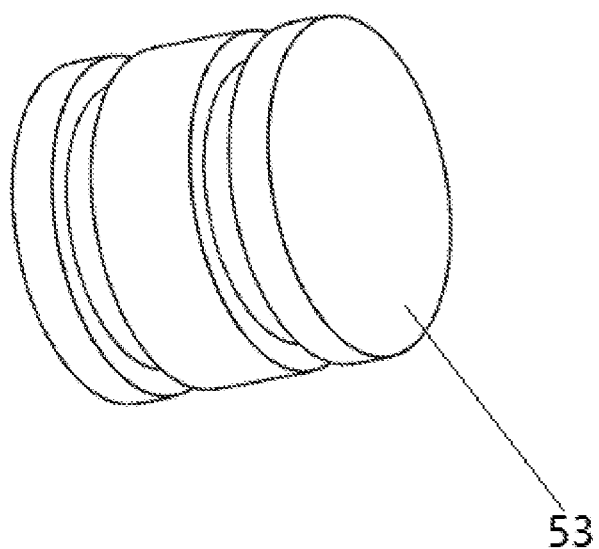
FIG. 73 is a schematic diagram of a second pipetting element according to an embodiment of the present invention.
Figure 74:
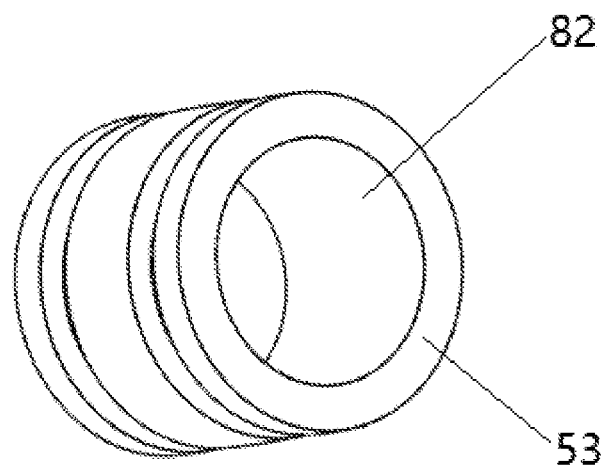
FIG. 74 is a schematic diagram of a second pipetting element from another angle according to an embodiment of the present invention.
Figure 75:
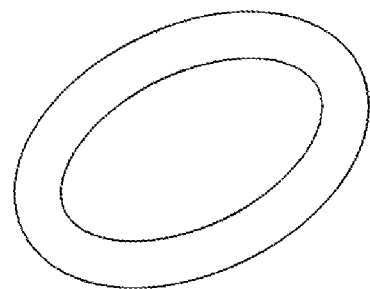
FIG. 75 is a schematic diagram of a sealing structure on the first pipetting element and the second pipetting element according to an embodiment of the present invention.
Figure 76:
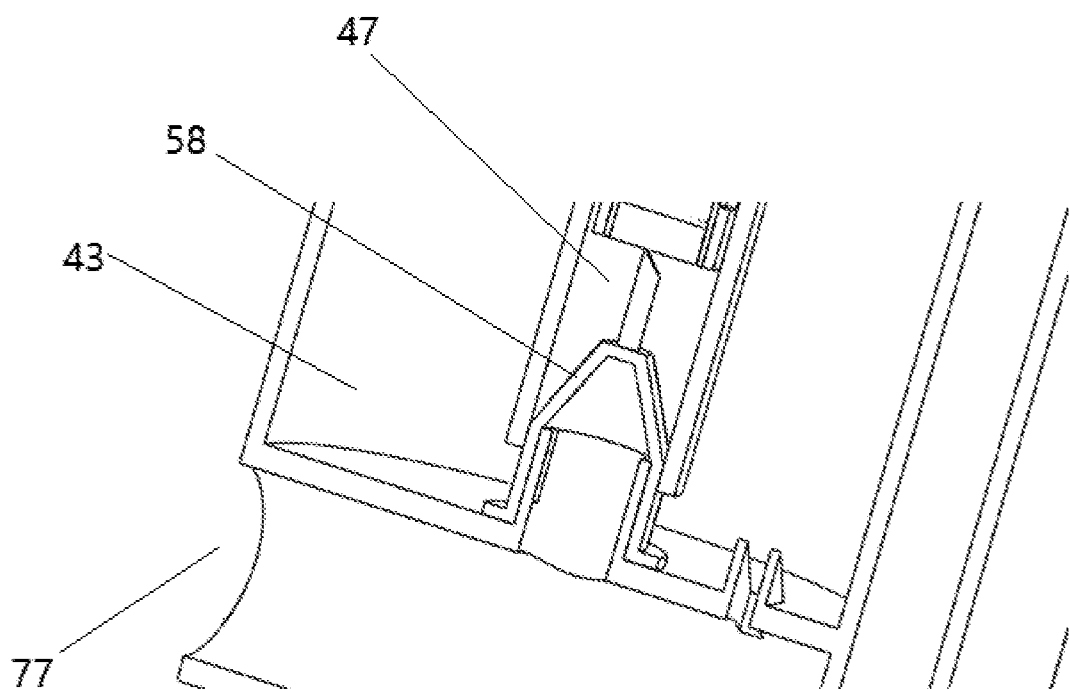
FIG. 76 is a schematic diagram of an assembly relationship between a connector and a first channel.
Figure 77:
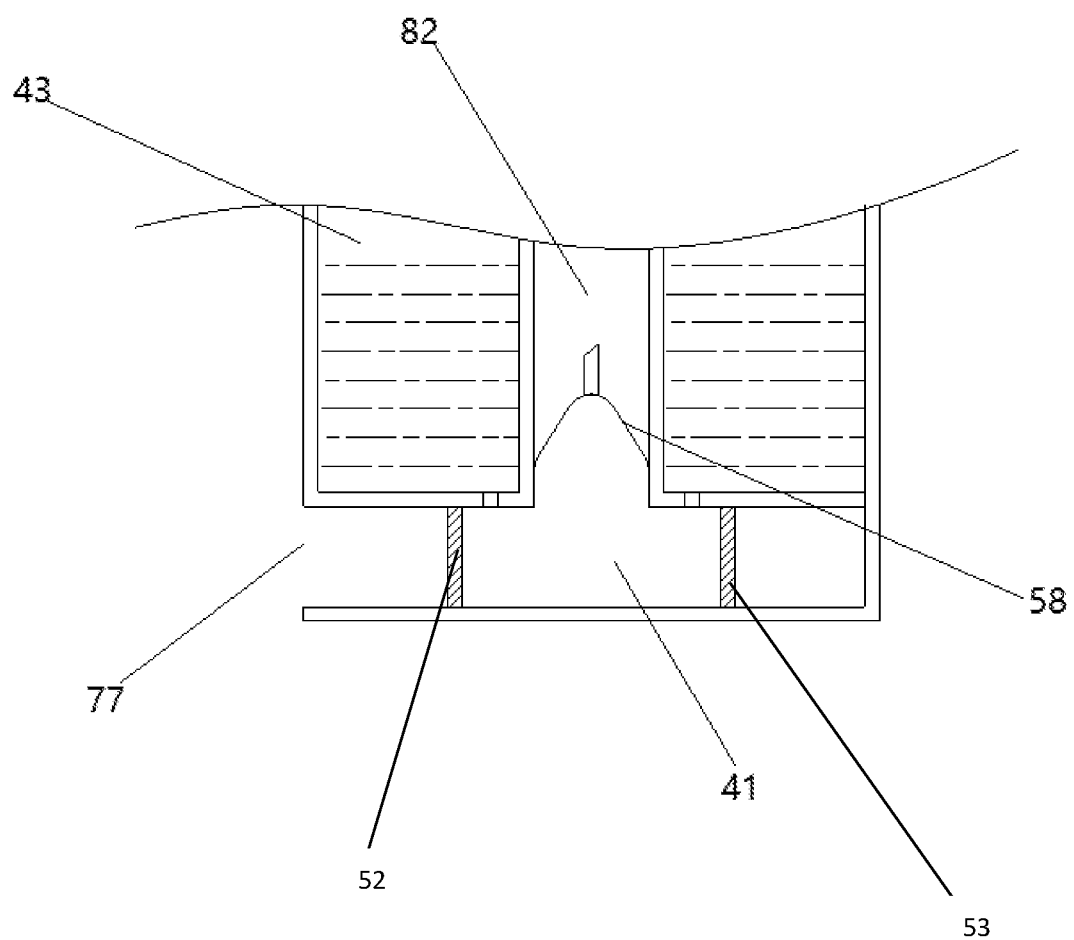
FIG. 77 is a schematic diagram of a first chamber, a third chamber, and a connector according to an embodiment of the present invention.
Figure 78:
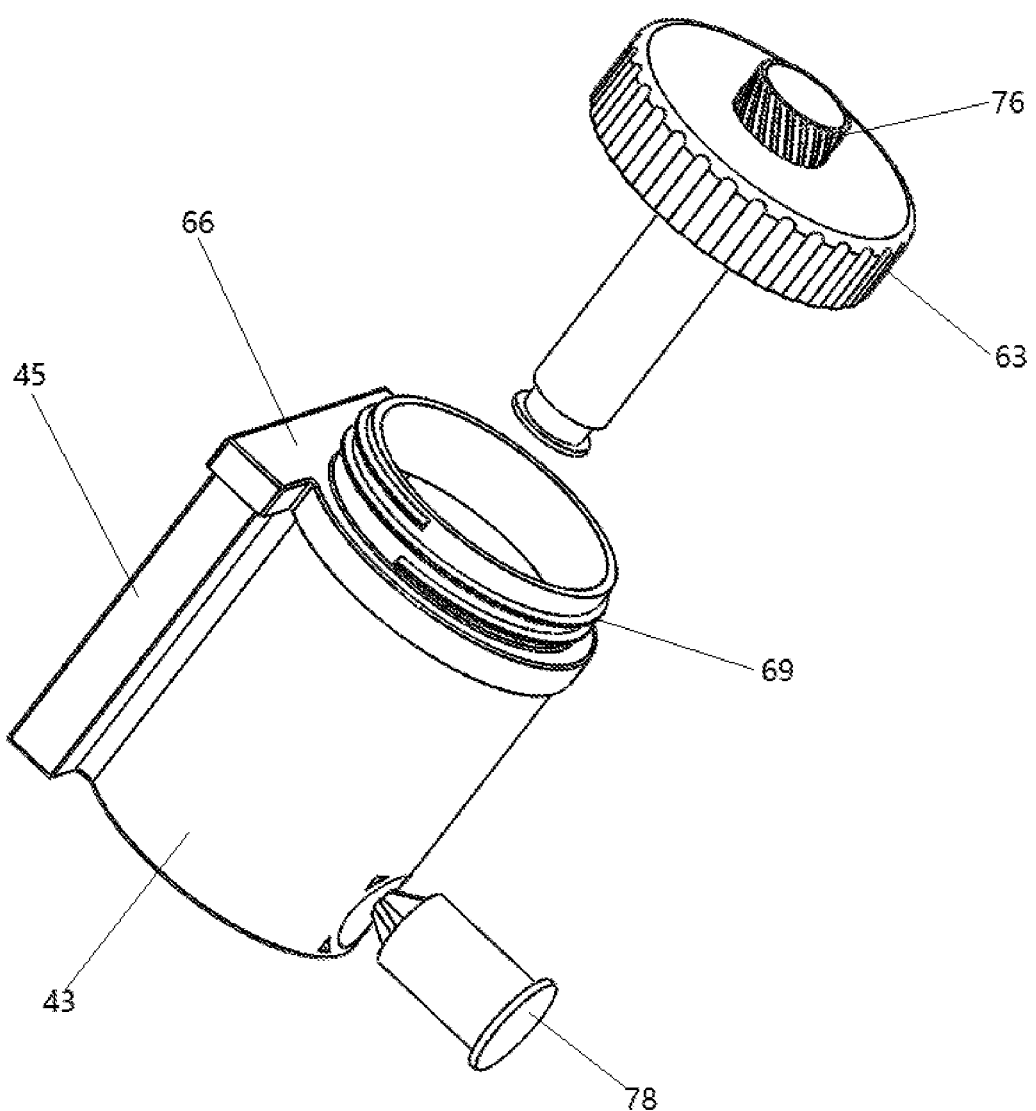
FIG. 78 is a perspective view of a cover body, a first chamber, a third chamber, and a connector according to an embodiment of the present invention.

As shown in FIGS. 73-74, in a specific embodiment, the second pipetting element 53 comprises a second moving chamber 82 into which the power component can partially extend to push the second pipetting element 53, thereby pushing the samples in the fourth chamber to the testing area. FIG. 29 shows the state when the samples in the fourth chamber are pushed into the testing area completely. In some preferred embodiments, the second moving chamber 82 may not be provided.

Method for Collecting Liquid Samples

The present invention provides a method of collecting a liquid sample. The method uses An apparatus for collecting samples as described previously. The sample collection apparatus comprises a first chamber for collecting a liquid sample and a second chamber for collecting samples for confirmatory detection. The first chamber and the second chamber can be in a fluid communication state or in a partitioned state. When the first chamber and the second chamber are in a fluid communication state, the liquid in the first chamber can be transferred to the second chamber.

In some preferred embodiments, the apparatus further comprises a third chamber for collecting samples. The third chamber and the first chamber are in a fluid communication state or in a partitioned state. Initial samples can be collected in the third chamber, and the samples collected in the first chamber may be transferred to the second chamber for second detection.

In some preferred embodiments, when the first chamber and the third chamber are in fluid communication state, the liquid collected in the third chamber can enter the first chamber at the same time, that is, when initial samples are collected in the third chamber, the initially collected samples can also be loaded in the first chamber.

In some preferred embodiments, when the liquid in the first chamber is transferred into the second chamber, the first chamber and the third chamber are in a liquid partition state. Since the sample in the second chamber is used for second confirmatory detection, in order to ensure that the sample in the second chamber is not contaminated, the first chamber is isolated from the other chambers prior to transfer.

In some preferred embodiments, it further comprises a fourth chamber for collecting the sample to be detected, and the fourth chamber being in fluid communication with or partitioned with the third chamber.

In some preferred embodiments, when the fourth chamber is in fluid communication with the third chamber, the liquid collected in the third chamber can enter the fourth chamber at the same time. The fourth chamber can also be in communication with the third chamber when collecting samples initially, by this way, the fourth chamber can basically complete the required samples synchronously with the third chamber. The samples collected in the fourth chamber are mainly used for initial detection. The initial detection can be performed directly in the fourth chamber, or can be transferred to other areas through the fourth chamber, for example, to the testing area.

In some preferred embodiments, it further comprises a testing area. The fourth chamber is in fluid communication with or partitioned with the testing area. When initially collecting samples in the fourth chamber, the fourth chamber can be separated from the testing area, that is, sample collection and detection can be carried out independently.

In some preferred embodiments, when the fourth chamber is in fluid communication with the testing area, the fourth chamber and the third chamber are in a liquid parturition state, which, on one hand, can ensure that the testing area is not affected by contamination of other chambers, and on the other hand, the quantitative detection can be achieved. As long as the volume of the fourth chamber is set, the quantitative detection of samples entering the testing area can be achieved.

In some preferred embodiments, the second chamber and the third chamber can be combined or separated. In some preferred embodiments, the second chamber and the first chamber can be combined or separated. Since the second chamber needs to acquire the collected samples from the first chamber or the third chamber, the second chamber must establish a liquid communication relationship with the first chamber or the third chamber or one of them. After the desired samples are acquired, the second chamber must be independently sealed and preserved, or even transported independently and sent to a second detection agency. So, the second chamber must be separated from the first chamber or the third chamber or one of them, in some preferred embodiments, the second chamber can be detachably combined or connected to the first chamber or the third chamber or one of them.

In some preferred embodiments, it further comprises a communicating device between the first chamber and the second chamber. The communicating device provides a convenient channel and path for the samples in the first chamber to enter the second chamber.

In some preferred embodiments, when samples are collected initially, the communicating device is not mounted. When a secondary confirmatory test is required, the communicating device is mounted.

In some preferred embodiments, the communicating device can allow the first chamber and the second chamber to be in a fluid communication state or in a partition state.

In some preferred embodiments, the communicating device can block the communication between the first chamber and the third chamber. After initial collection of samples is completed, the first chamber and the third chamber may be partitioned to ensure that the samples for a second confirmatory test are not contaminated.

In the present invention, since the initially collected samples cannot naturally enter the second chamber, an external force must be exerted. In such cases, it is necessary to take a force on the initially collected samples.

Therefore, in some preferred embodiments, the method of the present invention further provides a pipetting element. After the initial collection is completed, there is a sufficient amount of samples in the first chamber, at this time, the pipetting element is pushed to squeeze the samples in the first chamber, to allow samples to enter the second chamber directly or through a communicating device, while the volume of the first chamber itself is reduced. In some preferred embodiments, the pipetting element can also transfer samples in the fourth chamber. In some preferred embodiments, samples in the fourth chamber can be transferred after the first chamber. In some preferred embodiments, the first chamber and the fourth chamber may be extruded using different pipetting elements, respectively. In some preferred embodiments, a linkage can be achieved for pipetting elements between the first chamber and the fourth chamber.

In some preferred embodiments, the method of the present invention further provides a pipetting channel. The foregoing pipetting elements can be moved in the pipetting channel to squeeze the liquid in the first chamber or the fourth chamber. In some preferred embodiments, the first chamber or the fourth chamber may be a segment within the pipetting channel that is separated by different pipetting elements to form a chamber. In some preferred embodiments, the first chamber can be in fluid communication with the second chamber. In some preferred embodiments, the fourth chamber can be in fluid communication with the testing area. In other words, the pipetting channel itself can be in communication with the second chamber or testing area or both.

In some preferred embodiments, the method of the present invention further provides a pipetting plug, which is mainly used to provide power for moving the pipetting element, so that the pipetting element generates an extrusion force on samples in the first chamber and/or the fourth chamber when moving in the pipetting channel, to transfer these samples.

In some preferred embodiments, the method of the present invention further provides a sealing structure between the pipetting element and the pipetting channel, to ensure that no gap is generated between the pipetting element and the inner wall of the pipetting channel when the pipetting element is forced to move, and no sample leakage occurs.

Method for Detecting Samples

The present invention provides a method for detecting the presence or absence of an analyte in a liquid sample. The detection method comprises an apparatus for collecting samples of any one of the foregoing embodiments. By collecting samples to be detected with An apparatus for collecting samples, after samples are collected in the fourth chamber, samples are detected. In some preferred embodiments, after samples are collected in the third chamber, the samples are detected. In some preferred embodiments, the samples in the fourth chamber are transferred to the testing area for detection. In some preferred embodiments, the samples in the third chamber are transferred to the testing area for detection. After obtaining the detection results, the second chamber is separated from the sample collection apparatus in any of the foregoing ways.

Third Design (Shown in FIGS. 79-92)

Combination and Separation of First Chamber and Second Chamber

The sample detection apparatus of the present invention comprises two chambers for collecting liquid samples—a first chamber 1 and a second chamber 2. The first chamber 1 is used for collecting liquid samples for initial detection, and the second chamber 2 is used for collecting liquid samples for second confirmatory detection. The first chamber 1 and the second chamber 2 can be combined to simultaneously receive liquid samples collected initially, that is, users can realize the injection of liquid samples into the first chamber 1 and the second chamber 2 simultaneously through one-time collection operation when using the product of the present invention.

Figure 10:
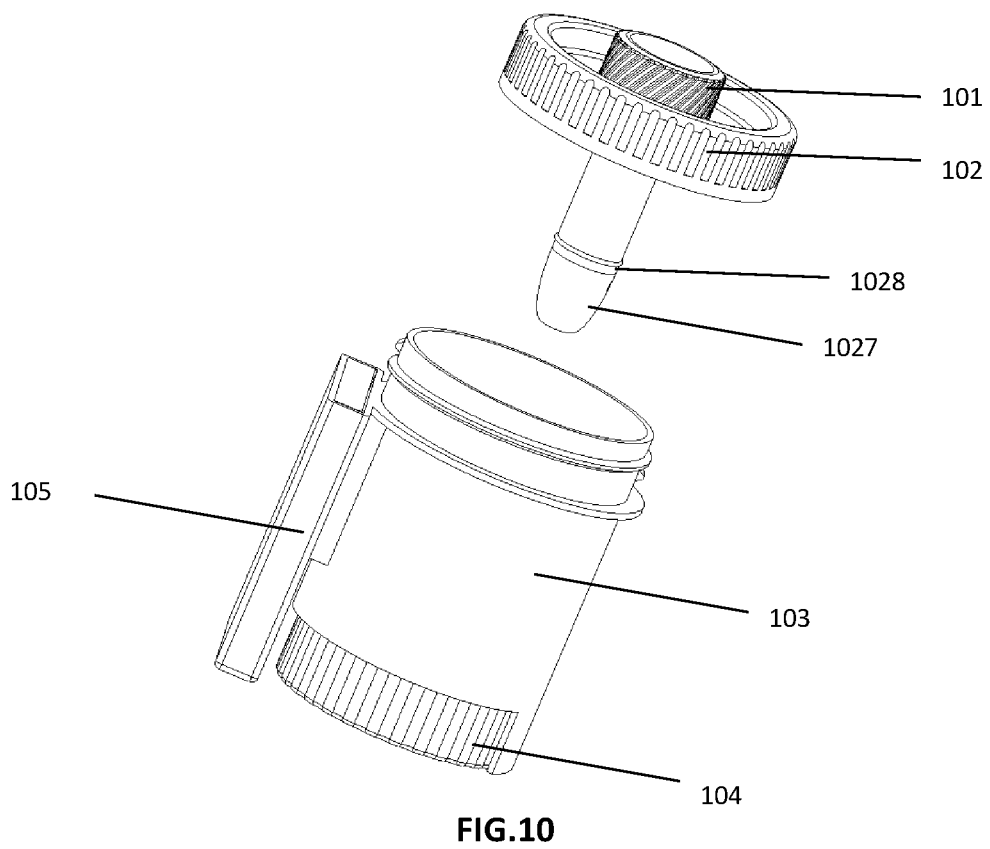
FIG. 10 is a perspective structural view for the operation process of covering the first chamber opening by a first cover body according to an embodiment of the present invention.
Figure 11:
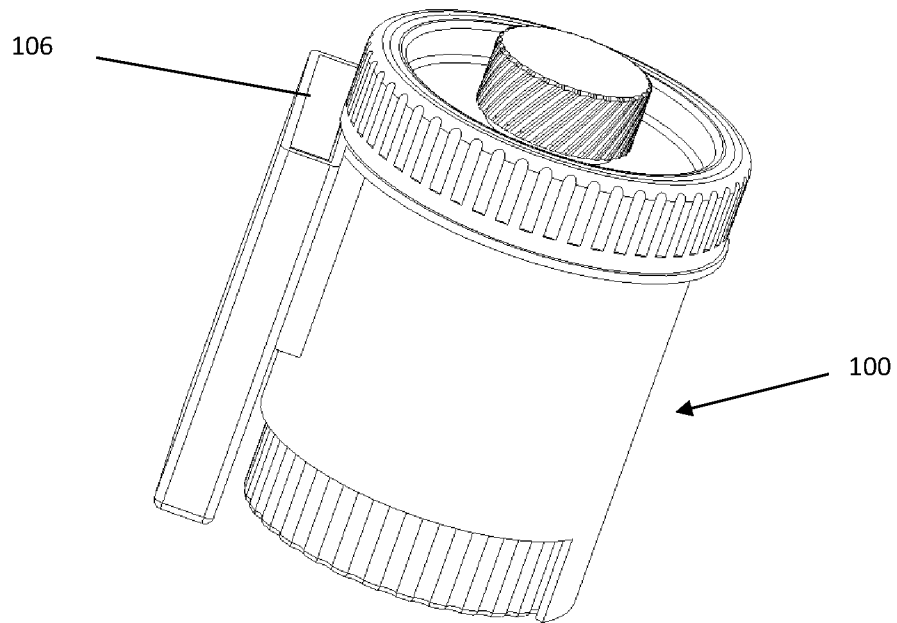
FIG. 11 is a perspective structural view after covering the first chamber opening by a first cover body according to an embodiment of the present invention.

In some embodiments of the present invention, as shown in FIGS. 2, 7, and 8, the bottom of the first chamber 1 is provided with a channel 5, one end of the channel 5 is in communication with the inside of the first chamber 1 and the other end is in communication with outside. The second chamber 2 can be assembled to the channel 5. The bottom of the second chamber 2 is sealed to form a plug of the channel 5. As described previously, as samples have fluidity, the collection port is usually facing upwards when users collection samples, for example, as shown in FIGS. 9 and 10, the first collection port 6 faces upward, and the position of channel 5 (i.e., the port 7 of the second chamber 2) is located below the first collection port 6. When users inject flowing samples from the first collection port 6, samples will flow to the second chamber 2 along the inner wall of the first chamber 1 due to the action of gravity, thus samples are collected in the second chamber, that is, the second chamber 2 at the bottom is preferentially loaded into samples, then the first chamber 1 will continue to be loaded until the amount for one-time detection is reached.

The liquid samples in the first chamber 1 are used for detection directly, while the liquid samples in the second chamber 2 may be sealed and transported to a confirmatory detection agency for second confirmatory detection. The liquid samples in the first chamber 1 have undergone one-time initial detection to become non-original samples, so the detection on the samples in the first chamber will affect the accuracy of the results of second confirmatory detection. Therefore, the first chamber 1 needs to be separated from the second chamber 2, and form a sealed chamber independently after separation to seal their respective liquid samples, in addition, the samples will not be sealed at the separation portion when the first chamber 1 is separated from the second chamber 2, which proposes requirements for the structure of separation portion and their respective sealing structures of the first chamber and the second chamber.

In some preferred embodiments, the second chamber 2 collects samples through the first chamber 1, the second chamber 2 can be detachably connected or combined with the first chamber 1, and the second chamber 2 is combined with the first chamber 1 during sample collection, and after sample collection, the second chamber 2 is pushed out of the first chamber.

In some preferred embodiments, the second chamber 2 includes a second collection port for collecting samples, and the second collection port is in fluid communication with the interior of the first chamber when collecting samples in the second chamber. In some preferred embodiments, the second chamber is disposed at the bottom of the first chamber. In some preferred embodiments, the first chamber 1 has a first collection port 37 for collecting samples. In some preferred embodiments, the opening direction of the first collection port 37 is the same as that of the second collection port 38, so as to enhance the collection efficiency of the second chamber 2 to the greatest extent. If the direction of the first collection port 37 is different from that of the second collection port 38, samples will not enter the second chamber through the first chamber as smoothly as that of the same direction of the collection port, which easily causes retention on the surface or side wall, and because of different direction, it is inevitable to produce corners, and samples may be accumulated in the corners, which is not conducive to collection. Excessively accumulated samples will increase the possibility of leakage. In addition, if the collection ports are in different directions, the linkage may not be smooth when sealed.

In some preferred embodiments, while the liquid samples are loaded into the first chamber, the liquid samples can naturally enter the second chamber. In some preferred embodiments, while the liquid samples are loaded into the first chamber, the liquid samples can enter the second chamber under an external force.

In some preferred embodiments, the bottom of the first chamber is provided with a channel capable of assembling a second chamber. In some preferred embodiments, the second chamber can move within the channel. In some preferred embodiments, the second chamber and the channel are detachably combined or connected. In some preferred embodiments, the first channel is in fluid communication with the interior of the first chamber. In some preferred embodiments, when the second chamber channel collects the sample, the second chamber is assembled in the channel. In some preferred embodiments, after the sample collection is completed, the second chamber can move in a direction separating from the first chamber under an external force.

Separation Portion

The present invention further provides a separation portion of the first chamber 1 and the second chamber 2, as shown in FIG. 7, the separation portion is embodied in the form of channel 5. When the first chamber 1 and the second chamber 2 are combined, the separation portion is presented as a combination portion of the first chamber 1 and the second chamber 2. In the initial stage, when the sample collection apparatus has not been used, the second chamber 2 is assembled on the first chamber 1, as described above, the second chamber 2 acts as a plug at the channel 5, to prevent samples from leaking out of the channel 5 at the time of initial loading, moreover, after samples are loaded, the second chamber 2 must be able to withdraw from the channel 5 without taking out unnecessary samples, which proposes a high requirement for assembly and sealing between the second chamber 2 and the channel 5. The liquid samples should flow inside the second chamber 2 and inside the first chamber 1 beyond the channel 5 as much as possible, instead of being accumulated in the assembly location of the second chamber 2 and the channel 5.

To this end, the following forms have been designed.

First, one form that can be taken is as follows: the port 7 of the second chamber 2 (i.e., the opening of the second chamber 2 toward the first chamber 1) must be at least flush with the surface of the opening 15 of the channel 5 facing the first chamber. The flush surface is relatively difficult to form an accumulation point, particularly it should be avoided that the surface of the opening of channel 5 is lower than the surface of the port of the second chamber 2. In this case, the liquid samples will inevitably enter the gap between the channel 5 and the port of the second chamber 2, and flow out when the second chamber 2 is withdrawn. Further, it should be noted that, as the second chamber 2 needs to have a second sealing portion 13 of the second sealing element 11, this second sealing portion 13 may exceed its port 7 to form a shoulder 14 between the second sealing portion 13 and the port 7, as shown in FIGS. 3 and 6. At this time, we should ensure that the shoulder 14 is flush with the surface of the opening 15 of the channel 5 facing towards the first chamber.

Then, the form may also be as follows. The second collection port 7 is slightly higher than the opening 15 of channel 5, or the second chamber's shoulder 14 is slightly higher than the opening of channel 5, so that liquid samples that are not loaded by the second chamber 2 will usually flow into the first chamber 1 outside of the channel 5 along the high-to-low layered structure.

Or alternatively, the second collection port 7 and the surface of the opening 15 of the channel 5 form a slope which gradually slopes downward from the inside, or the shoulder 14 of the second chamber and the surface of the opening 15 of channel 5 form a slope which gradually slopes downward from the inside, and this kind of slope can facilitate the liquid samples that are not loaded in the second chamber to enter the first chamber 1 along it.

The separation portion is embodied in the form of channel 5. The channel 5 is a component that is open at both ends, one end is in communication with the outside, and the other end is in communication with the first chamber. Since the second chamber 2 can be assembled, in some cases, the second chamber 2 may enter into the first chamber 1 along the channel 5, which must be absolutely avoided. On the one hand, the outer leakage part of the second chamber 2 will contaminate the liquid samples in the first chamber 1. On the second hand, if the second chamber 2 is not plugged or pulled out, the channel 5 becomes a hole of the first chamber, and the liquid samples will be leaked in a large amount, therefore, it is necessary to provide a limiting structure in which the second chamber 2 moves inwardly.

As shown in FIG. 2, 7, 8, or 9, the channel 5 is provided with an outer stepped surface 8. When the outer stepped surface 8 is taken as a dividing line, the inner diameter of the portion of the channel 5 on the outer stepped surface 8 close to the first chamber 1 is smaller than the inner diameter of the portion on the outer stepped surface 8 close to the outside, so that the inner wall of the channel 5 has formed a structure with small inside and large outside, in addition, the outer stepped surface 8 is exactly the dividing line of the size, that is, the outer stepped surface 8 can be used as a limiting structure.

In order to better fit this limiting structure, an inner stepped surface 9 can be disposed on the outer wall of the second chamber 2. Taking this inner stepped surface 9 as a dividing line, the inner diameter of the second chamber outer wall on the inner stepped surface 9 close to the first chamber 1 is smaller than that of the second chamber outer wall on the inner stepped surface 8 close to the outside, that is, the inner stepped surface 9 can form a fit with the outer stepped surface 8 to limit the inward movement of the second chamber 2. In the initial state, the second chamber 2 is assembled in the first chamber 1. At this time, the inner stepped surface 8 and the outer stepped surface 9 are usually in contact fit. When the inner stepped surface 8 is in contact fit with the outer stepped surface 9, the bottom of the second chamber 2 is flush with the surface of the port of the channel 5 facing outward. Later, as the sealing progresses, the inner stepped surface 8 and the outer stepped surface 9 are separated, and the second chamber 2 is gradually withdrawn outwards.

The foregoing description is only one implementation manner of this limiting structure. It should be understood that the limiting structure is a conventional mechanical structure that can be expanded and applied, as long as it is a structure that can meet the condition of preventing second chamber 2 from moving inwards indefinitely, for example, a snap ring, an elastic piece, etc.

In some preferred embodiments, a sealing structure can be disposed on the assembly surface of the second chamber and the channel. The said assembly surface refers to the outer surface of the second chamber and the inner surface of the channel. The sealing structure may be in the form of a seal retainer 37, and the seal retainer 37 may limit the assembly of the second chamber and the channel, that is, serving the same function as the aforementioned limiting structure, also it can play a sealing role on the separation of the second chamber and the channel. In some preferred embodiments, the seal retainer adopts an O-ring. In some preferred embodiments, the seal retainer 37 adopts a brush structure, and the brush structure can scrape the surface of the second chamber when the second chamber withdraws from the channel, to scrape off the samples which may be attached thereto. Of course, the O-ring can also have the aforesaid functions.

In some preferred embodiments, the sealing structure and the limiting structure may not be provided on the assembly surface of the channel and the second chamber. As long as the above functions can be performed, the assembly position of the structure is not within the scope of the present invention.

Method for Collecting Samples

The present invention provides a method of collecting the aforementioned samples, using a sample collection apparatus having the aforementioned first chamber 1 and second chamber 2. The first chamber 1 is used for collecting liquid samples, having a sample inlet 4, the second chamber 2 is used for collecting liquid samples for confirmatory detection. The detection timing and detection purpose of the first chamber 1 and the second chamber 2 are different, but the detection is for the same batch of collected samples. In order to achieve the same batch collection and separate detection, the first chamber 1 and the second chamber 2 can be combined and separated. When combined, they are used for collecting the same batch of samples, and when separated, detection is performed respectively, or detection is performed before separation, and the second chamber 2 enters the second detection procedure separately. The sample detection apparatus further comprises a first sealing element 10 for sealing the first chamber 1, and a second sealing element 11 for sealing the second chamber 2, and a third sealing element 16 for sealing the separation portion of the first chamber 1 and the second chamber 2. The separation portion is the aforementioned channel 5.

In some preferred embodiments, in the process of sealing the first chamber 1 by the first sealing element 10, the second chamber 2 can be sealed by the second sealing element 11. In some preferred embodiments, the channel 5 can be sealed by the third sealing element 16 in the process of sealing the first chamber 1 by the first sealing element 10. In some preferred embodiments, one of the second sealing element 11 and third sealing element 16 is linked with the first sealing element 10, and the second sealing element 11 is linked with the third sealing element 16; or both the second sealing element 11 and third sealing element 16 are linked with the first sealing element 10. In some preferred embodiments, the channel 5 is plugged by the second chamber 2 prior to all sealing processes, at this time, the first chamber 1 and the second chamber 2 form a whole body that is closed from outside and communicates with the inside. In some preferred embodiments, the second chamber 2 moves outward relative to the channel 5 during the sealing process.

In some preferred embodiments, the sample collection method comprises: the first chamber 1 and second chamber 2 are in liquid communication via the channel 5, and liquid samples can flow from the first chamber 1 to the second chamber 2 through the channel 5 or a port of the channel 5 (for example, the opening 15), so that the liquid samples can naturally enter the second chamber 2 while the liquid samples are loaded into the first chamber 1. In some preferred embodiments, before the first chamber 1 is separated from the second chamber 2, the channel 15 is sealed by the third sealing element 16. In some preferred embodiments, during the process of separating the first chamber 1 from the second chamber 2, the channel 5 is sealed by the third sealing element 16.

In some preferred embodiments, the method for collecting samples comprises a process of sealing the first chamber 1 and the second chamber 2 in which the samples are collected. During the sealing process, the first chamber 1 and the second chamber 2 can move relatively to make a portion of the second chamber 2 to be pushed out from the first chamber 1. In some preferred embodiments, a portion of the second chamber 2 is exposed outside of the first chamber 1 during the sealing process. In some preferred embodiments, the sealing of the first chamber 1 is accompanied by sealing of the second chamber 2.

In some preferred embodiments, the method for collecting samples comprises a process of sealing the channel 5 that communicates the first chamber 1 and the second chamber 2, and during the sealing process, the first chamber 1 and the second chamber 2 can move relatively to make a portion of the second chamber 2 to be pushed out from the first chamber 1. In some preferred embodiments, a portion of the second chamber 2 is exposed outside of the first chamber 1 during the sealing process. In some preferred embodiments, the sealing of the first chamber 1 is accompanied by sealing of the channel 5. In some preferred embodiments, the process for sealing the channel 5 follows the process for sealing the second chamber 2. In some preferred embodiments, the second chamber 2 is pushed out while sealing the channel 5.

Method for Detecting Samples

The present invention provides a sample detection method for detecting the presence or absence of an analyte in a collected liquid sample. The detection method comprises collecting the samples to be detected by using the foregoing collection apparatus or collecting method, and performing initial detection on the samples in the first chamber 1 after collected.

In some preferred embodiments, firstly perform sealing on the second chamber 2 that completes the sample collection, and then conduct detection on samples in the first chamber 1 by the testing element. In some preferred embodiments, firstly separate the first chamber 1 and the second chamber 2, then conduct detection on samples in the first chamber 1 by the testing element. Since the liquid samples collected by the second chamber 2 are used for second detection, the second chamber is first separated to prevent contamination on the liquid samples for second detection in the second chamber by the testing elements in the initial detection. In some preferred embodiments, firstly seal the channel that communicates the first chamber 1 and the second chamber 2, and then conduct detection on samples in the first chamber by the testing element. The channel is sealed to prevent leakage of test samples.

In some preferred embodiment, a blocking element 31 capable of preventing liquid samples from flowing into the testing is provided in the first chamber 1. The blocking element 31 can open or close the inlet 32 that communicates the first chamber 1 and the testing area, thereby preventing or releasing the liquid samples from flowing into the testing area 3; while the third sealing element 16 seals the channel, the blocking element 31 is triggered to open the inlet of the testing area. in some preferred embodiments, in the process of collecting the sample, the testing area 3 and the sample collection area (ie, the inside of the first chamber) are separated by the blocking element 31, and after the sample collection is completed, the blocking by the blocking element 31 is released between the testing area and the sample collection area, so that samples can enter the testing area.

In some preferred embodiments, the testing area 3 is provided in the first chamber 1. The testing area usually has externally visible characteristics. For example, the testing area can be made of a transparent material. In some preferred embodiments, the testing element is provided in the testing area 3. In some preferred embodiments, there is an inlet 32 between the testing area 3 and the first chamber 1 that can be communicated or closed. In some preferred embodiments, the inlet 32 can cooperate with the blocking element 31, and it will be blocked and closed by the blocking element, or be opened to communicate the testing area and the first chamber.

Sealing Element

As mentioned previously, when the first chamber 1 and the second chamber 2 are in the combined state, only one of the chambers can be sealed because the two chambers have a common opening and pass through a channel 5 for communicating the two chambers. After the first chamber 1 and the second chamber 2 are separated, the second chamber 2 needs to be sealed independently, so that the second chamber 2 can independently seal the liquid sample therein, therefore, a separate sealing device for the second chamber 2 is required, when the first chamber 1 and the second chamber 2 are separated, the first chamber 1 will inevitably generate a new opening which may leak liquid in addition to the original opening (this original opening will be sealed by the first sealing element 10) due to the withdrawal of the second chamber 2 (That is, the opening 15 of the channel 5 outwards), at this time, it is also necessary to seal the opening 15 to prevent the liquid sample from flowing out, thus a device for sealing the separation portion is necessary.

In view of the above, the present invention provides a specific sealing structure for the first chamber 1 and the second chamber 2, the specific sealing structure comprises a first sealing element 10 for sealing the first chamber 1, a second sealing element 11 for sealing the second chamber 2, and a third sealing element 16 for sealing the separation portion of the first chamber 1 and the second chamber 2 (ie, the channel 5).

In some preferred embodiments, the first sealing element 10 and the port 6 of the first chamber 1 are sealed by a first thread structure 17, and the second sealing element 11 and the port 7 of the second chamber 2 are sealed by a second thread structure 18; the third sealing element 16 and the separation portion (i.e. channel 5 are sealed by third thread structure 19.

FIG. 7 shows the state of the whole apparatus before sealing. At this time, the first sealing element 10, the second sealing element 11, and the third sealing element 16 are not sealed, when a user collects the appropriate amount of liquid samples from the port 6 of the first chamber 1, the apparatus can be sealed. The first sealing element 10 is capped to the port 6 of the first chamber 1, and the first sealing element 10 is rotatably capped to the port 6 of the first chamber 1 to achieve sealing the first chamber 1. During the sealing of the first chamber 1 by the first sealing element 10, the second sealing element 11 seals the port 7 of the second chamber 2, or during the sealing of the first chamber 1 by the first sealing element 10, the third sealing element 16 seals the channel 5, or during the sealing of the first chamber 1 by the first sealing element 10, the second sealing element 11 and the third sealing element 16 seal the second chamber 2 and the channel 5, respectively. When the first sealing element 10 completes the sealing of the first chamber 1, the second sealing element 11 and the third sealing element 16 have completely sealed the second chamber 2 and the channel 5, respectively. Or, during the sealing of the first chamber 1 by the first sealing element 10, the second sealing element 11 rotates with the first sealing element 10 to seal the second chamber 2. At the same time, the third sealing element 16 also seals the channel 5 while rotating. The sealing order is: the second sealing element 11 firstly seals the second chamber 2, at this time, the second chamber 2 is assembled to form a whole in the first chamber, but actually it has been separated as an independent chamber by the second sealing element 11, which can be separated from the first chamber 1 at any time, and then the third sealing element 11 completes sealing of the channel 5, the first sealing element 1 continues to rotate until the sealing of the first chamber 1 is completed.

As can be seen from the above description, the sealing process of the second chamber 2 by the second sealing element 11 must be performed during the process of sealing the first chamber by the first sealing element 10, and the sealing of channel 5 by the third sealing element 16 must be performed during the process of sealing the first chamber by the first sealing element 10, while the sealing process of the second chamber 2 by the second sealing element 11 and the sealing process of channel 5 by the third sealing element 16 can be performed sequentially or overlapped partially, or fully synchronized.

FIG. 8 shows an intermediate process of sealing. In the state shown in FIG. 8, the second sealing element 11 has completed the sealing of the second chamber 2, at this time, the third sealing element 16 is about to begin sealing the channel 5, and the first sealing element 1 is in the process of sealing the first chamber 1, that is, for the length of the screw thread, the length of the first thread structure 17 is equal to the sum of the lengths of the second thread structure 18 and the third thread structure 19, so that during the process of sealing the first chamber 1 by the first sealing element 10, .

. . .

It should be noted that, during the sealing process, since the first sealing element 1, the second sealing element 2 and the third sealing element 3 are sealed by tightening screw threads, these sealing elements have a reduction in the height during the process of screw thread cooperation. In terms of the linkage, it will push the second chamber 2 out in the direction away from the first chamber 1, so that a portion of the second chamber 2 is exposed outside the first chamber 1, thereby facilitating to take the second chamber 2 out of the first chamber 1, which will be described in detail in the linkage element below.

In some preferred embodiments, the sealing element can also achieve the sealing of the respective chambers by means of a plug. For example, the first sealing element 1, the second sealing element 2, and the third sealing element 3 may take the form of a sealing plug.

In some preferred embodiments, a seal retainer may be provided on the inner wall of the channel or on the outer wall of the second chamber. In some preferred embodiments, the seal retainer adopts a flexible structure or a brush structure. The seal retainer can prevent the second chamber from oozing samples during separation when the second chamber withdraws from the channel.

In some preferred embodiments, the sealing element only needs to include a second sealing element 11 for sealing the second chamber 2 and a third sealing element 16 for sealing the channel 5. The second sealing element and the third sealing element can seal the second chamber and the channel separately in a linkage way.

In some preferred embodiments, the second sealing element 11 first seals the second chamber 2, and then the third sealing element 16 seals the channel 5. In some preferred embodiments, the third sealing element 16 can move the second chamber 2 in a direction separating from the first chamber 1 while sealing the channel 5. In some preferred embodiments, the second chamber 2 only needs to partially withdraw from the first chamber 1.

In some preferred embodiments, the second sealing element 11 is combined with the second chamber 2 during the sealing of the second chamber 2. In some preferred embodiments, the third sealing element 16 is combined with the channel 5 during the sealing of the channel 5, while pressing the second chamber outwards. Here, the combination means that the sealing element and the sealed component are getting closer or closer, or in the case of assembly, it is more tightly assembled. This assembly can further shorten the length or height of the entire assembly structure. For example, for the screw thread structure, the height or length of the entire apparatus will be shorter as the screw thread is screwed in.

In some preferred embodiments, the second sealing element 11 can be detachably combined or connected to the port of the second chamber 2, the combination here is the same as the above, and the second collection port refers to a collection port used by the second chamber for collecting samples. In general, this collection port should also be the only opening in the second chamber. When this opening is closed, the second chamber will be sealed.

In some preferred embodiments, the second sealing element 11 is a second cover body, and the second cover body is detachably combined or connected to the second collection port by a second thread structure. In some preferred embodiments, the screw thread may be disposed on the outer wall of the second chamber port and the inner wall of the second cover body. In some preferred embodiments, the screw thread may be disposed on the outer wall of the second cover body and the inner wall of the second chamber port. The internal and external threads can be selected according to actual needs, and the present invention is not limited to one type of connection as shown in the figure. In some preferred embodiments, the second sealing element is a second plug body, and the second plug body can be tightly fitted with the inner wall of the second chamber port. By pressing inwardly and covering the port in the form of a plug, it can also achieve the above sealing effect, in addition, during the insertion process of the plug, it can achieve the linkage between plugs. For the purposes of the present invention, the sealing of the sealing element and the linkage of the sealing process are solutions to be protected by the present invention.

In some preferred embodiments, the third sealing element can be detachably combined or connected to the port of the channel. In some preferred embodiments, the third sealing element is a third cover body, and the third cover body is detachably combined or connected to the port of the channel by a third thread structure. In some preferred embodiments, the third sealing element is a third plug body, and the third plug body can be fitted to the inner wall of the port of the channel. Similarly, the connection or combination of the third sealing element and the port of the channel can also adopt a structure similar to that in the previous paragraph, and the present invention is not limited to the connecting way as shown in the figure. In some cases, different connection modes can be selected for different cover body according to the needs, that is, a combined connection mode, which should also be within the scope of protection of the present invention.

Linkage Element

In order to achieve a sealing sequence of first chamber 1, second chamber 2 and channel 5, it is required to set a linkage structure for the first sealing element, second sealing element and third sealing element. The role of the linkage structure: when the first sealing element seals the first chamber, the second sealing element can seal the second chamber. Possibly, when the first sealing element completes sealing, the second sealing element also completes the sealing, or, before the first sealing element completes sealing, the second sealing element has completed the sealing.

These linkage structures include a first linkage element 20 for linking the first sealing element 10 and the third sealing element 16, and a second linkage element 21 for linking the second sealing element 11 and the third sealing element or the second sealing element 11 and the first sealing element 10.

The first linkage element 20 is a linkage rod, and the first sealing element 10 and the third sealing element 16 are respectively connected to the two ends of the linkage rod, so that when one of the first sealing element 10 and the third sealing element 16 is rotated, the other one can be driven to rotate accordingly. The subsequent rotation can be either synchronous or intermittent, but usually in the same direction, of course, possibly in the opposite direction.

As a specific implementation form of the linkage rod, the first sealing element 10 is a cup cover having a relatively flat inner cover surface 22, and the inner cover surface 22 is provided with an inner shaft hole 23. The upper end of the linkage rod is inserted in the inner shaft hole 23, a portion of the first sealing element 10 as shown in FIGS. 2, 7, and 8. In some cases, the third sealing element 16 is also a cover structure having a relatively flat outer cover surface 24, and the outer cover surface 24 is provided with an outer shaft hole, and the lower end of the linkage rod is inserted into the outer shaft hole. Therefore, the linkage rod can link the first sealing element 10 and the third sealing element 16 through the inner and outer shaft holes, so that the synchronous rotation can be performed, and users only need to rotate the outermost first sealing element 10 when using, to synchronously drive the third sealing element 16 to seal the channel 5.

Alternatively, the portion of the third sealing element 16 may also be as shown in FIGS. 2, 7, and 8. The lower end of the linkage rod is provided with a linkage hole 25, and a coupling pin 26 is provided on the outer cover surface 24 of the third sealing element 16. The coupling pin 26 is inserted into the linkage hole 25 to realize the linkage of the third sealing element 16 and the linkage rod. In this way, it can achieve the purpose of synchronously rotating the first sealing element 1 and the third sealing element 16. Alternatively, the lower end of the linkage rod is directly attached to the outer cover surface 24 of the third sealing element 16, in which case the detachable separation and combination of the first linkage element 20 and the third sealing element 16 cannot be achieved, but it does not affect the function of this apparatus for collecting samples.

Regardless of which of the above implementations, the linkage rod connects the first sealing element 10 and the third sealing element 16 by passing through the first chamber 1. Also, the linkage rod or the portion for the connection thereon needs to have a certain shape. Generally, the shape is not a perfect circle, and may be, for example, a square, a semicircle, or a triangle. Accordingly, the inner and outer shaft holes on the first sealing element 10 and the third sealing element 16 are of the same shape, then the circumferential limit between the linkage rod and the shaft hole is achieved through such shape, without relative rotation, thus, the linkage rod can drive the first sealing element and the third sealing element to rotate through the two shaft holes, to achieve linkage. In some other embodiments, the linkage rod and the shaft hole can also be tightly fitted round holes, at this time, the force of linkage comes from the friction between the linkage rod and the shaft hole abutting surface. In other possible embodiments, the linkage rod and the shaft hole can also be in a step-by-step linkage relationship. In this step-by-step linkage relationship, the linkage rod or the shaft hole can be rotated independently by a certain angle, and then rotated synchronically.

Correspondingly, in the cooperation mode of the linkage hole 25 and the coupling pin 26, the linkage hole 25 and the coupling pin 26 can also implement the linkage coordination using the similar shapes described above or adopting a similar principle.

As another implementation form of linkage, the linkage rod is provided with a shaft hole, and the first sealing element or the third sealing element is provided with a matching component that links with the inner and outer shaft holes. The matching component has the same shape as the shaft hole, and the shape is deviated from the axis core of the linkage rod, or non-circular, so that the linkage rod and the mating component can realize the linkage. In some preferred embodiments, the linkage rod can also be matched with mating component by stepwise linkage.

The second linkage element 21 may directly link the first sealing element 10 and the second sealing element 11, and may also link the second sealing element 11 and the third sealing element 16. The linkage is not a specific implementation to be defined by the present invention, and the object of the present invention is to achieve the priority of the sealing. As shown in FIGS. 2, 7, and 8, the second linkage element 21 is a linkage pin or a short object with similar shape. The second linkage element 21 is attached to the upper cover surface of the second sealing element 27, and of course may be attached to the lower cover surface 28 of the third sealing element 16 (not shown in this manner), whether the second linkage element 21 is attached to the second sealing element 11 or to the third sealing element 16, a hole that matches with the second linkage element 21 is provided on one of the second sealing element 11 and the third sealing element (that is, the one that is not attached to the second linkage element 21). Similarly, the second linkage element 21 and the hole with which it is fitted also have a certain shape. The shape is similar to the foregoing linkage rod, which can be deviated from the self-rotation center of the second sealing element or the third sealing element, or can be non-spherical, such as square, semi-circular or triangular, etc. Its purpose is to make one of the linkage pin and or the linkage hole to drive another to rotate, and such rotation can be synchronic or intermittent, in the same direction or the opposite direction.

When the first sealing element 10 is linked with the first sealing element 10, the second sealing element 11 can seal the second chamber 2 by the second thread structure 18. When the second sealing element 11 is linked with the third sealing element 16, as the third sealing element 16 is linked with the first sealing element 10, the second sealing element 11 is also driven to seal the second chamber 2. Whether the direct linkage component of the second sealing element 11 is the first sealing element 10 or the third sealing element 16 can be considered according to the structural arrangement of the actual product, and selected according to actual needs.

In some preferred embodiments, the linkage structure comprises a first sealing element for sealing the first chamber and a second sealing element for sealing the second chamber, and the first sealing element is linked with the second sealing element via a first linkage element. In some preferred embodiments, the linkage structure comprises a first sealing element for sealing the first chamber and a third sealing element for sealing the channel, and the first sealing element is linked with the third sealing element via a first linkage element. In some preferred embodiments, the linkage structure comprises a second sealing element for sealing the second chamber and a third sealing element for sealing the channel, and the second sealing element is linked with the third sealing element via a second linkage element. In some preferred embodiments, the linkage structure comprises a first sealing element for sealing the first chamber and a second sealing element for sealing the second chamber, and a third sealing element for sealing the channel, the first sealing element is linked with the second sealing element via a first linkage element and the second sealing element is linked with the third sealing element via a second linkage element. In some preferred embodiments, the linkage structure comprises a first sealing element for sealing the first chamber, a second sealing element for sealing the second chamber, and a third sealing element for sealing the channel. The first sealing element is linked with the second sealing element via a first linkage element and the second sealing element is linked with the third sealing element via tight fitting or fixed connection.

In some preferred embodiments, the linkage between the second sealing element and the third sealing element may be implemented by a fixed connection. In some preferred embodiments, the linkage between the first sealing element and the third sealing element may be implemented by a fixed connection. That is, as shown in FIG. 13, the second sealing element 11 and the third sealing element 16 may be connected in a fixed manner, and the second sealing element 11 and the third sealing element 16 are integrated as a whole, to naturally realize linkage. This kind of fixed connection may be an integrated one itself, for example, a surface of the two seals may be fixedly connected or adhered together, or they may be fixedly connected by other components, such as a connecting rod. The present does not limit the fixed connection manner, as long as the linkage effect can be achieved. Similarly, the linkage can be realized naturally in this way between the first sealing element and the second sealing element, and between the first sealing element and the third sealing element.

In some preferred embodiments, the first linkage element is a linkage pole. In some preferred embodiments, the second linkage element is a linkage pin. In some preferred embodiments, the linkage refers to synchronous rotation. In some preferred embodiments, the linkage refers to moving in a direction close to the inside of the sample synchronically. In the present invention, the linkage particularly means that the sealing process is synchronous, for example, synchronous rotation, which is particularly suitable for the connection way of a screw thread structure, and for example, synchronous loading, which is particularly suitable for the connection way of a plug. In the connecting ways such as snapping, knob, etc., similar linkage structure can be used.

Limiting Structure

As foregoing stated, the channel 5 is an implementation manner of the separation portion, which is used to allow the second chamber 2 to be plugged in and sealed. As foregoing stated, it is required to limit the matching between the second chamber 2 and channel 5, otherwise, the second chamber 2 may slide into the first chamber 1 through this channel 5, causing contamination of the liquid samples or causing a large amount of leakage of the liquid samples at the channel 5. Therefore, a matching limiting structure is provided on the inner wall of the channel 5 and the outer wall of the second chamber 2. This limiting structure limits the limit position for the installation of the second chamber 2 to a place inside the channel, and once installed well, the second chamber 2 will not continue to move inwardly.

Referring to FIGS. 2, 7, 8, an outer stepped surface 36 is disposed on the inner wall of the channel 5, and using the outer stepped surface 36 as the dividing line, the inner diameter of the portion of channel 5 close to the first chamber is larger than that of the portion close to the outer portion. At the same time, referring to FIGS. 5-6, an inner stepped surface 29 that matches with the outer stepped surface 36 is provided on the outer wall of the second chamber 2. Using the inner stepped surface 29 as the dividing line, the inner diameter of the portion of the second chamber 2 close to the first chamber 1 is smaller than the inner diameter of the portion close to the outer portion, then through the matching of the inner stepped surface 29 and the outer stepped surface 36, the limit installation position of the second chamber 2 can be limited to this mating point. When the second chamber 2 is loaded, the stepped surface is snapped and unable to move further inward, to achieve the limit of the second chamber. 2.

The channel 5 is a structure that allows the first chamber to be assembled with the second chamber 2. The channel 5 can be regarded as a part of the first chamber 1. In an ideal state, after installation, the second chamber 2 (for example, the bottom surface) does not extend beyond the outer surface of the channel 5. By this way, the first chamber 1 and the second chamber 2 form an integral part before use. However, in such case, the second chamber 2 cannot be removed from the first chamber 1. So, the linkage structure in the present invention can achieve to gradually eject the second chamber outwards when the sealing element seals the first chamber 1, the second chamber 2 and channel 5. When all the sealing processes (including the sealing of the first chamber 1 by the first sealing element 10, sealing of the second chamber 2 by the second sealing element 11, and the sealing of the channel 5 by the third sealing element 16), a part of the second chamber 2 protrudes beyond the external contour of the first chamber 1 (as shown in FIG. 2), the second chamber 2 can be separated from the first chamber 1 by the extended portion, and the second chamber 2 after sealing by the second sealing element 11 is a chamber that has been sealed. The liquid samples inside can be used for second confirmatory detection, and the second chamber 2 can be transported separately to a second detection agency after detaching from the first chamber 1.

In order to achieve the gradual pushing out of the second chamber 2 with the sealing process, the length of the screw thread structure and the length of the linkage element need to meet certain requirements. For example, as described above, the second chamber 2 is first sealed by the second sealing element 11, and then the channel 5 is sealed by the third sealing element 16, during the sealing process, the first sealing element 11 is always in the process of sealing the first chamber 1, ideally, the third sealing element just completes the sealing while the first sealing element 11 completes the sealing. In this case, the length of the first thread structure 17 is equal to the sum of the lengths of the second thread structure 18 and the third thread structure 19, and the length of the linkage rod should meet the following condition: when the first sealing element 1 is turned down to the second sealing element 11 to completely seal the second chamber 2, the relative position of the second chamber 2 and the channel 5 is unchanged. When the third sealing element 16 begins to seal the channel 5, the second chamber 2 starts to be pushed out. That is, in the initial stage of the covering, the first sealing element 11 drives the second sealing element and the third sealing element to rotate by the linkage rod, and the third sealing element is in an idling state at this time, which is not in contact with other components, while the second sealing element has begun to coordinate with the screw thread structure on the second chamber 2. When the sealing of the second chamber 2 is finished, continue to rotate the first sealing element 11, and the first thread structure 17 continues to close, drive the third sealing element and the sealed second chamber downwardly through the linkage rod, when the second chamber 2 begins to move outward along the channel 5, the third sealing element begins to seal channel 5 until channel 5 is completely sealed, at this time, the first sealing element 11 has completed the sealing of the first chamber 1.

Since it is impossible to completely seal between the second sealing element 11 and the third sealing element 16, a gap 30 exists between them, and liquid samples may enter the gap when the second sealing element 11 seals the second chamber. Therefore, ideally, after the sealing of the second sealing element 11 is completed, the third sealing element 16 will still idle for a short distance, to squeeze out the liquid in the gap, and then seal the channel 5. By this way, the remaining liquid samples in the gap are as less as possible, to reduce the leakage of liquid samples when separation. In this case, the length of the first thread structure 17 needs to be slightly larger than the sum of the lengths of the second thread structure 18 and the third thread structure 19. In practice, the specific size can be adjusted as needed. The main technical solution to be achieved by the invention is the linkage relationship and the sequence of sealing.

Blocking Element

In addition to the above structure, the initial detection of the samples using the apparatus of the present invention is also an aspect of the present invention. Then, in a preferred state, the present invention is expected to be used in initial detection after the sample collection is completed, especially after the liquid samples in the second chamber 2 for the second confirmatory detection are collected and sealed. By this way, the samples for second confirmatory detection will not be contaminated for the initial detection, to ensure the accuracy of the second detection. To this end, the present invention further provides a blocking element 31. As mentioned above, the function of the blocking element is to temporarily partition the testing element and the liquid samples collected in the detection chamber (ie, first chamber 1), and temporarily prevent the liquid samples from entering the testing area 3. Of course, the blocking element can also release samples. Therefore, the blocking element is a component for blocking or opening the communication relationship between the first chamber 1 and the testing area 3. In the initial state of collecting samples, the blocking element 31 will separate the first chamber 1 from the testing area 3, at this time, the liquid samples cannot enter the testing area 3, and the testing element will not contact with or react with the liquid samples. When samples are collected to a certain extent or time, the blocking element 31 opens the detection inlet 32 that communicates the first chamber 1 and testing area 3, to allow a part of the liquid samples to enter the testing area 31 from the detection inlet 31, and carry out initial detection by the testing element, to obtain a preliminary test result.

As shown in FIGS. 2-4, the blocking element 31 can be a rotating piece that can rotate around the axis of the first chamber 1. A rotating piece can be provided with a blocking piece 33. The blocking piece 33 can block the inlet 32 before use and in the initial state of sample collection. At this time, even if the liquid samples enter the first chamber 1 and the second chamber 2, it is impossible to enter the testing area 3 to contact with the testing element, then the blocking element can interfere with one of the sealing elements at appropriate time during the rotation process of sealing element, thereby opening the inlet 32, to allow the liquid samples for initial detection to enter the testing area 3 for initial detection.

For example, the blocking element 31 is linked with the second sealing element, while the second sealing element completes the sealing of the second chamber, the blocking element is activated to open the inlet that communicates with the testing area. At this time, the second chamber has been sealed, to ensure that liquid samples in the second chamber will not have any contact with the samples in the testing area, and ensure the accuracy of second detection.

Alternatively, as shown in FIG. 2-4, the blocking element 31 is sleeved on the periphery of the channel 5 and can be rotated around it. The third sealing element 16 is provided with a protrusion portion 34. The protrusion portion 34 can be lowered to a position that interferes with the blocking piece 33 when sealing by third sealing element 16 and channel 5. When the third sealing element 16 completes the sealing of the channel 5, the protrusion portion 34 interferes with the blocking piece 33, pushing the blocking piece 33 to drive the blocking element 31 to rotate, open the inlet 32 that communicates with the testing area. Since the second sealing element has sealed the second chamber during the sealing of separation portion by the third sealing element, the second chamber has been sealed when the third sealing element completes the sealing of the separation portion. Therefore, when the opening of the testing area is opened, the liquid samples in the second chamber will not have any contact with the samples in the testing area, to ensure the accuracy of second detection.

In some preferred embodiments, blocking element is used to open the testing area for detecting the initial detection samples. When the second chamber does not collect the sample or when collecting samples, the testing area is closed. When the collection of the second chamber is completed and sealed, the samples can enter the testing area.

In some preferred embodiments, it comprises a second sealing element for sealing the second chamber, the second sealing element can open or close the detection inlet, and when the second sealing element completes the sealing of the second chamber, the detection inlet is opened. In some preferred embodiments, the second sealing element is linked with the blocking element, while the second sealing element completes the sealing of the second chamber, the blocking element is activated to open the inlet that communicates with the testing area.

In some preferred embodiments, the first chamber can be in liquid communication with or partition with the testing area. When the detection inlet is opened, the first chamber and the testing area achieve liquid communication. When the detection inlet is closed, the first chamber and the testing area are partitioned. In some preferred embodiments, first sealing element is linked with the second sealing element, and the first sealing element can open or close the detection inlet, when the second sealing element completes the sealing of the second chamber, the first sealing element is driven to open the detection inlet. In some preferred embodiments, the first sealing element is linked with the blocking element, and when the second sealing element completes the sealing of the second chamber, the blocking element is activated by the first sealing element to open the inlet that communicates with the testing area.

In some preferred embodiments, the third sealing element is linked with the second sealing element, the third sealing element can open or close the detection inlet, and when the second sealing element completes the sealing of the second chamber, the third sealing element is driven to open the detection inlet. In some preferred embodiments, the third sealing element is linked with the blocking element, while the second sealing element completes the sealing of the second chamber, the blocking element is activated by the third sealing element to open the inlet that communicates with the testing area.

Example 1

The assembling and operation methods are described below with reference to specific embodiments.

For example, referring to the apparatus shown in FIG. 1-3, 6-14, the apparatus includes a first chamber 103 and a second chamber 104, and the first chamber 103 has an opening 1031 for leading in liquid samples. Referring to FIG. 1, the first chamber is enclosed by the side wall and the bottom, and there is a protrusion area at the bottom of the first chamber, for example, referring to FIG. 9, the protrusion area is located in the center of the whole bottom, and an opening 1091 is provided in the protrusion area and there is a section of connecting channel 109, of which the first opening 1091 is connected with the first chamber 103 and the other opening 1092 is connected with the opening 1042 of the second chamber. A groove is formed around the protrusion area inside the first chamber, and the groove forms two collection areas 1035 and 1036 of liquid samples (see FIG. 7). A screw thread structure 1101 is arranged on the wall 110 opposite the outer side of the connecting channel 109 near the second opening 1092, and a screw thread structure 1041 is arranged on the outer wall of the opening 1042 of the second chamber 104, which cooperates with the screw thread 1101 on the wall 110 for rotation, so that the second chamber 104 can cooperate with the first chamber through the connecting channel 109 in a detachable manner. At the same time, the apparatus further includes a detection chamber 105, and liquids in the detection chamber are connected with those in the first chamber through the through hole 1038. The detection chamber includes a testing element, and the testing element is arranged in the card slot 1061 of the testing carrier 106. Generally, the sample application area of the testing element is located in the area of the testing carrier near the bottom of the second chamber or the bottom 1051 of the detection chamber, while the water absorption area of the testing element is close to the other end of the detection chamber (the end near the opening 1031 of the first chamber).

The present invention further provides a cover body 102 in the center of which is connected with a connecting rod 1023 at the terminal of which is provided with a sealing element 1028 on which a seal ring 108 is provided. At the same time, a discharge element 1027 is provided below the sealing element and the discharge element 1027 and the sealing element and the connecting rod 1023 are an integral structure, and they are only different functional areas. Generally, the length of the connecting rod 1023, the sealing element 1038 and the discharge element 1027 is slightly larger than the distance between the opening 1031 of the first chamber 103 and the opening 1042 of the second chamber 104, so that the discharge element 1027 can enter the second chamber 104, so as to discharge some liquid samples in the second chamber. At the same time, a liquid inlet 1025 of the drain channel is provided below the sealing element 1028 (FIG. 2 and FIG. 3), and the liquid inlet 1025 can be located between the discharge element 1027 and the sealing element 1028. At the same time, the sealing element, the discharge element and the connecting rod are of a hollow structure, and the interior includes a receiving chamber 1029 for collecting redundant liquid samples. When in use, first allow the opening of the first chamber to collect liquid samples, and as liquid samples enter, they are collected at the bottom of the first chamber and then enter the detection chamber through the through hole 1038, and liquid samples entering the detection chamber contact the sample reagent area of the testing element, so as to perform assay and detection. With the increase of liquids, liquid samples enter the second chamber through the opening 1091 of the connecting channel, and then the second chamber 104 is gradually filled with liquid samples and the first opening 1091 of the connecting channel is submerged, finally, the liquid level is higher than the first opening 1091 of the connecting channel 109. At this time, stop collecting the liquid samples. Then, use the first cover body 102 to cover the opening 1031 of the first chamber 103. As the cover body covers the opening 1031, the rotary covering of the cover body drives the sealing element 1028, the discharge element 1027 and the liquid inlet 1025 of the drain channel to approach the opening of the connecting channel 109 (see FIGS. 10, 11 and 12). With the rotation of the cover body, the discharge element 1027 first enters the connecting channel 109, and the seal ring of the sealing element has not approached the first opening 1091 of the connecting channel. Liquids can enter the first chamber 103 through the gap between the discharge element 1027 and the connecting channel 109. As the sealing element enters the connecting channel 109, the discharged liquid enters the receiving chamber 1029 through the liquid inlet 1025 of the drain channel so as to discharge redundant liquid samples and relieve the pressure on the sealing element when entering the connecting channel to obtain a better sealing effect more easily. After the discharge element enters the second chamber, the sealing element also seals the connecting channel 109. At this time, the first detection has been completed by the testing element of the detection chamber, and it is believed that it is necessary to reserve the residual samples for second confirmatory detection, after which the second chamber is separated from the first chamber by rotating the second chamber. The sealing element has sealed the connecting channel, so liquid samples in the first chamber will not leak out. Then, the second cover body 101 provided on the first cover body 102 is used to seal the opening 1042 of the second chamber 104 (see FIG. 14 and FIG. 13). In this way, the second cover body can be separately stored or packed and transported to the assay organization for second confirmatory detection.

Example 2

For example, referring to the apparatus shown in FIGS. 15-18, 23-28, the apparatus includes a first chamber 203 and a second chamber 204, and the first chamber 203 has an opening 2031 for leading in liquid samples. Referring to FIG. 16, the first chamber is enclosed by the side wall and the bottom, and there is a protrusion area at the bottom of the first chamber, for example, referring to FIG. 24, the protrusion area is located in the center of the whole bottom, and an opening 2091 is provided in the protrusion area and there is a section of connecting channel 209, of which the first opening 2091 is connected with the first chamber 203 and the other opening 2092 is connected with the opening 2042 of the second chamber. A groove is formed around the protrusion area inside the first chamber, and the groove forms two collection areas 2035,2034 of liquid samples (see FIG. 24). A screw thread structure 2101 is arranged on the wall 210 opposite the outer side of the connecting channel 209 near the second opening 2092, and a screw thread structure 2043 is arranged on the outer wall of the opening 2042 of the second chamber 204, which cooperates with the screw thread 2101 on the wall 210 for rotation, so that the second chamber 204 can cooperate with the first chamber through the connecting channel 209 in a detachable manner. At the same time, a carrier 206 is provided. The carrier has a plurality of channels with seals 2062 on one end and openings 2063 on the other end. One or more test strips are provided in the channel, and the sample application area of the test strip is located at one end of the opening 2063. One or more channels for accommodating test strips are provided in the carrier 206, and each channel is provided with a testing element. When there are multiple channels, test elements of different analytes can be set in each channel, so that a plurality of analytes can be detected by the same sample. Such a carrier 206 is placed in the first chamber 203 with two stop strips 2032 and 2033 on the wall of the chamber 203. The carrier 206 is inserted or snapped into the two limit grooves, allowing the end 2065 of the channel with opening to be close to the bottom of the first chamber, and the end 2064 with sealing channel to be close to the opening 2031 of the first chamber (FIG. 16). When the liquid sample flows into the first chamber through the opening 2031 of the first chamber, the liquid sample comes into contact with the sample application area of the test strip, thereby completing the detection.

The present invention further provides a cover body 202 in the center of which is connected with a connecting rod 2023 at the terminal of which is provided with a sealing element 2028 on which a seal ring 208 is provided. At the same time, a discharge element 2027 is provided below the sealing element, and the discharge element 2027 and the sealing element 2028 and the connecting rod 2023 are an integral structure, and they are only different functional areas. Generally, the length of the connecting rod 2023, the sealing element 2028 and the discharge element 2027 is slightly larger than the distance between the opening 2031 of the first chamber 203 and the opening 2042 of the second chamber 204, so that the discharge element 2027 can enter the second chamber 204, so as to discharge some liquid samples in the second chamber. At the same time, a liquid inlet 2025 of the drain channel is provided below the sealing element 2028 (FIG. 18 and FIG. 26), and the liquid inlet 2025 can be located between the discharge element 2027 and the sealing element 2028. At the same time, the sealing element, the discharge element and the connecting rod are of a hollow structure, and the interior includes a receiving chamber 2029 for collecting redundant liquid samples. When in use, first allow the opening of the first chamber to collect liquid samples, and as liquid samples enter, they are collected at the bottom of the first chamber, to contact the application area of testing element on the carrier for assay and detection. With the increase of liquids, liquid samples enter the second chamber through the opening 2091 of the connecting channel, and then the second chamber 204 is gradually filled with liquid samples and the first opening 2091 of the connecting channel is submerged, finally, the liquid level is higher than the first opening 2091 of the connecting channel 209. With the increase in the liquid, stop receiving the liquid samples when arriving at the set position At this time, stop collecting the liquid samples. Then, use the first cover body 202 to cover the opening 2031 of the first chamber 203. As the cover body covers the opening 2031, the rotary covering of the cover body drives the sealing element 2028, the discharge element 2027 and the liquid inlet 2025 of the drain channel to approach the opening of the connecting channel 209 (see FIG. 12). With the rotation of the cover body, the discharge element 2027 first enters the connecting channel 209, and the seal ring of the sealing element has not approached the first opening 2091 of the connecting channel, without sealing the first opening 2091 of the connecting channel. Liquids can enter the first chamber 203 through the gap 809 between the discharge element 2027 and the connecting channel 209. As the sealing element enters the connecting channel 209, the discharged liquid enters the receiving chamber 2029 through the liquid inlet 2025 of the drain channel so as to discharge redundant liquid samples and relieve the pressure on the sealing element when entering the connecting channel to obtain a better sealing effect more easily. After the discharge element enters the second chamber, the sealing element also seals the connecting channel 209. At this time, the first detection or initialed detection has been completed by the testing element of the detection chamber, and it is believed that it is necessary to reserve the residual samples for second confirmatory detection, after which the second chamber is separated from the first chamber by rotating the second chamber. The sealing element has sealed the connecting channel, so liquid samples in the first chamber will not leak out. Then, the second cover body 201 provided on the first cover body 202 is used to seal the opening 2042 of the second chamber 204 (see FIG. 24). In this way, the second cover body can be separately stored or packed and transported to the assay organization for second confirmatory detection.

Example 3

For example, referring to the apparatus shown in FIGS. 25-30, the apparatus includes a first chamber 303 and a second chamber 304, and the first chamber 303 has an opening 3031 for leading in liquid samples. Referring to FIG. 27, the first chamber is enclosed by the side wall and the bottom, and there is a protrusion area at the bottom of the first chamber, for example, referring to FIG. 27, the protrusion area is located in the center of the whole bottom, and an opening 3091 is provided in the protrusion area and there is a section of connecting channel 309, of which the first opening 3091 is connected with the first chamber 303 and the other opening 3092 is connected with the opening 3042 of the second chamber. A groove is formed around the protrusion area inside the first chamber, and the groove forms two collection areas 3035 and 3036 of liquid samples (see FIG. 27). A groove is formed around the protrusion area inside the first chamber, which forms liquid sample collection areas 3035, 3036 (FIG. 27). The second opening 3092 of the connecting channel 309 is a smooth outer wall and an inner wall. There is a tray structure 1004, with an internal thread 10041 that matches with the external thread at the bottom of the first chamber.

The second chamber 304 is located on a base structure or a tray structure 1004, and the base tray 1004 is detachably connected with the first chamber, while the second chamber is also detachably connected with the base tray 1004. Specifically, the tray structure 1004 has an internal thread, and the internal thread matches with the extended external thread 3031 at the bottom of the first chamber 303, thereby realizing a detachable combination between the tray structure 1004 and the first chamber 303. In this way, if there is still a connecting channel, as shown in FIG. 27, the connecting channel 309 can still have a first opening 3091 through which liquid can flow from or to the first chamber and a second opening 3092 through which liquid can flow from or to the second chamber, while the connecting channel has an extension 3098 which goes deep into the opening 3052 of the second chamber, and contacts the inner wall of the opening 3041, and they can be connected together by snapping, that is, the outer diameter of the extended area matches with the inner diameter of the opening 3041. Although the second chamber and the first chamber can also be connected through the connecting channel 109 by snapping as shown in FIG. 27, such connection is not required to be very firm, or as close as that shown in FIGS. 8-9 (by a screw thread or other ways). This is because the tray structure 1004 matches with the external thread 3031 of the extension of the first chamber 103 through the screw thread 10041, so no matter how many liquids are collected by the second chamber 304, the leakage problem between the connecting channel 109 and the opening 1042 of the second chamber will not caused. Therefore, the inner diameter of the connecting channel 109 can be less than that of the opening 1042 of the second chamber, so that the connecting channel can be easily inserted into the opening 3042 of the second chamber, as shown in FIG. 27. A screw thread is only set at the outer edge of the opening 3042 to cover the second cover body (as shown in FIG. 27). At this time, the connection between the connecting channel and the opening of the second chamber only needs to ensure no liquid leakage when collecting liquid samples, that is to ensure liquid can enter the second chamber, and more structural constraints are not required. Such connection can be achieved in the forms of snapping, piston or locking. In fact, the detachable combination, connection or assembly between the first chamber and the second chamber is completed in an indirect way.

After the collection is completed, and after the connecting channel is sealed or/and the drainage function of the second chamber body is conducted according to the method described below, if it is necessary to perform the second confirmatory test, separate the tray structure 1004 from the first chamber 103, for example, reversely rotate the screw thread structure of the tray that matches with the bottom of the first chamber, then the second chamber 104 on the tray is also separated from the first chamber 103 together with the tray structure, as shown in FIG. 27, at this time, take down the second cover body 101 to cover the opening 3042 of the second chamber. Then, let the second chamber separate from the tray 1004 (as shown in FIG. 29). Because the bottom of the second chamber and the bottom of the tray have a snapping structure 10042, so the tray and the second chamber will separate from the first chamber 103 together. Then, disassemble the tray 1004 from the second chamber 304, and connect or combine the tray 1004 alone with the first chamber 103 again. At this time, the integrity of the first chamber shall be still maintained, while the second chamber can be sent to the approved assay agency for the second confirmatory test. To allow the second chamber 304 to separate from the first chamber with the movement of the tray, a snapping ring 10042 is provided on the tray. The shape of the snapping ring is suitable for the shape of the second chamber 304, for example, the second chamber body is U-shaped, and the snapping ring 10042 is also U-shaped. In this way, the second chamber 304 will rotate when the tray structure 1004 rotates. The second chamber can slightly and closely cooperate with the snapping ring, so naturally, the second chamber 304 and the tray structure 1004 can separate from the first chamber 303 together. Of course, in some embodiments, the second chamber is a structure similar to a cube, and 4 snap joint structures are set on the tray. The second chamber is connected to the snap joint structure by snapping, so that the movement of the tray can drive the movement of the second chamber, and the second chamber can be separated from the first chamber.

The present invention further provides a cover body 302 in the center of which is connected with a connecting rod 3023 at the terminal of which is provided with a sealing element 3028 on which a seal ring is provided. The seal ring and sealing element are made of the same material by one-time injection moulding. At the same time, a discharge element 3027 is provided below the sealing element and the discharge element 3027 and the sealing element and the connecting rod 3023 are an integral structure, and they are only different functional areas. Generally, the length of the connecting rod 3023, the sealing element 3038 and the discharge element 3027 is slightly larger than the distance between the opening 3031 of the first chamber 303 and the opening 3042 of the second chamber 304, so that the discharge element 3027 can enter the second chamber 304, so as to discharge some liquid samples in the second chamber. At the same time, a liquid inlet 3025 of the drain channel is provided below the sealing element 3028 (FIG. 27), and the liquid inlet 3025 can be located between the discharge element 3027 and the sealing element 3028, or located on the discharge element. At the same time, the sealing element, the discharge element and the connecting rod are of a hollow structure, and the interior includes a receiving chamber 3029 for collecting redundant liquid samples. When in use, first allow the opening of the first chamber to collect liquid samples, and as liquid samples enter, they are collected at the bottom of the first chamber. With the increase in the liquid, the liquid samples enter the second chamber through the opening of 1091 of the connecting channel, and then the second chamber 304 is gradually filled with liquid samples and the first opening 3091 of the connecting channel is submerged, finally, the liquid level is higher than the first opening 3091 of the connecting channel 309. At this time, stop collecting the liquid samples. Then, use the first cover body 302 to cover the opening 3031 of the first chamber 303. As the cover body covers the opening 3031, the rotary covering of the cover body drives the sealing element 3028, the discharge element 3027 and the liquid inlet 3025 of the drain channel to approach the opening of the connecting channel 309. With the rotation of the cover body, the discharge element 3027 first enters the connecting channel 309, and the seal ring of the sealing element has not approached the first opening 3091 of the connecting channel. Liquids can enter the first chamber 303 through the gap between the discharge element 3027 and the connecting channel 309. As the sealing element enters the connecting channel 309, the discharged liquid enters the receiving chamber 3029 through the liquid inlet 3025 of the drain channel so as to discharge redundant liquid samples and relieve the pressure on the sealing element when entering the connecting channel to obtain a better sealing effect more easily. After the discharge element enters the second chamber, the sealing element also seals the connecting channel 309.

Figure 30:
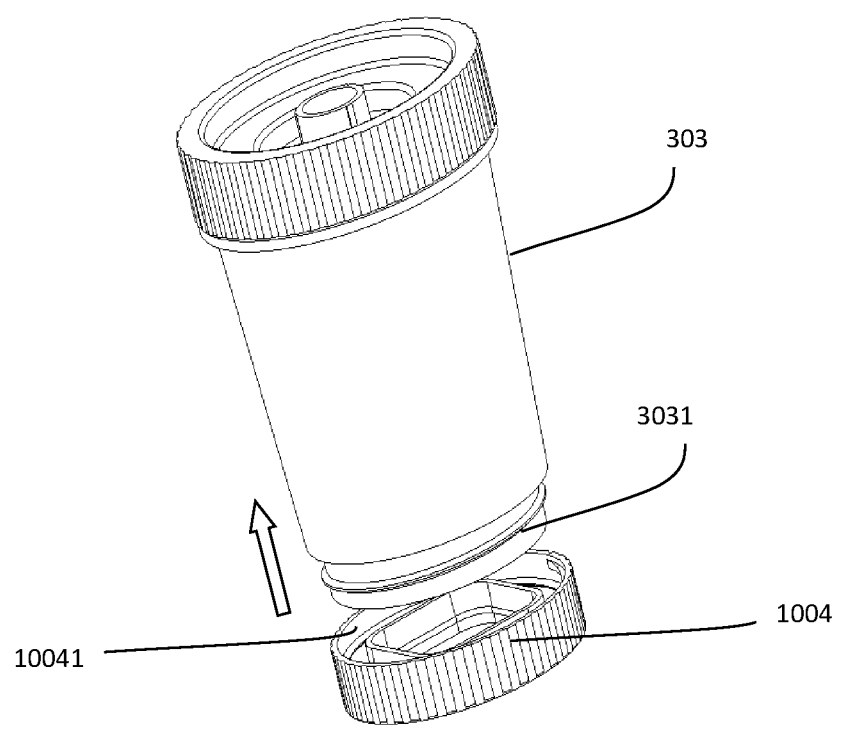
FIG. 30 is a perspective structural view showing a tray of a second chamber combining with a first chamber.

At this time, the liquid of the first chamber can be used for subsequent initial detection. When it is considered necessary to retain the remaining sample for the second confirmatory test, by rotating the tray structure, the tray structure is separated from the first chamber, thereby driving the second chamber to separate from the first chamber. The sealing element has sealed the connecting channel, so liquid samples in the first chamber will not leak out. Then, the second cover body 301 provided on the first cover body 302 is used to seal the opening 3042 of the second chamber 304 (see FIG. 28). At this time, the tray structure and the second chamber can be packaged and sent to a testing agency for second testing. Alternatively, the second chamber is removed from the tray and packaged for a second confirmatory test (FIG. 29). At this time, the tray is transferred to the first chamber again to form the integral structure (FIG. 30).

Example 4 (The Second Design)

As shown in FIG. 42, the sample collection apparatus of the present invention may comprises a cover body 63 and a third chamber 43, and the cover body and the third chamber are detachably connected by a joint portion 69. The sample collection apparatus may also comprise some components that may be separate and unassembled prior to use, for example, a second chamber 42, an assembly structure 62, a connector 58, a pipetting plug 78, etc. When packed and transported, these components can be put in the third chamber 43. A plug can be pre-configured on the assembly channel of the cover body 63, to plug the assembly channel for preventing dust accumulation or internal contamination of the assembly channel. In some cases, the connector 58 can also be used as a component and assembled to the cover body when in use. During use, the plug is removed, and the second chamber 42 is assembled into the assembly channel of the cover body 63. The second chamber itself can be mounted on an assembly structure. The assembly structure and the second chamber form an assembly body, and the assembly body can be placed into the assembly channel of the cover body 63, and then the connector 58 is also placed the lower end of the assembly channel 70. The connector 58 can seal the lower end of the assembly channel. Before use, as shown in FIG. 36, the connector 58 will not pierce the second chamber. In some cases, the connector 58 may be pre-assembled at the bottom of the assembly channel of the cover body 62, but it is not assembled to the limit position for matching.

When collecting the sample, open the cover body, assemble the second chamber and other components into the cover body according to the above relationship, then collect samples into the third chamber. While collecting samples in the third chamber, samples will automatically flow into the first chamber and the fourth chamber until the required amount is reached, and then the cover body 63 is closed. During the cover body sealing process, the connector 58 will initially close the first channel, then the cover body continues to cover downwards, and the assembly channel is pressed down, so that the connector further enters the assembly channel until the seal 57 on the second chamber is pierced. At this time, the first channel is closed by the connector, the first chamber and the third chamber are in an isolated state, while the first chamber is in fluid communication with the second chamber by the connector. However, as the connector is connected by a needle and the liquid in the first chamber is located below the second chamber, the liquid in the first chamber will not actively flow into the second chamber, and the samples in the fourth chamber will not actively flow into the testing area.

When detecting samples, the first pipetting element 52 is pushed inward by the pipetting plug 78. At this time, the inward movement of the first pipetting element 52 makes the volume of the first chamber 41 to become smaller, and the liquid samples in the first chamber are squeezed to move to the second chamber. At the same time, it will produce an inward thrust on the second pipetting element 53, but before this inward thrust overcomes the frictional resistance between the second pipetting element 53, however, before inward thrust overcomes the frictional resistance between the second pipetting element 53 and the inner wall of the pipetting channel 51, the second pipetting element 53 is immobile, until the first pipetting element 52 is in contact with the second pipetting element 53. At this time, the second chamber has substantially completed the collection of the samples. By further pushing the pipetting plug inwardly, the second pipetting element 53 begins to squeeze the liquid samples in the fourth chamber and push them in the testing area, then detection is carried out by the testing element. As shown in FIG. 29, the samples in the fourth chamber are completely pushed into the testing area. Since the position of the second pipetting element 51 is determined in the initial state, the volume of the fourth chamber 44 can be determined to achieve quantitative detection.

In the mode of this embodiment, a testing element can be placed in the testing area. The initial detection of samples is carried out by the testing element. The testing area is made of a transparent material, and the test result can be directly observed through the outer surface of the testing area. If the result may be positive or weakly positive or undetermined and it is required to conduct a second confirmatory detection, the second chamber and the assembly structure are taken out by turning the knob 76. At this time, the connector is left in the detection apparatus, and the second chamber can be independently transported to a detection agency for second confirmatory detection.

Example 5 (The Third Design)

Before use, the linkage rod and the first sealing element 10, the second sealing element 11 and the third sealing element 16 can be in a separated or partially separated state. Under such circumstances, the first sealing element 10 in a separated state can be used to close the entire apparatus. The second sealing element 11, the third sealing element 16 and the linkage rod in a separated state can be placed in the first chamber 1 as a complete product package.

During use, the first sealing element 10 is opened to take out accessories (including the second sealing element, the third sealing element and the linkage rod) therefrom. In some cases, these accessories can also be placed separately in other packages. The present invention does not limit the packaging way of the accessories. Liquid samples are loaded inwards from the first collection port. At this time, a part of the liquid samples will enter the second chamber simultaneously. As the second chamber is located at the bottom of the first chamber, in general, the second chamber is preferentially loaded into liquid samples. Liquid samples are continuously loaded into the apparatus until the desired amount is reached.

After liquid samples are collected, the apparatus will be sealed. The relevant accessories are connected together as shown in FIG. 85, and then the first sealing element 10 is rotated to seal the first chamber. During the process, as shown in FIG. 8, the linkage rod firstly drives the second sealing element and the third sealing element to move down until the second sealing element is in contact with the second collection port. When further rotating, the second sealing element can seal the second chamber, while sealing the second chamber, the sealing elements that form an integrated portion through the linkage elements will continue to rotate downwards. At this time, the third sealing element starts to seal the channel. Since the second sealing element and the third sealing element or the first sealing element are still in the linkage state, the second sealing element will drive the sealed second chamber to move downward while rotating. At this time, the downward movement of the second chamber is pushed outwards relative to the channel. The bottom of the second chamber is gradually exposed outside the bottom of the first chamber, until the channel is sealed. At this time, the first chamber is sealed. To prevent excessive rotation, a seal limiting element is provided at the outside of the first collection port, as shown in FIG. 80, 82, 85 or 86. It can be a spacing ring 35. The periphery of the spacing ring is larger than the periphery of the first sealing element. So, when the first sealing element is rotated into contact with the spacing ring, it can no longer continue to move downwards. The seal limiting structure can protect the internal structure and prevent excessive rotation and damage to the internal structure. Of course, the seal limiting element can also be a limiting block or a snap joint, or the seal limiting element can be realized by the end of the screw thread. When the first sealing element is rotated to the end of the first thread structure, it is naturally limited.

The following content is a part of technical solution of the present invention.

The present invention includes, but not limited to the following embodiments.

The First Design

Clause 1. An apparatus for collecting liquid samples, comprising a first chamber for collecting liquid samples; and a second chamber for collecting samples for confirmatory detection; wherein the first chamber and the second chamber can be detachably combined, assembled or connected.

Clause 2. The apparatus according to clause 1, wherein the first chamber and the second chamber are in a liquid communication state.

Clause 3. The apparatus according to clause 1, wherein the first chamber and the second chamber are in a liquid communication state before the second chamber is separated from the first chamber.

Clause 4. The apparatus according to clause 1, wherein the first chamber and the second chamber are not in a liquid communication state before the second chamber leaves the first chamber or before the second chamber is about to leave the first chamber.

Clause 5. The apparatus according to clause 1, wherein the first chamber and the second chamber are assembled together in a detachable manner.

Clause 6. The apparatus according to clause 1, wherein the second chamber is located below the first chamber, or, when collecting liquid, the liquid first enters the first chamber and then enters the second chamber, or the second chamber is located downstream of the first chamber; alternatively, when collecting liquid, liquid enters the first chamber and the second chamber simultaneously; or, a portion of the liquid samples enter the first chamber and another portion of the liquid samples enter the second chamber.

Clause 7. The apparatus according to clause 1, wherein the fluid communication state between the first chamber and the second chamber comprises one or more of the following states: fluid communication, fluid non-communication.

Clause 8. The apparatus according to clause 1, wherein the first chamber and the second chamber are first in a liquid non-communication state, then in a liquid communication state, and finally in a liquid non-communication state.

Clause 9. The apparatus according to clause 1, wherein the first chamber and the second chamber are first in a liquid communication state, and then in a liquid non-communication state.

Clause 10. The apparatus according to any one of clauses 1 to 9, wherein the first chamber and the second chamber are detachably combined when they are in a liquid communication state, or the first chamber and the second chamber can be separated or have been separated when they are in a liquid non-communication state.

Clause 11. The apparatus according to clause 10, wherein the first chamber and the second chamber are detachably combined when they are in a liquid non-communication state.

Clause 12. The apparatus according to any one of clauses 1 to 11, wherein the apparatus further comprises a sealing element, the sealing element may change a liquid communication state between the first chamber and the second chamber; or the apparatus further comprises a piercing element, the piercing element can change the state from liquid non-communication to liquid communication; or the apparatus further comprises a sealing element and a piercing element, firstly the first chamber and the second chamber are in a liquid communication state by the piercing element, then in a liquid non-communication state by the sealing element.

Clause 13. The apparatus according to clause 12, wherein the sealing element makes the first chamber and the second chamber in a liquid non-communication state before the second chamber leaves the first chamber or before second chamber is separated or is about to be separated from the first chamber.

Clause 14. The apparatus according to any one of clauses 1 to 13, the apparatus further comprises a connecting channel, the second chamber is detachably combined, connected or assembled with the first chamber via the connecting channel, or/and the second chamber is or is not in fluid communication with the first chamber via the connecting channel.

Clause 15. The apparatus according to any one of clauses 1 to 13, wherein the apparatus further comprises a connecting channel; the second chamber is in fluid communication with the first chamber via the connecting channel.

Clause 16. The apparatus according to clause 15, wherein the connecting channel is not sealed when the second chamber does not leave the first chamber; or the connecting channel is sealed before or after the second chamber leaves the first chamber.

Clause 17. The apparatus according to clause 16, wherein the connecting channel is sealed via a sealing element.

Clause 18. The apparatus according to clause 15, wherein the apparatus further comprises a sealing element for sealing the channel so that the first chamber and the second chamber are not in a liquid communication state.

Clause 19. The apparatus according to any one of clauses 1 to 13, or any one of clauses 17 to 18, wherein the apparatus further comprises a drain channel having a liquid inlet.

Clause 20. The apparatus according to clause 19, wherein the liquid inlet is located below the sealing element, or the liquid inlet is close to the connecting channel prior to the sealing element when the sealing element seals the channel, or the liquid inlet is located below the horizontal position of the sealing element when the sealing element enters the connecting channel; or the liquid inlet enters the connecting channel prior to the sealing element when the sealing element enters the connecting channel.

Clause 21. The apparatus according to clause 20, wherein the liquid inlet is located on a sealing element.

Clause 22. The apparatus according to clause 20, wherein the liquid inlet is located on a side wall of a connecting channel.

Clause 23. The apparatus according to clause 20, wherein the drain channel further has a liquid outlet, and the liquid outlet is in fluid communication with a receiving chamber.

Clause 24. The apparatus according to clause 23, wherein the receiving cavity is located on a sealing element.

Clause 25. The apparatus according to clause 20, wherein the drain channel further has a liquid outlet, and the liquid outlet is in fluid communication with the first chamber.

Clause 26. The apparatus according to any one of clauses 1 to 25, wherein the apparatus further comprises a discharge element for removing a portion of liquid samples in the second chamber.

Clause 27. The apparatus according to clause 26, wherein the discharge element is located in the second chamber or partially in the second chamber before the second chamber is separated from the first chamber.

Clause 28. The apparatus according to clause 26, wherein the second chamber does not contain a discharge element or does not contain a portion of discharge element after the second chamber is separated from the first chamber.

Clause 29. The apparatus according to any one of clauses 12 to 25, wherein the apparatus further comprises a discharge element for removing a portion of the liquid samples in the second chamber; the discharge element is located on a sealing element or is connected with a sealing element.

Clause 30. The apparatus according to clause 29, wherein the discharge element enters a connecting channel prior to the sealing element, or the discharge element enters the second chamber prior to the sealing element; or the discharge element is located in the second chamber when the sealing element is located in a connecting channel.

Clause 31. The apparatus according to clause 29, wherein the apparatus further comprises a drain channel having a liquid inlet, the liquid inlet is located on a discharge element; or the apparatus comprises a receiving chamber and the receiving chamber is located on the discharge element.

Clause 32. The apparatus according to clause 28, wherein the liquid inlet is in liquid communication with a receiving chamber, and the receiving chamber is located in a discharge element.

Clause 33. The apparatus according to clause 17, wherein a partial region of the sealing element is used as a discharge element for discharging a part of liquid in the second chamber.

Clause 34. The apparatus according to clause 33, wherein a portion of the sealing element is used for sealing a connecting channel, and a portion of the sealing element is used for discharging part of liquid in the second chamber.

Clause 35. The apparatus according to clause 33, wherein a portion of the sealing element is used for sealing a connecting channel, and a portion of the sealing element is located in the second chamber.

Clause 36. The apparatus according to clause 29, wherein the vertical projection area of the discharge element is located within the vertical projection area of the sealing element.

Clause 37. The apparatus according to any one of clauses 12 to 19 or 17 to 18, wherein the apparatus further comprises a drain channel having a liquid inlet, and the vertical projection of the liquid inlet is within the vertical projection area of the sealing element.

Clause 38. The apparatus according to any one of clauses 17 to 39, wherein the sealing element or the discharge element is moved by linkage.

Clause 39. The apparatus according to clause 41, wherein the linkage is used to cover the cover body of the first chamber opening for motion.

Clause 40. The apparatus according to clause 41 or 42, wherein the motion is a rotational motion.

Clause 41. A method of collecting liquid samples, comprising: Providing a collection apparatus, comprising a first chamber and a second chamber for collecting liquid samples, wherein the first chamber and the second chamber are detachably combined, connected or assembled; Allowing the first chamber and the second chamber in a liquid communication state before collecting liquid samples, so that the liquid that enters the first chamber can flow into the second chamber.

Clause 42. The method according to clause 41, wherein the first chamber and the second chamber are not in a liquid communication state after the first chamber collects liquid samples.

Clause 43. The method according to clause 42, wherein the second chamber is separated from the first chamber or the first chamber is separated from the second chamber when the first chamber and the second chamber are not in a liquid communication state.

Clause 44. The method according to clause 41, wherein liquid samples entering the second chamber are from the liquid samples in the first chamber; liquid enters the first chamber and the second chamber simultaneously; or, a portion of liquid samples enter the first chamber and another portion of liquid samples enter the second chamber.

Clause 45. The method according to clause 41, wherein the first chamber is connected to the second chamber by a connecting channel, the second chamber is detachably combined, connected or assembled with the connecting channel; or, the first chamber and the second chamber are in a liquid communication state through the connecting channel.

Clause 46. The method according to clause 45, wherein a sealing element is used to sealing the channel, to achieve non-communication state between the first chamber and the second chamber.

Clause 47. The method of clause 46, wherein the channel has a first opening in fluid communication with the first chamber and a second opening in fluid communication with the second chamber, allowing the sealing element to seal the first opening of the connecting channel.

Clause 48. The method according to clause 47, wherein a portion of the sealing element enters the channel after the sealing element seals the first opening of the connecting channel.

Clause 49. The method according to any one of clauses 41 to 48, wherein the apparatus further comprises a drain channel, and the drain channel includes a liquid inlet.

Clause 50. The method according to clause 49, wherein, when a portion of the sealing element enters the channel, liquid samples discharged by the sealing element are discharged out of the connecting channel or the second chamber through the liquid inlet in the case of presence of liquid samples.

Clause 51. The method according to clause 50, wherein liquid samples discharged by the sealing element are discharged to a receiving chamber through the drain channel.

Clause 52. The method according to clause 46, wherein the apparatus further comprises a drain channel, and the drain channel comprises a liquid inlet, and the liquid inlet enters the connecting channel prior to the sealing element.

Clause 53. The method according to any one of clauses 46 to 52, wherein the apparatus further comprises a discharge element for discharging a portion of liquid in the second chamber.

Clause 54. The method according to clause 53, wherein, when a sealing element is provided, the discharge element enters or approaches to the connecting channel prior to the sealing element.

Clause 55. The method according to clause 54, wherein the discharge element is allowed to enter the second chamber, or a portion of the discharge element is allowed to enter the second chamber.

Clause 56. The method according to clause 51, wherein, after the second chamber is separated from the first chamber, the discharge element is not located in the second chamber.

Clause 57. The method according to clause 54, wherein, when the sealing element seals the first opening of the connecting channel, the discharge element is allowed to enter the second chamber, or when the sealing element enters the connecting channel, the discharge element is allowed to enter the second chamber.

Clause 58. The method according to clause 54, wherein the sealing element and the discharge element move by linkage.

Clause 59. The method according to clause 58, wherein the linkage is performed by covering the cover body of the first chamber.

The present invention further includes the following embodiments.

Clause 1. An apparatus for collecting liquid samples, comprising: a first chamber for collecting liquid samples; and a second chamber for collecting liquid samples for confirmatory detection; wherein the first chamber has an opening for receiving liquid samples and the second chamber has an opening for receiving liquid samples from the first chamber.

Clause 2. The apparatus according to clause 1, wherein the apparatus further comprises a tray structure, the second chamber is detachably disposed on the tray structure, and the tray structure is detachably combined with the first chamber.

Clause 3. The apparatus according to clause 2, wherein the first chamber and the second chamber are in a liquid communication state when the tray structure is combined with the first chamber.

Clause 4. The apparatus according to clause 3, wherein the first chamber comprises a hole which is in a liquid communication state with the opening of the second chamber; or the liquid samples of the first chamber can flow into the second chamber by the action of gravity of liquid itself.

Clause 5. The apparatus according to clause 3, wherein the hole is a first opening of the connecting channel, the second chamber is in a fluid communication state with the first chamber through a connecting channel; or the hole has an extended channel, and the second chamber achieves a fluid communication state with the first chamber through the extended channel.

Clause 6. The apparatus according to clause 5, wherein the connecting channel or the extended channel has a first opening and a second opening, the first opening is in fluid communication with the first chamber, and the second opening is in fluid communication with the second chamber.

Clause 7. The apparatus according to clause 5 or 6, wherein the apparatus further comprises a sealing element for sealing the connecting channel, the extended channel or the hole.

Clause 8. The apparatus according to clause 7, wherein the sealing element can pass through the first opening of the connecting channel or extended channel or a portion of sealing element enters the connecting channel or extended channel to achieve sealing.

Clause 9. The apparatus according to any one of clauses 1 to 7, wherein the apparatus further comprises a drain channel.

Clause 10. The apparatus according to clause 9, wherein the drain channel comprises a liquid inlet, the liquid inlet is located below the sealing element, or when the sealing element seals the connecting channel or the extended channel, the liquid inlet approaches to the connecting channel or extended channel prior to the sealing channel, or when the sealing channel enters the connecting channel or extended channel, the liquid inlet is located below the horizontal position of the sealing element; or, when the sealing element enters the connecting channel, the liquid inlet enters the channeling channel prior to the sealing element.

Clause 11. The apparatus according to clauses 1 to 7, wherein the apparatus further comprises a drain channel, the drain channel includes a liquid inlet, and the projection area of the liquid inlet is located within the projection area of the sealing element.

Clause 12. The apparatus according to clause 10 or 11, wherein the liquid inlet is located on the sealing element.

Clause 13. The apparatus according to clause 10 or 11, wherein the liquid inlet is located on a side wall of the connecting channel.

Clause 14. The apparatus according to clause 13, wherein the liquid inlet is lower than the position of the connecting channel opening.

Clause 15. The apparatus according to clauses 9 to 14, wherein the drain passage further has a liquid outlet, and the liquid outlet is in fluid communication with a receiving chamber.

Clause 16. The apparatus according to clause 15, wherein the receiving cavity is located on the sealing element.

Clause 17. The apparatus according to clauses 9 to 14, wherein the drain channel further has a liquid outlet, and the liquid outlet is in fluid communication with the first chamber.

Clause 18. The apparatus according to clause 7, wherein the apparatus further comprises a drain channel, the drain channel has a liquid inlet, and a portion of liquid forced by the sealing element enters the drain channel through the liquid inlet, to discharge to the channel and/or outside of the second chamber.

Clause 19. The apparatus according to clauses 1 to 18, wherein the apparatus comprises a discharge element that is used to discharge a portion of liquid samples in the second chamber.

Clause 20. The apparatus according to clause 19, wherein the apparatus further comprises a drain channel, the drain channel includes a liquid inlet, and the liquid inlet is located on the discharge element.

Clause 21. The apparatus according to clause 19, wherein the discharge member and the sealing member are connected as an integral structure when there is a sealing element.

Clause 22. The apparatus according to clause 21, wherein the discharge element enters the second chamber prior to the sealing element when a sealing element is used to seal the channel.

Clause 23. The apparatus according to any one of clauses 1 to 22, wherein the drain channel comprises a liquid outlet, the liquid outlet opening is in fluid communication with a receiving chamber.

Clause 24. The apparatus according to clause 23, wherein the receiving chamber is used to receive liquid samples discharged when a portion of the sealing element enters the connecting channel.

Clause 25. The apparatus according to clause 24, wherein the receiving chamber is located in a sealing element or a discharge element.

Clause 26. The apparatus according to clause 21, wherein the projection area of the discharge element is located within a vertical projection area of the sealing element.

Clause 27. The apparatus according to clause 26, wherein the discharge element has a transverse diameter that is less than the transverse diameter of the sealing element.

Clause 28. The apparatus according to clause 27, wherein the connecting channel is cylindrical and the sealing element is also cylindrical.

Clause 29. The apparatus according to any one of clauses 1 to 28, wherein the apparatus further comprises a first cover body for covering the opening of the first chamber.

Clause 30. The apparatus according to clause 29, wherein the cover body moves by linkage with the sealing element, or the cover body moves by linkage with the discharge element, or the cover body moves by linkage with the sealing element and the discharge element.

Clause 31. The apparatus according to clause 30, wherein, when the first cover body covers the opening of the first chamber, the sealing element seals the first opening of the connecting channel with the covering by the cover body or a portion of the element enters the connecting channel.

Clause 32. The apparatus according to clause 30, wherein the apparatus further comprises a discharge element, and the discharge element is connected with the sealing element.

Clause 33. The apparatus according to clause 32, wherein the discharge element is farther from the first cover body than the sealing element.

Clause 34. The apparatus according to clause 30, wherein the sealing element is connected to the first cover body by a connecting rod.

Clause 35. The apparatus according to clause 34, wherein the sealing element is detachably connected to the connecting rod.

Clause 36. The apparatus according to any one of clauses 1 to 35, wherein the apparatus further comprises a drain channel, the drain channel includes a liquid inlet, and the projection area of the liquid inlet is located within the projection area of the sealing element.

Clause 37. The apparatus according to clause 36, wherein the liquid inlet is farther from the first cover body than the sealing element.

Clause 38. The apparatus according to clause 37, wherein the liquid inlet is located on the discharge element.

Clause 39. The apparatus according to claim 37, wherein the discharge element or a portion of discharge element is located in the second chamber when the sealing element seals the connecting channel.

The present invention further includes the following embodiments.

Clause 1. A method for collecting liquid samples, comprising:
  an apparatus for collecting liquid samples is provided, wherein the apparatus comprises: a first chamber for collecting liquid samples, wherein the first chamber has an opening for receiving liquid samples; and
  a second chamber for collecting liquid samples for confirmatory detection, the second chamber has an opening for receiving the liquid samples from the first chamber;
  a tray structure, the tray structure comprises a second chamber, wherein the tray structure is detachably connected, combined or assembled with the first chamber;
  use the first chamber to collect liquid samples, and allow liquid samples to enter the first chamber through the opening of the first chamber.

Clause 2. The method according to clause 1, wherein the first chamber has a hole, and the hole and the second chamber form a liquid communication.

Clause 3. The method according to clause 2, wherein before liquid is collected, allow the first chamber and the second chamber to form a liquid communication state through the hole.

Clause 4. The method according to clause 2, wherein when liquid is collected, allow liquid to enter the first chamber, then allow liquid to automatically flow to the second chamber form the first chamber; or, allow liquid to enter the first chamber and the second chamber simultaneously; or, allow some liquid to enter the first chamber, and another liquid to enter the second chamber.

Clause 5. The method according to clause 2, wherein the hole has an extended channel, part of the extended channel is located in the second chamber, or, part of the opening of the second chamber is located in the part of channel, thus forming liquid communication.

Clause 6. The method according to clause 5, wherein after liquid samples are collected, allow a sealing element to seal the hole or the extended channel, thus, the second chamber and the first chamber are not in fluid communication.

Clause 7. The method according to clause 6, wherein after the second chamber and the first chamber are not in fluid communication, allow the tray to leave the first chamber, thus driving the second chamber to leave the first chamber.

Clause 8. The method according to clause 7, wherein allow the second chamber to separate from the tray.

Clause 9. The method according to clause 8, wherein before or after allowing the second chamber to separate from the tray, use the second cover body to cover the opening of the second chamber, thus sealing the second chamber.

Clause 10. The method according to one of the clauses 1 to 9, wherein the first cover body for covering the opening of the first chamber is provided, the sealing element is provided on the cover body, so that the cover body and the sealing element can move in a linkage manner.

Clause 11. The method according to clause 10, wherein, in the process of covering the opening of the first chamber, the cover body drives the sealing element to form a liquid partition state between the first chamber and the second chamber.

Clause 12. The method according to clause 10, wherein the cover body drives the sealing element to seal the hole or the extended channel between the first chamber and the second chamber.

Clause 13. The method according to clause 10, wherein the cover body drives the sealing element, so that part of the sealing element enters the extended channel.

Clause 14. The method according to clause 10, wherein the cover body further comprises a discharge element, and the discharge element is farther from the cover body than the sealing element.

Clause 15. The method according to clause 10, wherein the cover body further comprises a drain channel, the drain channel comprises a liquid inlet, and the position of the liquid inlet is farther from the cover body than the sealing element; or, the liquid inlet enters the extended channel earlier than the sealing element.

Clause 16. The method according to clause 15, wherein the projection area of the liquid inlet is located in the projection area of the sealing element.

Clause 17. The method according to clause 15, wherein the sealing element forces some liquid to enter the drain channel through the liquid inlet, and then the liquid is discharged outside of the channel and/or the second chamber.

Clause 18. The method according to one of the clauses 14 to 17, wherein the drain channel comprises a liquid outlet, and the liquid outlet is in liquid communication with a receiving chamber.

Clause 19. The method according to clause 18, wherein the receiving chamber is located in the sealing element or the discharge element or the cover body.

Clause 20. The method according to clause 19, wherein when part of the sealing element enters the connecting channel, the receiving chamber is used for receiving the liquid samples discharged because the sealing element enters the connecting channel.

Clause 21. The method according to clause 19, wherein, when the discharge element enters the second chamber, a part of samples discharged by the discharge element also enters the receiving chamber.

The present invention further includes the following embodiments:

Clause 1. A detection apparatus for detecting the analyte in sample, comprising: a first chamber for collecting liquid samples and a second chamber for collecting liquid samples for confirmatory detection, wherein the first chamber has an opening for receiving liquid samples, and the second chamber has an opening for receiving the liquid samples from the first chamber, wherein the apparatus further comprises a testing element.

Clause 2. The apparatus according to clause 1, wherein the apparatus further comprises a tray structure, the tray structure is detachably connected with the first chamber, wherein the second chamber is provided on the tray, and the second chamber is detachably connected, combined or assembled with the first chamber through the tray.

Clause 3. The apparatus according to clause 2, wherein the second chamber achieves fluid communication with the first chamber through a channel.

Clause 4. The apparatus according to clause 2, wherein the channel has a first opening and a second opening, the first opening is in fluid communication with the first chamber, and the second opening is in fluid communication with the second chamber.

Clause 5. The apparatus according to clause 4, wherein the apparatus further comprises a sealing element for sealing the connecting channel.

Clause 6. The apparatus according to clause 5, wherein the sealing element for sealing the connecting channel can seal the connecting channel by sealing the first opening of the channel or letting part of the sealing element enter the connecting channel.

Clause 7. The apparatus according to clause 5, wherein the apparatus further comprises a drain channel, the drain channel comprises a liquid inlet and a liquid outlet, and the liquid inlet is located under the sealing element.

Clause 8. The apparatus according to clause 5, wherein the apparatus further comprises a drain channel, the drain channel comprises a liquid inlet and a liquid outlet, and the projection area of the liquid inlet is located within the projection area of the sealing element.

Clause 9. The apparatus according to clause 5, wherein the apparatus further comprises a discharge element for discharging some liquid in the second chamber, and the discharge element is connected with the sealing element.

Clause 10. The apparatus according to clause 9, wherein the apparatus further comprises a drain channel, the drain channel comprises a liquid inlet, and the liquid inlet is located on the discharge element.

Clause 11. The apparatus according to clause 10, wherein the drain channel comprises a liquid outlet, the liquid outlet is in liquid communication with the receiving chamber, and the receiving chamber is used for receiving the liquid discharged by the discharge element.

Clause 12. The apparatus according to clause 11, wherein when part of the sealing element enters the channel, the receiving chamber is used for receiving the liquid samples discharged because the sealing element enters the connecting channel.

Clause 13. The apparatus according to clause 11, wherein the receiving chamber is located in the sealing element or the discharge element.

Clause 14. The apparatus according to clause 9, wherein the projection area of the discharge element is located in the vertical projection area of the sealing element.

Clause 15. The apparatus according to clause 14, wherein the horizontal diameter of the discharge element is less than that of the sealing element.

Clause 16. The apparatus according to clause 5, wherein the connecting channel is cylindrical, and the sealing element is also cylindrical.

Clause 17. The apparatus according to clause 4, wherein the apparatus further comprises a first cover body for covering the opening of the first chamber, and the sealing element is provided on the cover body, thus when the first cover body covers the opening of the first chamber, the sealing element seals the first opening of the connecting channel or part of the element enters the connecting channel with the covering of the cover body.

Clause 18. The apparatus according to clause 17, wherein the apparatus further comprises a discharge element, and the discharge element is connected with the sealing element.

Clause 19. The apparatus according to clause 18, wherein the discharge element is farther from the first cover body than the sealing element.

Clause 20. The apparatus according to clause 19, wherein the sealing element is connected with the first cover body through a connecting rod.

Clause 21. The apparatus according to clause 20, wherein the sealing element is detachably connected with the connecting rod.

Clause 22. The apparatus according to clause 18, wherein the apparatus further comprises a drain channel, the drain channel comprises a liquid inlet, and the projection area of the liquid inlet is located within the projection area of the sealing element.

Clause 23. The apparatus according to clause 22, wherein the liquid inlet is farther from the first cover body than the sealing element.

Clause 24. The apparatus according to clause 23, wherein the liquid inlet is located on the discharge element.

Clause 25. The apparatus according to clause 18, wherein when the sealing element seals the channel, the discharge element or part of the discharge element is located in the second chamber.

Clause 26. The apparatus according to clause 1, wherein the apparatus further comprises a detection chamber, the detection chamber is in fluid communication with the first chamber, and the testing element is located in the detection chamber.

Clause 27. The apparatus according to clause 1, wherein the apparatus further comprises a carrier, on which there are multiple channels for accommodating the testing element, and the carrier is located in the first chamber.

Clause 28. The apparatus according to clause 27, wherein the sample application area of the testing element is located on the bottom of the first chamber.

The present invention further includes the following embodiments.

Clause 1. An apparatus for collecting liquid samples, comprising: a first chamber and a second chamber for collecting liquid samples, and the second chamber further comprises a detection chamber for initial detection that is in fluid communication with the second chamber, wherein there is an opening on the bottom of the first chamber, and the opening is sealed by a sealing element.

Clause 2. The apparatus according to clause 1, wherein the first chamber and the second chamber are detachably connected, combined or assembled.

Clause 3. The apparatus according to clause 1, wherein the sealing element is a sealing element that can be pierced.

Clause 4. The apparatus according to clause 3, wherein the sealing element belongs to one or more of the plastic films, double-sided adhesive tape, single-sided adhesive tape and aluminum foil.

Clause 5. The apparatus according to clause 1, wherein the opening has a channel extending outwards, and the channel comprises a second opening that is fluid communication with the second chamber.

Clause 6. The apparatus according to clause 1, wherein the apparatus further comprises a piercing element for piercing the sealing element and/or another sealing element.

Clause 7. The apparatus according to clause 6, wherein the apparatus further comprises another sealing element, and the another sealing element is used for sealing the opening after the sealing element is pierced by the piercing element.

Clause 8. The apparatus according to clause 7, wherein the piercing element and another sealing element are provided on a first cover body, and the first cover body is used for covering the opening of the first chamber.

Clause 9. The apparatus according to clause 8, wherein the piercing element is far from the cover body relative to another sealing element.

Clause 10. The apparatus according to clause 8, wherein the piercing element and another sealing element are provided in such a manner, that is to allow the piercing element to pierce the sealing element that seals the opening first, and then release some liquid to the second chamber, then allow another sealing element to seal the opening.

Clause 11. The apparatus according to clause 5, wherein the apparatus further comprises a second cover body for sealing the second opening of the channel.

Clause 12. The apparatus according to clause 2, wherein the detachable manner is achieved by cooperation between the thread structure of the first chamber and that of the second chamber.

Clause 13. The apparatus according to clause 13, wherein the first chamber comprises an external thread, and the second chamber comprises an internal thread.

Clause 14. The apparatus according to clause 6, wherein the apparatus further comprises a cover body for covering the opening of the first chamber, and the piercing element for piercing the sealing element and/or another sealing element move(s) with the cover body in a linkage manner.

Clause 15. The apparatus according to clause 14, wherein the piercing element is far from the cover body relative to another sealing element.

Clause 16. The apparatus according to clause 15, wherein the piercing element and another sealing element are provided in such a manner, that is to allow the piercing element to pierce the sealing element that seals the opening first, and then release some liquid to the second chamber, then allow another sealing element to seal the opening.

Clause 17. A method for collecting or/and detecting liquid samples, comprising:
An apparatus for collecting liquid samples is provided, wherein the apparatus comprises: a first chamber and a second chamber for collecting liquid samples, and the second chamber further comprises a detection chamber for initial detection that is in fluid communication with the second chamber, wherein there is an opening for discharging liquid on the bottom of the first chamber, the opening is sealed by a sealing element, and there is an opening for receiving samples; the first chamber is used for collecting liquid samples.

Clause 18. The method according to clause 17, wherein after the first chamber collects liquid, allow a piercing element to pierce the sealing element, thus releasing liquid to the second chamber.

Clause 19. The method according to clause 18, wherein allow the liquid in the second chamber to enter the detection chamber.

Clause 20. The method according to clause 18, wherein allow another sealing element to seal the opening on the piercing element or allow another sealing element to seal the opening.

Clause 21. The method according to clause 19, wherein allow the liquid samples entering the detection chamber to receive initial detection.

Clause 22. The method according to clause 21, wherein before, or after initial detection, allow the first chamber to separate from the second chamber for second confirmatory detection.

Clause 23. The method according to clause 22, wherein there is a channel extending outwards at the opening of the second chamber, when or after the second chamber is separated from the first chamber, a cover body is used to seal the opening of the channel.

Clause 24. The method according to clause 18, wherein a cover body for covering the opening of the first chamber for receiving liquid samples is provided, and the cover body is in linkage movement with another sealing element and the piercing element.

Clause 25. The method according to clause 24, wherein allow the linkage to be a rotary movement.

Clause 26. The method according to clause 24, wherein in the process of allowing the cover body to cover the opening of the first chamber for receiving liquid samples, allow the piercing element to pierce the element that seals the opening for discharging liquid, so as to release liquid to the second chamber; then allow another sealing element to seal the opening for discharging liquid.

The present invention further includes the following embodiments.

Clause 1. A chamber for collecting liquid samples, comprising:
  a side wall;
  a bottom; and an opening for receiving liquid, wherein the bottom has a hole for allowing liquid samples entering the chamber to flow to the outside of the chamber.

Clause 2. The chamber according to clause 1, wherein there is a protrusion area towards the interior chamber on the bottom of the chamber, and the protrusion area and the side wall form a collection area of liquid samples.

Clause 3. The chamber according to clause 2, wherein the sample collection area is set for receiving the testing carrier.

Clause 4. The chamber according to clause 3, wherein the testing carrier comprises a testing element.

Clause 5. The chamber according to clause 2, wherein the hole is provided on the protrusion area.

Clause 6. The chamber according to clause 5, wherein the hole has an extended channel.

Clause 7. The chamber according to clause 6, wherein the channel extends towards the inside and/or outside of the chamber.

Clause 8. The chamber according to clause 6, wherein the channel extends towards the outside of the chamber.

Clause 9. The chamber according to clause 5, wherein the protrusion area has a platform structure inside the chamber, and the hole is provided on the platform structure.

Clause 10. The chamber according to clause 7 or 8, wherein the chamber further comprises an extended area on the bottom, and the length of the extended area exceeds or equals to that of the extended channel.

Clause 11. The chamber according to clause 6, wherein the position of the hole is higher than that of the bottom of the collecting area, or, when collected, liquid arrives at the collecting area first, then flows into the hole.

The present invention further includes the following embodiments.

Clause 1. A cover body, comprising: a sealing element.

Clause 2. The cover body according to clause 1, wherein the cover body is a cover body for covering the opening of the chamber.

Clause 3. The cover body according to clause 1, wherein the cover body further comprises a connecting rod structure, one end of the connecting rod is connected with the cover body, and the other end is connected with the sealing element.

Clause 4. The cover body according to clause 3, wherein the sealing element is part of the end of the connecting rod, or the sealing element and the connecting rod are an integral structure.

Clause 5. The cover body according to clause 3, wherein the sealing element belongs to elastic materials.

Clause 6. The cover body according to clause 3, wherein the sealing element and the connecting rod are detachably connected.

Clause 7. The cover body according to clause 3, wherein the sealing element and the connecting rod are connected by plugging, screw threads or snapping.

Clause 8. The cover body according to clause 3, wherein the sealing element and the connecting rod are a hollow structure.

Clause 9. The cover body according to clause 3, wherein the sealing element and the connecting rod are connected by one-time injection molding.

Clause 10. The cover body according to clause 3, wherein the sealing element comprises a sealing ring.

Clause 11. The cover body according to clause 10, wherein the sealing ring has the same texture as the sealing element, or the sealing element with a sealing ring is formed by one-time injection molding.

Clause 12. The cover body according to clause 1, wherein there is one or more circular protrusion(s) on the sealing element, and the protrusion has the same texture as the sealing element.

The present invention further includes the following embodiments.

Clause 1. A cover body, comprising: a sealing element and a discharge element.

Clause 2. The cover body according to clause 1, wherein the cover body is a cover body for covering the opening of the chamber.

Clause 3. The cover body according to clause 1, wherein the cover body further comprises a connecting rod structure, one end of the connecting rod is connected with the cover body, and the other end is connected with the sealing element and the discharge element.

Clause 4. The cover body according to clause 3, wherein the sealing element is part of the end of the connecting rod, or the sealing element and the connecting rod are an integral structure.

Clause 5. The cover body according to clause 3, wherein the sealing element belongs to elastic materials.

Clause 6. The cover body according to clause 3, wherein the sealing element is connected with the discharge element.

Clause 7. The cover body according to clause 6, wherein the discharge element is farther from the cover body than the sealing element.

Clause 8. The cover body according to clause 7, wherein the vertical projection of the discharge element is located in or overlaps with the vertical projection area of the sealing element.

Clause 9. The cover body according to clause 7, wherein the horizontal diameter of the discharge element is less than that of the sealing element.

Clause 10. The cover body according to clause 7, wherein the discharge element is cone-shaped.

Clause 11. The cover body according to clause 1, wherein the sealing element and the discharge element are a structure of one-time injection molding.

The present invention further includes the following embodiments.

Clause 1. A cover body, comprising: a sealing element, a discharge element and a receiving chamber.

Clause 2. The cover body according to clause 1, wherein the cover body further comprises a connecting rod structure, one end of the connecting rod is connected with the cover body, and the other end is connected with the sealing element and the discharge element.

Clause 3. The cover body according to clause 3, wherein the sealing element is part of the end of the connecting rod, or the sealing element and the connecting rod are an integral structure.

Clause 4. The cover body according to clause 3, wherein the sealing element belongs to elastic materials.

Clause 5. The cover body according to clause 3, wherein the sealing element is connected with the discharge element.

Clause 6. The cover body according to clause 5, wherein the discharge element is farther from the cover body than the sealing element.

Clause 7. The cover body according to clause 1, wherein one of the sealing element, the connecting rod and the discharge element comprises a hollow chamber, or, the sealing element, the connecting rod and the discharge element are all of a hollow structure, and the receiving chamber is part of the hollow chamber or the hollow structure.

Clause 8. The cover body according to clause 7, wherein the horizontal diameter of the discharge element is less than that of the sealing element.

Clause 9. The cover body according to clause 7, wherein the discharge element is cone-shaped.

Clause 10. The cover body according to clause 1, wherein the receiving chamber is located in the connecting rod, the sealing element or the discharge element.

The cover body according to clause 1 or one of the clauses 6 to 10, wherein there is a hole in liquid communication with the receiving chamber provided on the sealing element, the discharge element and the connecting rod.

The present invention further includes the following embodiments.

Clause 1. A cover body, comprising: a sealing element and a drain channel, and the drain channel comprises a liquid inlet and a liquid outlet.

Clause 2. The cover body according to clause 1, wherein the cover body further comprises a connecting rod structure, one end of the connecting rod is connected with the cover body, and the other end is connected with the sealing element.

Clause 3. The cover body according to clause 1 or 2, wherein the liquid inlet of the drain channel is farther from the cover body than the sealing element.

Clause 4. The cover body according to clause 3, wherein the sealing element is connected with the discharge element.

Clause 5. The cover body according to clause 4, wherein the liquid inlet of the drain channel is located on the discharge element.

Clause 6. The cover body according to clause 3, wherein the sealing element comprises a seal ring, and the liquid inlet of the drain channel is farther from the cover body than the seal ring.

Clause 7. The cover body according to clause 3, wherein the cover body further comprises a receiving chamber, and the liquid outlet of the drain channel is in fluid communication with the receiving chamber.

Clause 8. The cover body according to clause 1, wherein one of the sealing element, the connecting rod and the discharge element comprises a hollow chamber, or, the sealing element, the connecting rod and the discharge element are all of a hollow structure, and the liquid inlet of the drain channel is in fluid communication with the hollow chamber or the hollow structure.

Clause 9. The cover body according to clause 3, wherein the liquid outlet of the drain channel is farther from the cover body than the sealing element.

Clause 10. The cover body according to one of clauses 1 to 9, wherein the vertical projection of the discharge element is located in or overlaps with the vertical projection area of the sealing element.

The cover body according to one of clauses 1 to 9, wherein the vertical projection of the liquid inlet is located in that of the sealing element.

The present invention further includes the following embodiments:

Clause 1. An apparatus for collecting liquid samples, comprising: a first chamber and a second chamber, wherein a protrusion area toward the interior chamber is provided on the bottom of the chamber, and the protrusion area forms a protrusion space relative to the first chamber, thus forming a sunken space relative to the bottom, and part of the second chamber is located in the sunken area.

Clause 2. The sample collection apparatus according to clause 1, wherein there is a hole in the first chamber, and the hole and the opening of the second chamber are in a liquid communication state.

Clause 3. The sample collection apparatus according to clause 1, wherein the apparatus further comprises a connecting channel, and the second chamber is detachably connected, combined or assembled with the connecting channel.

Clause 4. The sample collection apparatus according to clause 3, wherein the opening of the second chamber comprises an external thread, the connecting channel comprises an internal thread, and the external thread of the second chamber and the internal thread of the connecting channel are connected, combined or assembled through a screw thread.

Clause 5. The sample collection apparatus according to clause 3, wherein the hole has a section of extended channel, and the extended section is part of the connecting channel, wherein the extended channel is located in the sunken space.

Clause 6. The sample collection apparatus according to clause 5, wherein part of the extended channel is located in the second chamber.

Clause 7. The sample collection apparatus according to clause 6, wherein the outer diameter of the part of extended channel is equal to or less than the inner diameter of the opening of the second chamber.

Clause 8. The sample collection apparatus according to clause 6, wherein the extended channel is inserted into the second chamber.

Clause 9. The sample collection apparatus according to clause 2, wherein the apparatus further comprises a connecting channel, the hole is the first opening of the connecting chamber, the first opening is in fluid communication with the first chamber, and the second chamber is in fluid communication with the second opening of the connecting channel.

Clause 10. The sample collection apparatus according to clause 1, wherein the apparatus further comprises a tray structure, the second chamber is detachably provided on the tray structure, and the tray structure is detachably combined with the first chamber.

The present invention further includes the following embodiments.

Clause 1. A chamber for collecting fluid samples, comprising:
a side wall;
a bottom; and an opening for receiving liquid, wherein the bottom has an opening for allowing liquid samples entering the chamber to flow to the outside of the chamber, wherein the apparatus further comprises a detection chamber for accommodating the testing element, and the detection chamber is in liquid communication with the chamber through a through hole.

Clause 2. The chamber according to clause 1, wherein the position of the opening is higher than that of the through hole, or the opening is closer to the opening of the chamber than the through hole; or the through hole is closer to the bottom of the chamber than the opening.

Clause 3. The chamber according to clause 1, wherein when the chamber collects liquid samples, liquid enters the through hole first, and then enters the opening, or, some liquid samples enter the through hole, and some enter the opening.

Clause 4. The chamber according to clause 1, wherein the opening comprises a channel extending towards outside of the bottom.

Clause 5. The chamber according to clause 1, wherein there is a protrusion area towards the interior chamber on the bottom of the chamber, and the protrusion area and the side wall form a collection area of liquid samples.

Clause 6. The chamber according to clause 5, wherein the collection area comprises a bottom, and the opening is higher than the bottom position of the collection area.

Clause 7. The chamber according to clause 6, wherein the bottom of the collection area is the bottom area of part of the chamber.

Clause 8. The chamber according to clause 1, wherein the detection chamber comprises a testing element.

Clause 9. The chamber according to clause 8, wherein the testing element is located on a carrier, and the carrier is located in the detection chamber.

Clause 10. The chamber according to clause 1, wherein the testing element comprises a sample application area for contacting the liquid samples in the detectable quantity.

The Second Design

The present invention further includes the following embodiments.

Clause 1. An apparatus for collecting samples, comprising a first chamber for collecting liquid samples and a second chamber for collecting samples for confirmatory detection, wherein the first chamber is in fluid communication or partition with the second chamber, when the first chamber is in fluid communication with the second chamber, liquid in the first chamber can be transferred to the second chamber.

Clause 2. The apparatus for collecting samples according to clause 1, wherein the liquid in the first chamber can be transferred to the second chamber under the action of an external force; or the volume of the second chamber is variable, or/and the liquid in the first chamber can be transferred to the second chamber under non-gravity forces.

Clause 3. The apparatus for collecting samples according to clause 1, wherein it further comprises a third chamber for collecting samples, the third chamber can be in a fluid communication or partition with the first chamber.

Clause 4. The apparatus for collecting samples according to clause 3, wherein, when the first chamber and the third chamber are in a fluid communication state, the liquid collected in the third chamber simultaneously enter the first chamber.

Clause 5. The apparatus for collecting samples according to clause 3, wherein it comprises a first channel that allows the first chamber to be in fluid communication with the third chamber.

Clause 6. The apparatus for collecting samples according to clause 3, wherein the first channel is located at the bottom of the third chamber.

Clause 7. The apparatus for collecting samples according to clause 3, wherein a collecting tank is provided on the side wall of the first chamber, and the collecting tank is flush with the bottom of the third chamber or slightly higher than the bottom of the third chamber.

Clause 8. The apparatus for collecting samples according to clause 7, wherein the collecting tank can be closed individually or simultaneously with the first channel.

Clause 9. The apparatus for collecting samples according to clause 3, wherein samples are loaded into the third chamber preferentially.

Clause 10. The apparatus for collecting samples according to clause 9, wherein samples collected in the third chamber can be transferred to a pipetting channel under the action of an external force.

Clause 11. The apparatus for collecting samples according to clause 9, wherein the third chamber is provided with a third channel, the third channel is in communication with the first chamber and in partition with the third chamber.

Clause 12. The apparatus for collecting samples according to clause 9, wherein the third chamber and the first chamber have a common wall surface.

Clause 13. The apparatus for collecting samples according to clause 12, wherein the common wall surface is provided with a channel or opening which can be opened or closed.

Clause 14. The apparatus for collecting samples according to clause 12, wherein the third channel and the third chamber have a coincident opening, and the opening of the third channel is provided with a detachable closed structure.

Clause 15. The apparatus for collecting samples according to clause 9, wherein the flow direction of the samples in the apparatus is from third chamber into the first chamber, and then from the first chamber into the third channel.

Clause 16. The apparatus for collecting samples according to clause 9, wherein the second chamber can be loaded into the third channel.

Clause 17. The apparatus for collecting samples according to clause 9, wherein the second chamber is capable of collecting samples from the third channel.

Clause 18. The apparatus for collecting samples according to clause 2, wherein the first chamber and the third chamber are in a liquid partition state when the liquid in the first chamber is transferred into the second chamber.

Clause 19. The apparatus for collecting samples according to clause 2, wherein it further comprises a fourth chamber for collecting samples to be detected, and the fourth chamber and the third chamber can be in a fluid communication or partition state.

Clause 20. The apparatus for collecting samples according to clause 3, wherein, when the fourth chamber and the third chamber are in a fluid communication state, the liquid collected in the third chamber simultaneously enter the fourth chamber.

Clause 21. The apparatus for collecting samples according to clause 3, wherein it further comprises a testing area, and the fourth chamber and the testing area can be in a fluid communication or partition state.

Clause 22. The apparatus for collecting samples according to clause 3, wherein the fourth chamber and the third chamber are in a liquid partition state when the fourth chamber and the testing area are in a fluid communication state.

Clause 23. The apparatus for collecting samples according to clause 3, wherein the second chamber and the third chamber can be combined or separated.

Clause 24. The apparatus for collecting samples according to clause 3, wherein it further comprises a communication device between the first chamber and the second chamber.

Clause 25. The apparatus for collecting samples according to clause 24, wherein the communication device is detachably connected or combined with the second chamber.

Clause 26. The apparatus for collecting samples according to clause 24, wherein the communication device is capable of realizing fluid communication between the inside second chamber and the first chamber or outside when the second chamber is connected or combined with the communication device.

Clause 27. The apparatus for collecting samples according to clause 24, wherein it comprises a cover body that can cover the sample collection port of the sample collection apparatus.

Clause 28. The apparatus for collecting samples according to clause 27, wherein an assembly channel of the second chamber is provided on the cover body.

Clause 29. The apparatus for collecting samples according to clause 27, wherein the second chamber can be detachably combined or connected with the cover body.

Clause 30. The apparatus for collecting samples according to clause 29, wherein it comprises an assembly structure of the second chamber.

Clause 31. The apparatus for collecting samples according to clause 30, wherein the assembly structure is detachably combined or connected with the cover body.

Clause 32. The apparatus for collecting samples according to clause 31, wherein the assembly structure is detachably combined or connected with the assembly channel.

Clause 33. The apparatus for collecting samples according to clause 30, wherein the assembly structure has a handle member or a knob member that facilitates combination or separation of the assembly structure and the cover body.

Clause 34. The apparatus for collecting samples according to clause 30, wherein the assembly structure is provided with some hollow structures.

Clause 35. The apparatus for collecting samples according to clause 30, wherein it further comprises a connector.

Clause 36. The apparatus for collecting samples according to clause 35, wherein the connector has a communicating chamber.

Clause 37. The apparatus for collecting samples according to clause 30, wherein the connector can be detachably connected or combined with the second chamber.

Clause 38. The apparatus for collecting samples according to clause 37, wherein the connector is separated from the second chamber when the second chamber is detached from the cover body.

Clause 39. The apparatus for collecting samples according to clause 35, wherein the connector has a piercing element.

Clause 40. The apparatus for collecting samples according to clause 39, wherein the piercing element is capable of piercing the second chamber to achieve communication with other chamber or outside.

Clause 41. The apparatus for collecting samples according to clause 35, wherein the connector can be assembled on the cover body.

Clause 42. The apparatus for collecting samples according to clause 41, wherein the connector can be assembled onto the assembly channel.

Clause 43. The apparatus for collecting samples according to clause 41, wherein the connector is movable in the assembly channel.

Clause 44. The apparatus for collecting samples according to clause 43, wherein it further comprises a limiting structure of the connector, and the limiting structure can block the connector from being taken away from the cover body.

Clause 45. The apparatus for collecting samples according to clause 30, wherein the assembly structure comprises an outer wall and an inner chamber.

Clause 46. The apparatus for collecting samples according to clause 45, wherein the second chamber can be loaded into the inner chamber.

Clause 47. The apparatus for collecting samples according to clause 45, wherein the second chamber and the inner chamber are assembled together in a fixed combination, a fixed connection or a detachable combination, or a detachable connection.

Clause 48. The apparatus for collecting samples according to clause 19, wherein it further comprises a pipetting channel.

Clause 49. The apparatus for collecting samples according to clause 48, wherein samples can be transferred between chambers, between a chamber and a pipetting channel.

Clause 50. The apparatus for collecting samples according to clause 48, wherein the samples collected in the chamber can naturally flow into the pipetting channel, or the samples collected in the chamber can flow into the pipetting channel under an external force.

Clause 51. The apparatus for collecting samples according to clause 48, wherein the pipetting channel is located at the bottom of the third chamber.

Clause 52. The apparatus for collecting samples according to clause 48, wherein it further comprises a pipetting element.

Clause 53. The apparatus for collecting samples according to clause 52, wherein the pipetting element separates a portion of the pipetting channel into a first chamber.

Clause 54. The apparatus for collecting samples according to clause 53, wherein the pipetting element can move in the pipetting channel to change the volume of the first chamber.

Clause 55. The apparatus for collecting samples according to clause 53, wherein the pipetting element is capable of applying a force to the samples in the first chamber, to transfer the samples in the first chamber to other chamber or outside.

Clause 56. The apparatus for collecting samples according to clause 52, wherein the pipetting element separates a portion of the pipetting channel into a fourth chamber.

Clause 57. The apparatus for collecting samples according to clause 56, wherein the pipetting element can move in the pipetting channel to change the volume of the fourth chamber.

Clause 58. The apparatus for collecting samples according to clause 56, wherein the pipetting element is capable of applying a force to the samples in the fourth chamber to transfer the samples in the fourth chamber to other chamber or outside.

Clause 59. The apparatus for collecting samples according to clause 56, wherein it comprises a testing area.

Clause 60. The apparatus for collecting samples according to clause 59, wherein it comprises a detection inlet that allows the pipetting channel to communicate with the testing area, and the detection inlet can be opened or closed.

Clause 61. A method for collecting samples, providing An apparatus for collecting samples, wherein the apparatus comprises a first chamber for collecting liquid samples and a second chamber for collecting samples for confirmatory detection, the first chamber is in fluid communication or partition with the second chamber, when the first chamber is in fluid communication with the second chamber, liquid in the first chamber can be transferred to the second chamber.

Clause 62. The method for collecting samples according to clause 61, wherein the first chamber is loaded with samples, allowing samples in the first chamber to enter the second chamber, or the volume of the second chamber is variable, to allow liquid to transfer from the first chamber to the second chamber, or/and allow liquid in the first chamber to be transferred to the second chamber under non-gravity forces.

Clause 63. The method for collecting samples according to clause 61, wherein the method further comprises a third chamber for collecting samples, the third chamber can be in a fluid communication or partition with the first chamber.

Clause 64. The method for collecting samples according to clause 63, wherein samples are first loaded into the third chamber to allow the samples to enter the first chamber.

Clause 65. The method for collecting samples according to clause 63, wherein samples are allowed to enter the first chamber while loaded into the third chamber.

Clause 66. The method for collecting samples according to clause 65, wherein the liquid communication between the first chamber and the third chamber is blocked to allow the first chamber to communicate with the second chamber after sample collection is completed in the third chamber.

Clause 67. The method for collecting samples according to clause 66, wherein liquid communication between the first chamber and the second chamber is achieved through a connector.

Clause 68. The method for collecting samples according to clause 66, wherein liquid communication between the first chamber and the second chamber is achieved through an external force.

Clause 69. The method for collecting samples according to clause 67, wherein samples in the first chamber are transferred to the second chamber through an external force.

Clause 70. The method for collecting samples according to clause 62, wherein it further comprises a fourth chamber for collecting test samples, and the fourth chamber and the third chamber are in a fluid communication or partition state.

Clause 71. The method for collecting samples according to clause 70, wherein samples are first loaded into the third chamber to allow the samples to enter the fourth chamber.

Clause 72. The method of collecting samples according to clause 71, wherein the liquid collected in the third chamber can naturally flow into the fourth chamber or flow into the fourth chamber under the action of an external force when the fourth chamber and the third chamber are in a fluid communication state.

Clause 73. The method for collecting samples according to clause 71, wherein samples in the fourth chamber can enter the testing area under the action of an external force.

Clause 74. A method for detecting samples, wherein the method uses the sample collection apparatus clauseed in any one of clauses 1 to 60 to collect samples, and detects samples collected by the testing element.

Clause 75. A method for detecting samples, wherein the method collects samples according to the method clauseed in any one of clauses 61 to 74, and detects samples collected by the testing element.

The Third Design

The present invention further includes the following embodiments.

Clause 1. A sample collection and/or detection apparatus, comprising a first chamber for collecting liquid samples and a second chamber for collecting samples for confirmatory detection, wherein the first chamber and the second chamber can be combined or separated; the sample detection apparatus further comprises a second sealing element for sealing the second chamber, and a third sealing element for sealing the separation portion of the first chamber and the second chamber.

Clause 2. The sample collection and detection apparatus according to clause 1, wherein the first chamber and the second chamber are in fluid communication state when the first chamber is combined with the second chamber.

Clause 3. The sample collection and detection apparatus according to clause 1, wherein the third sealing chamber seals the separation portion after the second sealing element seals the second chamber.

Clause 4. The sample collection and detection apparatus according to clause 1, wherein the third sealing element seals the separation portion after the second sealing element seals the second chamber.

Clause 5. The sample collection and detection apparatus according to clause 1, wherein it further comprises a first sealing element for sealing the first chamber.

Clause 6. The sample collection and detection apparatus according to clause 5, wherein the second chamber can be sealed by a second sealing element while the first sealing element seals the first chamber.

Clause 7. The sample collection and detection apparatus according to clause 5, wherein the separation portion can be sealed by the third sealing element during sealing of the first chamber by the first sealing element.

Clause 8. The sample collection and detection apparatus according to clause 5, wherein the second sealing element or the third sealing element is linked with the first sealing element, and the second sealing element is linked with the third sealing element.

Clause 9. The sample collection and detection apparatus according to clause 5, wherein both the second sealing element and the third sealing element are linked with the first sealing element.

Clause 10. The sample collection and detection apparatus according to clause 8 or clause 9, wherein the sample detection apparatus further comprises a first linkage element that links the first sealing element and the third sealing element.

Clause 11. The sample collection and detection apparatus according to clause 8 or clause 9, wherein the linkage refers to synchronous rotation.

Clause 12. The sample collection and detection apparatus according to clause 8 or clause 9, wherein the linkage refers to moving in a direction close to the inside of the sample.

Clause 13. The sample collection and detection apparatus according to clause 1, wherein the separation portion comprises a channel, and the second chamber can move in the channel.

Clause 14. The sample collection and detection apparatus according to clause 8, wherein a limiting structure of a second chamber is provided in the channel.

Clause 15. The sample collection and detection apparatus according to clause 14, wherein after sealed, the second chamber can move along the channel in a direction away from the first chamber.

Clause 16. The sample collection and detection apparatus according to clause 1 or clause 4, wherein it comprises a testing area for collecting initial samples, and the testing area can be opened or closed.

Clause 17. The sample collection and detection apparatus according to clause 16, wherein when the second chamber does not collect samples or when samples are collected, the testing area is closed, when the second chamber completes collection and is sealed, samples can enter the testing area.

Clause 18. The sample collection and detection apparatus according to clause 17, wherein it further comprises a blocking element and the blocking element is capable of opening or closing the detection inlet.

Clause 19. The sample collection and detection apparatus according to clause 18, wherein the blocking element can be linked with the third sealing element, and the opening of the testing area can be opened when driven by the third sealing element.

Clause 20. The sample collection and detection apparatus according to clause 18, wherein the blocking element can be linked with the second sealing element, and the opening of the testing area can be opened when driven by the second sealing element.

Clause 21. The sample collection and detection apparatus according to clause 18, wherein the blocking element can be linked with the first sealing element, and the opening of the testing area can be opened when driven by the first sealing element.

All patents and publications mentioned in the specification of the present invention are disclosures of the prior art and they can be used in the present invention. All patents and publications referred to herein are incorporated in the references as if each individual publication is specifically referred to separately. The invention described herein may be practiced in the absence of any one or more of the elements, any one limitation or more limitations that are not specifically recited herein. For example, the terms "comprising," "consisting essentially of," and "consisting of" in each instance herein may be replaced with each of the remaining two terms. The terms and expressions which have been employed herein are descriptive rather than restrictive, and there is no intention to suggest that these terms and expressions in this description exclude any equivalents, but it is to be understood that any appropriate changes or modifications can be made within the scope of the present invention and appended claims. It should be understood that, the embodiments described in the present invention are some preferred embodiments and features, and any person skilled in the art may make some changes and variations based on the essence of the description of the present invention, and these changes and variations are also considered to fall into the scope of the present invention and the independent claims and the appended claims.

What is claimed is:

1. An apparatus for collecting liquid samples, comprising a first chamber for collecting liquid samples;
a second chamber for collecting samples for confirmatory detection; and
a connecting channel, wherein the second chamber is detachably combined, connected or assembled with the first chamber via the connecting channel;
wherein the connecting channel is not sealed when the second chamber does not leave the first chamber; or the connecting channel is sealed before or after the second chamber leaves the first chamber.

2. The apparatus according to claim 1, wherein the connecting channel is sealed via a sealing element.

3. The apparatus according to claim 1, wherein the apparatus further comprises a sealing element for sealing the channel so that the first chamber and the second chamber are not in a liquid communication state.

4. The apparatus according to claim 2, wherein the apparatus further comprises a drain channel having a liquid inlet.

5. The apparatus according to claim 4, wherein the liquid inlet is located below the sealing element, or the liquid inlet is close to the connecting channel prior to the sealing element when the sealing element seals the channel, or the liquid inlet is located below the horizontal position of the sealing element when the sealing element enters the connecting channel; or the liquid inlet enters the connecting channel prior to the sealing element when the sealing element enters the connecting channel.

6. The apparatus according to claim 5, wherein the liquid inlet is located on a sealing element.

7. The apparatus according to claim 4, wherein the drain channel further has a liquid outlet, and the liquid outlet is in fluid communication with a receiving chamber.

8. The apparatus according to claim 7, wherein the receiving cavity is located in a sealing element.

9. The apparatus according to claim 1, wherein the apparatus further comprises a discharge element for removing a portion of liquid samples in the second chamber.

10. The apparatus according to claim 9, wherein the discharge element is located in the second chamber or partially in the second chamber before the second chamber is separated from the first chamber.

11. The apparatus according to claim 9, wherein the second chamber does not contain a discharge element or does not contain a portion of discharge element after the second chamber is separated from the first chamber.

12. The apparatus according to any one of claim 2, wherein the apparatus further comprises a discharge element for removing a portion of the liquid samples in the second chamber; the discharge element is located on a sealing element or is connected with a sealing element.

13. The apparatus according to claim 12, wherein the discharge element enters a connecting channel prior to the sealing element or the discharge element enters the second chamber prior to the sealing element; or the discharge element is located in the second chamber when the sealing element is located in a connecting channel.

14. A method of collecting liquid samples, comprising:
providing a collection apparatus, wherein the collection apparatus comprises a first chamber and a second chamber for collecting liquid samples, the first chamber and the second chamber are detachably combined, connected or assembled;
allowing the first chamber and the second chamber in a liquid communication state before collecting liquid samples, so that the liquid that enters the first chamber can flow into the second chamber,
wherein the first chamber and the second chamber are not in a liquid communication state after the first chamber collects liquid samples,
wherein the first chamber is connected to the second chamber by a connecting channel, the second chamber is detachably combined, connected or assembled with the connecting channel,
wherein a sealing element is used to sealing the connecting channel, to achieve non-communication state between the first chamber and the second chamber,
wherein the connecting channel has a first opening in fluid communication with the first chamber and a second opening in fluid communication with the second chamber, allowing the sealing element to seal the first opening of the connecting channel,
wherein the apparatus further comprises a drain channel, and the drain channel comprises a liquid inlet.

15. The method according to claim 14, wherein, when a portion of the sealing element enters the channel, liquid samples discharged by the sealing element are discharged out of the connecting channel and/or the second chamber through the liquid inlet in the case of presence of liquid samples.

16. The method according to claim 15, wherein liquid samples discharged by the sealing element are discharged to a receiving chamber through the drain channel.

17. The method according to claim 16, wherein the apparatus further comprising a discharge element configure to discharging a portion of liquid from the second chamber.

18. The method according to claim 17, wherein the sealing element and the discharge element move by linkage.

19. The method according to claim 18, wherein the linkage is performed by covering the cover a opening of the first chamber.

* * * * *